(12) United States Patent
Findley et al.

(10) Patent No.: US 9,913,469 B2
(45) Date of Patent: Mar. 13, 2018

(54) EARLY APPLICATIONS OF ENCAPSULATED ACETAMIDES FOR REDUCED INJURY IN CROPS

(75) Inventors: Douglas A. Findley, Creve Coeur, MO (US); S. Douglas Prosch, Ballwin, MO (US); Matthew T. Faletti, St. Louis, MO (US); Alejandro Perez-Jones, St. Louis, MO (US); Ronald J. Brinker, Ellisville, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 13/497,565

(22) PCT Filed: Aug. 18, 2011

(86) PCT No.: PCT/US2011/048303
§ 371 (c)(1),
(2), (4) Date: Mar. 22, 2012

(87) PCT Pub. No.: WO2012/024524
PCT Pub. Date: Feb. 23, 2012

(65) Prior Publication Data
US 2013/0029847 A1   Jan. 31, 2013

Related U.S. Application Data

(60) Provisional application No. 61/375,029, filed on Aug. 18, 2010, provisional application No. 61/374,984, filed on Aug. 18, 2010.

(51) Int. Cl.
*A01N 37/18* (2006.01)
*A01N 57/20* (2006.01)
*A01N 43/84* (2006.01)
*A01N 37/26* (2006.01)

(52) U.S. Cl.
CPC .................... *A01N 37/26* (2013.01)

(58) Field of Classification Search
CPC .... A01N 37/26; A01N 2300/00; A01N 25/28; A01N 33/18; A01N 33/22; A01N 37/40
USPC ................ 504/127, 130, 133, 136, 138, 139
See application file for complete search history.

(56) References Cited

U.S. PATENT DOCUMENTS

| | | | |
|---|---|---|---|
| 3,516,846 A | 6/1970 | Matson | |
| 3,516,941 A | 6/1970 | Matson | |
| 3,959,464 A | 5/1976 | Savigny | |
| 4,021,224 A | 5/1977 | Pallos et al. | |
| 4,107,292 A | 8/1978 | Nemeth | |
| 4,193,889 A | 3/1980 | Baatz et al. | |
| 4,280,833 A | 7/1981 | Beestman et al. | |
| 4,285,720 A | 8/1981 | Scher | |
| 4,356,108 A | 10/1982 | Schwab et al. | |
| 4,417,916 A | 11/1983 | Beestman et al. | |
| 4,428,983 A | 1/1984 | Nehen et al. | |
| 4,480,082 A | 10/1984 | McLean et al. | |
| 4,489,017 A | 12/1984 | Alberts et al. | |
| 4,563,212 A | 1/1986 | Becher et al. | |
| 4,599,271 A | 7/1986 | Chao | |
| 4,640,709 A | 2/1987 | Beestman | |
| 4,643,764 A | 2/1987 | Scher | |
| 4,668,580 A | 5/1987 | Dahm et al. | |
| 4,670,246 A | 6/1987 | Dahl et al. | |
| 4,681,806 A | 7/1987 | Matkan et al. | |
| 4,738,898 A | 4/1988 | Vivant | |
| 4,847,152 A | 7/1989 | Jabs et al. | |
| 4,859,788 A | 8/1989 | Brindopke et al. | |
| 4,889,719 A | 12/1989 | Ohtsubo et al. | |
| 4,938,797 A | 7/1990 | Hasslin et al. | |
| 4,956,129 A | 9/1990 | Scher et al. | |
| 5,006,161 A | 4/1991 | Hasslin et al. | |
| 5,049,182 A | 9/1991 | Scher et al. | |
| 5,223,477 A | 6/1993 | Scher et al. | |
| 5,310,721 A | 5/1994 | Lo | |
| 5,342,556 A | 8/1994 | Traubel et al. | |
| 5,354,742 A | 10/1994 | Deming et al. | |
| 5,461,027 A | 10/1995 | Bergman | |
| 5,463,175 A | 10/1995 | Barry et al. | |
| 5,583,090 A | 12/1996 | Stern et al. | |

(Continued)

FOREIGN PATENT DOCUMENTS

EP    0008207 A2    2/1980
EP    0017409 A1    10/1980

(Continued)

OTHER PUBLICATIONS

Parker, D.C., et al., "Fall and Early Preplant Application Timing Effects on Persistence and Efficacy of Acetamide Herbicides,"2005, Weed Tech, 19:6-13.
Scher, H.B., et al. "Microencapsulation of Pesticides by Interfacial Polymerization Utilizing Isocyanate or Aminoplast Chemistry," 1998, Pest Sci, 54/4:394-400, XP-000804298.
Stern, A.J., et al., "Chapter 7. Microencapsulation Technology and Future Trends," 1996, Pesticide Formulation and Adjuvant Technology, Foy and Pritchard, Eds., pp. 93-114.
Wilson, R., "Chapter 20: Encapsulated Acetochlor for Selective Weed Control in Roundup-Ready Sugarbeets," 2010, 2009 Weed Control Report, http://panhandle.unl.edu/c/document_library/get_file?uuid+a97205bc-1618-4ffc-ac2d-45bf5ee801b5 &groupId=131817, 3 pages.

(Continued)

*Primary Examiner* — Johann R Richter
*Assistant Examiner* — Courtney Brown
(74) *Attorney, Agent, or Firm* — Senniger Powers LLP; Erin C. Robert

(57) ABSTRACT

Methods of reducing injury to crop foliage and achieving weed control using encapsulated acetamide herbicides in pre-plant or preemergence crop plant applications are described. A composition comprising a first population of a particulate microencapsulated acetamide herbicide and a second population of a particulate microencapsulated acetamide herbicide is described wherein the application mixture exhibits a bimodal acetamide release profile. The compositions provide reduced crop injury through controlled herbicide release.

44 Claims, No Drawings

(56) References Cited

U.S. PATENT DOCUMENTS

| | | |
|---|---|---|
| 5,783,520 A | 7/1998 | Anderson et al. |
| 5,925,464 A | 7/1999 | Mulqueen et al. |
| 5,925,595 A | 7/1999 | Seitz et al. |
| 6,020,066 A | 2/2000 | Weisser et al. |
| 6,133,197 A | 10/2000 | Chen et al. |
| 6,337,130 B1 | 1/2002 | Von Koppenhagen et al. |
| 6,340,653 B1 | 1/2002 | Scher et al. |
| 6,448,476 B1 | 9/2002 | Barry |
| 6,485,736 B1 | 11/2002 | Shirley et al. |
| 6,566,306 B1 | 5/2003 | Wolf et al. |
| 6,653,256 B1 | 11/2003 | Wolf et al. |
| 6,730,635 B2 | 5/2004 | Wolf et al. |
| 6,740,488 B2 | 5/2004 | Rangwala et al. |
| 6,992,047 B2 | 1/2006 | Asrar et al. |
| 7,056,522 B2 | 6/2006 | Voris et al. |
| 7,199,185 B2 | 4/2007 | Hemming et al. |
| 7,381,861 B2 * | 6/2008 | Cerny et al. ............ 800/300 |
| 7,687,434 B2 | 3/2010 | De Billot et al. |
| 7,718,572 B2 | 5/2010 | Igari et al. |
| 7,754,655 B2 | 7/2010 | Wolf et al. |
| 2003/0022791 A1 | 1/2003 | Asrar et al. |
| 2004/0137031 A1 | 7/2004 | Seitz et al. |
| 2005/0208089 A1 | 9/2005 | Asrar et al. |
| 2005/0233907 A1* | 10/2005 | Nabors et al. ............ 504/149 |
| 2005/0277549 A1 | 12/2005 | Seitz et al. |
| 2008/0242548 A1 | 10/2008 | Asrar et al. |
| 2009/0105077 A1 | 4/2009 | Bhatti et al. |
| 2012/0129694 A1 | 5/2012 | Ditmarsen et al. |

FOREIGN PATENT DOCUMENTS

| | | |
|---|---|---|
| EP | 0148149 A2 | 7/1985 |
| EP | 0165227 A2 | 12/1985 |
| EP | 0252896 A2 | 1/1988 |
| EP | 0369614 A1 | 5/1990 |
| EP | 0679333 A2 | 11/1995 |
| EP | 0780154 A1 | 6/1997 |
| EP | 0148149 A2 * | 10/2005 |
| JP | 09-249505 | 9/1997 |
| WO | 8102505 A1 | 9/1981 |
| WO | 9213450 A1 | 8/1992 |
| WO | 9911122 A1 | 3/1999 |
| WO | 0005951 A1 | 2/2000 |
| WO | 0005952 A1 | 2/2000 |
| WO | 0110414 A1 | 2/2001 |
| WO | 0194001 A2 | 12/2001 |
| WO | 0196010 A1 | 12/2001 |
| WO | 2002036782 A2 | 5/2002 |
| WO | 2002082901 A1 | 10/2002 |
| WO | 2003092360 A2 | 11/2003 |
| WO | 2004054362 A1 | 1/2004 |
| WO | 2004054362 A1 | 7/2004 |
| WO | 2004072235 A2 | 8/2004 |
| WO | 2005012488 A2 | 2/2005 |
| WO | 2005012515 A2 | 2/2005 |
| WO | 2005122759 A1 | 12/2005 |
| WO | 2009103455 A2 | 8/2009 |
| WO | 2010093970 A2 | 8/2010 |

OTHER PUBLICATIONS

2010 Research Progress Report, Mar. 8-11, 2010, Western Society of Weed Science, Waikoloa, Hawaii, http://www.wsweedscience.org/Research Report Archive/2010 WSWS RPR.pdf, 146 pages.

International Search Report and Written Opinion issued in PCT/US2010/024158, dated Sep. 28, 2011, 16 pages.

International Search Report and Written Opinion issued in PCT/US2011/048303 dated Nov. 2, 2011, 18 pages.

MICRO-TECH® Herbicide, by Monsanto, Product Label, EPA Reg. No. 524-344, Copyright 2010, 19 pages.

Huston, P. L., et al., "Degradation of Selected Pesticide Active Ingredients and Commercial Formulations in Water by the Photo-Assisted Fenton Reaction," 1999, Wat Res, 33/5:1238-1246.

Pilon, P., "Pre-emergent Herbicide Application Guidelines," 2010, retreived from http://betterplants.basf.us/news-&-events/featured-stories/archived-featured-stories/pre-emergent-herbicide-guide-lines-paul-pilon.html, 4.14.14.

Zhang, B., et al., "Pesticide Processing Technology," 1996, Central Plains Farmer Press, pp. 64-65 and 74-76, 11 pages.

Han, X., "Pesticide Introduction," 1995, China Agricultural University Press, pp. 37-38, 6 pages.

Specimen Label Degree® Herbicide, Monsanto Company, EPA Reg. No. 524-496, 2012, 8 pages.

Specimen Label Harness® Herbicide by Monsanto, EPA Reg. No. 524-473, 2012, 9 pages.

* cited by examiner

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Chimeric DNA of cotton genomic DNA and
      transgene insert DNA

<400> SEQUENCE: 1
attcaatgta gtcaaacact                                              20

<210> SEQ ID NO 2
<211> LENGTH: 20
<212> TYPE: DNA
<213> ORGANISM: Artificial Sequence
<220> FEATURE:
<223> OTHER INFORMATION: Chimeric DNA of cotton genomic DNA and
      transgene insert DNA

<400> SEQUENCE: 2
ttgaatatat attacaaagc                                              20

<210> SEQ ID NO 3
<211> LENGTH: 2880
<212> TYPE: DNA
<213> ORGANISM: Artificial sequence
<220> FEATURE:
<223> OTHER INFORMATION: Chimeric DNA of cotton genomic DNA and
      transgene insert DNA

<400> SEQUENCE: 3
gcttggtacc gagctcggat ccactagtaa cggccgccag tgtgctggaa ttcgcccttt     60
tttactacga tgttaagtcc tattttacac agtttcttta agacagattt gaccgctcct    120
acgatacttg gagaaacgtt ggtcgaatgt ctcttagaat acaacaacac gatgatcaaa    180
gcagtagcac ctctgtagtg attaacgaac aagcgttgtc ttttttctatc accaaaacat   240 tggaaaacat ggagaggaaa agagtagaat tttggaaaga aaataatctt ggtatgagag    300
```

-continued

```
agtgagattg agcaaaaaat tttgaagagg tcttagcctt ttatatgcgt tcaaagtgga    360
ggaattttgg aaatatccat gtataatgag acaaaatctg catttaaaat ggcatttcgc    420
gtcgcctgcg tcgtgcgagt gcgcccaac  cctgacgggt ttggacttac accctcatac    480
acgcgaggca ggattccaag tttagtcatt caatcactct taaagtgagc ttcaagctta    540
gacattacaa attaaattaa ataatataag ataattgcgc taaataaaca aacattttt    600 ttgtgatcct gaacgtaatc aacgagggta tgatggttat gattcacgga aagagcgaga    660
gaagagaacc gtcgctcgaa gaggatgatg attcatccta ttcatgcacg actgtccaac    720
tccccaccca atcaaattcc aaattatgac atgagaagaa catcatccca cgtggtctgt    780
gcttcacgcc accatgtccc acgtgggctc cattttggtg gggcccttcc ccaccgccca    840
agctgatccc gggttggcca tccctacttt taattatcag agccacctcc ccaatctgca    900
aaacgacgga aatggaaaac tataatttc  tttttttca  acgtacttat aaaatatttt    960 tcaaaaagt  atgaataaaa ttgtgatatt gcttggccta agaggccaat cttttgcaaa   1020
tctcgaagtc gggaggcaca ataaaaactt ggaaagtttt ttcaagtgtc tgctttataa   1080
aattattgaa atgcatgtat tcgtacttgc cttatttatc gacaatttaa acattattat   1140
ttcatgaaaa tgtccttcca ccgatttcaa tgacaaaacc aataattact acttttatt   1200 ttcaattatg tcacggttca catgtttatt agggtttagg ttgaggttaa aactttcgac   1260
tctctattcg taacgcttaa agatgtaggg tttaggttga ggttaaaaca atcatgtaat   1320
gtaaggatac ctgaaaagct gtcattagtg taagtgttta ttactagggt tgtttaaatt   1380
catgttgatg tcaagcttgg ataacccatt ttactaaaaa aataaatgaa gtcccaaagg   1440
gcattgggca tcctatcaaa gatgggaaat tttttcaaaa ttttaaccta aaaagaggt    1500 ggaaagtctt agtccaaata atcagccaca tcagaatttg attcgtttct ttcaagcaaa   1560
ttatacctat tggctgcaat atctttaagt ggaatggtcg gccaaacttt tccatatcag   1620
cttgattcat ctctaaactt gattattctt ttttattaat attaaattcc acaacttgaa   1680 cttttaatttt tttaattaat taaaaaaatt gtcacctttt caagctgaaa agaaaaaga   1740 aaccttaatt attatcacta gtattaaatt tcaaaacttg atttgtccta aatttgaaaa   1800
ggggtctcct tcaattcata tatgtagtca tgaagattat aacttagctg aaaatggcct   1860
ccattatttg gctattcaa  tcaaaagttt acaaaactag tgcaaattta atatgataat   1920
gtctacaaga accaaatacg aattgagtaa atttttttgg ctaaaataaa ttacgaattg   1980
atgaattatc atttaaaaa  gttcttttta accatttctt ttactgaatt aaaaaaaggt   2040
tttattaatc atatatatta caaattaccc attaagtagc caaattacaa attttaattc   2100
aatgtagtca aacactgata gtttaaacat gactctctta aggtagccaa agcccgggct   2160
taattaaggc gcgccggcca agtcggccgc ggccgcgtta tcaagcttct gcaggtcctg   2220
ctcgagtgga agctaattct cagtccaaag cctcaacaag gtcagggtac agagtctcca   2280
aaccattagc caaaagctac aggagatcaa tgaagaatct tcaatcaaag taaactactg   2340
ttccagcaca tgcatcatgg tcagtaagtt tcagaaaaag acatccaccg aagacttaaa   2400
gttagtgggc atctttgaaa gtaatcttgt caacatcgag cagctggctt gtggggacca   2460
gacaaaaaag gaatggtgca gaattgttag gcgcacctac caaaagcatc tttgccttta   2520
ttgcaaagat aaagcagatt cctctagtac aagtggggaa caaataacg  tggaaaagag   2580 ctgtcctgac agcccactca ctaatgcgta tgacgaacgc agtgacgacc acaaaagaat   2640
```

| | |
|---|---|
| tagcttgagc tcaggattta gcagcattcc agattgggtt caatcaacaa ggtacgagcc | 2700 |
| atatcacttt attcaaattg gtatcgccaa aaccaagaag gaactcccat cctcaaaggt | 2760 |
| ttgtaaggaa gaattcgata tcaagcttga tatcggaagt ttctctcttg agggaggttg | 2820 |
| ctcgtggaat gggacacata tggttgttat aataaaccat ttccattgtc atgagatttt | 2880 |

<210> SEQ ID NO 4
<211> LENGTH: 1675
<212> TYPE: DNA
<213> ORGANISM: Artificial sequence
<220> FEATURE:
<223> OTHER INFORMATION: Chimeric DNA of cotton genomic DNA and
      transgene insert DNA

<400> SEQUENCE: 4

| | |
|---|---|
| tgaccgaagt taatatgagg agtaaaacac ttgtagttgt accattatgc ttattcacta | 60 |
| ggcaacaaat atattttcag acctagaaaa gctgcaaatg ttactgaata caagtatgtc | 120 |
| ctcttgtgtt ttagacattt atgaactttc ctttatgtaa ttttccagaa tccttgtcag | 180 |
| attctaatca ttgctttata attatagtta tactcatgga tttgtagttg agtatgaaaa | 240 |
| tattttttaa tgcattttat gacttgccaa ttgattgaca acatgcatca atcgacctgc | 300 |
| agccactcga gtggaggcct catctaagcc cccatttgga cgtgaatgta gacacgtcga | 360 |
| aataaagatt tccgaattag aataaatttgt ttattgcttt cgcctataaa tacgacggat | 420 |
| cgtaatttgt cgttttatca aaatgtactt tcatttttata ataacgctgc ggacatctac | 480 |
| atttttgaat tgaaaaaaaa ttggtaatta ctctttctttt ttctccatat tgaccatcat | 540 |
| actcattgct gatccatgta gatttcccgg acatgaagcc atttacaatt gaatatatat | 600 |
| tacaaagcta tttgcttata acatatgcga aaaattttgt actataatca ggggtaaatt | 660 |
| taggaggggg cttgtaggtc tcgcttctct taaaatgaaa aatttttctat ttagttattt | 720 |
| aaaattttaa aagtaaaata taaaaatttc atttaatcct ttaaaaatta taagatata | 780 |
| gactattaaa atgatgaaat tacaattta ttatcataaa aattataatt taatttcgac | 840 |
| ccctaacaaa atttttctgat tttgccccta actgtaatat ttgtataaaa acatttttctt | 900 |
| tttgcattta atgatttctt taattcagtc caagaaagaa atttattaat tgcatatgcg | 960 |
| aaagttagtc cttgcctagt gatattaaag gaaagaaaca taaaatcaat aaattaattt | 1020 |
| ttaaagcaaa tagtaaaaat aaggaaaaac tttctacgat agtctataat tcaaaaaag | 1080 |
| aaataataat ctttaaccat tgaattttaa aataacatca gaataatcta tttatttaat | 1140 |
| ttaataaata ataataacat atatattaat attaaaattt ttattgagct tagtgtcaca | 1200 |
| aatcaataaa aaatttctta caaaataaat tatattattt tgagggtgtt ttattatttt | 1260 |
| atatatttta tacagacata tagaaatata aatacacata ataaaatttg aatccaaatt | 1320 |
| tttaatttt aacatttata atttactatt caaccaaaat ttatttatt atttatatca | 1380 |
| aatttttata aatatattta tcagataatg cgattttttt tacctatata tagatgacat | 1440 |
| aatctacttt aaattaagtc ctaaaaataa tatatcatac caaaaaaatt cttaaaatga | 1500 |
| atctgataat acttaaccc ttttataaaa caatcttaac cccttatata ttttaatatt | 1560 |
| aatatcatta taaatataaa tctattgagc atatgtttta aaccaagtaa tgttgagtgc | 1620 |
| ggtagtaaaa ctcattacac atttttaagta gaacgtagtt cgaaccttgg agaag | 1675 |

EARLY APPLICATIONS OF ENCAPSULATED ACETAMIDES FOR REDUCED INJURY IN CROPS

REFERENCE TO RELATED APPLICATIONS

This application is the U.S. National Stage Application of International Application No. PCT/US2011/048303 filed Aug. 18, 2011, and claims the benefit of U.S. Provisional Application No. 61/374,984, filed Aug. 18, 2010, and U.S. Provisional Application No. 61/375,029, filed Aug. 18, 2010, the entire disclosures of which are incorporated herein by reference.

FIELD OF THE INVENTION

The present invention generally relates to methods of reducing injury to crop foliage and achieving commercial weed control using encapsulated acetamide (e.g., encapsulated acetanilide) herbicides. In particular, the present invention provides encapsulated acetamide (e.g., encapsulated acetanilide) herbicide compositions and methods that enable application preemergence to crop plants whereby simultaneous commercially acceptable weed control and commercially acceptable crop injury can be attained.

BACKGROUND OF THE INVENTION

The emergence of glyphosate-resistant weeds has generated interest in the use of residual herbicides as tank-mix partners with glyphosate in glyphosate-tolerant (e.g., ROUNDUP READY or RR) crops. Acetamide herbicides, including, for example, acetanilide herbicides, typically do not offer significant post-emergence activity, but as a residual partner would provide control of newly emerging monocots and small-seeded dicot weed species. This would usefully supplement the activity of glyphosate which is effective on emerged weeds, but lacks significant residual activity.

Commercially available acetanilide herbicide formulations are typically applied after the emergence of the crop (i.e., post-emergent to the crop), but before the emergence of later germinating weeds (i.e., preemergent to the weeds). Application during this time window, however, may cause unexpected foliar injury to the crop. Moreover, application during this window has prevented the use of acetanilide herbicides for burndown prior to crop plant emergence. Crop plant injury has been observed with both commercially available conventional acetanilide emulsifiable concentrate (EC) formulations and with commercially available encapsulated acetanilide formulations.

Prior art microencapsulation procedures are generally adequate for producing formulations with good weed control. However, the practitioner of this art has had some difficulty optimizing the release rates to obtain acceptable bioefficacy for a given active while minimizing crop injury to commercially acceptable levels. In particular, commercial encapsulated formulations may show greater systemic crop plant injury over time in the form of leaf crinkling and plant stunting when compared to emulsifiable concentrates.

In microencapsulation technology known in the art, core herbicide is typically released from a microcapsule at least in part by molecular diffusion through the shell wall. Modification of shell wall thickness to increase or decrease herbicide rate has definite limitations.

Thin shell walls are sensitive to premature mechanical rupture during handling or in the field, resulting in immediate release. Poor package stability resulting from shell wall defects can also arise when the core material is in direct contact with the external vehicle. As a result, some core material may crystallize outside the capsule causing problems in spray applications, such as spray nozzle plugging. Further, higher shear encountered in certain application means, such as spray applications, can result in shell wall rupture and herbicide release. The microcapsule thus becomes little more than an emulsion stabilized against coalescence. When delivered to the field, herbicide release is so fast that little crop safety improvement is gained over conventional emulsion concentrate formulations.

If the wall thickness is increased, the bioefficacy quickly drops to a marginal performance level because herbicide release is delayed. There is also a practical limit to the wall thickness in interfacial polymerization. As the polymer precipitates, the reaction becomes diffusion controlled. The reaction rate can drop to such an extent that non-constructive side reactions can predominate.

Various formulation solutions have been attempted to address the release rate limitations. For example, two package or single package blends of microcapsules and dispersions or emulsions of free agricultural actives have been proposed in Scher, U.S. Pat. Nos. 5,223,477 and 5,049,182. Seitz et al., U.S. Pat. No. 5,925,595 and U.S. Publication No. 2004/0137031 A1, teach methods for producing microencapsulated acetochlor. The degree of permeability is regulated by a compositional change in the precursors for the wall. Although the Seitz compositions have proven effective for weed control, unacceptable crop injury has been observed in connection with the use of those compositions when applied to certain commercially important crops.

A need therefore exists for herbicide compositions and methods utilizing acetamide herbicides such as acetanilide herbicides whereby simultaneous commercially acceptable weed control and commercially acceptable crop injury can be attained. A further need exists for acetamide (e.g., acetanilide) herbicide compositions and methods that enable application preemergence to crop plants.

SUMMARY OF THE INVENTION

Among the various aspects of the present invention may be noted the provision of encapsulated acetamide herbicide compositions and methods for use thereof. The present invention provides for acetamide application prior to planting of the crop plant or preemergence to the crop plant wherein herbicide release rate is controlled in order to give both commercially acceptable weed control and commercially acceptable crop injury.

In accordance with one embodiment, the present invention provides a method for controlling weeds in a field of crop plants. The method comprises applying an application mixture to the field in an herbicidally effective amount, wherein the application mixture comprises at least one particulate microencapsulated acetamide herbicide and the application mixture is applied to the field (i) prior to planting of the crop plant or (ii) preemergence to the crop plant.

In accordance with another embodiment, the present invention provides a particulate microencapsulated acetamide herbicide composition. The composition comprises a first population of a particulate microencapsulated acetamide herbicide and a second population of the particulate microencapsulated acetamide herbicide. The first and the second populations of the particulate microencapsulated acetamide herbicide each comprise a water-immiscible core material comprising the acetamide herbicide and a microcapsule containing the core material and having a shell wall comprising a polyurea. The shell wall is formed in a polymerization medium by a polymerization reaction between a polyisocyanate component comprising a polyisocyanate or mixture of polyisocyanates and a polyamine component comprising a polyamine or mixture of polyamines to form the polyurea. The first population of the particulate microencapsulated acetamide herbicide has a mean particle size of from about 3 µm to 11 µm and the second population of the particulate microencapsulated acetamide herbicide has a mean particle size of between 11 µm and about 20 µm. In accordance with one particular embodiment, the composition exhibits a multi-modal acetamide herbicide release profile.

Aqueous mixtures comprising the particulate microencapsulated acetamide herbicide compositions in the form of a concentrate or diluted spray application mixture and comprising one or more co-herbicides are also provided.

Other objects and features will be in part apparent and in part pointed out hereinafter.

DESCRIPTION OF THE EMBODIMENTS OF THE INVENTION

In accordance with the present invention, compositions comprising encapsulated herbicides (e.g., particulate microencapsulated herbicides) having a low initial release rate and a sustained long term release, and methods for using such compositions, are provided that provide both commercially acceptable weed control and commercially acceptable crop injury. The compositions are useful for the control of weeds when applied in a herbicidally effective amount prior to planting of the crop plant or preemergence to the crop plant.

In accordance with the present invention, it has been discovered that particulate microencapsulated acetamide (e.g., encapsulated acetanilide) herbicides can be applied to a field before crops are planted or from planting up to, but not including, plant emergence in order to achieve commercially acceptable rates of weed control and commercially acceptable rates of crop plant emergence and injury. Preplant, preemergence acetamide herbicide application in accordance with the present invention increases the application window beyond post-emergence in order to provide the benefit of treating a field prior to weed germination thereby aiding the establishment of crop plants. In particular, early application of encapsulated acetanilide herbicide, such as 1-40 days prior to planting, enables acetanilide exposure to weeds at germination in order to provide control of newly emerging monocots and small seeded dicot species during the early growing season when the crop plant is more susceptible to competition for water, sunlight and nutrients.

It has been further discovered that, for a given acetamide herbicide, the combination of a first population of a particulate microencapsulated acetamide herbicide and a second population of a particulate microencapsulated acetamide herbicide, wherein the first and second microencapsulated acetamide herbicides have different average size and shell thickness, can provide a longer duration of weed control and reduced crop injury as compared to either population of microencapsulated acetamide herbicide applied individually. The combination provides a multi-modal (e.g. bimodal) release profile wherein early acetamide release provides initial weed control without significant crop injury and sustained release over time provides extended residual control.

As used herein, "prior to planting of the crop plant" refers, for example, to a time period of from about 40 days prior to planting of the crop plant to immediately before planting of the crop plant, from about 35 days prior to planting of the crop plant to immediately before planting of the crop plant, from about 30 days prior to planting of the crop plant to immediately before planting of the crop plant, from about 25 days prior to planting of the crop plant to immediately before planting of the crop plant, from about 20 days prior to planting of the crop plant to immediately before planting of the crop plant, from about 15 days prior to planting of the crop plant to immediately before planting of the crop plant, from about 10 days prior to planting of the crop plant to immediately before planting of the crop plant, or from about 5 days prior to planting of the crop plant to immediately before planting of the crop plant. "Preemergence to the crop plant" refers to anytime during the interval from planting of the crop plant up to, but not including, emergence of the crop plant (i.e., before cracking). For example, during the interval of from about 1 day after planting, from about 2 days after planting, from about 3 days after planting, from about 4 days after planting, from about 5 days after planting, from about 10 days after planting, from about 15 days after planting, or from about 20 days after planting of the crop plant up to, but not including, emergence of the crop plant.

As further used herein, "weed control" refers to any observable measure of control of plant growth, which can include one or more of the actions of (1) killing, (2) inhibiting growth, reproduction or proliferation, and (3) removing, destroying, or otherwise diminishing the occurrence and activity of plants. Weed control can be measured by any of the various methods known in the art. For example, weed control can be determined as a percentage as compared to untreated plants following a standard procedure wherein a visual assessment of plant mortality and growth reduction is made by one skilled in the art specially trained to make such assessments. In another control measurement method, control is defined as a mean plant weight reduction percentage between treated and untreated plants. In yet another control measurement method, control can be defined as the percentage of plants that fail to emerge following a preemergence herbicide application. A "commercially acceptable rate of weed control" varies with the weed species, degree of infestation, environmental conditions, and the associated crop plant. Typically, commercially effective weed control is defined as the destruction (or inhibition) of at least about 60%, 65%, 70%, 75%, 80%, or even at least 85%, or even at least 90%. Although it is generally preferable from a commercial viewpoint that 80-85% or more of the weeds be destroyed, commercially acceptable weed control can occur at much lower destruction or inhibition levels, particularly with some very noxious, herbicide-resistant plants. Advantageously, the herbicidal microcapsules used in accordance with the present invention achieve commercially acceptable weed control in the time period of from application of the herbicide microcapsules, for example as contained in an application mixture, to 3 weeks, 4 weeks, 5 weeks, 6 weeks, 7 weeks, 8 weeks, 9 weeks, 10 weeks, 11 weeks, or even 12 weeks after application of the herbicide microcapsules.

Crop damage can be measured by any means known in the art, such as those described above for weed control determination. A "commercially acceptable rate of crop injury" for the present invention likewise varies with the crop plant species. Typically, a commercially acceptable rate of crop injury is defined less than about 20%, 15%, 10% or even less than about 5%. The herbicidal microcapsules and methods of the present invention limit crop injury to a commercially acceptable rate as measured from about 24 hours (about 1

Day After Treatment or DAT) after application to two weeks (about 14 DAT), from about 24 hours (about 1 DAT) after application to three weeks (about 21 DAT), or from about 24 hours (about 1 DAT) to about four weeks (about 28 DAT).

Acetanilide herbicides within the scope of the present invention are classified as seedling growth inhibitors. Seedling growth inhibitors are absorbed and translocated in plants from germination to emergence primarily by subsurface emerging shoots and/or seedling roots. In general, seedling growth inhibitors retard plant cell division through interference with lipid and protein synthesis (acetanilides) or cell division (dinitroanilides) thereby inhibiting shoot elongation and lateral root formation. In dicots (e.g., broadleaf plants), an embryonic shoot comprising three main parts emerges from the seed: the cotyledons (seed leaves), the section of shoot below the cotyledons (hypocotyl), and the section of shoot above the cotyledons (epicotyl). Dicot seedling growth inhibitors are believed to absorb primarily by the hypocotyl and epicotyl. In monocots (e.g., grasses), a coleophile emerges from the seed and extends to the soil surface where elongation terminates and leaves emerge. Monocot seedling growth inhibitors are believed to absorb primarily by the coleophile.

In contrast to preemergent plants, emergent plants are typically relatively unaffected by seedling growth inhibitor herbicides. For that reason, prior art practice has been to apply seedling growth inhibitor herbicides after crop emergence, but before weed emergence.

Certain crop plants such as corn, soybean, cotton, peanut and sugar beets are less susceptible to the action of acetamide herbicides than are weeds. In accordance with the present invention and based on experimental evidence to date, it is believed that the controlled acetamide release rate from the microencapsulated acetamide herbicides in combination with crop plants having reduced acetamide susceptibility enables commercial control of weeds and commercially acceptable rates of crop damage when microencapsulated acetamide herbicides are applied to a field either pre-planting or preemergent to the crop plant. This critical discovery enables the use of seedling growth inhibitor acetamide herbicides, or optionally seedling growth inhibitor acetamide herbicides in combination with one or more co-herbicides, in crop plant pre-planting and preemergence applications, such as for burndown.

In some embodiments of the present invention, crop plants include, for example, corn, peanuts, potatoes, soybeans, canola, alfalfa, sugarcane, sugarbeets, peanuts, grain sorghum (milo), field beans, rice, sunflowers, wheat and cotton. Crop plants include hybrids, inbreds, and transgenic or genetically modified plants having specific traits or combinations of traits including, without limitation, herbicide tolerance (e.g., resistance to glyphosate, glufosinate, dicamba, sethoxydim, etc.), Bacillus thuringiensis (Bt), high oil, high lysine, high starch, nutritional density, and drought resistance. In some embodiments, the crop plants are resistant to organophosphorus herbicides, acetolactate synthase (ALS) or acetohydroxy acid synthase (AHAS) inhibitor herbicides, synthetic auxin herbicides and/or acetyl CoA carboxylase (ACCase) inhibitor herbicides, In other embodiments the crop plants are resistant to glyphosate, dicamba, 2,4-D, MCPA, quizalofop, glufosinate and/or diclofop-methyl. In other embodiments, the crop plant is glyphosate and/or dicamba resistant. In some embodiments of the present invention, crop plants are glyphosate and/or glufosinate resistant. In some other embodiments, the crop plants are glyphosate, glufosinate and dicamba tolerant. Preferred crops include corn, cotton, soybeans, peanuts and sugarbeets. Particularly preferred crop species are corn, cotton and soybean.

Acetamide herbicides suitable for the practice of the present invention include dimethenamid, napropamide, pronamide and acetanilide herbicides such as acetochlor, alachlor, butachlor, butenachlor, delachlor, diethatyl, dimethachlor, mefenacet, metazochlor, metolachlor, pretilachlor, propachlor, propisochlor, prynachlor, terbuchlor, thenylchlor and xylachlor, mixtures thereof and stereoisomers thereof. Some acetamide herbicides are available in their free forms, as salts, or as derivatized materials, for example, as esters. Any form of the herbicides described herein by name is potentially applicable. For instance, the present invention has utility for both racemic metolachlor and S-metolachlor, and racemic dimethenamid and dimethenamid-P. Preferred acetamide herbicides include dimethenamid and dimethenamid-P and preferred acetanilide herbicides include acetochlor, metolachlor and S-metolachlor.

An additional aspect of the present invention is the use of the encapsulated acetamide formulations as tank mix partners with foliar active herbicides. An example of a foliar active herbicide includes, but is not limited to, glyphosate. It is well known in the art that the mixing of foliar active herbicides with co-herbicides (such as acetamides) and/or other materials which cause foliar injury can, in some cases, result in antagonism wherein the uptake of the foliar herbicides is reduced thereby resulting in lower herbicidal effectiveness. It is believed that the release rate of the encapsulated acetamides of the present invention is reduced as compared to prior art compositions thereby minimizing antagonism such that the co-herbicide (e.g. glyphosate) is effectively absorbed and translocated within the plant before leaf damage induced by the acetamide herbicide can significantly interfere with absorption and translocation of the co-herbicide. Therefore, in addition to reducing foliar injury on crop plants, the encapsulated acetamide herbicides of this invention should minimize the initial localized foliar injury to previously emerged weeds and thereby allow the foliar active components of the co-herbicide to effectively and efficiently absorb into and translocate through the previously emerged weeds in order to achieve maximum activity in the absence of antagonism between the acetamide and co-herbicide.

In general, the encapsulated herbicides of the present invention are prepared by contacting an aqueous continuous phase containing a polyamine component comprising a polyamine source and a discontinuous oil phase containing the herbicide and a polyisocyanate component comprising a polyisocyanate source. A shell wall is formed in a polymerization reaction between the polyamine source and the isocyanate source at the oil/water interface thereby forming a capsule or microcapsule containing the herbicide. The polyamine source can be a mixture of a principal polyamine and one or more auxiliary polyamines, also termed a polyamine mixture. In some embodiments of the present invention, the polyamine source consists essentially of a principal polyamine. As used herein, a principal polyamine (also referred to as a principal amine) refers to a polyamine consisting essentially of a single polyamine species. The polyisocyanate source can be a polyisocyanate or mixture of polyisocyanates.

In accordance with the present invention and based on experimental evidence, it has been discovered that the objects of the invention can be achieved by encapsulating herbicides, in particular, acetamides, in microcapsules prepared by the selection of one or more certain compositional and process variables including the molar ratio of polyamine to polyisocyanate, the shell wall composition, the weight ratio of core material (herbicide component) to shell wall material, the core material components, the mean microcapsule particle size, process conditions such as mixing shear and time, and combinations thereof. Through the careful selection of these and other factors, aqueous dispersions of microencapsulated herbicides have been developed according to the compositions and methods described herein which, as compared to compositions and methods known in the art, reduce crop foliage injury for preemergent application to the crop plants to a commercially acceptable level while simultaneously achieving commercially acceptable weed control for preemergent application to the weeds. Improved crop safety of the present invention is achieved even in the absence of a safener.

The microcapsule shell of the present invention may preferably comprise a polyurea polymer formed by a reaction between a principal polyamine, and optionally an auxiliary polyamine, having two or more amino groups per molecule and at least one polyisocyanate having two or more isocyanate groups per molecule. Release of the herbicide core material is controlled by the microcapsule shell wall, preferably without the need for mechanical release (microcapsule rupture).

In some embodiments, the microcapsules may be prepared by encapsulating core material in a shell wall formed by reacting polyamine component and a polyisocyanate component in a reaction medium in concentrations such that the reaction medium comprises a molar equivalent excess of amine groups compared to the isocyanate groups. More particularly, the molar concentration of amine groups from the principal polyamine and optional auxiliary polyamine and the molar concentration of isocyanate groups from the at least one polyisocyanate (i.e., one polyisocyanate, a blend of two polyisocyanates, a blend of three polyisocyanates, etc.) in the reaction medium is such that the ratio of the concentration of amine molar equivalents to the concentration of isocyanate molar equivalents is at least 1.1:1. The molar ratio of concentration of amine molar equivalents to concentration of isocyanate molar equivalents may be calculated according to the following equation:

$$\text{Molar Equivalents Ratio} = \frac{\text{amine molar equivalents}}{\text{polyisocyanate molar equivalents}} \quad (1)$$

In the above equation (1), the amine molar equivalents is calculated according to the following equation: amine molar equivalents=$\Sigma$([polyamine]/equivalent weight). In the above equation (1), the isocyanate molar equivalents is calculated according to the following equation:

i. isocyanate molar equivalents=$\Sigma$([polyisocyanate]/equivalent weight)

wherein the polyamine concentration and the polyisocyanate concentration refer to the concentration of each in the reaction medium and are each in grams/L. The equivalent weight is generally calculated by dividing the molecular weight in grams/mole by the number of functional groups per molecules and is in grams/mole. For some molecules, such as triethylenetetramine ("TETA") and 4,4'-diisocyanato-dicyclohexyl methane ("DES W"), the equivalent weight is equal to the molecular weight divided by the number of functional groups per molecule. For example, TETA has a molecular weight of 146.23 g/mole and 4 amine groups. Therefore, the equivalent weight is 36.6 g/mol. This calculation is generally correct, but for some materials, the actual equivalent weight may vary from the calculated equivalent weight. In some components, for example, the biuret-containing adduct (i.e., trimer) of hexamethylene-1,6-diisocyanate, the equivalent weight of the commercially available material differs from the theoretical equivalent weight due to, for example, incomplete reaction. The theoretical equivalent weight of the biuret-containing adduct (i.e., trimer) of hexamethylene-1,6-diisocyanate is 159.5 g/mol. The actual equivalent weight of the trimer of hexamethylene-1,6-diisocyanate ("DES N3200"), the commercially available product, is about 183 g/mol. This actual equivalent weight is used in the calculations above. The actual equivalent weight may be obtained from the manufacturer or by titration with a suitable reactant by methods known in the art. The symbol, $\Sigma$, in the amine molar equivalents calculation means that the amine molar equivalents comprises the sum of amine molar equivalents for all polyamines in the reaction medium. Likewise, the symbol, $\Sigma$, in the isocyanate molar equivalents calculation means that the isocyanate molar equivalents comprises the sum of isocyanate molar equivalents for all polyisocyanates in the reaction medium.

It is advantageous to select a polyamine component and a polyisocyanate component such that the principal polyamine and optional auxiliary polyamine has an amine functionality of at least 2, i.e., 3, 4, 5 or more, and at least one of the polyisocyanates has an isocyanate functionality of at least 2, i.e., 2.5, 3, 4, 5, or more since high amine and isocyanate functionality increases the percentage of cross-linking occurring between individual polyurea polymers that comprise the shell wall. In some embodiments, the principal polyamine and optional auxiliary polyamine has an amine functionality of greater than 2 and the polyisocyanate is a mixture of polyisocyanates wherein each polyisocyanate has an isocyanate functionality of greater than 2. In other embodiments the principal polyamine and optional auxiliary polyamine comprises a trifunctional polyamine and the polyisocyanate component comprises one or more trifunctional polyisocyanates. In yet other embodiments, the shell wall is formed by the reaction between a polyisocyanate or mixture of polyisocyanates with a minimum average of 2.5 reactive groups per molecule and a principal polyamine and optional auxiliary polyamine with an average of at least three reactive groups per molecule. It is, moreover, advantageous to select concentrations of the polyamine component and the polyisocyanate component such that the polyisocyanate component is substantially completely reacted to form the polyurea polymer. Complete reaction of the polyisocyanate component increases the percentage of cross-linking between polyurea polymers formed in the reaction thereby providing structural stability to the shell wall. These factors, i.e., the ratio of weight of core material components compared to weight of shell wall components, the mean particle sizes of the herbicidal microcapsules, the degree of crosslinking, among other factors, may be selected to affect the release rate profile of the population of herbicidal microcapsules, thereby enabling the preparation of herbicidal microcapsules that balance enhanced crop safety and are still efficacious for weed control.

Preferably, the molar equivalents ratio of amine molar equivalents to isocyanate molar equivalents is at least about 1.15:1 or even at least about 1.20:1. In some embodiments, the molar equivalents ratio is less than about 1.7:1, less than about 1.6:1, less than about 1.5:1, less than about 1.4:1, or even less than about 1.3:1. In some embodiments, the molar equivalents ratio of amine molar equivalents to isocyanate molar equivalents in the polymerization medium is from 1.1:1 to about 1.7:1, from 1.1:1 to about 1.6:1, from 1.1:1 to about 1.5:1, from 1.1:1 to about 1.4:1, from 1.1:1 to about 1.3:1, from about 1.15:1 to about 1.7:1, from about 1.15:1 to about 1.6:1, from about 1.15:1 to about 1.5:1, from about 1.15:1 to about 1.4:1, or from about 1.15:1 to about 1.3:1 Examples of typical ratios include 1.1, 1.15:1, 1.2:1, 1.25:1, 1.3:1, 1.35:1, 1.4:1, 1.45:1 and 1.5:1. The molar equivalents ratio used in the practice of the present invention is greater than that typically employed in prior art compositions wherein a small stoichiometric excess of amine equivalents to isocyanate equivalents of about 1.01:1 to about 1.05:1 is used to ensure that the isocyanate is completely reacted. It is believed, without being bound to any particular theory, that increased excess of amine groups used in the present invention results in a significant number of unreacted amine functional groups thereby providing a shell having a large number of amine functional groups that are not cross-linked. It is believed, that the combination of a completely reacted and cross-linked polyisocyanate component and an amine component having a significant number of unreacted and uncross-linked functional groups may result in a structurally stable shell wall that is more flexible and/or supple and less likely to shear or rupture as compared to shell walls known in the art. It is further believed that unreacted amine groups may reduce the number of fissures or cracks in the shell wall thereby reducing leakage from the core.

In some other embodiments, the concentration of core material in comparison to the concentration of shell wall components in the reaction medium is controlled thereby resulting in a variation of the microcapsule shell wall thickness. Preferably, the reaction medium comprises core material and shell wall components in a concentration (weight) ratio from about 16:1 to about 3:1, such as from about 13:1 to about 8:1, from about 13:1 to about 6:1, from about 12:1 to about 6:1, or from about 10:1 to about 6:1. The ratio is calculated by dividing the core material concentration (grams/L), which consists of the herbicide active and any diluent solvent or solvents, in the reaction medium by the concentration of the shell wall components (grams/L) in the reaction medium. The shell wall components concentrations comprises the concentration of the polyamine component and the concentration of the polyisocyanate component. In general, it has been found that decreasing the ratio of core material to shell wall components tends to reduce, by increase of shell wall thickness, the release rate of the core materials. This tends to decrease both the crop injury and weed control, although the amounts of the effects are not always correlated.

In some embodiments, a diluent, such as a solvent, may be added to change the solubility parameter characteristics of the core material to increase or decrease the release rate of the active from the microcapsule, once release has been initiated. For example, the core material may comprise from 0% to about 35% by weight of a diluent, for example from 0.1 to about 25% by weight, from about 0.5% and about 20% by weight, or from about 1% and 10% by weight. In particular, the core material may comprise 0%, 0.5% 1%, 2%, 3%, 4%, 5%, 6%, 7%, 8%, 10%, 15%, 20%, 25%, 30% or even 35% diluent. In some embodiments, the weight ratio of total core material to diluent can be, for example, from 8 to 1, from 10 to 1, from 15 to 1, or from 20 to 1. In some embodiments, the diluent is a water-insoluble organic solvent having a solubility of less than 10, 5, 1, 0.5 or even 0.1 gram per liter at 25° C. Examples of suitable water-insoluble solvents include paraffinic hydrocarbons. Paraffinic hydrocarbons are preferably predominantly a linear or branched hydrocarbon. Examples include pentadecane and ISOPAR V.

A population of herbicidal microcapsules of the present invention may be prepared having at least one mean transverse dimension (e.g., diameter or mean particle size) of at least about 7 micrometers ("microns" or μm). The particle size may be measured with a laser light scattering particle size analyzer known to those skilled in the art. One example of a particle size analyzer is a Coulter LS Particle Size Analyzer. The microcapsules are essentially spherical such that the mean transverse dimension defined by any point on a surface of the microcapsule to a point on the opposite side of the microcapsule is essentially the diameter of the microcapsule. Preferably, the population of microcapsules has at least one mean transverse dimension, or mean particle size, of at least about 7 μm, more preferably at least about 8 μm, more preferably at least about 9 μm, more preferably at least about 10 μm. In preferred embodiments, the mean particle size of the population of microcapsules is less than about 15 μm, and more preferably less than 12 μm. In view thereof, a population of herbicidal microcapsules of the present invention preferably has a mean particle size of from about 7 μm to about 15 μm, from about 7 μm to about 12 μm, from about 8 μm to about 12 μm, or from about 9 μm to about 12 μm. In particularly preferred embodiments, the range varies from about 9 μm to about 11 μm.

In some embodiments of the present invention, the compositions comprise a blend of a first population of a particulate microencapsulated acetamide herbicide and a second population of a particulate microencapsulated acetamide herbicide. The first population of microencapsulated acetamide herbicide has a mean particle size of from about 3 μm to about 11 μm, from about 4 μm to 11 μm, from about 5 μm to 11 μm, from about 6 μm to 11 μm, from about 7 μm to 11 μm or from about 8 μm to 11 μm. The second population of microencapsulated acetamide herbicide has a mean particle size of between 11 μm and about 20 μm, from 11.5 μm to about 20 μm, from 12 μm to about 20 μm, from 11.5 μm to about 18 μm, from 12 μm to about 18 μm, from 11.5 μm to about 16 μm, from 12 μm to about 16 μm, from about 11.5 μm to about 15 μm, from 12 μm to about 15 μm, from 11.5 μm to about 14 μm or from 12 μm to about 14 μm. The weight ratio of the first population of particulate microencapsulated acetamide herbicide to the second population of particulate microencapsulated acetamide herbicide is about 10:1, 5:1, 3:1, 2:1, 1:1, 1:2, 1:3, 1:5 or about 1:10 and ranges thereof, such as from about 10:1 to about 1:10, from about 5:1 to about 1:5, from about 3:1 to about 1:3 from about 2:1 to about 1:2 or is about 1:1. The ratio of amine molar equivalents contained in the polyamine component to isocyanate molar equivalents contained in the polyisocyanate component, as well as other characteristics and methods related to as described herein for the microencapsulated acetamide herbicides, generally apply to both the first and second populations of particulate microencapsulated acetamides. In particular, the particle size shell wall characteristics for the first and second populations can be achieved as described above. It is believed, based on experimental evidence to date, that release rate decreases with increasing shell wall amount (calculated on the basis of acetamide herbicide content) and particle size. It is further believed that the release rate increases with increasing amine excess and ratio of acetamide to solvent (diluent, e.g., NORPAR). Release rate is generally decreased with an amine excess of from about 1% to about 10%, from about 2% to about 8% or from about 3% to about 7% and an acetamide to solvent ratio of from 1 to 10, from 5 to 10 or from 7 to 9. Release rate is generally increased with an amine excess of from about 10% to about 30%, from about 15% to about 25% or from about 18% to about 22% and an acetamide to solvent ratio of from 10 to 25, from 15 to 20 or from 17 to 19. The acetamide release rate for a mixture of the first and second particulate microencapsulated acetamide herbicide blend can be measured according to the methods described herein. A total acetamide release rate from the application mixture comprising the blended first and second particulate microencapsulated acetamide herbicide is preferably less than about 100 ppm after agitation for 6 hours at 25° C. and less than about 150 ppm after agitation for 24 hours at 25° C.; less than about 75 ppm after 6 hours, and less than about 125 ppm after 24 hours; less than about 60 ppm after 6 hours, and less than about 100 ppm after 24 hours; or even less than about 50 ppm after 6 hours, and less than about 75 ppm after 24 hours.

An example of a blend of a first particulate microencapsulated acetamide herbicide and a second particulate microencapsulated acetamide herbicide that provides a multimodal (e.g., bimodal) release rate when combined is as follows: (1) A first particulate microencapsulated acetamide herbicide wherein a population thereof has an acetochlor loading of about 33.0% by weight, a shell wall amount of about 8% (based on acetamide herbicide content), an amine excess over isocyanate of about 20%, an acetochlor to paraffin oil ratio of about 18.5:1, and a mean particle size of about 10 μm; and (2) A second particulate microencapsulated acetamide herbicide wherein a population thereof has an acetochlor loading of about 41% by weight, a shell wall amount of about 7.1% (based on acetamide herbicide content), an amine excess over isocyanate of about 5%, an acetochlor to paraffin oil ratio of about 8.4:1, and a mean particle size of from about 12 μm to about 13 μm. As compared to the particulate blend, the first population of microencapsulated acetochlor herbicide particulates provides a faster release rate and the second population of microencapsulated acetochlor herbicide particulates provides a slower release rate.

The particle size of the microcapsules of the present invention are larger than that typically employed in the art and is generally achieved by varying the composition, as described above, and by controlling the reaction conditions such as, for example, blending speed, shear forces, mixer design and mixing times. In general, reduced blending speed, shear forces and mixing time favor the preparation of larger microcapsules.

In other embodiments of the present invention, two or more of the above variables can be manipulated in order to achieve the objects of the present invention. Manipulation of the following variable combinations is within the scope of the present invention: (1) (i) the ratio of molar equivalent amine groups to isocyanate groups and (ii) the weight ratio of the core herbicide to the shell wall components; (2) (i) the ratio of molar equivalent amine groups to isocyanate groups and (iii) the weight ratio of the core herbicide to the diluent (e.g., solvent); (3) (i) the ratio of molar equivalent amine groups to isocyanate groups and (iv) the microcapsule particle size; (4) (ii) the weight ratio of the core herbicide to the shell wall components and (iii) the weight ratio of the core herbicide to the diluent; (5) (ii) the weight ratio of the core herbicide to the shell wall components and (iv) the microcapsule particle size; (6) (iii) the weight ratio of the core herbicide to the diluent and (iv) the microcapsule particle size; (7) (i) the ratio of molar equivalent amine groups to isocyanate groups, (ii) the weight ratio of the core herbicide to the shell wall components, and (iii) the weight ratio of the core herbicide to the diluent; (8) (i) the ratio of molar equivalent amine groups to isocyanate groups, (ii) the weight ratio of the core herbicide to the shell wall components, and (iv) the microcapsule particle size; (9) (i) the ratio of molar equivalent amine groups to isocyanate groups, (iii) the weight ratio of the core herbicide to the diluent and (iv) the microcapsule particle size; (10) (ii) the weight ratio of the core herbicide to the shell wall components, (iii) the weight ratio of the core herbicide to the diluent and (iv) the microcapsule particle size; and (11) (i) the ratio of molar equivalent amine groups to isocyanate groups, (ii) the weight ratio of the core herbicide to the shell wall components, (iii) the weight ratio of the core herbicide to the diluent and (iv) the microcapsule particle size.

The release rate of the core material from the microcapsules can be controlled by selecting capsule properties and composition and by selecting process parameters as previously described. Therefore, by appropriate choice of the parameters discussed previously and below, it is possible to create formulations that have acceptable safety when applied as a broadcast spray to a field either before crops are planted or after planting, but before emergence and maintain good weed control for agriculturally useful lengths of time.

The microcapsules of the present invention exhibit a release rate profile that provides a reduced rate of crop injury as compared to microcapsules known in the art. Under one theory, and without being bound to any particular theory, it is believed that increasing the mean particle size of the population of microcapsules decreases the total effective area per unit weight of the microcapsules. Since the diffusional release is proportional to the surface area, this tends, if everything else is held constant, to reduce the release rate. This in turn tends to reduce both the weed control and crop injury. However, it has been surprisingly discovered that the microcapsules of the present invention provide crop plant injury that is even less than would be expected based only on a particle size-mediated release rate. It is believed, without being bound to any particular theory, that the combination of increased particle size and the shell characteristics resulting from a large excess of unreacted amine groups significantly reduces the amount of herbicide that the crop plants are exposed to following a pre-planting or preemergent application, thereby providing enhanced crop safety and minimized crop plant injury. It is believed that, as compared to prior art microcapsules, the flexible shell of the present invention is resistant to rupturing such that the amount of herbicide that crop plants are initially exposed to upon application of a herbicidal formulation containing the microcapsules is reduced. Additionally or alternatively, it is believed that the shell wall of the microcapsules is characterized by reduced fissuring that decreases leakage and flow of herbicide through the shell wall. In addition, optimizing the weight ratio of the core to the shell and the weight ratio of the core herbicide to the diluent (solvent) may further affect release rate and achieve the objects of the present invention.

The release rate profile for the purposes of estimating the potential for crop injury of the herbicidal active from a population of herbicidal microcapsules of the present invention may be measured in the laboratory using an agitated dissolution test apparatus known in the art, such as a SOTAX AT-7 (SOTAX Corporation; Horsham, Pa. 19044) or a HANSON SR8-PLUS (available from Hitachi). In the dissolution rate method protocol of the present invention, an aqueous slurry consisting of 1% by weight of the encapsulated acetamide herbicide active ingredient in an aqueous medium consisting of deionized water is prepared. For example, a 100 mL aqueous slurry would contain a total of about 1 gram acetamide herbicide. For microcapsules comprising 50% by weight acetamide, the aqueous slurry therefore would contain 2% by weight of the microcapsules. The aqueous slurry is placed a cell of the dissolution test apparatus and agitated at a temperature of 25° C. The aqueous slurry is agitated at a rate sufficient to maintain the microcapsule particles in suspension throughout the test without mechanical rupture of the microcapsule particles. For example, in the case of a SOTAX AT-7 agitated dissolution test apparatus, the agitator is rotated at about 150 RPM. Aliquots are removed periodically to determine the concentration of herbicide, e.g., at 0, 1, 2, 4, 6, and 24 hours. Each aliquot is filtered through a syringe filter (TARGET Cellulose Acetate 0.2 μm, ThermoFisher Scientific) to remove any capsules. The resulting solution is then analyzed for the active by standard analytical methods known in the art, such as, for instance, HPLC.

According to the method described herein for determining the release rate profile and based on experimental evidence, it is believed that good crop safety correlates to an encapsulated acetamide herbicide contained within a shell of limited permeability wherein a concentration of acetamide herbicide (e.g., acetochlor) in the test aliquot at 6 hours is less than about 100 ppm (about 1% of the total acetamide) and a concentration of acetamide in the test aliquot at 24 hours is less than about 150 ppm (1.5% of the total acetamide. Preferably, the concentration of acetamide in the test aliquot at 6 hours is less than about 75 ppm (0.75% of the total acetamide), and the concentration of acetamide in the test aliquot at 24 hours is less than about 125 ppm (1.25% of the total acetamide). More preferably, the concentration of acetamide in the test aliquot at 6 hours is less than about 60 ppm (0.60% of the total acetamide) and less than 100 ppm (1.00% of the total acetamide) for the test aliquot at 24 hours. Even more preferably, the concentration of acetamide in the test aliquot at 6 hours is less than about 50 ppm (0.50% of the total acetamide) and less than about 75 ppm (0.75% of the total acetamide) in the test aliquot at 24 hours. It has been observed that herbicidal microcapsules having release rate profiles with the above-described parameters generally provide both commercially acceptable crop plant safety and efficacy on weeds. By comparison, a sample of DEGREE Herbicide, a commercially available microencapsulated acetochlor formulation available from Monsanto Company, typically releases from about 125 ppm to about 140 ppm in the aliquot at 6 hours and about 200 ppm (close to saturation) in the aliquot at 24 hours.

Preparation of the encapsulated acetamide herbicides of the present invention is described in more detail below.

Acetamide Encapsulation

The polyurea polymer shells of the present invention include a repeat unit having the general structure (I):

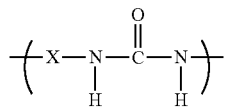

Structure (I)

wherein X generally represents some portion, or portions, of the repeat units which, as further defined herein below, may be independently selected from a number of different entities (e.g., different hydrocarbylene linkers, such as aromatic, aliphatic, and cycloaliphatic linking groups, and moieties having combinations of aromatic, aliphatic, and cycloaliphatic linking groups). The shell encapsulates an acetamide-containing core material such that, once initiated, molecular diffusion of the acetamide through the shell wall is preferably the predominant release mechanism (as further described elsewhere herein). Thus, the shell is preferably structurally intact; that is, the shell is preferably not mechanically harmed or chemically eroded so as to allow the acetamide to release by a flow mechanism. Further, the shell is preferably substantially free of defects, such as micropores and fissures, of a size which would allow the core material to be released by flow. Micropores and fissures may form if gas is generated during a microcapsule wall-forming reaction. For example, the hydrolysis of an isocyanate generates carbon dioxide. Accordingly, the microcapsules of the present invention are preferably formed in an interfacial polymerization reaction in which conditions are controlled to minimize the in situ hydrolysis of isocyanate reactants. The reaction variables that may preferably be controlled to minimize isocyanate hydrolysis include, but are not limited to: selection of isocyanate reactants, reaction temperature, and reaction in the presence of an excess of amine molar equivalents over isocyanate molar equivalents.

As used herein, "flow" of the core material from the microcapsule generally refers to a stream of the material that drains or escapes through a structural opening in the shell wall. In contrast, "molecular diffusion" generally refers to a molecule of, for example, an acetanilide, which is absorbed into the shell wall at the interior surface of the wall and desorbed from the shell wall at the exterior surface of the wall.

As described above, the polyurea polymer is preferably the product of a reaction between a polyamine component comprising a principal polyamine (and optional auxiliary polyamine) having two or more amino groups per molecule and a polyisocyanate component comprising at least one polyisocyanate having two or more isocyanate groups per molecule. In some embodiments, the at least one polyisocyanate comprises a blend of two or more polyisocyanates. In some preferred embodiments, the blend of polyisocyanates comprises at least one diisocyanate, i.e., having two isocyanate groups per molecule, and at least one triisocyanate, having three isocyanate groups per molecule. Preferably, neither the principal amine nor the auxiliary amine are the product of a hydrolysis reaction involving any of the polyisocyanates with which they react to form the polyurea polymer. More preferably, the shell wall is substantially free of a reaction product of a polyisocyanate with an amine generated by the hydrolysis of the polyisocyanate. This in situ polymerization of an isocyanate and its derivative amine is less preferred for a variety of reasons described elsewhere herein.

The shell wall of the microcapsules may be considered "semi-permeable," which, as used herein, generally refers to a microcapsule having a half-life that is intermediate between release from a substantially impermeable microcapsule and a microcapsule that essentially allows the immediate release of core material (i.e., a microcapsule having a half-life of less than about 24 hours, about 18 hours, about 12 hours, or even about 6 hours). For example, a "semi-permeable" microcapsule may have a half-life that is from about 5 to about 150 days, about 10 to about 125 days, about 25 to about 100 days, or about 50 to about 75 days.

Polyisocyanates

The polyurea polymer shell or wall of the microcapsules may be formed using one or more polyisocyanates, i.e., having two or more isocyanate groups per molecule. In some embodiments, the polyurea shell wall is formed using a blend of at least two polyisocyanates. In a preferred embodiment, the polyurea shell wall is formed in an interfacial polymerization reaction using at least one diisocyanate and at least one triisocyanate.

Polyisocyanates for use in forming the shell wall of the present invention have the following general structure (II):

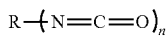

Structure (II)

wherein n is an integer that is at least 2, such as from 2 to five, from 2 to 4, and preferably is 2 or 3; and R is a group linking the 2 or more isocyanate groups together, including any aromatic, aliphatic, or cycloaliphatic groups, or combinations of any of aromatic, aliphatic, or cycloaliphatic groups, which are capable of linking the isocyanate groups together.

A wide variety of aliphatic diisocyanates, cycloaliphatic diisocyanates, and aromatic diisocyanates (wherein X is two in structure (II)) may be employed, for example, diisocyanates containing an aliphatic segment and/or containing a cycloaliphatic ring segment or an aromatic ring segment may be employed in the present invention as well.

General aliphatic diisocyanates include those having the following general structure (III):

  Structure (III)

wherein n is an integer having an mean value of from about 2 to about 18, from about 4 to about 16, or about 6 to about 14. Preferably, n is six, i.e., 1,6-hexamethylene diisocyanate. The molecular weight of 1,6-hexamethylene diisocyanate is about 168.2 g/mol. Since 1,6-hexamethylene diisocyanate comprises 2 isocyanate groups per molecule, its equivalent weight is about 84.1 g/mol. The equivalent weight of the polyisocyanate is generally defined as the molecular weight divided by the number of functional groups per molecule. As noted above, in some polyisocyanates, the actual equivalent weight may differ from the theoretical equivalent weight, some of which are identified herein.

In certain embodiments, the aliphatic diisocyanates include dimers of diisocyanates, for example, a dimer having the following structure (IV):

Structure (IV)

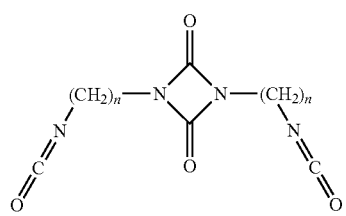

wherein n is an integer having an mean value of from about 2 to about 18, from about 4 to about 16, or about 6 to about 14. Preferably, n is six, i.e., structure (IV) is a dimer of 1,6-hexamethylene diisocyanate (molecular weight 339.39 g/mol; equivalent weight=183 g/mol).

A wide variety of cylcoaliphatic and aromatic diisocyanates may be used as well. In general, aromatic diisocyanates include those diisocyanates wherein the R linking group contains an aromatic ring, and a cycloaliphatic diisocyanates include those diisocyanates wherein the R linking group contains a cylcoaliphatic ring. Typically, the R group structure in both aromatic and cycloaliphatic diisocyanates contains more moieties than just an aromatic or cycloaliphatic ring. The nomenclature herein is used to classify diisocyanates.

Certain commercially available aromatic diisocyanates comprise two benzene rings, which may be directly bonded to each other or connected through an aliphatic linking group having from one to about four carbon atoms. One such aromatic diisocyanate is 4,4'-diisocyanato-diphenylmethane (bis(4-isocyanatophenyl)methane (Molecular weight=250.25 g/mol; equivalent weight=125 g/mol) having the following structure (V):

Structure (V)

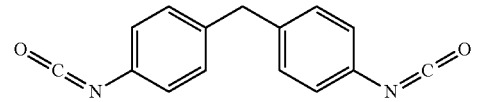

Aromatic diisocyanates having structures similar to structure (V) include 2,4'-diisocyanato-diphenylmethane (Molecular weight=250.25 g/mol; equivalent weight=125 g/mol) and 2,2'-diisocyanato-diphenyl methane (Molecular weight=250.25 g/mol; equivalent weight=125 g/mol).

Other aromatic diisocyanates, wherein the benzene rings are directly bonded to each other include, 4,4'-diisocyanato-1,1'-biphenyl and 4,4'-diisocyanato-3,3'-dimethyl-1,1'-biphenyl (Molecular weight=264.09 g/mol; equivalent weight=132 g/mol), which has the following structure (VI):

Structure (VI)

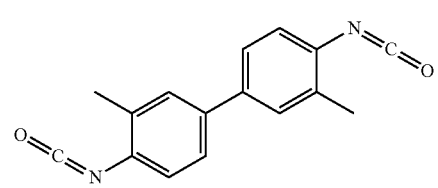

Yet another aromatic diisocyanate is dianisidine diisocyanate (4,4'-diisocyanato-3,3'-dimethoxybiphenyl) (Molecular weight=296 g/mol; equivalent weight=148 g/mol) having the following structure (VII):

Structure (VII)

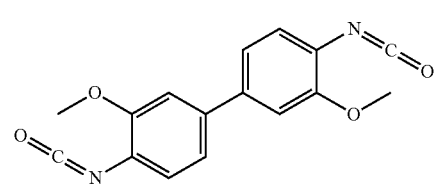

Certain commercially available aromatic diisocyanate comprise a single benzene ring. The isocyanate groups may be directly bonded to the benzene ring or may be linked through aliphatic groups having from one to about four carbon atoms. An aromatic diisocyanate having a single benzene ring is meta-phenylene diisocyanate (1,3-diisocyanatobenzene) (Molecular weight=160.1 g/mol; equivalent weight=80 g/mol) having the structure (VIII):

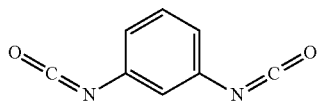

Structure (VIII)

Similar aromatic diisocyanates include para-phenylene diisocyanate (Molecular weight=160.1 g/mol; equivalent weight=80 g/mol), 2,4-toluene diisocyanate (2,4-diisocyanato-1-methylbenzene) (Molecular weight=174.2 g/mol; equivalent weight=85 g/mol), 2,6-toluene diisocyanate (Molecular weight=174.2 g/mol; equivalent weight=85 g/mol), and 2,4,6-triisopropyl-m-phenylene isocyanate. Similar diisocyanates having aliphatic groups linking the isocyanates to the benzene ring include 1,3-xylylene diisocyanate, 1,4-xylylene diisocyanate, tetramethyl-meta-xylylene diisocyanate, tetramethyl-para-xylylene diisocyanate, and meta-tetramethylxylene diisocyanate (1,3-bis(2-isocyanatopropan-2-yl)benzene).

Cycloaliphatic diisocyanate may include one or more cycloaliphatic ring groups having from four to about seven carbon atoms. Typically, the cycloaliphatic ring is a cyclohexane ring. The one or more cyclohexane rings may be bonded directly to each other or through an aliphatic linking group having from one to four carbon atoms. Moreover, the isocyanate groups may be directly bonded to the cycloaliphatic ring or may be linked through an aliphatic group having from one to about four carbon atoms. An example of a cycloaliphatic isocyanate is a 4,4'-diisocyanato-dicyclohexyl methane (bis(4-isocyanatocyclohexyl)methane) such as Desmodur W (Miles) having the structure (IX):

Structure (IX)

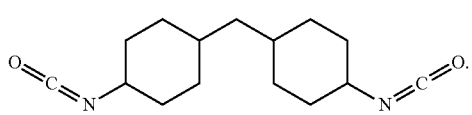

Desmodur W has an approximate molecular weight of 262.35 and an approximate equivalent weight of 131.2 g/mole. Additional cycloaliphatic diisocyanates include 1,3-bis(isocyanatomethyl)cyclohexane and isophorone diisocyanate (5-isocyanato-1-(isocyanatomethyl)-1,3,3-trimethylcyclohexane).

Certain aliphatic triisocyanates include, for example, trifunctional adducts derived from linear aliphatic diisocyanates. The linear aliphatic diisocyanate may have the following structure (III):

O=C=N—(CH$_2$)$_n$—N=C=O     Structure (III)

wherein n is an integer having an mean value of from about 2 to about 18, from about 4 to about 16, or about 6 to about 14. A particularly preferred linear aliphatic diisocyanate of structure (III) useful for preparing aliphatic triisocyanates is a trimer of hexamethylene-1,6-diisocyanate. The aliphatic triisocyanates may be derived from the aliphatic isocyanate alone, i.e., dimers, trimers, etc., or they may be derived from a reaction between the aliphatic isocyanate of structure (I), and a coupling reagent such as water or a low molecular weight triol like trimethylolpropane, trimethylolethane, glycerol or hexanetriol.

An exemplary aliphatic triisocyanate, wherein n is 6, is the biuret-containing adducts (i.e., trimers) of hexamethylene-1,6-diisocyanate corresponding to the structure (X):

Structure (X)

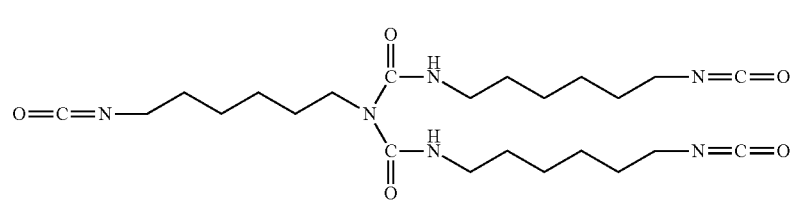

This material is available commercially under the trade name Desmodur N3200 (Miles) or Tolonate HDB (Rhone-Poulenc). Desmodur N3200 has an approximate molecular weight of 478.6 g/mole. The commercially available Desmodur N3200 has an approximate equivalent weight of 191 g/mol (Theoretical equivalent weight is 159 g/mol).

Another aliphatic triisocyanate derived from the aliphatic isocyanate of structure (III) corresponds to the following general structure:

Structure (XI)

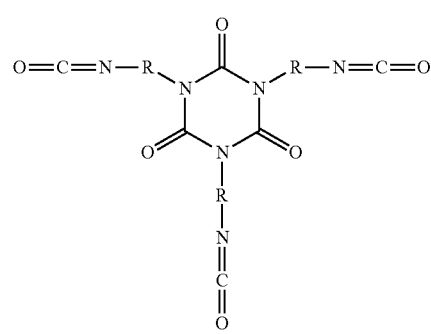

A specific aliphatic triisocyanate of the above structure wherein the R groups are linear hydrocarbons having six carbon atoms (trimers of hexamethylene-1,6-diisocyanate) having the name HDI isocyanurate trimer, which is available commercially under the trade names Desmodur N3300 (Miles) or Tolonate HDT (Rhone-Poulenc). Desmodur N3300 has an approximate molecular weight of 504.6 g/mol, and an equivalent weight of 168.2 g/mol.

Another exemplary aliphatic triisocyanate is the triisocyanate adduct of trimethylolpropane and hexamethylene-1,6-diisocyanate corresponding to the structure (XII):

Structure (XII)

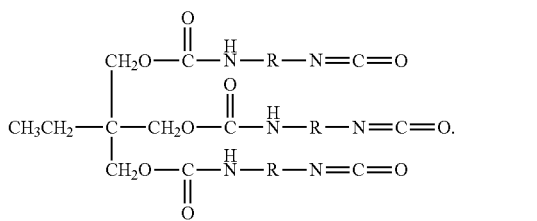

Aromatic triisocyanates containing an aromatic moiety are also useful in the present invention, including for example those which contain or comprise polymethylenepolyphenyl polyisocyanate (CAS #9016-87-9, 4,4'-(4-isocyanato-1,3-phenylene)bis(methylene)s(isocyanatobenzene)) having the structure (XIII):

Structure (XIII)

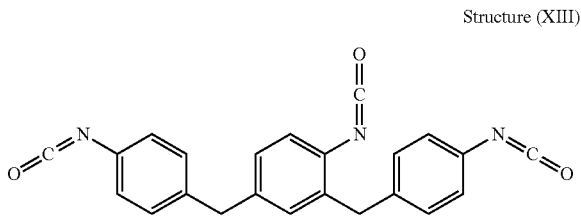 [SMILES: O=C=Nc1ccc(Cc2ccc(N=C=O)c(Cc3ccc(N=C=O)cc3)c2)cc1]

Isocyanates with an aromatic moiety may have a tendency to undergo in situ hydrolysis at a greater rate than aliphatic isocyanates. Since the rate of hydrolysis is decreased at lower temperatures, isocyanate reactants are preferably stored at temperatures no greater than about 50° C., and isocyanate reactants containing an aromatic moiety are preferably stored at temperatures no greater than about 20° C. to about 25° C., and under a dry atmosphere.

Still other polyisocyanates include toluene diisocyanate adducts with trimethylolpropane, xylene diisocyanate and polymethylenepolyphenyl polyisocyanate-terminated polyols.

It is to be noted that selection of the polyisocyanate, or blend of polyisocyanates, to be used may be determined experimentally using means known in the art (see, e.g., U.S. Pat. No. 5,925,595, the entire contents of which are incorporated herein for all relevant purposes). Where a blend of a triisocyanate and a diisocyanate is used, the ratio of the triisocyanate to the diisocyanate, on an isocyanate equivalent basis, is between about 90:10 and about 30:70.

Amines

A. Principal Amines

In some preferred embodiments of the present invention, the polyamine component consists essentially of the principal amine. Similarly stated, in some embodiments, the polyamine component is a principal amine in the absence of one or more auxiliary amines. The polyurea polymers, from which the microcapsule shell wall is prepared or formed, may comprise an amine or polyfunctional amine precursor (e.g., monomer). Among the amines or polyfunctional amines that may be employed to prepare a preferred microcapsule of the present invention are, for example, linear alkylamines or polyalkylamines, having the general structure:

$H_2N-X-NH_2$     Structure (XIV)

wherein "X" is selected from the group consisting of $-(CH_2)_a-$ and $-(C_2H_4)-Y-(C_2H_4)-$; "a" is an integer having a value from about 1 to about 8, 2 to about 6, or about 3 to about 5; and, "Y" is selected from the group consisting of $-S-S-$, $-(CH_2)_b-Z-(CH_2)_b-$, and $-Z-(CH_2)_a-Z-$, wherein "b" is an integer having a value from 0 to 4, or from 1 to 3, "a" is as defined above, and "Z" is selected from the group consisting of

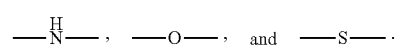

Examples of such amines or polyfunctional amines that may typically be employed in the present invention include substituted and unsubstituted polyethyleneamines, such as (i) amines of the structure $NH_2(CH_2CH_2NH)_mCH_2CH_2NH_2$ where m is 1 to 5, 1 to 3, or 2, (ii) diethylene triamine (molecular weight=103.17 g/mol, equivalent weight=34.4 g/mol) and (iii) triethylene tetramine (molecular weight=146.23 g/mol, equivalent weight=36.6 g/mol), as well as substituted and unsubstituted polypropylimines. However, it is to be noted that other, similar substituted and unsubstituted polyfunctional amines are also useful, including for example iminobispropylamine, bis(hexamethylene) triamine, cystamine, triethylene glycol diamine (e.g. Jeffamine EDR-148 from Huntsman Corp., Houston, Tex.) and the alkyl diamines, triamine and tetramine having a main alkyl chain of from about 2 to about 6, or about 2 to about 4, carbons in length (e.g., from ethylene diamine up to hexamethylene diamine, triamine or tetramine, with a few number of carbons typically being preferred and/or tetramines typically being preferred over triamines). The principal polyamine may comprise one or more of any of the above described amines having the general structure (XIV). Among the preferred amines are included, for example, substituted or unsubstituted polyethyleneamine, polypropyleneamine, diethylene triamine and triethylene tetramine.

B. Auxiliary Amines

In some optional embodiments of the present invention, the polyamine component comprises a principal amine and one or more auxiliary amines. Where the polyamine component comprises a principal amine and an auxiliary amine, the permeability of the shell wall, or the release rate of the core material, may be affected, for example, by varying the relative amounts of 2 or more amines used in the shell wall-forming polymerization reaction (see, e.g., U.S. Patent Pub. No. 2004/0137031 A1, the entire contents of which is incorporated by reference herein). Accordingly, in addition to those principal amines set forth above, auxiliary amines, such as a polyalkyleneamine or an epoxy-amine adduct, may be optionally included in combination with the principal amine to provide microcapsules having an altered shell wall permeability or release rate as compared to a shell wall prepared from an amine source consisting essentially of a principal amine, in addition to the permeability imparted thereto upon activation of the microcapsule (e.g., by cleavage of the blocking group from the polymer backbone).

This permeability, or release rate, may change (e.g., increase) as the ratio of the auxiliary amine to a principal amine increases. It is to be noted, however, that alternatively or additionally, as described in greater detail elsewhere herein, the rate of permeability may be further optimized by altering the shell wall composition by, for example, (i) the type of isocyanate employed, (ii) using a blend of isocyanates, (iii) using an amine having the appropriate hydrocarbon chain length between the amino groups, and/or (iv)

varying the ratios of the shell wall components and core components, all as determined, for example, experimentally using means standard in the art.

In some embodiments, the permeability-altering or auxiliary amine may be a polyalkyleneamine prepared by reacting an alkylene oxide with a diol or triol to produce a hydroxyl-terminated polyalkylene oxide intermediate, followed by amination of the terminal hydroxyl groups.

Alternatively, the auxiliary amine may be a polyetheramine (alternatively termed a polyoxyalkyleneamine, such as for example polyoxypropylenetri- or diamine, and polyoxyethylenetri- or diamine) having the following structure (XV):

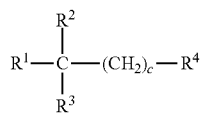

Structure (XV)

wherein: c is a number having a value of 0 or 1; "$R^1$" is selected from the group consisting of hydrogen and $CH_3(CH_2)_d$—; "d" is a number having a value from 0 to about 5; "$R^2$" and "$R^3$" are

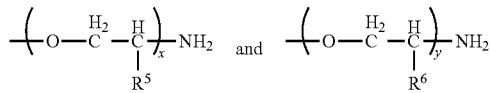

respectively; "$R^4$" is selected from the group consisting of hydrogen and

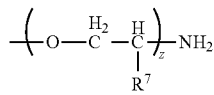

wherein "$R^5$", "$R^6$", and "$R^7$" are independently selected from a group consisting of hydrogen, methyl, and ethyl; and, "x", "y", and "z" are numbers whose total ranges from about 2 to about 40, or about 5 to about 30, or about 10 to about 20.

In some embodiments, the value of x+y+z is preferably no more than about 20, or more preferably no more than about 15 or even about 10. Examples of useful auxiliary amine compounds having this formula include amines of the Jeffamine ED series (Huntsman Corp., Houston, Tex.). One of such preferred amines is Jeffamine T-403 (Huntsman Corp., Houston, Tex.), which is a compound according to this formula wherein c, g and h are each 0, $R_1$ is $CH_3CH_2$ (i.e., $CH_3(CH_2)d$, where d is 1), $R_5$, $R_6$, and $R_7$ are each a methyl group and the average value of x+y+z is from about 5 and about 6.

The reaction of a polyfunctional amine with an epoxy functional compound has been found to produce epoxy-amine adducts that are also useful as auxiliary amines. Epoxy-amine adducts are generally known in the art. (See, e.g., Lee, Henry and Neville, Kris, Aliphatic Primary Amines and Their Modifications as Epoxy-Resin Curing Agents in Handbook of Epoxy Resins, pp. 7-1 to 7-30, McGraw-Hill Book Company (1967).) Preferably, the adduct has a water solubility as described for amines elsewhere herein. Preferably, the polyfunctional amine which is reacted with an epoxy to form the adduct is an amine as previously set forth above. More preferably, the polyfunctional amine is diethylenetriamine or ethylenediamine. Preferred epoxies include ethylene oxide, propylene oxide, styrene oxide, and cyclohexane oxide. Diglycidyl ether of bisphenol A (CAS #1675-54-3) is a useful adduct precursor when reacted with an amine in an amine to epoxy group ratio preferably of at least about 3 to 1.

It is to be noted, however, that permeability may also be decreased in some instances by the addition of an auxiliary amine. For example, it is known that the selection of certain ring-containing amines as the permeability-altering or auxiliary amine is useful in providing microcapsules with release rates which decrease as the amount of such an amine increases, relative to the other, principal amine(s) therein. Preferably, the auxiliary amine is a compound selected from the group consisting of cycloaliphatic amines and arylalkyl amines. Aromatic amines, or those having the nitrogen of an amine group bonded to a carbon of the aromatic ring, may not be universally suitable. Exemplary, and in some embodiments preferred, cycloaliphatic amines include 4,4'-diaminodicyclohexyl methane, 1,4-cyclohexanebis(methylamine) and isophorone diamine(5-Amino-1,3,3-trimethylcyclohexanemethylamine; molecular weight=170.30 g/mol; equivalent weight=85.2 g/mol). Exemplary, and in some embodiments preferred, arylalkyl amines have the structure of the following structure (XVI):

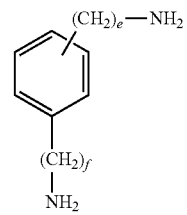

Structure (XVI)

wherein "e" and "f" are integers with values which independently range from about 1 to about 4, or about 2 to about 3. Meta-xylene diamine, from Mitsubishi Gas Co., Tokyo, JP, is a preferred example of an arylalkyl amine (molecular weight=136.19 g/mol; equivalent weight=68.1 g/mol). Another example is para-xylylenediamine. Alkyl substituted arylalkyl polyamines include 2,3,5,6-tetramethyl-1,4-xylylenediamine and 2,5-dimethyl-1,4-xylylenediamine.

C. Amine Properties

Preferably, the principal amine (and optional auxiliary polyamine) has at least about two amino groups or functionalities, and even more preferably, the amine comprises at least three amino groups. Without being held to any particular theory, it is generally believed that in an interfacial polymerization as described herein, the effective functionality of a polyfunctional amine is typically limited to only slightly higher than about 2 and less than about 4. This is believed to be due to steric factors, which normally prevent significantly more than about 3 amino groups in the polyfunctional amine shell wall precursor from participating in the polymerization reaction.

It is to be further noted that the molecular weight of the amine monomer, which may or may not possess an amine blocking group thereon, is preferably less than about 1000 g/mole, and in some embodiments is more preferably less than about 750 g/mole or even 500 g/mole. For example, the molecular weight of the amine monomer, which may or may not have one or more block amine functionalities therein, may range from about 75 g/mole to less than about 750 g/mole, or from about 100 g/mole to less than about 600 g/mole, or from about 150 g/mole to less than about 500 g/mole. Equivalent weights (the molecular weight divided by the number of amine functional groups) generally range from about 20 g/mole to about 250 g/mole, such as from about 30 g/mole to about 125 g/mole. Without being held to a particular theory, it is generally believed that steric hindrance is a limiting factor here, given that bigger molecules may not be able to diffuse through the early-forming protoshell wall to reach, and react to completion with, the isocyanate monomer in the core during interfacial polymerization.

Core Material Composition

Generally speaking, useful herbicidal core materials include those that are a single phase liquid at temperatures of less than about 80° C. Preferably, the core material is a liquid at temperatures of less than about 65° C. More preferably, the core material is a liquid at temperatures of less than about 50° C. The core material may also comprise solids suspended in a liquid phase. Whether liquid or solids in a liquid phase, the core material preferably has a viscosity such that it flows easily to facilitate transport by pumping and to facilitate the creation of an oil in water emulsion as part of the method for preparation of microcapsules discussed herein. Thus, the core material preferably has a viscosity of less than about 1000 centipoise (cps) (e.g., less than about 900, 800, 700, 600 or even 500 cps) at the temperature at which the emulsion is formed and the polymerization reaction occurs, typically from about 25° C. to about 65° C., typically, from about 40° C. to about 60° C. Preferably, the core material is water-immiscible, a property which promotes encapsulation by interfacial polymerization. Water-immiscibility refers to materials that have a relatively low water solubility at about 25° C., for example, less than about 500 mg/L, preferably less than about 250 mg/L, even more preferably less than about 100 mg/L. Certain core materials have even lower water solubilities, such as acetochlor, which is less than 25 mg/L at 25° C. In some preferred embodiments, the acetamide herbicidal core materials suitable for the practice of the present invention include dimethenamid, napropamide, pronamide and acetanilide herbicides such as acetochlor, alachlor, butachlor, butenachlor, delachlor, diethatyl, dimethachlor, mefenacet, metazochlor, metolachlor, pretilachlor, propachlor, propisochlor, prynachlor, terbuchlor, thenylchlor and xylachlor, mixtures thereof and stereoisomers thereof. Preferred acetamide herbicides include dimethenamid and dimethenamid-P and preferred acetanilide herbicides include acetochlor, metolachlor and S-metolachlor.

The core material may comprise multiple compounds for release (e.g., an acetamide and one or more additives compatible therewith which act to enhance its bioefficacy on weeds and/or reduce crop injury). For example, in some embodiments, the core material optionally comprises a safener. Suitable safeners include, for example, furilazole ((RS)-3-(dichloroacetyl)-5-(2-furanyl)-2,2-dimethyl-1,3-oxazolidine 95%), commercially available from Monsanto Company; AD 67 (4-(dichloroacetyl)-1-oxa-4-azaspiro[4,5]decane); benoxacor (CGA 154281, (RS)-4-dichloroacetyl-3,4-dihydro-3-methyl-2H-1,4-benzoxazine); cloquintocet-mexyl (CGA 184927, (5-chloroquinolin-8-yloxy)acetic acid); cyometrinil (CGA 43089, (Z)-cyanomethoxyimino (phenyl)acetonitrile); cyprosulfamide(N-[4-(cyclopropyl-carbamoyl)phenylsulfonyl]-o-anisamide); dichlormid (DDCA, R25788, N,N-diallyl-2,2-dichloroacetamide); dicyclonon ((RS)-1-dichloroacetyl-3,3,8a-trimethylperhydropyrrolo[1,2-a]pyrimidin-6-one); dietholate (O,O-diethyl O-phenyl phosphorothioate) fenchlorazole-ethyl (HOE 70542, 1-(2,4-dichlorophenyl)-5-trichloromethyl-1H-1,2,4-triazole-3-carboxylic acid); fenclorim (CGA 123407 4, 6-dichloro-2-phenylpyrimidine); flurazole (benzyl 2-chloro-4-trifluoromethyl-1,3-thiazole-5-carboxylate); fluxofenim (CGA 133205, 4'-chloro-2,2,2-trifluoroacetophenone (EZ)-O-1,3-dioxolan-2-ylmethyloxime); isoxadifen (4,5-dihydro-5,5-diphenyl-1,2-oxazole-3-carboxylic acid); mefenpyr ((RS)-1-(2,4-dichlorophenyl)-5-methyl-2-pyrazoline-3,5-dicarboxylic acid); mephenate (4-chlorophenyl methylcarbamate); MG 191; naphthalic anhydride; oxabetrinil (CGA 92194, (Z)-1,3-dioxolan-2-ylmethoxyimino(phenyl)acetonitrile); and others as are known in the art. It is to be noted that the herbicidal microcapsules, through selection of processing and structural parameters, achieve commercially acceptable crop safety even in the absence of a safener. Therefore, the safener is an optional core material.

It is to be further noted, as previously described, that the core material may optionally comprise a diluent. The diluent may be added to change the solubility parameter characteristics of the core material to increase or decrease the release rate of the active from the microcapsule, once release has been initiated. The preferred diluent content in the core material is as previously described.

The diluent may be selected from essentially any of those known in the art. The compatibility of the diluent with the core material (e.g., the acetamide active) and/or the shell wall may be determined, for example, experimentally using means standard in the art (see, e.g., U.S. Patent Pub. No. 2004/0137031 A1 and U.S. Pat. No. 5,925,595, the entire contents of which are incorporated herein for all relevant purposes). Exemplary diluents include, for example: alkyl-substituted biphenyl compounds (e.g., SureSol 370, commercially available from Koch Co.); normal paraffin oil (e.g., NORPAR 15, commercially available from Exxon); mineral oil (e.g., ORCHEX 629, commercially available from Exxon); isoparaffin oils (e.g., ISOPAR V and ISOPAR L, commercially available from Exxon); aliphatic fluids or oils (e.g., EXXSOL D110 and EXXSOL D130, commercially available from Exxon); alkyl acetates (e.g., EXXATE 1000, formerly commercially available from Exxon); aromatic fluids or oils (A 200, commercially available from Exxon); citrate esters (e.g., Citroflex A4, commercially available from Morflex); and, plasticizing fluids or oils used in, for examples, plastics (typically high boiling point esters).

Preparation of Microcapsules and Dispersions Thereof

In general, an aqueous dispersion of the microcapsules of the present invention may be produced by an interfacial polymerization reaction, either continuously or batchwise, using means generally known in the art. However, preferably a principal amine is polymerized with one or more polyisocyanates at the interface of an oil-in-water emulsion. The discontinuous oil phase (also referred to herein as "internal phase") preferably comprises one or more polyisocyanates and a continuous aqueous phase (also referred to herein as "external phase") comprises the principal amine. The oil phase further comprises a core material that preferably comprises an acetamide herbicide as the active ingredient. In other embodiments, when more than one amine is used (e.g., a principal amine and an auxiliary amine), these amines may be reacted in a ratio such that the microcapsules have a predetermined permeability with respect to the core material, either prior to activation or additionally upon activation.

In this regard it is to be noted that preferably the amine is not the hydrolysis product of the isocyanate. Rather, it is preferred that the reactants are selected from, for example, the amines and polyisocyanates disclosed elsewhere herein.

The oil-in-water emulsion is preferably formed by adding the oil phase to the continuous aqueous phase to which an emulsifying agent has been added (e.g., previously dissolved therein). The emulsifying agent is selected to achieve the desired oil droplet size in the emulsion. The size of the oil droplets in the emulsion is impacted by a number of factors in addition to the emulsifying agent employed and determines the size of microcapsules formed by the process, as described elsewhere herein. The emulsifying agent is preferably a protective colloid. Polymeric dispersants are preferred as protective colloids. Polymeric dispersants provide steric stabilization to an emulsion by adsorbing to the surface of an oil drop and forming a high viscosity layer which prevents drops from coalescing. Polymeric dispersants may be surfactants and are preferred to surfactants which are not polymeric, because polymeric compounds form a stronger interfacial film around the oil drops. If the protective colloid is ionic, the layer formed around each oil drop will also serve to electrostatically prevent drops from coalescing. SOKALAN (BASF), a maleic acid-olefin copolymer, is a preferred protective colloid, as is Invalon and Lomar D (Cognis).

Other protective colloids useful in this invention are gelatin, casein, polyvinyl alcohol, alkylated polyvinyl pyrrolidone polymers, maleic anhydride-methyl vinyl ether copolymers, styrene-maleic anhydride copolymers, maleic acid-butadiene and diisobutylene copolymers, sodium and calcium lignosulfonates, sulfonated naphthalene-formaldehyde condensates, modified starches, and modified cellulosics like hydroxyethyl or hydroxypropyl cellulose, and carboxy methyl cellulose.

To prepare microcapsules of a preferred mean diameter, the selection of a protective colloid and the conditions of the emulsification step are to be given consideration. For example, the quality of the emulsion, and hence the size of the microcapsules produced, is dependent to some extent upon the stirring operation used to impart mechanical energy to the emulsion. Preferably, the emulsification is accomplished with a high shear disperser. Generally, the microcapsules produced by this process have a size roughly approximated by the size of the oil drops from which they formed. Therefore, the emulsion is typically mixed to create oil drops having a mean diameter preferably at least about 5 μm, but typically less than about 15 μm.

The time that the emulsion remains in a high shear mixing zone is preferably limited to only the time required to create an emulsion having the desired droplet size. The longer the emulsion remains in the high shear mixing zone, the greater the degree to which the polyisocyanate will hydrolyze and react in situ. A consequence of in situ reaction is the premature formation of shell walls. Shell walls formed in the high shear zone may be destroyed by the agitation equipment, resulting in wasted raw materials and an unacceptably high concentration of unencapsulated core material in the aqueous phase. Typically, mixing the phases with a Waring blender for about 45 seconds to about 90 seconds, or with an in-line rotor/stator disperser having a shear zone dwell time of much less than a second, is sufficient. After mixing, the emulsion is preferably agitated sufficiently to maintain a vortex.

The time at which the amine source is added to the aqueous phase is a process variable that may affect, for example, the size distribution of the resulting microcapsules and the degree to which in situ hydrolysis occurs. Contacting the oil phase with an aqueous phase which contains the amine source prior to emulsification initiates some polymerization at the oil/water interface. If the mixture has not been emulsified to create droplets having the preferred size distribution, a number of disfavored effects may result, including but not limited to: the polymerization reaction wastefully creates polymer which is not incorporated into shell walls; oversized microcapsules are formed; or, the subsequent emulsification process shears apart microcapsules which have formed.

In some instances, the negative effects of premature amine addition may be avoided by adding a non-reactive form of the amine to the aqueous phase and converting the amine to its reactive form after emulsion. For example, the salt form of amine reactants may be added prior to emulsification and thereafter converted to a reactive form by raising the pH of the emulsion once it is prepared. This type of process is disclosed in U.S. Pat. No. 4,356,108, which is herein incorporated by reference in its entirety. However, it is to be noted that the increase in pH required to activate amine salts may not exceed the tolerance of the protective colloid to pH swings, otherwise the stability of the emulsion may be compromised.

Accordingly, it may be preferable for the amine source to be added after the preparation of the emulsion. More preferably, the amine source may be added as soon as is practical after a suitable emulsion has been prepared. Otherwise, the disfavored in situ hydrolysis reaction may be facilitated for as long as the emulsion is devoid of amine reactant, because the reaction of isocyanate with water proceeds unchecked by any polymerization reaction with amines. Therefore, amine addition is preferably initiated and completed as soon as practical after the preparation of the emulsion.

There may be, however, situations where it is desirable to purposefully increase the period over which the amine source is added. For example, the stability of the emulsion may be sensitive to the rate at which the amine is added. Alkaline colloids, like SOKALAN, can generally handle the rapid addition of amines. However, rapid addition of amines to an emulsion formed with non-ionic colloids or PVA cause the reaction mixture to gel rather than create a dispersion. Furthermore, if relatively "fast reacting" polyisocyanates are used (e.g., polyisocyanates containing an aromatic moiety), gelling may also occur if the amines are added too quickly. Under the above circumstances, it is typically sufficient to extend the addition of the amine over a period of from about 3 to about 15 minutes, or from about 5 to about 10 minutes. The addition is still preferably initiated as soon as is practical after the emulsion has been prepared.

The viscosity of the external phase is primarily a function of the protective colloid present. The viscosity of the external phase is preferably less than about 50 cps, more preferably less than about 25 cps, and still more preferably less than about 10 cps at the temperature of emulsion preparation, which is typically from about 25° C. to about 65° C., preferably from about 40° C. to about 60° C. The external phase viscosity is measured with a Brookfield viscometer with a spindle size 1 or 2 and at about 20 to about 60 rpm speed. After reaction and without additional formulation, the microcapsule dispersion which is prepared by this process preferably has a viscosity of less than about 400 cps (e.g., less than about 350 cps, about 300 cps, about 250 cps, or even about 200 cps) at the temperature of emulsion preparation. More preferably the dispersion viscosity is from about 100 to about 200 cps, or from 125 to about 175 cps at the temperature of emulsion preparation.

It is preferred that the oil phase is in the liquid state as it is blended into the aqueous phase. Preferably, the acetamide herbicide or other active ingredient is melted or dissolved or otherwise prepared as liquid solution prior to the addition of the isocyanate reactant. To these ends, the oil phase may require heating during its preparation.

The discontinuous oil phase may also be a liquid phase which contains solids. Whether liquid, low melting solid, or solids in a liquid, the discontinuous oil phase preferably has a viscosity such that it flows easily to facilitate transport by pumping and to facilitate the creation of the oil-in-water emulsion. Thus, the discontinuous oil phase preferably has a viscosity of less than about 1000 cps (e.g., less than about 900 cps, about 800 cps, about 700 cps, about 600 cps, or even about 500 cps) at the temperature of emulsion preparation, which is typically from about 25° C. to about 65° C., preferably from about 40° C. to about 60° C.

To minimize isocyanate hydrolysis and in situ shell wall formation, a cooling step subsequent to heating the oil phase is preferred when the oil phase comprises a polyisocyanate comprising an aromatic moiety, because isocyanates comprising an aromatic moiety undergo the temperature-dependent hydrolysis reaction at a faster rate than non-aromatic isocyanates. It has been discovered that the hydrolysis reaction has a negative effect on the preparation of the microcapsules of the present invention. Among other problems, isocyanates hydrolyze to form amines that compete in situ with the selected amine in the polymerization reaction, and the carbon dioxide generated by the hydrolysis reaction may introduce porosity into the prepared microcapsules. Therefore, it is preferred to minimize the hydrolysis of isocyanate reactants at each step of the process of the present invention. Since the hydrolysis reaction rate is directly dependent on the temperature, it is particularly preferred that the internal phase (i.e., discontinuous phase) be cooled to less than about 50° C. subsequent to mixing the polyisocyanate and the core material. It is also preferred that the internal phase be cooled to less than about 25° C. if isocyanates comprising an aromatic moiety are used.

Hydrolysis may also be minimized by avoiding the use of oil phase compositions in which water is highly soluble. Preferably water is less than about 5% by weight soluble in the oil phase at the temperature of the emulsion during the reaction step. More preferably water is less than about 1% soluble in the oil phase. Still more preferably water is less than about 0.1% soluble in the oil phase. It is preferred that the oil phase has a low miscibility in water. Low miscibility in water also promotes the formation of a useful emulsion.

It is preferred that the principal polyamine (and optional auxiliary polyamine) is sufficiently mobile across an oil-water emulsion interface. Thus, it is preferred that amines selected for the wall-forming reaction have an n-octanol/water partition coefficient wherein the base-10 log of the partition coefficient is between about −4 and about 1. It is also preferred that the reaction occur on the oil side of the oil-water interface, but is it believed that at partition coefficient values lower than about −4 the amines may not be soluble enough in the oil phase to participate sufficiently in the wall-forming reaction. Therefore, the reaction may proceed too slowly to be economical, or the disfavored in situ reaction may predominate. Furthermore, at partition coefficient values above about 1, the amines may not be sufficiently soluble in the water phase to be evenly distributed enough throughout the aqueous phase to facilitate a consistent reaction rate with all the oil particles. Therefore, more preferably the base-10 log of the partition coefficient is between about −3 and about 0.25, or about −2 and about 0.1.

To further reduce the amount of poyisocyanate hydrolysis and in situ reaction, the reaction is preferably run at as low of a temperature as economics based on the reaction rate will allow. For example, the reaction step may preferably be performed at a temperature from about 40° C. to about 65° C. More preferably, the reaction step may be performed at a temperature from about 40° C. to about 50° C.

The reaction step may preferably be performed to convert at least about 90% of the polyisocyanate. The reaction step may more preferably be performed to convert at least about 95% of the polyisocyanate. In this regard it is to be noted that the conversion of polyisocyanate may be tracked by monitoring the reaction mixture around an isocyanate infrared absorption peak at 2270 $cm^{-1}$, until this peak is essentially no longer detectable. The reaction may achieve 90% conversion of the isocyanate at a reaction time which is within the range of, for example, about one-half hour to about 3 hours, or about 1 to about 2 hours, especially where the core material comprises an acetanilide.

Liquid Microcapsule Dispersions: Parameters and Compositions

The microcapsules of the present invention comprise a water-immiscible, agricultural chemical-containing core material encapsulated by a polyurea shell wall, which is preferably substantially non-microporous, such that core material release occurs by a molecular diffusion mechanism, as opposed to a flow mechanism through a pore or rift in the polyurea shell wall. As noted herein, the shell wall may preferably comprise a polyurea product of a polymerization of one or more polyisocyanates and a principal polyamine (and optional auxiliary polyamine). Additionally, a further embodiment of the present invention comprises a liquid dispersion of the microcapsules of the present invention. The liquid medium in which the microcapsules are dispersed is preferably aqueous (e.g., water). The dispersion may optionally, and/or preferably, be further formulated with additives as described elsewhere herein (e.g., a stabilizer, one or more surfactants, an antifreeze, an anti-packing agent, drift control agents, etc.).

The acetamide herbicide loading of the formulated microcapsule dispersions of the present invention is typically from about 5% to about 50% by weight on an active ingredient basis, such as 5%, 10%, 15%, 20%, 25%, 30%, 35%, 40%, 45% or even 50% by weight on an active ingredient basis. In application mixture formulations, the acetamide herbicide loading is typically no more than about 5% by weight or from about 0.1% to about 5% by weight on an active ingredient basis, such as 5%, 4%, 3%, 2%, 1%, 0.5% or 0.1% by weight on an active ingredient basis.

The aqueous dispersion of microcapsules of the present invention may preferably be formulated to further optimize its shelf stability and safe use. Dispersants and thickeners are useful to inhibit the agglomeration and settling of the microcapsules. This function is facilitated by the chemical structure of these additives as well as by equalizing the densities of the aqueous and microcapsule phases. Anti-packing agents are useful when the microcapsules are to be redispersed. A pH buffer can be used to maintain the pH of the dispersion in a range which is safe for skin contact and, depending upon the additives selected, in a narrower pH range than may be required for the stability of the dispersion.

Low molecular weight dispersants may solubilize microcapsule shell walls, particularly in the early stages of their formation, causing gelling problems. Thus, in some embodiments dispersants having relatively high molecular weights of at least about 1.5 kg/mole, more preferably of at least about 3 kg/mole, and still more preferably at least about 5, 10 or even 15 kg/mole. In some embodiments, the molecular weight may range from about 5 kg/mole to about 50 kg/mole. Dispersants may also be non-ionic or anionic. An example of a high molecular weight, anionic polymeric dispersant is polymeric naphthalene sulfonate sodium salt, such as Invalon (formerly Irgasol, Huntsman Chemicals). Other useful dispersants are gelatin, casein, ammonium caseinate, polyvinyl alcohol, alkylated polyvinyl pyrrolidone polymers, maleic anhydride-methyl vinyl ether copolymers, styrene-maleic anhydride copolymers, maleic acid-butadiene and diisobutylene copolymers, sodium and calcium lignosulfonates, sulfonated naphthalene-formaldehyde condensates, modified starches, and modified cellulosics like hydroxyethyl or hydroxypropyl cellulose, and sodium carboxy methyl cellulose.

Thickeners are useful in retarding the settling process by increasing the viscosity of the aqueous phase. Shear-thinning thickeners may be preferred, because they act to reduce dispersion viscosity during pumping, which facilitates the economical application and even coverage of the dispersion to an agricultural field using the equipment commonly employed for such purpose. The viscosity of the microcapsule dispersion upon formulation may preferably range from about 100 cps to about 400 cps, as tested with a Haake Rotovisco Viscometer and measured at about 10° C. by a spindle rotating at about 45 rpm. More preferably, the viscosity may range from about 100 cps to about 300 cps. A few examples of useful shear-thinning thickeners include water-soluble, guar- or xanthan-based gums (e.g. Kelzan from CPKelco), cellulose ethers (e.g. ETHOCEL from Dow), modified cellulosics and polymers (e.g. Aqualon thickeners from Hercules), and microcrystalline cellulose anti-packing agents.

Adjusting the density of the aqueous phase to approach the mean weight per volume of the microcapsules also slows down the settling process. In addition to their primary purpose, many additives may increase the density of the aqueous phase. Further increase may be achieved by the addition of sodium chloride, glycol, urea, or other salts. The weight to volume ratio of microcapsules of preferred dimensions is approximated by the density of the core material, where the density of the core material is from about 1.05 to about 1.5 g/cm$^3$. Preferably, the density of the aqueous phase is formulated to within about 0.2 g/cm$^3$ of the mean weight to volume ratio of the microcapsules. More preferably, the density of the aqueous phase ranges from about 0.2 g/cm$^3$ less than the weight mean weight to volume ratio of the microcapsules to about equal to the weight mean weight to volume ratio of the microcapsules.

In order to enhance shelf stability and prevent gelling of the aqueous dispersion of microcapsules, particularly upon storage in high temperature environments, the formulated microcapsule dispersions may further include urea or similar structure-breaking agent at a concentration of up to about 20% by weight, typically about 5% by weight.

Surfactants can optionally be included in the formulated microcapsule dispersions of the present invention. Suitable surfactants are selected from non-ionics, cationics, anionics and mixtures thereof. Examples of surfactants suitable for the practice of the present invention include, but are not limited to: alkoxylated tertiary etheramines (such as TOMAH E-Series surfactants); alkoxylated quaternary etheramine (such as TOMAH Q-Series surfactant); alkoxylated etheramine oxides (such as TOMAH AO-Series surfactant); alkoxylated tertiary amine oxides (such as AROMOX series surfactants); alkoxylated tertiary amine surfactants (such as the ETHOMEEN T and C series surfactants); alkoxylated quaternary amines (such as the ETHOQUAD T and C series surfactants); alkyl sulfates, alkyl ether sulfates and alkyl aryl ether sulfates (such as the WITCOLATE series surfactants); alkyl sulfonates, alkyl ether sulfonates and alkyl aryl ether sulfonates (such as the WITCONATE series surfactants); alkoxylated phosphate esters and diesters (such as the PHOSPHOLAN series surfactants); alkyl polysaccharides (such as the AGRIMUL PG series surfactants); alkoxylated alcohols (such as the BRIJ or HETOXOL series surfactants); and mixtures thereof.

Anti-packing agents facilitate redispersion of microcapsules upon agitation of a formulation in which the microcapsules have settled. A microcrystalline cellulose material such as LATTICE from FMC is effective as an anti-packing agent. Other suitable anti-packing agents are, for example, clay, silicon dioxide, insoluble starch particles, and insoluble metal oxides (e.g. aluminum oxide or iron oxide). Anti-packing agents which change the pH of the dispersion are preferably avoided, for at least some embodiments.

Drift control agents suitable for the practice of the present invention are known to those skilled in the art and include the commercial products GARDIAN, GARDIAN PLUS, DRI-GARD, PRO-ONE XL ARRAY, COMPADRE, IN-PLACE, BRONC MAX EDT, EDT CONCENTRATE, COVERAGE and BRONC Plus Dry EDT.

The formulated microcapsule dispersions of the present invention are preferably easily redispersed, so as to avoid problems associated with application (e.g., clogging a spray tank). Dispersability may be measured by the Nessler tube test, wherein Nessler tubes are filled with 95 ml of water, then 5 ml of the test formulation is added by syringe. The tube is stoppered, and inverted ten times to mix. It is then placed in a rack, standing vertically, for 18 hours at 20° C. The tubes are removed and smoothly inverted every five seconds until the bottom of the tube is free of material. The number of inversions required to remix the settled material from the formulation is recorded. Preferably, the dispersions of the present invention are redispersed with less than about 100 inversions as measured by a Nessler tube test. More preferably, less than about 20 inversions are required for redispersion.

The pH of the formulated microcapsule dispersion may preferably range from about 4 to about 9, in order to minimize eye irritation of those persons who may come into contact with the formulation in the course of handling or application to crops. However, if components of a formulated dispersion are sensitive to pH, such as for example the blocking agent, buffers such as disodium phosphate may be used to hold the pH in a range within which the components are most effective. Additionally, a pH buffer such as citric acid monohydrate may be particularly useful in some systems during the preparation of microcapsules, to maximize the effectiveness of a protective colloid such as SOKALAN CP9.

Other useful additives include, for example, biocides or preservatives (e.g., PROXEL, commercially available from Avecia), antifreeze agents (such as glycerol, sorbitol, or urea), and antifoam agents (such as Antifoam SE23 from Wacker Silicones Corp.).

Controlling Plant Growth with Microcapsule Dispersions

The microcapsule dispersions disclosed herein are useful as controlled-release herbicides or concentrates thereof. Therefore, the present invention is also directed to a method of applying a dispersion of the microencapsulated herbicides for controlling plant growth. In some embodiments, herein, the dispersion of herbicidal microcapsules is applied to the soil, before planting the crop plants or after planting, but preemergent to the crop plants.

A microcapsule dispersion may be applied to a field according to practices known to those skilled in the art. The microcapsules are preferably applied as a controlled release delivery system for an agricultural chemical (e.g., acetanilide herbicide) or blend of agricultural chemicals contained therein. Because the mean release characteristics of a population of microcapsules of the present invention are adjustable, the timing of release initiation (or increase release) can be controlled thereby giving both commercially acceptable weed control and a commercially acceptable rate of crop injury.

When blended for end use on an agricultural field, the dispersion of herbicide-containing microcapsules prior to dilution by the end user may be, for example, less than about 62.5 weight percent microcapsules, or alternatively, less than about 55 weight percent herbicide or other active. If the dispersion is too concentrated with respect to microcapsules, the viscosity of the dispersion may be too high to pump and also may be too high to easily redisperse if settling has occurred during storage. It is for these reasons that the dispersion preferably has a viscosity of less than about 400 cps, as describe above.

The microcapsule dispersions may be as dilute with respect to microcapsule weight percent as is preferred by the user, constrained mainly by the economics of storing and transporting the additional water for dilution and by possible adjustment of the additive package to maintain a stable dispersion. Typically, the dispersion is at least about 25 weight percent herbicidal active (about 30 weight percent microcapsules) for these reasons. These concentrations are useful compositions for the storage and transport of the dispersions.

For a stand-alone (i.e., in the absence of a co-herbicide) application of the microcapsules of the present invention, the dispersion is preferably diluted with water to form an application mixture prior to application. Typically, no additional additives are required to place the dispersion in a useful condition for application as a result of dilution. The optimal concentration of a diluted dispersion is dependent in part on the method and equipment which is used to apply the herbicide.

The effective amount of microcapsules to be applied to an agricultural field is dependent upon the identity of the encapsulated herbicide, the release rate of the microcapsules, the crop to be treated, and environmental conditions, especially soil type and moisture. Generally, application rates of herbicides, such as, for example, acetochlor, are on the order of about 0.1, 0.5, 1, 2, 3, 4, 5, 6, 7, 8, 9 or 10 kilograms of herbicide per hectare, or ranges thereof, such as from 0.5 to 10 kilograms per hectare, from 0.5 to 10 kilograms per hectare, from 0.5 to 5 kilograms per hectare, or from 1 to 5 kilograms per hectare. In some embodiments, an application rate for sorghum, rice and wheat of from about 0.85 to about 1 kilograms per hectare is preferred. For other crops, e.g., corn, peanuts, potatoes, soybeans, canola, alfalfa, sugarcane, sugarbeets, peanuts, field beans, sunflowers and cotton, an application rate of about 1.1 to about 1.4 kilograms per hectare is preferred.

Application mixtures of the dispersions of the microencapsulated acetamide herbicides are preferably applied to an agricultural field within a selected timeframe of crop plant development. In some embodiments of the present invention, as described above, the dispersion of the microencapsulated herbicides, optionally including one or more co-herbicides, is applied to a field from 1-40 days prior to planting of the crop plant and/or preemegence (i.e., from planting of the crop plant up to, but not including, emergence or cracking) in order to provide control of newly emerging monocots and small seeded dicot species without significant crop damage. In other embodiments, a particulate microencapsulated acetamide herbicide composition comprising a first particulate microencapsulated acetamide herbicide and a second microencapsulated acetamide herbicide, optionally further comprising one or more co-herbicides, is applied to a field from 1-40 days prior to crop planting and/or preemegence.

Application mixtures of the aqueous dispersions of herbicidal microcapsules of the present invention are useful for controlling a wide variety of weeds, i.e., plants that are considered to be a nuisance or a competitor of commercially important crop plants, such as corn, soybean, cotton, etc. In some embodiments, the microcapsules of the present invention are applied before the weeds emerge (i.e., preemergence application). Examples of weeds that may be controlled according to the method of the present invention include, but are not limited to, Meadow Foxtail (*Alopecurus pratensis*) and other weed species with the *Alopecurus* genus, Common Barnyard Grass (*Echinochloa crus-galli*) and other weed species within the *Echinochloa* genus, crabgrasses within the genus *Digitaria*, White Clover (*Trifolium repens*), Lambsquarters (*Chenopodium berlandieri*), Redroot Pigweed (*Amaranthus retroflexus*) and other weed species within the *Amaranthus* genus, Common Purslane (*Portulaca oleracea*) and other weed species in the *Portulaca genus, Chenopodium album* and other *Chenopodium* spp., *Setaria lutescens* and other *Setaria* spp., *Solanum nigrum* and other *Solanum* spp., *Lolium multiflorum* and other *Lolium* spp., *Brachiaria platyphylla* and other *Brachiaria* spp., *Sorghum halepense* and other *Sorghum* spp., *Conyza Canadensis* and other *Conyza* spp., and *Eleusine indica*. In some embodiments, the weeds comprise one or more glyphosate-resistant species, 2,4-D-resistant species, dicamba-resistant species and/or ALS inhibitor herbicide-resistant species. In some embodiments, the glyphosate-resistant weed species is selected from the group consisting of *Amaranthus palmeri, Amaranthus rudis, Ambrosia artemisiifolia, Ambrosia trifida, Conyza bonariensis, Conyza canadensis, Digitaria insularis, Echinochloa colona, Eleusine indica, Euphorbia heterophylla, Lolium multiflorum, Lolium rigidum, Plantago lancelata, Sorghum halepense*, and *Urochloa panicoides*.

As used herein transgenic glyphosate-tolerant corn, soybean, cotton, etc. plants includes plants grown from the seed of any corn, soybean, cotton, etc. event that provides glyphosate tolerance and glyphosate-tolerant progeny thereof.

Such glyphosate-tolerant events include, without limitation, those that confer glyphosate tolerance by the insertion or introduction, into the genome of the plant, the capacity to express various native and variant plant or bacterial EPSPS enzymes by any genetic engineering means known in the art for introducing transforming DNA segments into plants to confer glyphosate resistance as well as glyphosate-tolerant cotton events that confer glyphosate tolerance by other means such as described in U.S. Pat. Nos. 5,463,175 and 6,448,476 and International Publication Nos. WO 2002/36782, WO 2003/092360 and WO 2005/012515.

Non-limiting examples of transgenic glyphosate-tolerant cotton events include the glyphosate-tolerant (ROUNDUP READY) cotton event designated 1445 and described in U.S. Pat. No. 6,740,488. Of particular interest in the practice of one embodiment of the present invention are methods for weed control in a crop of transgenic glyphosate-tolerant cotton plants in which glyphosate resistance is conferred in a manner that allows later stage application of glyphosate herbicides without incurring significant glyphosate-mediated reproductive injury. Non-limiting examples of such transgenic glyphosate-tolerant cotton plants include those grown from the seed of the glyphosate-tolerant (ROUNDUP READY) FLEX cotton event (designated MON 88913 and having representative seed deposited with American Type Culture Collection (ATCC) with Accession No. PTA-4854) and similar glyphosate-tolerant cotton events and progeny thereof as described in International Publication No. WO 2004/072235. Glyphosate-tolerant (ROUNDUP READY FLEX) cotton event MON 88913 and similar glyphosate-tolerant cotton events may be characterized in that the genome comprises one or more DNA molecules selected from the group consisting of SEQ ID NO:1, SEQ ID NO:2, SEQ ID NO:3, and SEQ ID NO:4; or the genome in a DNA amplification method produces an amplicon comprising SEQ ID NO:1 or SEQ ID NO:2; or the transgenic glyphosate-tolerant cotton plants comprise a glyphosate tolerant trait that is genetically linked to a complement of a marker polynucleic acid, and the marker polynucleic acid molecule is homologous or complementary to a DNA molecule selected from the group consisting of SEQ ID NO:1 and SEQ ID NO:2 as described in International Publication No. Wo 2004/072235, the entire contents of which are incorporated herein by reference. A sequence listing containing each of SEQ ID NOS: 1, 2, 3, and 4 as disclosed in International Publication No. WO 2004/072235 is contained herein. These sequences are listed as SEQ ID NOS: 1, 2, 3, and 4, respectively.

As noted above, the glyphosate-tolerant (ROUNDUP READY FLEX) cotton event MON 88913 allows for over-the-top application of glyphosate herbicides at advanced stages of plant development without incurring significant glyphosate-mediated reproductive injury (e.g., as quantified, for example, by flower pollen shed and/or lint yield). As compared to the previous commercial glyphosate-tolerant (ROUNDUP READY) cotton event designated 1445, glyphosate-tolerant (ROUNDUP READY FLEX) cotton event MON 88913 is particularly advantageous in allowing foliar application of glyphosate herbicide for weed control at a developmental age characterized by at least five leaf nodes present on a cotton plant of the crop. As used herein, a node having a leaf branch is referred to as a leaf node in accordance with the conventional node method used in assessing cotton plant developmental age. Furthermore, cotyledons are leaves originally contained in the seed and are not considered as plant leaves or nodes for purposes of determination of the stage of cotton development. That is, as generally accepted by those skilled in the art and as used herein, the stem point of cotyledon attachment is referenced as Node 0. The fifth and subsequent leaf nodes are typically the first reproductive (i.e., fruiting) branches and may develop a fruiting bud and associated leaf. A leaf node having a reproductive branch may be referred as a reproductive node. Cotton plants can develop as many as about 25 leaf nodes, with nodes 5-25 potentially developing into reproductive nodes. In practicing weed control in a crop of transgenic glyphosate-tolerant cotton grown from seed of glyphosate-tolerant (ROUNDUP READY FLEX) cotton event MON 88913 or similar cotton events and progeny thereof, glyphosate herbicidal formulations can be applied over-the-top of the crop at more advanced developmental ages characterized, for example, by six, ten, twelve, fourteen or more leaf nodes present on a cotton plant of the crop and up to and including layby without incurring significant glyphosate-mediated reproductive injury to the crop. Herbicidal glyphosate formulation may be applied over-the-top of the cotton crop at various intervals of advanced development, characterized, for example, by six or more leaf nodes and no more than ten, twelve, fourteen, sixteen, eighteen, twenty or twenty-five leaf nodes on a cotton plant of the crop.

In some embodiments as described previously, the herbicidal microcapsules of the present invention, including blends of a first and second particulate microencapsulated acetamide herbicide, can be dispersed in combination with one or more co-herbicides in an aqueous concentrate or spray application tank mix, such as a co-herbicide selected from ACCase inhibitors (such as aryloxyphenoxypropionics), enolpyruvyl shikimate-3-phosphate synthaste (EPSPS) inhibitor (glyphosate), glutamine synthetase inhibitor (glufosinate), synthetic auxins (such as aromatic acid, phenoxy and pyridine herbicides), photosystem II (PS II) inhibitors (such as ureas and triazines), ALS or AHAS inhibitors (such as sulfonyl ureas, triazolopyrimidines and imidazolinones), photosystem I (PS I) inhibitors (such as quaternary ammonium herbicides), protoporphyrinogen oxidase (PPO) inhibitors (such as diphenyl ethers, phenyl pyrazoles, aryl triazones and oxadiazoles), mitosis inhibitors (such as anilide, amide, certain organophosphorus and carbanilate herbicides), cellulose inhibitors (such as nitrile and oxazole herbicides), oxidative phosphorylation uncouplers, dihydropteroate synthase inhibitors, fatty acid and lipid biosynthesis inhibitors (such as thiocarbamate and certain organophosphorus herbicides), auxin transport inhibitors (such as amide and urea herbicides) and carotenoid biosynthesis inhibitors (such as isoxazolidinone, benzoylcyclohexanedione and benzoylpyrazole herbicides), salts and esters thereof, and mixtures thereof. Application mixtures of the co-herbicide formulations can likewise be prepared. A weight ratio of acetamide to co-herbicide of from 10:1 to 1:10 or from 5:1 to 1:5 is preferred. In some embodiments of the present invention, the one or more co-herbicides are not encapsulated.

Where an herbicide is referenced generically herein by name, unless otherwise restricted, that herbicide includes all commercially available forms known in the art such as salts, esters, free acids and free bases, as well as stereoisomers thereof. For example, where the herbicide name "glyphosate" is used, glyphosate acid, salts and esters are within the scope thereof.

An EPSPS herbicide is glyphosate or a salt or ester thereof. A glutamine synthetase herbicide is glufosinate or glufosinate-P, or a salt or and ester thereof.

ACCase inhibitors include, for example, alloxydim, butroxydim, clethodim, cycloxydim, pinoxaden, sethoxydim, tepraloxydim and tralkoxydim, salts and esters thereof, and mixtures thereof. Another group of acetyl CoA carboxylase inhibitors include chlorazifop, clodinafop, clofop, cyhalofop, diclofop, diclofop-methyl, fenoxaprop, fenthiaprop, fluazifop, haloxyfop, isoxapyrifop, metamifop, propaquizafop, quizalofop and trifop, salts and esters thereof, and mixtures thereof. Acetyl CoA carboxylase inhibitors also include mixtures of one or more "dims" and one or more "fops", salts and esters thereof.

Synthetic auxin herbicides include, for example, 2,4-D, 2,4-DB, dichloroprop, MCPA, MCPB, aminopyralid, clopyralid, fluoroxypyr, triclopyr, diclopyr, mecoprop, dicamba, picloram and quinclorac, salts and esters thereof, and mixtures thereof.

PS II inhibitors include, for example, ametryn, amicarbazone, atrazine, bentazon, bromacil, bromoxynil, chlorotoluron, cyanazine, desmedipham, desmetryn, dimefuron, diuron, fluometuron, hexazinone, ioxynil, isoproturon, linuron, metamitron, methibenzuron, metoxuron, metribuzin, monolinuron, phenmedipham, prometon, prometryn, propanil, pyrazon, pyridate, siduron, simazine, simetryn, tebuthiuron, terbacil, terbumeton, terbuthylazine and trietazine, salts and esters thereof, and mixtures thereof.

ALS and AHAS inhibitors include, for example, amidosulfuron, azimsulfruon, bensulfuron-methyl, bispyribac-sodium, chlorimuron-ethyl, chlorsulfuron, cinosulfuron, cloransulam-methyl, cyclosulfamuron, diclosulam, ethametsulfuron-methyl, ethoxysulfuron, flazasulfuron, florazulam, flucarbazone, flucetosulfuron, flumetsulam, flupyrsulfuron-methyl, foramsulfuron, halosulfuron-methyl, imazamethabenz, imazamox, imazapic, imazapyr, imazaquin, imazethapyr, imazosulfuron, iodosulfuron, metsulfuron-methyl, nicosulfuron, penoxsulam, primisulfuron-methyl, propoxycarbazone-sodium, prosulfuron, pyrazosulfuron-ethyl, pyribenzoxim, pyrithiobac, rimsulfuron, sulfometuron-methyl, sulfosulfuron, thiencarbazone, thifensulfuron-methyl, triasulfuron, tribenuron-methyl, trifloxysulfuron and triflusulfuron-methyl, salts and esters thereof, and mixtures thereof.

Mitosis inhibitors include anilofos, benefin, DCPA, dithiopyr, ethalfluralin, flufenacet, mefenacet, oryzalin, pendimethalin, thiazopyr and trifluralin, salts and esters thereof, and mixtures thereof.

PPO inhibitors include, for example, acifluorfen, azafenidin, bifenox, butafenacil, carfentrazone-ethyl, flufenpyr-ethyl, flumiclorac, flumiclorac-pentyl, flumioxazin, fluoroglycofen, fluthiacet-methyl, fomesafen, lactofen, oxadiargyl, oxadiazon, oxyfluorfen, pyraflufen-ethyl, saflufenacil and sulfentrazone, salts and esters thereof, and mixtures thereof.

Carotenoid biosynthesis inhibitors include, for example, aclonifen, amitrole, beflubutamid, benzofenap, clomazone, diflufenican, fluridone, fluorochloridone, flurtamone, isoxaflutole, mesotrione, norflurazon, picolinafen, pyrazolynate, pyrazoxyfen, sulcotrione, tembotrione and topramezone, salts and esters thereof, and mixtures thereof.

PS I inhibitors include diquat and paraquat, salts and esters thereof, and mixtures thereof.

Cellulose inhibitors include dichlobenil and isoxaben.

An oxidative phosphorylation uncoupler is dinoterb, and esters thereof.

Auxin transport inhibitors include diflufenzopyr and naptalam, salts and esters thereof, and mixtures thereof.

A dihydropteroate synthase inhibitor is asulam and salts thereof.

Fatty acid and lipid biosynthesis inhibitors include bensulide, butylate, cycloate, EPIC, esprocarb, molinate, pebulate, prosulfocarb, thiobencarb, triallate and vernolate, salts and esters thereof, and mixtures thereof.

Some preferred co-herbicides include flumioxazin, fluometuron, diuron, sulfentrazone, fomesafen, metribuzen, saflufenacil, thiencarbazone, mesotrione, atrazine, isoxaflutole, 2,4-D, dicamba and glyphosate, salts and esters thereof, racemic mixtures and resolved isomers thereof, and mixtures thereof.

In some embodiments of the present invention, the co-herbicide is flumioxazin and the crop plant is cotton or soy; the co-herbicide is fomesafen and the crop plant is cotton or soy; the co-herbicide is metribuzen and the crop plant is soy; the co-herbicide is saflufenacil and the crop plant is cotton or soy; the co-herbicide is thiencarbazone and the crop plant is corn; the co-herbicide is mesotrione and the crop plant is corn, cotton or soy; the co-herbicide is atrazine and the crop plant is corn; the co-herbicide is isoxaflutole and the crop plant is corn, cotton or soy; or the co-herbicide is 2,4-D or dicamba and the crop plant is not limited, but can be, for example, corn, peanuts, potatoes, soybeans, canola, alfalfa, sugarcane, sugarbeets, peanuts, grain sorghum (milo), field beans, rice, sunflowers, wheat or cotton.

In some embodiments the herbicidal microcapsules of the present invention can be dispersed with two co-herbicides to form a three-way herbicidal composition. The compositions can be concentrate compositions or application mixtures. A weight ratio of acetamide to total co-herbicide of from 10:1 to 1:10 or from 5:1 to 1:5 is preferred. A table of co-herbicide combinations within the scope of the present invention is provided below where "Comb" is a combination reference number, "Gly or glu" refers to glyphosate or glufosinate, and "1st co-herb" and "2nd co-herb" refer to the first and second non-encapsulated co-herbicide classes that are combined with the encapsulated acetamide (e.g. acetanilide).

| Comb | 1st co-herb | 2nd co-herb |
| --- | --- | --- |
| 1 | Gly or glu | ACCase |
| 2 | Gly or glu | Auxin |
| 3 | Gly or glu | PS II |
| 4 | Gly or glu | ALS |
| 5 | Gly or glu | Mitosis |
| 6 | Gly or glu | PPO |
| 7 | Gly or glu | Carotenoid |
| 8 | ACCase | Auxin |
| 9 | ACCase | PS II |
| 10 | ACCase | ALS |
| 11 | ACCase | Mitosis |
| 12 | ACCase | PPO |
| 13 | ACCase | Carotenoid |
| 14 | Auxin | PS II |
| 15 | Auxin | ALS |
| 16 | Auxin | Mitosis |
| 17 | Auxin | PPO |
| 18 | Auxin | Carotenoid |
| 19 | PS II | ALS |
| 20 | PS II | Mitosis |
| 21 | PS II | PPO |
| 22 | PS II | Carotenoid |
| 23 | ALS | Mitosis |
| 24 | ALS | PPO |
| 25 | ALS | Carotenoid |
| 26 | Mitosis | PPO |
| 27 | Mitosis | Carotenoid |
| 28 | PPO | Carotenoid |

In some embodiments, the encapsulated acetamides are combined in an aqueous application mixture with an auxin herbicide and an organophosphate herbicide, or salt or ester thereof. In some embodiments, the encapsulated acetamide herbicide is selected from acetochlor, metolachlor, S-metolachlor, dimethenamide and dimethenamide-P salts and esters thereof, the first co-herbicide is selected from dicamba and 2,4-D, salts and esters thereof, and the second co-herbicide is selected from glyphosate, glufosinate and glufosinate-P, salts and esters thereof. Examples include: encapsulated acetochlor, dicamba and glyphosate; encapsulated metolachlor and/or S-metolachlor, dicamba and glyphosate; encapsulated dimethenamid and/or dimethenamid-P, dicamba and glyphosate; encapsulated acetochlor, 2,4-D and glyphosate; encapsulated metolachlor and/or S-metolachlor, 2,4-D and glyphosate; encapsulated dimethenamid and/or dimethenamid-P, 2,4-D and glyphosate; encapsulated acetochlor, dicamba and glufosinate and/or glufosinate-P;

encapsulated metolachlor and/or S-metolachlor, dicamba and glufosinate and/or glufosinate-P; encapsulated dimethenamid and/or dimethenamid-P, dicamba and glufosinate and/or glufosinate-P; encapsulated acetochlor, 2,4-D and glufosinate and/or glufosinate-P; encapsulated metolachlor and/or S-metolachlor, 2,4-D and glufosinate and/or glufosinate-P; and encapsulated dimethenamid and/or dimethenamid-P, 2,4-D and glufosinate and/or glufosinate-P.

In some preferred embodiments the first co-herbicide is an organophosphorus herbicide and the second co-herbicide is a PS II herbicide. Examples include glyphosate and atrazine, metribuzen or fluometuron.

In some other preferred embodiments, the first co-herbicide is an organophosphorus herbicide and the second co-herbicide is a PPO herbicide. Examples include glyphosate and flumioxazin, fomesafen, lactofen, sulfentrazone, oxyfluorfen or saflufenacil.

In other preferred embodiments the first co-herbicide is a PS II herbicide and the second co-herbicide is a PPO herbicide. Examples include atrazine, metribuzen or fluometuron as PS II herbicides in combination with flumioxazin, fomesafen, lactofen, sulfentrazone, oxyfluorfen or saflufenacil as PPO herbicides.

In other preferred embodiments, the present microcapsules are used in the preparation of an aqueous concentrate composition or tank mix comprising glyphosate or a salt thereof (e.g., the potassium or monoethanolammonium salt). In such a tank mix, a percent by weight acetamide from about 5% to about 0.1% a.i. and from about 3% by weight to about 0.25% a.e. by weight is preferred. Such an aqueous composition is particularly useful for burndown applications prior to crop emergence to control glyphosate susceptible plants and several commercially important weeds that have been reported to be glyphosate resistant, including, for example, palmer amaranth (*Amaranthus palmeri*), waterhemp (*Amaranthus rudis*), common ragweed (*Ambrosia artemisiifolia*), giant ragweed (*Ambrosia trifida*), hairy fleaane (*Conyza bonariensis*), horseweed (*Conyza canadensis*), sourgrass (*Digitaria insularis*), junglerice (*Echinochloa colona*), goosegrass (*Eleusine indica*), wild poinsettia (*Euphorbia heterophylla*), Italian ryegrass (*Lolium multiflorum*), rigid ryegrass (*Lolium rigidum*), buckhorn plantain (*Plantago Lancelata*), Johnsongrass (*Sorghum halepense*), and liverseedgrass (*Urochloa panicoides*).

As used throughout this specification, the expression "predominantly comprises" means more than 50%, preferably at least about 75%, and more preferably at least about 90% by weight of the component is made up of the specified compound(s).

EXAMPLES

The following non-limiting Examples are provided to further illustrate the present invention. The materials shown in the following Table were used in the following Examples. Throughout the Examples, these components are referred to by the term stated in the Reference column.

| Material | Function | Reference | Supplier |
|---|---|---|---|
| Acetochlor | Herbicide | Acetochlor | Monsanto |
| Furilazole | Safener | | Monsanto |
| n-Pentadecane | Internal Phase Solvent (dilutent) | NORPAR 15 | Exxon Mobil |
| Isoparaffinic hydrocarbon (approximate MW 234) | Internal Phase Solvent (dilutent) | ISOPAR V | Exxon Mobil |
| Isoparaffinic hydrocarbon (approximate MW 163) | Internal Phase Solvent (dilutent) | ISOPAR L | Exxon Mobil |
| Dearomatized hydrocarbon (approximate MW 229) | Internal Phase Solvent (dilutent) | EXXSOL D-130 | Exxon Mobil |
| Dearomatized hydrocarbon (approximate MW 200) | Internal Phase Solvent (dilutent) | EXXSOL D-110 | Exxon Mobil |
| Triethylenetetramine 50% solution | Amine shell wall component | TETA | Huntsman Chemical |
| Meta-Xylylenediamine 50% solution | Amine shell wall component | XDA | |
| Desmodur N3200 Trimer of hexamethylene-1,6-diisocyanate | Triisocyanate shell wall component | DES N3200 | Bayer |
| Desmodur W 4,4'-diisocyanato-dicyclohexyl methane | Diisocyanate shell wall component | DES W | Bayer |
| 85% by weight trimer of hexamethylene-1,6-diisocyanate: 15% by weight 4,4'-diisocyanato-dicyclohexyl methane | Blend of DES N3200 and DES W | MISTAFLEX | Monsanto |
| Water | External Phase Solvent | Water | |
| Ammonium caseinate | Dispersant | Ammonium caseinate | American Casein Company |
| Glycerin | | Glycerin | Cargill |
| Maleic acid-olefin copolymer, 25% solution | surfactant | SOKALAN CP9 | BASF |
| Citric Acid, 50% solution | pH adjustment | Acid | ADM |
| Invalon DAM Naphthalene formaldehyde condensate sulfonate | Dispersant | Invalon | Huntsman Chemical |
| Kelzan CC | Thickener | Kelzan CC | Kelco |
| Proxel GXL | Preservative | Proxel GXL | Avecia |
| NAOH, 20% solution | pH adjustment | Caustic | Dow Chemical |
| Antifoam SE23 | Antifoam | Antifoam | Wacker Silicone |
| Na$_2$HPO$_4$ | Buffer | Buffer | ICL Performance Products |

The herbicidal effectiveness data set forth herein report crop damage and weed inhibition as a phytotoxicity percentage following a standard procedure in the art which reflects a visual assessment of plant mortality and growth reduction by comparison with untreated plants, made by technicians specially trained to make and record such observations. In all cases, a single technician makes all assessments of percent inhibition within any one experiment or trial.

The selection of application rates that are biologically effective for a specific acetamide herbicide is within the skill of the ordinary agricultural scientist. Those of skill in the art will likewise recognize that individual plant conditions, weather and growing conditions, as well as the specific exogenous chemical and formulation thereof selected, will affect the efficacy on weeds and associated crop injury achieved in practicing this invention. Useful application rates for the acetamide herbicides employed can depend upon all of the above factors. With respect to the use of the method of this invention, much information is known about appropriate acetamide application rates. Over four decades of acetamide use and published studies relating to such use have provided abundant information from which a weed control practitioner can select acetamide application rates that are herbicidally effective on particular species at particular growth stages in particular environmental conditions.

Effectiveness in greenhouse tests, usually at exogenous chemical rates lower than those normally effective in the field, is a proven indicator of consistency of field performance at normal use rates. However, even the most promising composition sometimes fails to exhibit enhanced performance in individual greenhouse tests. As illustrated in the Examples herein, a pattern of enhancement emerges over a series of greenhouse tests; when such a pattern is identified this is strong evidence of biological enhancement that will be useful in the field.

The compositions of the present invention can be applied to soil or plants by spraying, using any conventional means for spraying liquids, such as spray nozzles, atomizers, or the like. Compositions of the present invention can be used in precision farming techniques, in which apparatus is employed to vary the amount of exogenous chemical applied to different parts of a field, depending on variables such as the particular plant species present, soil composition, and the like. In one embodiment of such techniques, a global positioning system operated with the spraying apparatus can be used to apply the desired amount of the composition to different parts of a field.

The composition, at the time of application to soil or plants, is preferably dilute enough to be readily sprayed using standard agricultural spray equipment. Preferred application rates for the present invention vary depending upon a number of factors, including the type and concentration of active ingredient and the plant species involved. Selection of appropriate rates of application is within the capability of one skilled in the art. Useful rates for applying an aqueous application mixture to a field can range from about 50 to about 1,000 liters per hectare (L/ha) by spray application. The preferred application rates for aqueous application mixtures are in the range from about 100 to about 300 L/ha.

Damage to the foliage of a crop plant may cause the plant to be stunted or otherwise reduce the yield of the desired agricultural commodity. Thus, it is important that a herbicidal composition not be applied in such a manner as to excessively injure and interrupt the normal functioning of the plant tissue. However, some limited degree of local injury can be insignificant and commercially acceptable.

A large number of compositions of the invention are illustrated in the examples that follow. Many concentrate acetamide compositions have provided sufficient herbicidal effectiveness in greenhouse tests to warrant field testing on a wide variety of weed species under a variety of application conditions.

Some of the experiments were carried out in a greenhouse. The herbicidal compositions were applied using a research track sprayer. The dilution of the dispersion of herbicidal microcapsules were varied in order achieve different concentrations of active applied.

Example 1

Preparation of Aqueous Dispersions of Microencapsulated Acetochlor

Aqueous dispersions of microencapsulated acetochlor were prepared according to the protocol described in this example. The aqueous dispersions were prepared using a method that resulted in microcapsules having a mean diameter greater than those found in DEGREE, a commercially available microencapsulated herbicidal product containing about 42% by weight acetochlor, available from Monsanto Company. The microcapsules in DEGREE have a mean diameter of about 2.5 μm. The test formulations resulted in aqueous dispersions of microcapsules having mean diameters significantly greater, such as about 5 μm to about 13 μm. Field studies indicated that the aqueous dispersions of herbicidal microcapsules having larger mean diameters exhibited improved crop safety when tested on soybean and cotton compared to DEGREE and also compared to HARNESS, a commercially available herbicidal product containing emulsified concentrate of unencapsulated acetochlor, also available from Monsanto Company.

The internal phases were prepared to contain the components and amounts shown in the following table. The percentages indicate the approximate weight percentage of each component in the aqueous dispersion.

TABLE

| Internal Phase Components | | | | | | |
|---|---|---|---|---|---|---|
| | Acetochlor | | NORPAR 15 | | MISTAFLEX | |
| Form. | (g) | (%) | (g) | (%) | (g) | (%) |
| 5291 | 447.25 | 43.19 | 23.56 | 2.35 | 30.84 | 3.07 |
| 5297 | 894.21 | 43.19 | 46.99 | 2.35 | 61.53 | 3.07 |
| 5295 | 841.2 | 40.63 | 107.01 | 5.00 | 61.73 | 3.07 |

To prepare the internal phase of formulations 5291, 5297, and 5295, acetochlor was charged to the mixing vessels in the amounts shown in the above internal phase components table. Next, NORPAR 15 was charged to the mixing vessels, followed by the MISTAFLEX blend of DES N3200 and DES W polyisocyanates. The solution was agitated to obtain a clear homogenous solution. The solution may be sealed within the mixing vessel and stored until needed. Prior to use, the mixture was heated to 50° C. in an oven.

The external aqueous phases were prepared containing the components and amounts shown in the following table:

TABLE

| External Phase Components | | | | | |
|---|---|---|---|---|---|
| | Weight of Components in grams | | | | |
| Form. | Water | Ammonium Caseinate | Glycerin | SOKALAN CP9 | Acid |
| 5291 | 278.2 | 0.45 | 81.1 | 23.0 | 1.64 |
| 5297 | 556.61 | 0.98 | 162.28 | 46.04 | 3.09 |
| 5295 | 556.32 | 0.93 | 162.27 | 46.63 | 3.23 |

To prepare the external phase of formulations 5291, 5297, and 5295, mixing vessels were charged with water in the amounts shown in the above external phase components table, and the remaining components were added in the order shown in the above table. The solution was agitated to obtain a clear homogenous solution. The solution may be sealed within the mixing vessel and stored until needed. Prior to use, the mixture was heated to 50° C. in an oven.

The interfacial polymerization medium was prepared by first charging the external phase to a Waring blender cup that has been preheated to 50° C. The commercial Waring blender (Waring Products Division, Dynamics Corporation of America, New Hartford, Conn., Blender 700) was powered through a 0 to 120 volt variable autotransformer. The blender mix speed was varied by controlling power to the blender as shown below in the emulsification parameters table. The internal phase was added to the external phase over a 16 second interval and blending was continued to obtain an emulsion.

TABLE

Emulsification Parameters

| Form. | Voltage (V) | Power (%) | Duration (s) |
|---|---|---|---|
| 5297 | 120 | 40 | 120 |
| 5295 | 120 | 40 | — |

To initiate polymerization and encapsulation of the internal phase, a 50% by weight solution of TETA was added to the emulsion to the amounts shown in the following Amine Table over a period of about 5 seconds. The blender speed is then reduced to a speed which just produces a vortex for approximately five to fifteen minutes. The emulsion was then transferred to a hot plate and stirred. The reaction vessel is covered and maintained at about 50° C. for approximately two hours which has been found is sufficient time for the isocyanate to react essentially completely.

TABLE

Amine

| | TETA, 50% by weight solution | |
|---|---|---|
| Form. | (g) | (%) |
| 5291 | 14.14 | 1.39% |
| 5297 | 27.72 | 1.39% |
| 5295 | 27.92 | 1.39% |

The capsule slurry is then allowed to cool to close to room temperature. The components shown in the stabilizer components table with the exception of the buffer are previously premixed with a high speed mixer (Waring Blender or Cowles Dissolver). The resulting stabilizer premix is then added to the capsule slurry to stabilize the dispersion of microcapsules. Finally the buffer is added and the mixture is stirred for at least 15 minutes until visually homogeneous.

Due to variations in the blender design and other uncontrollable variables, it was found to be difficult to correlate blender speed and particle size accurately. In consequence, some samples were discarded because they did not have the desired size. Samples were chosen for evaluation based on their measured particle size.

TABLE

Stabilizer Components

| | Weight of Components in grams | | |
|---|---|---|---|
| Form. | Invalon | Glycerin | Kelzan CC |
| 5291 | 58.41 | 39.2 | 0.53 |
| 5297 | 116.83 | 78.37 | 1.04 |
| 5295 | 116.83 | 78.37 | 1.04 |

| Form. | Proxel GXL | Caustic | Antifoam | Buffer |
|---|---|---|---|---|
| 5291 | 0.53 | 0.23 | 0.01 | 1.18 |
| 5297 | 1.04 | 0.354 | 0.01 | 2.38 |
| 5295 | 1.04 | 0.354 | 0.01 | 2.38 |

Formulations 5291, 5297, and 5295 were stabilized aqueous dispersions of microcapsules containing acetochlor at an approximate active concentration of 42.5% ai by weight (which approximately the same active concentration as DEGREE).

Each formulation was prepared to have an excess molar equivalents ratio of amine molar equivalents to isocyanate molar equivalents and herbicide to shell wall component ratios. TETA has an approximate equivalent weight of 36.6 g/mol. DES N3200 has an approximate equivalent weight of 183 g/mol (theoretical equivalent weight is 159.53 g/mol). DES W has an approximate equivalent weight of 132 g/mol. Formulation 5295 was prepared with an excess of internal phase solvent (diluent), NORPAR 15. The formulations had the following weight ratios:

TABLE

Formulation Characteristics

| Form. | Molar equivalents ratio | Ratio of Herbicide to Shell Wall Components | Ratio of Herbicide to Internal Phase Solvent |
|---|---|---|---|
| 5291 | 1.08:1 | 9.94:1 | 18.98:1 |
| 5297 | 1.06:1 | 10.02:1 | 19.03:1 |
| 5295 | 1.06:1 | 9.38:1 | 7.86:1 |

The blender speed was controlled to produce an increased microcapsule size compared to the microcapsules in DEGREE, which is about 2.5 μm. The particle size parameters were measured using a Beckman Coulter LS Particle Size Analyzer. The mean particle sizes and standard deviations of the microcapsules in the slurry for each formulation are shown in the following table:

TABLE

Particle Size Parameters

| Form. | Mean Particle size (μm) | Standard Deviation (μm) |
|---|---|---|
| 5291 | 5.57 | 3.99 |
| 5297 | 13.97 | 8.5 |
| 5295 | 12.70 | 7.85 |

Example 2

Preparation of Aqueous Dispersions of Microencapsulated Acetochlor

Aqueous dispersions of two microencapsulated acetochlor formulations, referenced as 410P9M and 403U7N, were prepared according to the method of Example 1. Composition 410P9M comprised the weight percent amounts shown in the following table.

TABLE

410P9M

| Component | Weight Percent |
|---|---|
| Internal Phase | |
| Acetochlor (95.4%) | 34.59 (33.0) |
| NORPAR 15 | 1.78 |
| MISTAFLEX H9915 | 2.52 |
| External Phase | |
| Glycerin | 9.66 |
| SOKALAN CP9 (25%) | 2.85(0.71) |
| Ammonium Caseinate | 0.057 |
| Citric Acid | 0.21 |
| Water | 34.81 |
| TETA, 50% solution | 1.28 (0.64) |
| Stabilizer | |
| Invalon (40%) | 7.15 (2.86) |
| Kelzan CC | 0.064 |
| Antifoam | 0.001 |
| Glycerin | 4.80 |
| Proxel GXL | 0.064 |
| Caustic | 0.022 |
| Buffer | 0.14 |

Composition 403U7N was prepared from similar components, but wherein the acetochlor loading and ratio of amine to isocyanate was altered to provide higher acetochlor loading and larger particle size. Composition 403U7N comprised the weight percent amounts shown in the following table.

TABLE

403U7N

| Component | Weight Percent |
|---|---|
| Internal Phase | |
| Acetochlor (95.4%) | 42.95 (41.0) |
| NORPAR 15 | 5.00 |
| MISTAFLEX H9915 | 3.08 |
| External Phase | |
| Glycerin | 7.73 |
| SOKALAN CP9 (25%) | 2.28(0.57) |
| Ammonium Caseinate | 0.046 |
| Citric Acid | 0.164 |
| Water | 27.85 |
| TETA, 50% solution | 1.37 (0.69) |
| Stabilizer | |
| Invalon (40%) | 5.56 (2.22) |
| Kelzan CC | 0.05 |
| Antifoam | 0.001 |
| Glycerin | 3.73 |
| Proxel GXL | 0.05 |
| Caustic | 0.017 |
| Buffer | 0.14 |

The particle size parameters for compositions 410P9M and 403U7N were measured using a Beckman Coulter LS Particle Size Analyzer. Compositions 410P9M and 403U7N are characterized in the table below:

TABLE

410P9M and 403U7N Characterization

| | 410P9M | 403U7N |
|---|---|---|
| Acetochlor loading | 33.0% | 41% |
| Shell Wall Amount (% organic premix) | 8% | 7.1% |
| Amine excess | 20% | 5% |
| Acetochlor/NORPAR | 18.5 | 8.4 |
| Mean Particle size | 10 μm | 12-13 μm |

Example 3

Study of Soybean, Cotton, Rice, Peanut and Wheat Safety in Preemergent Crop Application of Microencapsulated Acetochlor Formulations Aqueous dispersions of the two microencapsulated acetochlor formulations, referenced as 410P9M and 403U7N, prepared in Example 2 were applied to soil immediately after seeding with glyphosate-tolerant (ROUNDUP READY) soybean, glyphosate-tolerant (ROUNDUP READY) cotton, rice, peanut or wheat. Formulations were tested against commercial formulations HARNESS and DEGREE. Formulations were applied preemergent to soybean, cotton, rice, peanut and wheat and measured for phytotoxicity at 19, 20, 21, 22, or 25 DAT. The results are shown in tables below (Soybean % Injury 22 DAT), (Soybean % Injury 22 DAT), (Soybean % Injury 20 DAT), (Cotton % Injury 20 DAT), (Rice % Injury 25 DAT), (Peanut % Injury 25 DAT), (Winter Wheat % Injury 21 DAT).

Pots were seeded with RR2Y soybeans and then immediately treated with HARNESS, DEGREE or an aqueous dispersion of 410P9M or 403U7N with application rates of 420, 700, 980, 1260 or 1543 g/ha (0.375, 0.625, 0.875, 1.125 or 1.375 lb/A). Plants were watered by overhead irrigation (0.25" or 6.4 mm) 3 days after herbicide treatment followed by sub-irrigation to start germination. After germination pots were sub-irrigated as needed. Plants were evaluated 22 DAT for foliar injury and the results are reported in the table below.

TABLE

Soybean % Injury 22 DAT

| TRT | Product Formulation | % AI | Rate g/ha AI | Soybean GLXMG (Avg. 6 reps) |
|---|---|---|---|---|
| 1 | HARNESS | 74.8 | 420 | 2.0 |
| 2 | HARNESS | 74.8 | 700 | 4.2 |
| 3 | HARNESS | 74.8 | 980 | 11.2 |
| 4 | HARNESS | 74.8 | 1260 | 22.0 |
| 5 | HARNESS | 74.8 | 1540 | 24.2 |
| 6 | DEGREE | 42.0 | 420 | 0.5 |
| 7 | DEGREE | 42.0 | 700 | 3.3 |
| 8 | DEGREE | 42.0 | 980 | 2.7 |
| 9 | DEGREE | 42.0 | 1260 | 4.7 |
| 10 | DEGREE | 42.0 | 1540 | 6.3 |
| 11 | 403U7N | 41.0 | 420 | 0.7 |
| 12 | 403U7N | 41.0 | 700 | 1.3 |
| 13 | 403U7N | 41.0 | 980 | 2.0 |
| 14 | 403U7N | 41.0 | 1260 | 2.7 |
| 15 | 403U7N | 41.0 | 1540 | 3.8 |
| 16 | 410P9M | 33.0 | 420 | 0.3 |
| 17 | 410P9M | 33.0 | 700 | 0.8 |
| 18 | 410P9M | 33.0 | 980 | 0.8 |
| 19 | 410P9M | 33.0 | 1260 | 1.3 |
| 20 | 410P9M | 33.0 | 1540 | 3.0 |
| 21 | Untreated | | 0 | 0.0 |

Pots were seeded with RR2Y soybeans and then immediately treated with HARNESS, DEGREE or an aqueous dispersion of 410P9M, 403U7N or a 50:50 blend of 410P9M:403U7N with application rates of 420, 700, 980, 1260 or 1540 g/ha (0.375, 0.625, 0.875, 1.125, or 1.375 lb/A). Plants were evaluated 22 DAT for injury and the results are reported in the table below.

TABLE

Soybean % Injury 22 DAT

| TRT | Product Formulation | % AI | Rate g/ha AI | Soybean GLXMG (Avg. 6 reps) |
|---|---|---|---|---|
| 1 | HARNESS | 74.8 | 420 | 4.0 |
| 2 | HARNESS | 74.8 | 700 | 6.2 |
| 3 | HARNESS | 74.8 | 980 | 9.0 |
| 4 | HARNESS | 74.8 | 1260 | 12.3 |
| 5 | HARNESS | 74.8 | 1540 | 30.0 |
| 6 | DEGREE | 42.0 | 420 | 1.7 |
| 7 | DEGREE | 42.0 | 700 | 3.7 |
| 8 | DEGREE | 42.0 | 980 | 5.0 |
| 9 | DEGREE | 42.0 | 1260 | 17.3 |
| 10 | DEGREE | 42.0 | 1540 | 5.0 |
| 11 | 403U7N | 41.0 | 420 | 2.3 |
| 12 | 403U7N | 41.0 | 700 | 3.7 |
| 13 | 403U7N | 41.0 | 980 | 8.0 |
| 14 | 403U7N | 41.0 | 1260 | 2.3 |
| 15 | 403U7N | 41.0 | 1540 | 4.0 |
| 16 | 410P9M | 33.0 | 420 | 2.0 |
| 17 | 410P9M | 33.0 | 700 | 1.7 |
| 18 | 410P9M | 33.0 | 980 | 3.3 |
| 19 | 410P9M | 33.0 | 1260 | 2.0 |
| 20 | 410P9M | 33.0 | 1540 | 7.0 |
| 21 | 403U7N | 41.0 | 210 | 2.0 |
|    | 410P9M | 33.0 | 210 |     |
| 22 | 403U7N | 41.0 | 350 | 1.7 |
|    | 410P9M | 33.0 | 350 |     |
| 23 | 403U7N | 41.0 | 490 | 3.3 |
|    | 410P9M | 33.0 | 490 |     |
| 24 | 403U7N | 41.0 | 630 | 1.7 |
|    | 410P9M | 33.0 | 630 |     |
| 25 | 403U7N | 41.0 | 770 | 4.3 |
|    | 410P9M | 33.0 | 770 |     |
| 26 | Untreated | — | 0 | 0.0 |

Soybean injury was greatest with HARNESS compared to any of the encapsulated acetochlor treatments used.

Pots were seeded with RR2Y soybean then immediately treated with HARNESS, DEGREE or an aqueous dispersion of 410P9M, 403U7N or a 50:50 blend of 410P9M:403U7N with application rates of 560, 1120, 2240 or 4485 g/ha (0.5, 1.0, 2.0, or 4.0 lb/A). Plants were evaluated 20 DAT for foliar injury and the results are reported in the table below.

TABLE

Soybean % Injury 20 DAT

| TRT | Product Formulation | % AI | Rate g/ha AI | Soybean GLXMG (Avg. 6 reps) |
|---|---|---|---|---|
| 1 | HARNESS | 74.8 | 560 | 6.3 |
| 2 | HARNESS | 74.8 | 1120 | 6.8 |
| 3 | HARNESS | 74.8 | 2240 | 12.0 |
| 4 | HARNESS | 74.8 | 4485 | 28.3 |
| 5 | DEGREE | 42.0 | 560 | 4.0 |
| 6 | DEGREE | 42.0 | 1120 | 3.7 |
| 7 | DEGREE | 42.0 | 2240 | 5.3 |
| 8 | DEGREE | 42.0 | 4485 | 17.5 |
| 9 | 403U7N | 41.0 | 560 | 4.7 |
| 10 | 403U7N | 41.0 | 1120 | 3.0 |
| 11 | 403U7N | 41.0 | 2240 | 4.3 |
| 12 | 403U7N | 41.0 | 4485 | 5.3 |
| 13 | 410P9M | 33.0 | 560 | 2.7 |
| 14 | 410P9M | 33.0 | 1120 | 4.7 |
| 15 | 410P9M | 33.0 | 2240 | 4.3 |
| 16 | 410P9M | 33.0 | 4485 | 5.3 |
| 17 | 403U7N | 41.0 | 280 | 1.3 |
|    | 410P9M | 33.0 | 280 |     |
| 18 | 403U7N | 41.0 | 560 | 3.3 |
|    | 410P9M | 33.0 | 560 |     |
| 19 | 403U7N | 41.0 | 1120 | 3.0 |
|    | 410P9M | 33.0 | 1120 |     |
| 20 | 403U7N | 41.0 | 2242 | 4.7 |
|    | 410P9M | 33.0 | 2243 |     |
| 21 | Untreated |   | 0 | 0.0 |

In this study, HARNESS caused more soybean injury than any of the encapsulated acetochlor formulations tested. At the two highest rates tested, the formulations containing encapsulated acetochlor compositions 410P9M and 403U7N caused less injury to soybeans than DEGREE.

Pots were seeded with ROUNDUP READY Flex Cotton and then immediately treated with HARNESS, DEGREE or an aqueous dispersion of 410P9M, 403U7N or a 50:50 blend of 410P9M:403U7N with application rates of 560, 1120, 2240 or 4485 g/ha (0.5, 1.0, 2.0, or 4.0 lb/A). Plants were evaluated 20 DAT for foliar injury and the results are reported in the table below.

TABLE

Cotton % Injury 20 DAT

| TRT | Product Formulation | % AI | Rate g/ha AI | Cotton GOSHI (Avg. 6 reps) |
|---|---|---|---|---|
| 1 | HARNESS | 74.8 | 560 | 2.7 |
| 2 | HARNESS | 74.8 | 1120 | 3.3 |
| 3 | HARNESS | 74.8 | 2240 | 8.0 |
| 4 | HARNESS | 74.8 | 4485 | 35.8 |
| 5 | DEGREE | 42.0 | 560 | 2.3 |
| 6 | DEGREE | 42.0 | 1120 | 2.0 |
| 7 | DEGREE | 42.0 | 2240 | 3.7 |
| 8 | DEGREE | 42.0 | 4485 | 4.7 |
| 9 | 403U7N | 41.0 | 560 | 0.2 |
| 10 | 403U7N | 41.0 | 1120 | 1.2 |
| 11 | 403U7N | 41.0 | 2240 | 6.6 |
| 12 | 403U7N | 41.0 | 4485 | 6.7 |
| 13 | 410P9M | 33.0 | 560 | 0.8 |
| 14 | 410P9M | 33.0 | 1120 | 1.3 |
| 15 | 410P9M | 33.0 | 2240 | 3.7 |
| 16 | 410P9M | 33.0 | 4485 | 3.3 |
| 17 | 403U7N | 41.0 | 280 | 0.7 |
|    | 410P9M | 33.0 | 280 |     |
| 18 | 403U7N | 41.0 | 560 | 3.0 |
|    | 410P9M | 33.0 | 560 |     |
| 19 | 403U7N | 41.0 | 1120 | 4.6 |
|    | 410P9M | 33.0 | 1120 |     |
| 20 | 403U7N | 41.0 | 2242 | 4.8 |
|    | 410P9M | 33.0 | 2243 |     |
| 21 | Untreated |   | 0 | 0.0 |

In this study, the encapsulated acetochlor formulations caused less injury to cotton than HARNESS.

Pots were seeded with rice and then immediately treated with HARNESS, DEGREE or an aqueous dispersion of 410P9M, 403U7N or a 50:50 blend of 410P9M:403U7N with application rates of 560, 1120, 2240 or 4485 g/ha (0.5, 1.0, 2.0, or 4.0 lb/A). Plants were evaluated 25 DAT for foliar injury and the results are reported in the table below.

TABLE

Rice % Injury 25 DAT

| TRT | Product Formulation | % AI | Rate g/ha AI | Rice ORYSS (Avg. 5 reps) |
|---|---|---|---|---|
| 1 | HARNESS | 74.8 | 560 | 4.3 |
| 2 | HARNESS | 74.8 | 1120 | 12.5 |
| 3 | HARNESS | 74.8 | 2240 | 19.2 |
| 4 | HARNESS | 74.8 | 4485 | 79.2 |
| 5 | DEGREE | 42.0 | 560 | 4.3 |
| 6 | DEGREE | 42.0 | 1120 | 6.7 |
| 7 | DEGREE | 42.0 | 2240 | 15.0 |
| 8 | DEGREE | 42.0 | 4485 | 22.5 |
| 9 | 403U7N | 41.0 | 560 | 3.3 |
| 10 | 403U7N | 41.0 | 1120 | 5.7 |
| 11 | 403U7N | 41.0 | 2240 | 10.0 |
| 12 | 403U7N | 41.0 | 4485 | 13.3 |
| 13 | 410P9M | 33.0 | 560 | 2.7 |
| 14 | 410P9M | 33.0 | 1120 | 6.0 |
| 15 | 410P9M | 33.0 | 2240 | 8.7 |
| 16 | 410P9M | 33.0 | 4485 | 14.2 |
| 17 | 403U7N | 41.0 | 280 | 6.8 |
|  | 410P9M | 33.0 | 280 |  |
| 18 | 403U7N | 41.0 | 560 | 9.2 |
|  | 410P9M | 33.0 | 560 |  |
| 19 | 403U7N | 41.0 | 1120 | 10.8 |
|  | 410P9M | 33.0 | 1120 |  |
| 20 | 403U7N | 41.0 | 2242 | 24.2 |
|  | 410P9M | 33.0 | 2243 |  |
| 21 | Untreated |  | 0 | 0.0 |

In this study, rice foliar injury was greater with HARNESS compared to any of the encapsulated acetochlor formulations.

Pots were seeded with peanuts and then immediately treated with HARNESS, DEGREE or an aqueous dispersion of 410P9M, 403U7N or a 50:50 blend of 410P9M:403U7N with application rates of 560, 1120, 2240 or 4485 g/ha (0.5, 1.0, 2.0, or 4.0 lb/A). Plants were evaluated 25 DAT for foliar injury and the results are reported in the table below.

TABLE

Peanut % Injury 25 DAT

| TRT | Product Formulation | % AI | Rate g/ha AI | Peanut ARHHY (Avg. 5 reps) |
|---|---|---|---|---|
| 1 | HARNESS | 74.8 | 560 | 7.5 |
| 2 | HARNESS | 74.8 | 1120 | 7.0 |
| 3 | HARNESS | 74.8 | 2240 | 12.5 |
| 4 | HARNESS | 74.8 | 4485 | 18.3 |
| 5 | DEGREE | 42.0 | 560 | 4.0 |
| 6 | DEGREE | 42.0 | 1120 | 4.8 |
| 7 | DEGREE | 42.0 | 2240 | 6.5 |
| 8 | DEGREE | 42.0 | 4485 | 7.3 |
| 9 | 403U7N | 41.0 | 560 | 2.3 |
| 10 | 403U7N | 41.0 | 1120 | 2.0 |
| 11 | 403U7N | 41.0 | 2240 | 4.7 |
| 12 | 403U7N | 41.0 | 4485 | 4.8 |
| 13 | 410P9M | 33.0 | 560 | 3.7 |
| 14 | 410P9M | 33.0 | 1120 | 4.7 |
| 15 | 410P9M | 33.0 | 2240 | 3.7 |
| 16 | 410P9M | 33.0 | 4485 | 7.0 |
| 17 | 403U7N | 41.0 | 280 | 2.0 |
|  | 410P9M | 33.0 | 280 |  |
| 18 | 403U7N | 41.0 | 560 | 5.5 |
|  | 410P9M | 33.0 | 560 |  |
| 19 | 403U7N | 41.0 | 1120 | 6.4 |
|  | 410P9M | 33.0 | 1120 |  |
| 20 | 403U7N | 41.0 | 2242 | 8.2 |
|  | 410P9M | 33.0 | 2243 |  |
| 21 | Untreated |  | 0 | 0.0 |

The encapsulated acetochlor formulations showed greater crop safety in peanut than HARNESS.

Pots containing a 50:50 silt loam:redi-earth soil mix were seeded with winter wheat. Immediately after planting, preemergence applications of HARNESS, DEGREE or an aqueous dispersion of 410P9M or 403U7N at application rates of 420, 841, 1261, and 1681 g/ha were conducted. Plants were evaluated 21 DAT for foliar injury and the results are reported in the table below.

TABLE

Winter Wheat % Injury 21 DAT

| TRT | Product Formulation | g/l AI | Rate g/ha AI | Wheat TRZAW (Avg 6 reps) |
|---|---|---|---|---|
| 1 | 410P9M | 359 | 420 | 0.0 |
| 2 | 410P9M | 359 | 841 | 3.3 |
| 3 | 410P9M | 359 | 1261 | 3.3 |
| 4 | 410P9M | 359 | 1681 | 2.5 |
| 5 | 403U7N | 455 | 420 | 0.8 |
| 6 | 403U7N | 455 | 841 | 2.5 |
| 7 | 403U7N | 455 | 1261 | 2.5 |
| 8 | 403U7N | 455 | 1681 | 3.3 |
| 9 | DEGREE | 455 | 420 | 2.5 |
| 10 | DEGREE | 455 | 841 | 2.5 |
| 11 | DEGREE | 455 | 1261 | 5.0 |
| 12 | DEGREE | 455 | 1681 | 6.7 |
| 13 | HARNESS | 839 | 420 | 7.5 |
| 14 | HARNESS | 839 | 841 | 10.8 |
| 15 | HARNESS | 839 | 1261 | 10.0 |
| 16 | HARNESS | 839 | 1681 | 19.2 |
| 17 | Untreated |  | 0 | 0.0 |

The encapsulated acetochlor formulations showed greater crop safety in wheat than HARNESS.

Example 4

Study of Weed Control Efficacy and Soybean and Cotton Safety in Preemergent Crop Application of Microencapsulated Acetochlor Formulations and Tank Mixes with Other Herbicides Formulations and mixtures were applied to soil immediately after seeding with herbicide-tolerant soybean (glyphosate-tolerant, ROUNDUP READY soy or dicamba-tolerant, DT-SOY) or herbicide-tolerant cotton (glyphosate-tolerant, ROUNDUP READY cotton or dicamba-tolerant, DT-COTTON) to assess crop safety and Proso Millet (PANMI), Velvetleaf (ABUTH), Purslane (POROL), Morningglory (IPOLA), or Rox Orange *Sorghum* (SORSS) to assess weed efficacy.

Aqueous dispersions of microencapsulated acetochlor formulation 410P9M prepared in Example 2, alone and in tank mix combination with VALOR SX (flumioxazin), REFLEX (fomesafen), SHARPEN (saflufenacil), or CLARITY (dicamba, diglycolamine salt) were tested. Formulations and mixtures were tested against commercial formulation HARNESS. All treatments were applied immediately to seeded soil and allowed to sit for 3 days (to obtain release of acetochlor in formulations of 410P9M) in the greenhouse prior to receiving 0.25 or 0.5 inches (6.4 or 13 mm) of overhead irrigation to incorporate the herbicide treatments into the soil surface and evaluated 14, 16, or 17 DAT. The results are shown in the first Table below (Soybean and Cotton % Injury 16 DAT and IPOLA and SORSS Weed Control Efficacy 16 DAT) and the second Table below (Soybean and Cotton % Injury 17 DAT and PANMI, ABUTH, POROL Weed Control Efficacy 14 DAT).

TABLE

Soybean and Cotton % Injury 16 DAT and IPOLA and SORSS Weed Control Efficacy 16 DAT

| TRT | Product Formulation | % AI | Rate g/ha | RR Soy GLXMV | RR Cotton GOSHX | IPOLA | SORSS |
|---|---|---|---|---|---|---|---|
| 1 | 410P9M | 33.0 | 1120 | 8.3 | 2.5 | 0.8 | 5.8 |
| 2 | 410P9M | 33.0 | 1682 | 10.8 | 5.8 | 3.3 | 30.0 |
| 3 | 410P9M | 33.0 | 2244 | 17.5 | 16.7 | 30.8 | 45.8 |
| 4 | HARNESS | 74.8 | 1120 | 33.3 | 22.5 | 18.3 | 48.3 |
| 5 | HARNESS | 74.8 | 1682 | 63.3 | 35.0 | 41.7 | 65.8 |
| 6 | HARNESS | 74.8 | 2244 | 84.2 | 46.7 | 78.3 | 82.5 |
| 7 | VALOR SX | 50.0 | 35 | 0.0 | 0.0 | 12.5 | 30.8 |
| 8 | VALOR SX | 50.0 | 70 | 5.8 | 22.5 | 21.7 | 35.8 |
| 9 | VALOR SX | 50.0 | 140 | 17.5 | 20.0 | 55.0 | 60.0 |
| 10 | REFLEX | 22.8 | 95 | 0.0 | 0.0 | 1.7 | 15.8 |
| 11 | REFLEX | 22.8 | 190 | 4.2 | 15.8 | 61.7 | 30.0 |
| 12 | REFLEX | 22.8 | 380 | 6.7 | 12.5 | 81.7 | 79.2 |
| 13 | SHARPEN | 34.2 | 25 | 0.0 | 0.0 | 56.7 | 3.3 |
| 14 | SHARPEN | 34.2 | 50 | 1.7 | 7.5 | 100.0 | 27.5 |
| 15 | SHARPEN | 34.2 | 100 | 21.7 | 12.5 | 100.0 | 32.5 |
| 16 | 410P9M VALOR SX | 33.0 50.0 | 1120 35 | 5.0 | 0.0 | 2.5 | 20.8 |
| 17 | 410P9M VALOR SX | 33.0 50.0 | 1682 35 | 7.5 | 8.3 | 5.8 | 35.0 |
| 18 | 410P9M VALOR SX | 33.0 50.0 | 2244 35 | 20.8 | 9.2 | 33.3 | 53.3 |
| 19 | 410P9M VALOR SX | 33.0 50.0 | 1120 70 | 6.7 | 0.0 | 17.5 | 31.7 |
| 20 | 410P9M VALOR SX | 33.0 50.0 | 1682 70 | 3.3 | 5.8 | 30.8 | 49.2 |
| 21 | 410P9M VALOR SX | 33.0 50.0 | 2244 70 | 24.2 | 10.0 | 46.7 | 70.0 |
| 22 | 410P9M VALOR SX | 33.0 50.0 | 1120 140 | 10.0 | 0.0 | 35.8 | 51.7 |
| 23 | 410P9M VALOR SX | 33.0 50.0 | 1682 140 | 9.2 | 10.0 | 43.3 | 59.2 |
| 24 | 410P9M VALOR SX | 33.0 50.0 | 2244 140 | 43.3 | 9.2 | 61.7 | 71.7 |
| 25 | 410P9M REFLEX | 33.0 50.0 | 1120 95 | 0.0 | 3.3 | 7.5 | 20.0 |
| 26 | 410P9M REFLEX | 33.0 50.0 | 1682 95 | 4.2 | 5.8 | 29.2 | 34.2 |
| 27 | 410P9M REFLEX | 33.0 50.0 | 2244 95 | 14.2 | 10.8 | 45.0 | 38.3 |
| 28 | 410P9M REFLEX | 33.0 50.0 | 1120 190 | 0.8 | 5.0 | 15.8 | 38.3 |
| 29 | 410P9M REFLEX | 33.0 50.0 | 1682 190 | 1.7 | 10.0 | 60.0 | 37.5 |
| 30 | 410P9M REFLEX | 33.0 50.0 | 2244 190 | 21.7 | 12.5 | 55.0 | 47.5 |
| 31 | 410P9M REFLEX | 33.0 50.0 | 1120 380 | 4.2 | 0.0 | 53.3 | 81.7 |
| 32 | 410P9M REFLEX | 33.0 50.0 | 1682 380 | 5.0 | 10.0 | 64.2 | 74.2 |
| 33 | 410P9M REFLEX | 33.0 50.0 | 2244 380 | 7.5 | 18.3 | 76.7 | 76.7 |
| 34 | 410P9M SHARPEN | 33.0 34.2 | 1120 25 | 5.8 | 1.7 | 25.8 | 25.0 |
| 35 | 410P9M SHARPEN | 33.0 34.2 | 1682 25 | 5.8 | 14.2 | 86.7 | 30.0 |
| 36 | 410P9M SHARPEN | 33.0 34.2 | 2244 25 | 10.0 | 16.7 | 89.2 | 33.3 |
| 37 | 410P9M SHARPEN | 33.0 34.2 | 1120 50 | 6.7 | 7.5 | 93.3 | 45.0 |
| 38 | 410P9M SHARPEN | 33.0 34.2 | 1682 50 | 15.0 | 5.0 | 100.0 | 55.8 |
| 39 | 410P9M SHARPEN | 33.0 34.2 | 2244 50 | 15.8 | 26.7 | 93.3 | 51.7 |
| 40 | 410P9M SHARPEN | 33.0 34.2 | 1120 100 | 5.0 | 9.2 | 100.0 | 40.8 |
| 41 | 410P9M SHARPEN | 33.0 34.2 | 1682 100 | 10.0 | 11.7 | 85.0 | 49.2 |
| 42 | 410P9M SHARPEN | 33.0 34.2 | 2244 100 | 19.2 | 13.3 | 98.3 | 54.2 |
| 43 | Untreated | 0 | 0 | 0.0 | 0.0 | 0.0 | 0.0 |

Encapsulated acetochlor formulation 410P9M showed acceptable levels of crop safety at the 1120 g/ha rate, both alone and in combination with commercial herbicides VALOR SX, REFLEX and SHARPEN. Encapsulated acetochlor formulation 410P9M showed acceptable levels of crop safety at the 1682 g/ha rate with commercial herbicide VALOR SX and REFLEX.

After the incorporation of the herbicide treatments, the pots were only overhead irrigated as needed to ensure proper incorporation of the herbicides in the germination zone.

The plants were rated visually and percentage of crop injury was determined 19 days after the herbicide treatments. The results are reported in the table below.

TABLE

Soybean and Cotton % Injury 17 DAT and PANMI, ABUTH, POROL Weed Control Efficacy 14 DAT

| TRT | Product Formulation | % AI | Rate g/ha | DT-SOY GLXMD | DT-COTTON GOSHD | PANMI | ABUTH | POROL |
|---|---|---|---|---|---|---|---|---|
| 1 | HARNESS | 74.8 | 840 | 6.7 | 1.7 | 98.3 | 7.5 | 99.5 |
| 2 | | | 1260 | 29.2 | 12.5 | 99.3 | 25.8 | 100.0 |
| 3 | 410P9M | 33.0 | 840 | 0.0 | 0.0 | 76.5 | 0.0 | 35.0 |
| 4 | | | 1260 | 9.2 | 0.8 | 88.0 | 19.2 | 64.2 |
| 5 | VALOR SX | 50.0 | 35 | 0.8 | 0.0 | 50.8 | 31.7 | 99.7 |
| 6 | | | 70 | 6.7 | 15.0 | 66.7 | 63.3 | 100.0 |
| 7 | REFLEX | 22.8 | 95 | 4.2 | 2.5 | 20.0 | 21.7 | 81.7 |
| 8 | | | 190 | 5.0 | 10.0 | 40.8 | 48.3 | 96.8 |
| 9 | SHARPEN | 34.2 | 25 | 2.5 | 4.2 | 39.2 | 46.7 | 99.7 |
| 10 | | | 50 | 6.7 | 12.5 | 56.7 | 87.5 | 100.0 |
| 11 | CLARITY | 38.5 | 140 | 0.0 | 0.0 | 16.7 | 28.3 | 58.3 |
| 12 | | | 280 | 0.0 | 0.0 | 41.7 | 46.7 | 77.5 |
| 13 | 410P9M VALOR SX | 33.0 50.0 | 840 35 | 1.7 | 0.0 | 52.5 | 14.2 | 83.3 |
| 14 | 410P9M VALOR SX | 33.0 50.0 | 1260 35 | 10.0 | 4.2 | 70.0 | 38.3 | 93.3 |
| 15 | 410P9M VALOR SX | 33.0 50.0 | 840 70 | 7.5 | 7.5 | 62.5 | 11.7 | 88.8 |
| 16 | 410P9M VALOR SX | 33.0 50.0 | 1260 70 | 23.3 | 8.3 | 73.0 | 46.7 | 93.3 |
| 17 | 410P9M REFLEX | 33.0 50.0 | 840 95 | 0.8 | 4.2 | 31.7 | 2.5 | 63.3 |
| 18 | 410P9M REFELX | 33.0 50.0 | 1260 95 | 12.5 | 6.7 | 58.3 | 27.5 | 72.5 |
| 19 | 410P9M REFLEX | 33.0 50.0 | 840 190 | 10.8 | 7.5 | 75.0 | 15.8 | 85.0 |
| 20 | 410P9M REFELX | 33.0 50.0 | 1260 190 | 15.8 | 10.8 | 83.0 | 29.2 | 91.3 |
| 21 | 410P9M SHARPEN | 33.0 34.2 | 840 25 | 8.3 | 5.8 | 62.5 | 30.0 | 88.0 |
| 22 | 410P9M SHARPEN | 33.0 34.2 | 1260 25 | 10.0 | 9.2 | 77.5 | 50.0 | 99.3 |
| 23 | 410P9M SHARPEN | 33.0 34.2 | 840 50 | 15.0 | 7.5 | 65.8 | 92.5 | 99.7 |
| 24 | 410P9M SHARPEN | 33.0 34.2 | 1260 50 | 17.5 | 25.8 | 82.2 | 97.5 | 100.0 |
| 25 | 410P9M CLARITY | 33.0 38.5 | 840 140 | 0.0 | 0.0 | 65.8 | 25.8 | 60.8 |
| 26 | 410P9M CLARITY | 33.0 38.5 | 1260 140 | 11.7 | 4.2 | 82.5 | 33.3 | 71.7 |
| 27 | 410P9M CLARITY | 33.0 38.5 | 840 280 | 0.0 | 0.0 | 65.0 | 30.0 | 79.2 |
| 28 | 410P9M CLARITY | 33.0 38.5 | 1260 280 | 12.5 | 5.0 | 82.0 | 45.0 | 89.3 |
| 29 | Untreated | 0.0 | 0 | 0.0 | 0.0 | 0.0 | 0.0 | 0.0 |

Tank mixtures of encapsulated acetochlor formulation 410P9M with SHARPEN provided the best weed control compared to other tank mixtures tested.

Pots containing a 50:50 silt loam:redi-earth soil mix were seeded with winter wheat. Immediately after planting, encapsulated acetochlor formulation 410P9M at 840, 1260, and 1680 g ai/ha and SENCOR DF (metribuzin) at 210, 420, and 840 g ai/ha were applied. In addition, encapsulated acetochlor formulation 410P9M was tank-mixed with SENCOR DF (metribuzin) at each rate. Then, the herbicide treatments were incorporated into the germination zone with 0.25 inches (6.4 mm) overhead irrigation three days after application.

TABLE

Winter Wheat % Injury 19 DAT

| TRT | Product Formulation | g/l AI | % AI | Rate g/ha AI | Wheat TRZAW |
|---|---|---|---|---|---|
| 1 | 410P9M | 359 | | 840 | 1.7 |
| 2 | 410P9M | 359 | | 1260 | 1.7 |
| 3 | 410P9M | 359 | | 1680 | 1.7 |
| 4 | SENCOR DF | | 75 | 210 | 90.8 |
| 5 | SENCOR DF | | 75 | 420 | 100.0 |
| 6 | SENCOR DF | | 75 | 840 | 100.0 |
| 7 | 410P9M SENCOR DF | 359 | 75 | 840 210 | 100.0 |

TABLE-continued

Winter Wheat % Injury 19 DAT

| TRT | Product Formulation | g/l AI | % AI | Rate g/ha AI | Wheat TRZAW |
|---|---|---|---|---|---|
| 8 | 410P9M | 359 | | 840 | 91.7 |
| | SENCOR DF | | 75 | 420 | |
| 9 | 410P9M | 359 | | 840 | 100.0 |
| | SENCOR DF | | 75 | 840 | |
| 10 | 410P9M | 359 | | 1260 | 95.8 |
| | SENCOR DF | | 75 | 210 | |
| 11 | 410P9M | 359 | | 1260 | 97.5 |
| | SENCOR DF | | 75 | 420 | |
| 12 | 410P9M | 359 | | 1260 | 100.0 |
| | SENCOR DF | | 75 | 840 | |
| 13 | 410P9M | 359 | | 1680 | 100.0 |
| | SENCOR DF | | 75 | 210 | |
| 14 | 410P9M | 359 | | 1680 | 100.0 |
| | SENCOR DF | | 75 | 420 | |
| 15 | 410P9M | 359 | | 1680 | 100.0 |
| | SENCOR DF | | 75 | 840 | |
| 16 | Untreated | 0 | | 0 | 0.0 |

Example 5

Field Trial Study of Weed Control Efficacy and Soybean and Cotton Safety in Preemergent Crop Application of Microencapsulated Acetochlor Formulations and Tank Mixtures with Other Herbicides Aqueous dispersions of microencapsulated acetochlor formulation 410P9M prepared in Example 2, alone and in tank mix combination with VALOR SX (flumioxazin), COTORAN 4 (fluometuron) and SENCOR DF (metribuzin) were tested. The commercial formulation DUAL MAGNUM, available from Syngenta and comprising s-metalochlor as the active ingredient and proprietary ingredients was also tested. All treatments were applied to soil seeded with glyphosate-tolerant ROUNDUP READY soybeans or ROUNDUP READY Flex Cotton on the same day as planting and the associated crop injury was evaluated. Crop injury was evaluated in terms of growth reduction (% GR), stand reduction (% SR) and leaf crinkle (% LF). The results from three field trials are reported in the tables below.

TABLE

RR Soybean % Crop Injury 14 DAT in Three Field Trials

| Product Formulation | Rate g AI/ha | Trial 2010530037 % GR | % LF | Trial 2010530038 % GR | % LF | Trial 2010530039 % GR | % LF |
|---|---|---|---|---|---|---|---|
| 410P9M | 840 | 0.0 | 0.0 | 0.8 | 3.3 | 6.3 | 10.0 |
| 410P9M | 1260 | 0.0 | 2.0 | 1.3 | 5.8 | 6.3 | 11.3 |
| DUAL MAGNUM | 930 | 0.0 | 0.0 | 0.0 | 0.8 | 5.0 | 8.8 |
| DUAL MAGNUM | 1400 | 0.0 | 1.6 | 0.0 | 0.0 | 5.0 | 11.3 |
| COTORAN 4 | 1120 | 0.0 | 0.8 | 0.0 | 0.0 | 7.5 | 1.3 |
| COTORAN 4 | 1800 | 0.0 | 1.5 | 0.0 | 0.8 | 32.5 | 0.0 |
| VALOR SX | 48 | 0.0 | 0.8 | 0.8 | 0.0 | 25.0 | 7.5 |
| VALOR SX | 70 | 0.0 | 2.8 | 0.0 | 0.0 | 30.0 | 7.5 |
| SENCOR DF | 370 | 0.0 | 0.0 | 0.0 | 0.0 | 66.3 | 0.0 |
| SENCOR DF | 560 | 0.0 | 0.0 | 3.8 | 0.0 | 73.8 | — |
| 410P9M<br>VALOR SX | 840<br>48 | 0.0 | 4.0 | 1.3 | 9.5 | 36.3 | 18.8 |
| 410P9M<br>VALOR SX | 1260<br>48 | 0.0 | 5.8 | 1.3 | 11.3 | 32.5 | 15.0 |
| 410P9M<br>VALOR SX | 840<br>70 | 0.0 | 5.8 | 3.3 | 9.3 | 48.8 | 15.0 |
| 410P9M<br>VALOR SX | 1260<br>70 | 0.0 | 9.0 | 4.5 | 13.8 | 51.3 | 17.5 |
| 410P9M<br>COTORAN 4 | 840<br>1120 | 0.0 | 0.0 | 2.8 | 7.5 | 22.5 | 15.0 |
| 410P9M<br>COTORAN 4 | 1260<br>1120 | 0.0 | 0.8 | 2.0 | 10.0 | 21.3 | 12.5 |
| 410P9M<br>COTORAN 4 | 840<br>1800 | 0.0 | 2.0 | 7.0 | 8.3 | 32.5 | 15.0 |
| 410P9M<br>COTORAN 4 | 1260<br>1800 | 0.0 | 3.3 | 5.8 | 11.3 | 42.5 | 15.0 |
| 410P9M<br>SENCOR DF | 840<br>370 | 0.0 | 2.0 | 3.8 | 9.3 | 70.0 | 11.3 |
| 410P9M<br>SENCOR DF | 1260<br>370 | 0.0 | 4.0 | 2.0 | 8.3 | 85.0 | 7.5 |
| 410P9M<br>SENCOR DF | 840<br>560 | 0.0 | 0.8 | 11.3 | 7.5 | 90.0 | 15.0 |
| 410P9M<br>SENCOR DF | 1260<br>560 | 0.0 | 3.5 | 12.5 | 9.5 | 100.0 | — |

Data from these field trials demonstrate that the encapsulated acetochlor formulation 410P9M exhibited good soybean crop safety alone at all three locations tested and exhibited good soybean crop safety in combination with co-herbicides VALOR SX, COTORAN 4 and SENCOR DF at two of the three locations tested.

SX and SENCOR DF did not exhibit acceptable levels of crop safety. This is not unexpected since SENCOR DF is not labeled for use in cotton and VALOR SX requires a 14-28 day waiting period after application prior to planting cotton.

The efficacy of the same formulations on morningglory (IPOHE), *amaranthus* (AMASS) and sicklepod (CASOB)

TABLE

RR Flex Cotton % Crop Injury 14 DAT in Three Field Trials

| Product Formulation | Rate g AI/ha | Trial 2010530037 % GR | Trial 2010530037 % SR | Trial 2010530038 % GR | Trial 2010530038 % SR | Trial 2010530039 % GR | Trial 2010530039 % SR |
|---|---|---|---|---|---|---|---|
| 410P9M | 840 | 0.0 | 0.0 | 2.5 | 0.0 | 2.5 | 0.0 |
| 410P9M | 1260 | 0.0 | 0.0 | 0.0 | 0.0 | 6.3 | 0.0 |
| DUAL MAGNUM | 930 | 1.3 | 0.0 | 3.8 | 0.0 | 3.8 | 0.0 |
| DUAL MAGNUM | 1400 | 6.5 | 0.0 | 7.8 | 0.0 | 20.0 | 3.8 |
| COTORAN 4 | 1120 | 0.0 | 0.0 | 0.8 | 0.0 | 2.5 | 0.0 |
| COTORAN 4 | 1800 | 2.5 | 2.5 | 0.8 | 0.0 | 1.3 | 0.0 |
| VALOR SX | 48 | 22.5 | 25.0 | 12.0 | 7.0 | 47.5 | 11.3 |
| VALOR SX | 70 | 38.8 | 41.3 | 37.5 | 28.8 | 65.0 | 30.0 |
| SENCOR DF | 370 | 99.3 | 99.3 | 86.3 | 86.3 | 92.5 | 92.5 |
| SENCOR DF | 560 | 99.5 | 99.5 | 100.0 | 100.0 | 98.8 | 98.8 |
| 410P9M VALOR SX | 840 48 | 6.3 | 3.8 | 46.3 | 33.8 | 71.3 | 55.0 |
| 410P9M VALOR SX | 1260 48 | 6.3 | 0.0 | 56.3 | 56.3 | 60.0 | 32.5 |
| 410P9M VALOR SX | 840 70 | 12.5 | 11.3 | 66.3 | 66.3 | 80.0 | 66.3 |
| 410P9M VALOR SX | 1260 70 | 21.3 | 15.0 | 65.0 | 57.5 | 83.8 | 75.0 |
| 410P9M COTORAN 4 | 840 1120 | 0.0 | 0.0 | 1.3 | 0.0 | 8.8 | 1.3 |
| 410P9M COTORAN 4 | 1260 1120 | 0.0 | 0.0 | 0.0 | 0.0 | 22.5 | 7.5 |
| 410P9M COTORAN 4 | 840 1800 | 1.3 | 1.3 | 0.0 | 0.0 | 11.3 | 5.0 |
| 410P9M COTORAN 4 | 1260 1800 | 1.3 | 1.3 | 0.0 | 0.0 | 22.5 | 5.0 |
| 410P9M SENCOR DF | 840 370 | 87.3 | 87.3 | 62.5 | 68.8 | 100.0 | 100.0 |
| 410P9M SENCOR DF | 1260 370 | 91.3 | 90.0 | 68.3 | 70.8 | 100.0 | 100.0 |
| 410P9M SENCOR DF | 840 560 | 98.5 | 98.5 | 95.8 | 95.8 | 100.0 | 100.0 |
| 410P9M SENCOR DF | 1260 560 | 92.5 | 87.5 | 97.5 | 97.5 | 100.0 | 100.0 |

Data from these field trials demonstrate that the encapsulated acetochlor formulation 410P9M both alone and in combination with COTORAN 4 has good crop safety on cotton. Tank mixes of formulation 410P9M with VALOR by preemergent application on the same day as planting the crop was also determined with the results reported in the table below.

TABLE

IPOHE, AMASS and CASOB Weed Control Efficacy 28 and 56 DAT

| Product Formulation | Rate g AI/ha | IPOHE 28 DAT | IPOHE 56 DAT | AMASS 28 DAT | AMASS 56 DAT | CASOB 28 DAT | CASOB 56 DAT |
|---|---|---|---|---|---|---|---|
| 410P9M | 840 | 0.0 | 6.3 | 55.0 | 42.5 | 5.0 | 0.0 |
| 410P9M | 1260 | 8.8 | 6.3 | 85.0 | 72.5 | 21.3 | 28.8 |
| DUAL MAGNUM | 930 | 0.0 | 0.0 | 77.5 | 47.5 | 25.0 | 5.0 |
| DUAL MAGNUM | 1400 | 3.8 | 0.0 | 80.0 | 50.0 | 32.5 | 10.0 |
| COTORAN 4 | 1120 | 0.0 | 12.5 | 0.0 | 0.0 | 17.5 | 0.0 |
| COTORAN 4 | 1800 | 10.0 | 0.0 | 10.0 | 10.0 | 36.3 | 0.0 |
| VALOR SX | 48 | 73.8 | 40.0 | 100.0 | 85.0 | 60.0 | 27.5 |
| VALOR SX | 70 | 73.8 | 72.5 | 100.0 | 75.0 | 50.0 | 7.5 |
| SENCOR DF | 370 | 10.0 | 0.0 | 92.5 | 60.0 | 75.0 | 60.0 |
| SENCOR DF | 560 | 7.5 | 0.0 | 100.0 | 65.0 | 97.0 | 100.0 |
| 410P9M VALOR SX | 840 48 | 66.3 | 60.0 | 100.0 | 87.5 | 55.0 | 42.5 |
| 410P9M VALOR SX | 1260 48 | 48.8 | 31.3 | 100.0 | 100.0 | 56.3 | 26.3 |

TABLE-continued

IPOHE, AMASS and CASOB Weed Control Efficacy 28 and 56 DAT

| Product Formulation | Rate g AI/ha | IPOHE 28 DAT | IPOHE 56 DAT | AMASS 28 DAT | AMASS 56 DAT | CASOB 28 DAT | CASOB 56 DAT |
|---|---|---|---|---|---|---|---|
| 410P9M<br>VALOR SX | 840<br>70 | 92.5 | 82.5 | 100.0 | 100.0 | 80.0 | 70.0 |
| 410P9M<br>VALOR SX | 1260<br>70 | 65.0 | 52.5 | 100.0 | 100.0 | 75.8 | 37.5 |
| 410P9M<br>COTORAN 4 | 840<br>1120 | 3.8 | 0.0 | 100.0 | 100.0 | 56.3 | 32.5 |
| 410P9M<br>COTORAN 4 | 1260<br>1120 | 7.5 | 0.0 | 100.0 | 85.0 | 35.0 | 25.0 |
| 410P9M<br>COTORAN 4 | 840<br>1800 | 16.3 | 10.0 | 100.0 | 100.0 | 38.8 | 5.0 |
| 410P9M<br>COTORAN 4 | 1260<br>1800 | 7.5 | 6.3 | 100.0 | 100.0 | 36.3 | 0.0 |
| 410P9M<br>SENCOR DF | 840<br>370 | 3.8 | 0.0 | 100.0 | 96.3 | 80.0 | 60.0 |
| 410P9M<br>SENCOR DF | 1260<br>370 | 3.8 | 0.0 | 100.0 | 100.0 | 67.5 | 36.3 |
| 410P9M<br>SENCOR DF | 840<br>560 | 0.0 | 0.0 | 100.0 | 100.0 | 94.5 | 67.5 |
| 410P9M<br>SENCOR DF | 1260<br>560 | 16.3 | 0.0 | 100.0 | 100.0 | 100.0 | 80.0 |

The efficacy of the same formulations on velvetleaf (ABUTH), barnyardgrass (ECHCG) and signalgrass (BRAPP) by preemergent application on the same day as planting the crop was also determined with the results reported in the table below.

The efficacy of the same formulations on *amaranthus* (AMASS), velvetleaf (ABUTH) and morningglory (IPOHE) by preemergent application on the same day as planting the crop was also determined with the results reported in the table below.

TABLE

ABUTH, ECHCG and BRAPP Weed Control Efficacy 28 and 56 DAT

| Product Formulation | Rate g AI/ha | ABUTH 28 DAT | ABUTH 56 DAT | ECHCG 28 DAT | ECHCG 56 DAT | BRAPP 28 DAT | BRAPP 56 DAT |
|---|---|---|---|---|---|---|---|
| 410P9M | 840 | 0.0 | 0.0 | 80.0 | 50.0 | 10.0 | 0.0 |
| 410P9M | 1260 | 3.8 | 0.0 | 100.0 | 100.0 | 35.0 | 0.0 |
| DUAL MAGNUM | 930 | 11.3 | 0.0 | 100.0 | 100.0 | 75.0 | 27.5 |
| DUAL MAGNUM | 1400 | 32.5 | 15.0 | 92.5 | 100.0 | 85.0 | 15.0 |
| COTORAN 4 | 1120 | 0.0 | 0.0 | 25.0 | 0.0 | 0.0 | 0.0 |
| COTORAN 4 | 1800 | 3.8 | 0.0 | 60.0 | 0.0 | 32.5 | 0.0 |
| VALOR SX | 48 | 100.0 | 82.5 | 75.0 | 20.0 | 20.0 | 5.0 |
| VALOR SX | 70 | 100.0 | 100.0 | 75.0 | 72.5 | 25.0 | 20.0 |
| SENCOR DF | 370 | 100.0 | 90.0 | 97.5 | 27.5 | 25.0 | 10.0 |
| SENCOR DF | 560 | 100.0 | 100.0 | 90.0 | 75.0 | 45.0 | 10.0 |
| 410P9M<br>VALOR SX | 840<br>48 | 89.5 | 82.5 | 99.8 | 87.5 | 58.8 | 22.5 |
| 410P9M<br>VALOR SX | 1260<br>48 | 90.0 | 85.0 | 100.0 | 100.0 | 26.3 | 5.0 |
| 410P9M<br>VALOR SX | 840<br>70 | 100.0 | 100.0 | 97.5 | 100.0 | 45.0 | 35.0 |
| 410P9M<br>VALOR SX | 1260<br>70 | 91.3 | 80.0 | 100.0 | 100.0 | 40.0 | 0.0 |
| 410P9M<br>COTORAN 4 | 840<br>1120 | 0.0 | 0.0 | 100.0 | 100.0 | 47.5 | 12.5 |
| 410P9M<br>COTORAN 4 | 1260<br>1120 | 3.8 | 0.0 | 85.0 | 100.0 | 28.8 | 0.0 |
| 410P9M<br>COTORAN 4 | 840<br>1800 | 10.0 | 5.0 | 95.0 | 100.0 | 82.5 | 35.0 |
| 410P9M<br>COTORAN 4 | 1260<br>1800 | 3.8 | 0.0 | 100.0 | 100.0 | 40.0 | 5.0 |
| 410P9M<br>SENCOR DF | 840<br>370 | 95.0 | 85.0 | 100.0 | 100.0 | 75.0 | 17.5 |
| 410P9M<br>SENCOR DF | 1260<br>370 | 100.0 | 97.5 | 100.0 | 100.0 | 72.5 | 25.0 |
| 410P9M<br>SENCOR DF | 840<br>560 | 100.0 | 100.0 | 100.0 | 100.0 | 87.5 | 46.3 |
| 410P9M<br>SENCOR DF | 1260<br>560 | 95.0 | 97.5 | 100.0 | 100.0 | 97.5 | 47.5 |

TABLE

AMASS, ABUTH and IPOHE Weed Control Efficacy 28 DAT

| Product Formulation | Rate g AI/ha | AMASS 28 DAT | ABUTH 28 DAT | IPOHE 28 DAT |
|---|---|---|---|---|
| 410P9M | 840 | 100.0 | 16.3 | 17.5 |
| 410P9M | 1260 | 100.0 | 23.8 | 17.5 |
| DUAL MAGNUM | 930 | 100.0 | 22.5 | 16.3 |
| DUAL MAGNUM | 1400 | 100.0 | 18.8 | 21.3 |
| COTORAN 4 | 1120 | 95.0 | 16.3 | 18.8 |
| COTORAN 4 | 1800 | 92.5 | 28.8 | 21.3 |
| VALOR SX | 48 | 100.0 | 94.5 | 58.8 |
| VALOR SX | 70 | 100.0 | 99.8 | 88.8 |
| SENCOR DF | 370 | 100.0 | 80.0 | 16.3 |
| SENCOR DF | 560 | 100.0 | 97.5 | 18.8 |
| 410P9M / VALOR SX | 840 / 48 | 100.0 | 93.8 | 81.3 |
| 410P9M / VALOR SX | 1260 / 48 | 100.0 | 97.0 | 89.5 |
| 410P9M / VALOR SX | 840 / 70 | 100.0 | 100.0 | 85.0 |
| 410P9M / VALOR SX | 1260 / 70 | 100.0 | 100.0 | 78.8 |
| 410P9M / COTORAN 4 | 840 / 1120 | 100.0 | 22.5 | 22.5 |
| 410P9M / COTORAN 4 | 1260 / 1120 | 100.0 | 66.3 | 28.8 |
| 410P9M / COTORAN 4 | 840 / 1800 | 100.0 | 36.3 | 41.3 |
| 410P9M / COTORAN 4 | 1260 / 1800 | 100.0 | 41.3 | 25.0 |
| 410P9M / SENCOR DF | 840 / 370 | 62.5 | 100.0 | 25.0 |
| 410P9M / SENCOR DF | 1260 / 370 | 68.3 | 94.5 | 20.0 |
| 410P9M / SENCOR DF | 840 / 560 | 95.8 | 100.0 | 28.8 |
| 410P9M / SENCOR DF | 1260 / 560 | 97.5 | 99.8 | 21.3 |

The efficacy of the same formulations on sicklepod (CASOB), hemp sesbania (SEBEX) and signalgrass (BRAPP) by preemergent application on the same day as planting the crop was also determined with the results reported in the table below.

TABLE

CASOB, SEBEX and BRAPP Weed Control Efficacy 28 DAT

| Product Formulation | Rate g AI/ha | CASOB 28 DAT | SEBEX 28 DAT | BRAPP 28 DAT |
|---|---|---|---|---|
| 410P9M | 840 | 22.5 | 8.8 | 60.0 |
| 410P9M | 1260 | 16.3 | 18.8 | 66.3 |
| DUAL MAGNUM | 930 | 10.0 | 3.8 | 90.0 |
| DUAL MAGNUM | 1400 | 21.3 | 23.8 | 92.5 |
| COTORAN 4 | 1120 | 25.0 | 13.8 | 5.0 |
| COTORAN 4 | 1800 | 30.0 | 41.3 | 48.8 |
| VALOR SX | 48 | 47.5 | 78.3 | 15.0 |
| VALOR SX | 70 | 58.8 | 81.3 | 27.5 |
| SENCOR DF | 370 | 56.3 | 54.5 | 40.0 |
| SENCOR DF | 560 | 74.5 | 78.3 | 58.8 |
| 410P9M / VALOR SX | 840 / 48 | 63.8 | 85.8 | 86.3 |
| 410P9M / VALOR SX | 1260 / 48 | 62.5 | 90.0 | 85.0 |
| 410P9M / VALOR SX | 840 / 70 | 66.3 | 88.8 | 66.3 |
| 410P9M / VALOR SX | 1260 / 70 | 72.5 | 95.8 | 83.8 |
| 410P9M / COTORAN 4 | 840 / 1120 | 21.3 | 36.3 | 88.8 |
| 410P9M / COTORAN 4 | 1260 / 1120 | 23.8 | 51.3 | 60.8 |
| 410P9M / COTORAN 4 | 840 / 1800 | 42.5 | 71.3 | 93.8 |
| 410P9M / COTORAN 4 | 1260 / 1800 | 45.0 | 83.3 | 100.0 |
| 410P9M / SENCOR DF | 840 / 370 | 56.3 | 73.8 | 93.8 |
| 410P9M / SENCOR DF | 1260 / 370 | 56.3 | 66.3 | 97.5 |
| 410P9M / SENCOR DF | 840 / 560 | 72.0 | 91.3 | 96.3 |
| 410P9M / SENCOR DF | 1260 / 560 | 80.8 | 100.0 | 100.0 |

The efficacy of the same formulations on crowfootgrass (DTTAE), barnyardgrass (ECHCG) and goosegrass (ELEIN) by preemergent application on the same day as planting the crop was also determined with the results reported in the table below.

TABLE

DTTAE, ECHCG and ELEIN Weed Control Efficacy 28 DAT

| Product Formulation | Rate g AI/ha | DTTAE 28 DAT | ECHCG 28 DAT | ELEIN 28 DAT |
|---|---|---|---|---|
| 410P9M | 840 | 93.8 | 97.5 | 100.0 |
| 410P9M | 1260 | 100.0 | 100.0 | 100.0 |
| DUAL MAGNUM | 930 | 100.0 | 100.0 | 100.0 |
| DUAL MAGNUM | 1400 | 92.5 | 100.0 | 100.0 |
| COTORAN 4 | 1120 | 57.5 | 97.5 | 100.0 |
| COTORAN 4 | 1800 | 87.5 | 83.8 | 100.0 |
| VALOR SX | 48 | 95.0 | 86.3 | 100.0 |
| VALOR SX | 70 | 90.0 | 95.0 | 92.5 |
| SENCOR DF | 370 | 92.5 | 90.0 | 100.0 |
| SENCOR DF | 560 | 93.8 | 100.0 | 100.0 |
| 410P9M / VALOR SX | 840 / 48 | 100.0 | 100.0 | 100.0 |
| 410P9M / VALOR SX | 1260 / 48 | 100.0 | 100.0 | 100.0 |
| 410P9M / VALOR SX | 840 / 70 | 100.0 | 100.0 | 100.0 |
| 410P9M / VALOR SX | 1260 / 70 | 100.0 | 100.0 | 100.0 |
| 410P9M / COTORAN 4 | 840 / 1120 | 100.0 | 97.5 | 100.0 |
| 410P9M / COTORAN 4 | 1260 / 1120 | 90.0 | 100.0 | 100.0 |
| 410P9M / COTORAN 4 | 840 / 1800 | 92.5 | 100.0 | 100.0 |
| 410P9M / COTORAN 4 | 1260 / 1800 | 100.0 | 100.0 | 100.0 |
| 410P9M / SENCOR DF | 840 / 370 | 100.0 | 100.0 | 100.0 |
| 410P9M / SENCOR DF | 1260 / 370 | 100.0 | 100.0 | 100.0 |
| 410P9M / SENCOR DF | 840 / 560 | 100.0 | 100.0 | 100.0 |
| 410P9M / SENCOR DF | 1260 / 560 | 100.0 | 100.0 | 100.0 |

The efficacy of the same formulations on amaranth (AMARE), velvetleaf (ABUTH) and crabgrass (DIGSA) by preemergent application on the same day as planting the crop was also determined with the results reported in the table below.

TABLE

AMARE, ABUTH and DIGSA Weed Control Efficacy 28 DAT

| Product Formulation | Rate g AI/ha | AMARE 28 DAT | ABUTH 28 DAT | DIGSA 28 DAT |
|---|---|---|---|---|
| 410P9M | 840 | 92.5 | 7.5 | 100.0 |
| 410P9M | 1260 | 96.3 | 10.0 | 98.8 |
| DUAL MAGNUM | 930 | 94.5 | 11.3 | 100.0 |
| DUAL MAGNUM | 1400 | 95.0 | 11.3 | 100.0 |
| COTORAN 4 | 1120 | 87.5 | 26.3 | 86.3 |
| COTORAN 4 | 1800 | 88.8 | 68.8 | 87.5 |
| VALOR SX | 48 | 60.0 | 85.0 | 82.5 |
| VALOR SX | 70 | 91.3 | 100.0 | 100.0 |
| SENCOR DF | 370 | 96.3 | 91.3 | 93.8 |
| SENCOR DF | 560 | 71.3 | 92.5 | 88.8 |
| 410P9M VALOR SX | 840 48 | 100.0 | 95.0 | 98.8 |
| 410P9M VALOR SX | 1260 48 | 97.0 | 90.0 | 92.5 |
| 410P9M VALOR SX | 840 70 | 99.8 | 93.4 | 93.9 |
| 410P9M VALOR SX | 1260 70 | 100.0 | 96.3 | 100.0 |
| 410P9M COTORAN 4 | 840 1120 | 100.0 | 33.8 | 99.5 |
| 410P9M COTORAN 4 | 1260 1120 | 100.0 | 40.0 | 100.0 |
| 410P9M COTORAN 4 | 840 1800 | 100.0 | 57.0 | 100.0 |
| 410P9M COTORAN 4 | 1260 1800 | 100.0 | 76.3 | 100.0 |
| 410P9M SENCOR DF | 840 370 | 100.0 | 90.0 | 100.0 |
| 410P9M SENCOR DF | 1260 370 | 100.0 | 90.0 | 100.0 |
| 410P9M SENCOR DF | 840 560 | 100.0 | 98.8 | 100.0 |
| 410P9M SENCOR DF | 1260 560 | 97.5 | 97.5 | 100.0 |

The efficacy of the same formulations on prickly *sida* (SIDSP), hemp sesbania (SEBEX) and sicklepod (CASOB) by preemergent application on the same day as planting the crop was also determined with the results reported in the table below.

TABLE

SIDSP, SEBEX and CASOB Weed Control Efficacy 28 DAT

| Product Formulation | Rate g AI/ha | SIDSP 28 DAT | SEBEX 28 DAT | CASOB 28 DAT |
|---|---|---|---|---|
| 410P9M | 840 | 21.3 | 10.0 | 8.8 |
| 410P9M | 1260 | 26.3 | 21.3 | 20.0 |
| DUAL MAGNUM | 930 | 16.3 | 12.5 | 15.0 |
| DUAL MAGNUM | 1400 | 23.8 | 30.0 | 23.8 |
| COTORAN 4 | 1120 | 73.3 | 47.8 | 30.8 |
| COTORAN 4 | 1800 | 91.3 | 59.3 | 50.0 |
| VALOR SX | 48 | 83.8 | 64.5 | 25.0 |
| VALOR SX | 70 | 100.0 | 66.8 | 32.5 |
| SENCOR DF | 370 | 87.0 | 58.3 | 57.0 |
| SENCOR DF | 560 | 85.0 | 56.3 | 55.0 |
| 410P9M VALOR SX | 840 48 | 92.5 | 67.0 | 51.3 |
| 410P9M VALOR SX | 1260 48 | 82.5 | 73.8 | 47.0 |
| 410P9M VALOR SX | 840 70 | 100.0 | 84.9 | 58.3 |
| 410P9M VALOR SX | 1260 70 | 100.0 | 74.0 | 55.8 |
| 410P9M COTORAN 4 | 840 1120 | 70.8 | 57.5 | 36.0 |
| 410P9M COTORAN 4 | 1260 1120 | 83.8 | 64.5 | 42.8 |
| 410P9M COTORAN 4 | 840 1800 | 77.5 | 65.8 | 52.5 |
| 410P9M COTORAN 4 | 1260 1800 | 83.8 | 68.8 | 61.8 |
| 410P9M SENCOR DF | 840 370 | 93.8 | 71.3 | 55.8 |
| 410P9M SENCOR DF | 1260 370 | 95.0 | 68.8 | 60.0 |
| 410P9M SENCOR DF | 840 560 | 100.0 | 76.5 | 75.0 |
| 410P9M SENCOR DF | 1260 560 | 100.0 | 79.0 | 74.5 |

The efficacy of the same formulations on barnyardgrass (ECHCG) by preemergent application on the same day as planting the crop was also determined with the results reported in the table below.

TABLE

ECHCG Weed Control Efficacy 28 DAT

| Product Formulation | Rate g AI/ha | ECHCG 28 DAT |
|---|---|---|
| 410P9M | 840 | 98.8 |
| 410P9M | 1260 | 100.0 |
| DUAL MAGNUM | 930 | 100.0 |
| DUAL MAGNUM | 1400 | 100.0 |
| COTORAN 4 | 1120 | 100.0 |
| COTORAN 4 | 1800 | 100.0 |
| VALOR SX | 48 | 100.0 |
| VALOR SX | 70 | 97.5 |
| SENCOR DF | 370 | 100.0 |
| SENCOR DF | 560 | 88.8 |
| 410P9M VALOR SX | 840 48 | 100.0 |
| 410P9M VALOR SX | 1260 48 | 97.5 |
| 410P9M VALOR SX | 840 70 | 100.0 |
| 410P9M VALOR SX | 1260 70 | 97.5 |
| 410P9M COTORAN 4 | 840 1120 | 100.0 |
| 410P9M COTORAN 4 | 1260 1120 | 100.0 |
| 410P9M COTORAN 4 | 840 1800 | 100.0 |
| 410P9M COTORAN 4 | 1260 1800 | 100.0 |
| 410P9M SENCOR DF | 840 370 | 100.0 |
| 410P9M SENCOR DF | 1260 370 | 100.0 |
| 410P9M SENCOR DF | 840 560 | 100.0 |
| 410P9M SENCOR DF | 1260 560 | 100.0 |

The encapsulated acetochlor formulation 410P9M alone exhibited greater than 98.8% control of crabgrass (DIGSA) and barnyardgrass (ECHCG) and 92.5% or greater control in tank mixes with COTORAN 4, VALOR SX or SENCOR DF at all rate combinations evaluated 28 DAT. Amaranth (AMARE) control efficacy was greater than 92.5% with the encapsulated acetochlor formulation 410P9M alone and greater than 97.0% with tank mixes of formulation 410P9M with VALOR SX, COTORAN 4 or SENCOR DF at the rates evaluated in this trial. VALOR SX>SENCOR DF>COTORAN 4 for prickly *sida* (SIDSP) control efficacy as individual products at 28 DAT. Tank mix combinations of the encapsulated acetochlor formulation 410P9M with SENCOR DF exhibited greater control than tank mixes of 410P9M with VALOR SX in this trial 28 DAT with respect to SIDSP. Neither hemp sesbania (SEBEX) nor sicklepod (CASOB) were controlled to acceptable levels in this trial at 28 DAT.

Example 6

Field Trial Study of Weed Control Efficacy and Soybean and Cotton Safety in Preemergent Crop Application of Microencapsulated Acetochlor Formulations and Tank Mixtures with Other Herbicides Aqueous dispersions of microencapsulated acetochlor formulation 410P9M prepared in Example 2, alone and in tank mix combination with COBRA (lactofen), SPARTAN 4L (sulfentrazone) and PROWL (pendimethalin) were tested on glyphosate-tolerant ROUNDUP READY Flex Cotton or ROUNDUP READY Soy and various weeds. All treatments were applied to soil seeded with ROUNDUP READY soybeans or ROUNDUP READY Flex Cotton on the same day as planting the crop and the associated crop injury was evaluated. The results from three field trials are reported in the tables below.

TABLE

RR Flex Cotton % Crop Injury 14 DAT in Three Field Trials

| Product Formulation | Rate g AI/ha | Trial 2010530040 % GR | Trial 2010530040 % SR | Trial 2010530041 % GR | Trial 2010530041 % SR | Trial 2010530042 % GR | Trial 2010530042 % SR |
|---|---|---|---|---|---|---|---|
| 410P9M | 840 | 2.0 | 0.0 | 0.0 | 0.0 | 7.0 | 3.8 |
| 410P9M | 1260 | 0.0 | 0.0 | 0.0 | 0.0 | 15.8 | 7.5 |
| COBRA | 175 | 0.0 | 0.0 | 1.3 | 0.0 | 66.3 | 47.5 |
| COBRA | 262 | 3.8 | 2.0 | 6.3 | 0.0 | 88.8 | 86.3 |
| SPARTAN 4L | 233 | 80.0 | 73.8 | 94.8 | 94.8 | 87.5 | 76.3 |
| SPARTAN 4L | 350 | 99.8 | 99.8 | 100.0 | 100.0 | 97.5 | 96.3 |
| PROWL | 1120 | 0.0 | 0.0 | 1.3 | 0.0 | 21.3 | 10.0 |
| PROWL | 1680 | 0.0 | 0.0 | 7.5 | 0.0 | 46.3 | 8.8 |
| 410P9M COBRA | 840 175 | 3.3 | 2.5 | 2.5 | 0.0 | 78.8 | 75.0 |
| 410P9M COBRA | 1260 175 | 2.5 | 0.0 | 6.3 | 0.0 | 82.5 | 67.5 |
| 410P9M COBRA | 840 262 | 3.8 | 1.3 | 8.3 | 0.0 | 87.5 | 86.3 |
| 410P9M COBRA | 1260 262 | 8.3 | 2.5 | 8.8 | 0.0 | 90.0 | 83.8 |
| 410P9M SPARTAN 4L | 840 233 | 85.0 | 80.0 | 90.0 | 90.0 | 86.3 | 81.3 |
| 410P9M SPARTAN 4L | 1260 233 | 97.5 | 97.5 | 93.8 | 93.8 | 91.3 | 87.5 |
| 410P9M SPARTAN 4L | 840 350 | 95.8 | 95.8 | 99.8 | 99.8 | 93.8 | 91.3 |
| 410P9M SPARTAN 4L | 1260 350 | 98.5 | 98.5 | 100.0 | 100.0 | 96.3 | 96.3 |
| 410P9M PROWL | 840 1120 | 1.3 | 0.0 | 6.3 | 0.0 | 25.0 | 10.0 |
| 410P9M PROWL | 1260 1120 | 3.8 | 0.0 | 6.3 | 0.0 | 36.3 | 10.0 |
| 410P9M PROWL | 840 1680 | 2.5 | 0.0 | 10.0 | 0.0 | 47.5 | 15.0 |
| 410P9M PROWL | 1260 1680 | 4.5 | 1.3 | 16.3 | 0.0 | 58.8 | 13.8 |

TABLE

RR Soybean % Crop Injury 14 DAT in Three Field Trials

| Product Formulation | Rate g AI/ha | Trial 2010530040 % GR | Trial 2010530040 % LF Crinkle | Trial 2010530041 % GR | Trial 2010530041 % LF Crinkle | Trial 2010530042 % GR | Trial 2010530042 % LF Crinkle |
|---|---|---|---|---|---|---|---|
| 410P9M | 840 | 0.0 | 0.8 | 0.0 | 3.8 | 8.3 | 7.5 |
| 410P9M | 1260 | 0.0 | 1.5 | 1.3 | 7.0 | 16.3 | 8.8 |
| COBRA | 175 | 0.0 | 0.0 | 0.0 | 0.0 | 6.3 | 0.0 |
| COBRA | 262 | 0.0 | 0.8 | 0.0 | 0.0 | 20.8 | 1.3 |
| SPARTAN 4L | 233 | 0.0 | 0.0 | 0.0 | 0.0 | 16.3 | 0.0 |
| SPARTAN 4L | 350 | 0.0 | 0.0 | 5.0 | 0.8 | 33.8 | 0.0 |
| PROWL | 1120 | 0.0 | 0.0 | 0.0 | 0.8 | 21.3 | 1.3 |
| PROWL | 1680 | 0.0 | 0.0 | 0.0 | 0.0 | 45.0 | 2.5 |
| 410P9M COBRA | 840 175 | 0.0 | 2.0 | 1.3 | 6.5 | 30.0 | 15.0 |
| 410P9M COBRA | 1260 175 | 0.0 | 2.8 | 1.3 | 10.0 | 30.0 | 17.5 |
| 410P9M COBRA | 840 262 | 0.0 | 2.5 | 1.3 | 4.5 | 36.3 | 16.3 |
| 410P9M COBRA | 1260 262 | 0.0 | 5.8 | 0.0 | 8.8 | 35.0 | 17.5 |
| 410P9M SPARTAN 4L | 840 233 | 0.0 | 0.0 | 1.3 | 4.5 | 18.3 | 7.5 |
| 410P9M SPARTAN 4L | 1260 233 | 0.0 | 3.0 | 0.0 | 5.3 | 23.8 | 9.5 |
| 410P9M SPARTAN 4L | 840 350 | 0.0 | 2.0 | 1.3 | 2.5 | 27.5 | 7.0 |
| 410P9M SPARTAN 4L | 1260 350 | 0.0 | 0.8 | 0.0 | 5.0 | 35.0 | 8.8 |
| 410P9M PROWL | 840 1120 | 0.0 | 0.0 | 0.0 | 2.8 | 27.5 | 10.8 |
| 410P9M PROWL | 1260 1120 | 0.0 | 5.0 | 0.0 | 7.5 | 32.5 | 12.5 |
| 410P9M PROWL | 840 1680 | 0.0 | 1.5 | 0.0 | 6.3 | 52.5 | 25.0 |
| 410P9M PROWL | 1260 1680 | 0.0 | 3.8 | 5.0 | 7.5 | 53.8 | 28.8 |

No significant differences were observed in either growth reduction (% GR) or stand reduction (% SR) for RR Flex Cotton with formulations of the encapsulated acetochlor formulation 410P9M, COBRA (lactofen) or PROWL (pendimethalin) in field trials 2010530040 and 2010530041 at the rates evaluated in these trials. SPARTAN 4L (sulfentrazone) applied preemergent caused between 80.0-100.0% growth reduction and between 73.8-100.0% stand reduction compared to untreated rows when used alone or when tank mixed with the encapsulated acetochlor formulation 410P9M. This injury was not unexpected as the product is not labeled for use in cotton. Tank mix combinations of the encapsulated acetochlor formulation 410P9M with COBRA at all rate combinations showed less than 8.8% growth reduction and less than 2.5% stand reduction of RR Flex Cotton. The encapsulated acetochlor formulation 410P9M in tank mixtures with PROWL showed a 10% or less growth reduction at all but the highest application rate and 1.3% or less stand reduction.

RR Soybeans exhibited 5.0% or less growth reduction with any individual product or tank mix combination in these trials and leaf crinkle was 10.0% or less.

In field trial 2010530042, RR Flex Cotton was more severely injured in this trial compared to the previous trials with only the low rate of the encapsulated acetochlor formulation 410P9M (840 g ai/ha) having acceptable levels of growth reduction (7.0%) and stand reduction (3.8%). As in previous trials, SPARTAN 4L caused severe cotton injury both alone and as a tank mix partner with the encapsulated acetochlor formulation 410P9M. In this trial, COBRA also caused a high degree of injury to cotton both alone and as a tank mix partner with the encapsulated acetochlor formulation 410P9M.

RR Soybean injury was higher in this trial compared to the previous trials with the encapsulated acetochlor formulation 410P9M and COBRA having slightly less injury than SPARTAN 4L or PROWL. The tank mix combinations of the encapsulated acetochlor formulation 410P9M with PROWL tended to have slightly greater growth reductions than those of the encapsulated acetochlor formulation 410P9M with COBRA or with SPARTAN 4L.

The increased injury in this trial compared to the previous trials is most likely caused by the higher temperatures and humidity when this trial was initiated. Planting soybeans in these types of conditions is not a typical grower practice so the level of injury observed in this trial would not be considered typical.

The efficacy of the same formulations on morningglory (IPOHE), *amaranthus* (AMASS) and sicklepod (CASOB) by preemergent application on the same day as planting the crop was also determined with the results reported in the table below.

TABLE

IPOHE, AMASS and CASOB Weed Control Efficacy 28 and 56 DAT

| Product Formulation | Rate g AI/ha | IPOHE 28 DAT | IPOHE 56 DAT | AMASS 28 DAT | AMASS 56 DAT | CASOB 28 DAT | CASOB 56 DAT |
|---|---|---|---|---|---|---|---|
| 410P9M | 840 | 0.0 | 0.0 | 100.0 | 65.0 | 28.8 | 5.0 |
| 410P9M | 1260 | 15.0 | 0.0 | 100.0 | 87.5 | 27.5 | 26.3 |
| COBRA | 175 | 3.8 | 0.0 | 85.0 | 0.0 | 11.3 | 0.0 |
| COBRA | 262 | 20.0 | 12.5 | 62.5 | 0.0 | 48.8 | 25.0 |
| SPARTAN 4L | 233 | 99.8 | 95.0 | 100.0 | 73.8 | 21.3 | 0.0 |
| SPARTAN 4L | 350 | 100.0 | 99.8 | 100.0 | 100.0 | 30.0 | 10.0 |
| PROWL | 1120 | 15.0 | 16.3 | 100.0 | 42.5 | 30.8 | 18.8 |
| PROWL | 1680 | 17.5 | 0.0 | 92.5 | 42.5 | 28.8 | 0.0 |
| 410P9M COBRA | 840 175 | 11.3 | 12.5 | 90.0 | 85.0 | 18.8 | 0.0 |
| 410P9M COBRA | 1260 175 | 20.0 | 0.0 | 100.0 | 100.0 | 20.0 | 0.0 |
| 410P9M COBRA | 840 262 | 8.8 | 0.0 | 100.0 | 90.0 | 22.5 | 0.0 |
| 410P9M COBRA | 1260 262 | 6.3 | 0.0 | 100.0 | 100.0 | 35.0 | 0.0 |
| 410P9M SPARTAN 4L | 840 233 | 100.0 | 96.3 | 100.0 | 100.0 | 16.3 | 5.0 |
| 410P9M SPARTAN 4L | 1260 233 | 100.0 | 96.3 | 100.0 | 100.0 | 30.0 | 17.5 |
| 410P9M SPARTAN 4L | 840 350 | 100.0 | 93.5 | 100.0 | 100.0 | 32.5 | 11.3 |
| 410P9M SPARTAN 4L | 1260 350 | 100.0 | 100.0 | 100.0 | 100.0 | 33.8 | 35.0 |
| 410P9M PROWL | 840 1120 | 8.8 | 0.0 | 100.0 | 85.0 | 3.8 | 0.0 |
| 410P9M PROWL | 1260 1120 | 8.8 | 0.0 | 100.0 | 92.5 | 32.5 | 37.5 |
| 410P9M PROWL | 840 1680 | 30.0 | 30.0 | 100.0 | 92.5 | 23.8 | 12.5 |
| 410P9M PROWL | 1260 1680 | 32.5 | 10.0 | 100.0 | 100.0 | 27.5 | 10.0 |

All formulations in this trial except COBRA alone provided 90% or greater control of AMASS. The encapsulated acetochlor formulation 410P9M in combination with SPARTAN 4L provided 100% control of IPOHE.

The efficacy of the same formulations on velvetleaf (ABUTH), barnyardgrass (ECHCG) and signalgrass (BRAPP) by preemergent application on the same day as planting the crop was also determined with the results reported in the table below.

TABLE

ABUTH, ECHCG and BRAPP Weed Control Efficacy 28 and 56 DAT

| Product Formulation | Rate g AI/ha | ABUTH 28 DAT | ABUTH 56 DAT | ECHCG 28 DAT | ECHCG 56 DAT | BRAPP 28 DAT | BRAPP 56 DAT |
|---|---|---|---|---|---|---|---|
| 410P9M | 840 | 0.0 | 5.0 | 70.0 | 28.8 | 37.5 | 0.0 |
| 410P9M | 1260 | 0.0 | 0.0 | 82.5 | 90.0 | 42.5 | 0.0 |
| COBRA | 175 | 0.0 | 0.0 | 45.0 | 0.0 | 0.0 | 0.0 |
| COBRA | 262 | 0.0 | 0.0 | 52.5 | 25.0 | 0.0 | 0.0 |
| SPARTAN 4L | 233 | 86.3 | 62.5 | 77.5 | 5.0 | 15.0 | 0.0 |
| SPARTAN 4L | 350 | 97.5 | 93.8 | 96.3 | 57.5 | 31.3 | 25.0 |

TABLE-continued

ABUTH, ECHCG and BRAPP Weed Control Efficacy 28 and 56 DAT

| Product Formulation | Rate g AI/ha | ABUTH 28 DAT | ABUTH 56 DAT | ECHCG 28 DAT | ECHCG 56 DAT | BRAPP 28 DAT | BRAPP 56 DAT |
|---|---|---|---|---|---|---|---|
| PROWL | 1120 | 18.8 | 0.0 | 97.5 | 100.0 | 70.0 | 37.5 |
| PROWL | 1680 | 36.3 | 5.0 | 97.5 | 87.5 | 92.5 | 75.0 |
| 410P9M COBRA | 840 175 | 5.0 | 0.0 | 97.5 | 87.5 | 15.0 | 0.0 |
| 410P9M COBRA | 1260 175 | 5.0 | 0.0 | 100.0 | 87.5 | 36.3 | 20.0 |
| 410P9M COBRA | 840 262 | 7.5 | 0.0 | 77.5 | 65.0 | 21.3 | 0.0 |
| 410P9M COBRA | 1260 262 | 10.0 | 0.0 | 100.0 | 100.0 | 20.0 | 0.0 |
| 410P9M SPARTAN 4L | 840 233 | 78.8 | 48.8 | 98.8 | 75.0 | 36.3 | 21.3 |
| 410P9M SPARTAN 4L | 1260 233 | 85.0 | 81.3 | 100.0 | 100.0 | 61.3 | 25.0 |
| 410P9M SPARTAN 4L | 840 350 | 67.5 | 53.8 | 99.8 | 86.3 | 68.8 | 22.5 |
| 410P9M SPARTAN 4L | 1260 350 | 88.8 | 82.5 | 100.0 | 87.5 | 55.0 | 21.3 |
| 410P9M PROWL | 840 1120 | 17.5 | 0.0 | 65.0 | 87.5 | 50.0 | 18.8 |
| 410P9M PROWL | 1260 1120 | 26.3 | 0.0 | 96.3 | 92.5 | 82.5 | 27.5 |
| 410P9M PROWL | 840 1680 | 37.5 | 27.5 | 100.0 | 100.0 | 97.5 | 95.0 |
| 410P9M PROWL | 1260 1680 | 45.0 | 27.5 | 92.5 | 82.5 | 87.5 | 70.0 |

The encapsulated acetochlor formulation 410P9M in certain combinations with COBRA, SPARTAN 4L or PROWL provided as much as 100% control of ECHCG.

The efficacy of the same formulations on *amaranthus* (AMASS), velvetleaf (ABUTH) and morningglory (IPOHE) by preemergent application on the same day as planting the crop was also determined with the results reported in the table below.

TABLE

AMASS, ABUTH and IPOHE Weed Control Efficacy 28 DAT

| Product Formulation | Rate g AI/ha | AMASS 28 DAT | ABUTH 28 DAT | IPOHE 28 DAT |
|---|---|---|---|---|
| 410P9M | 840 | 100.0 | 16.3 | 7.5 |
| 410P9M | 1260 | 100.0 | 18.8 | 7.5 |
| COBRA | 175 | 100.0 | 22.5 | 17.5 |
| COBRA | 262 | 100.0 | 21.3 | 15.0 |
| SPARTAN 4L | 233 | 91.3 | 60.0 | 70.0 |
| SPARTAN 4L | 350 | 100.0 | 96.3 | 92.5 |
| PROWL | 1120 | 100.0 | 75.0 | 12.5 |
| PROWL | 1680 | 100.0 | 97.5 | 30.0 |
| 410P9M COBRA | 840 175 | 100.0 | 26.3 | 12.5 |
| 410P9M COBRA | 1260 175 | 100.0 | 25.0 | 17.5 |
| 410P9M COBRA | 840 262 | 100.0 | 40.0 | 32.5 |
| 410P9M COBRA | 1260 262 | 100.0 | 33.8 | 27.5 |
| 410P9M SPARTAN 4L | 840 233 | 100.0 | 68.8 | 85.0 |
| 410P9M SPARTAN 4L | 1260 233 | 100.0 | 77.5 | 91.3 |
| 410P9M SPARTAN 4L | 840 350 | 100.0 | 85.8 | 95.8 |
| 410P9M SPARTAN 4L | 1260 350 | 100.0 | 98.8 | 99.5 |
| 410P9M PROWL | 840 1120 | 100.0 | 84.5 | 21.3 |
| 410P9M PROWL | 1260 1120 | 100.0 | 82.0 | 25.0 |
| 410P9M PROWL | 840 1680 | 87.5 | 100.0 | 42.5 |
| 410P9M PROWL | 1260 1680 | 100.0 | 99.5 | 37.5 |

The encapsulated acetochlor formulation 410P9M in combination with COBRA, SPARTAN 4L, or PROWL provided 87.5-100% control of AMASS. The encapsulated acetochlor formulation 410P9M in combination with SPARTAN 4L provided 68.8-98.8% control of ABUTH and 85.0 to 99.5% control of IPOHE.

The efficacy of the same formulations on sicklepod (CASOB), hemp sesbania (SEBEX) and barnyardgrass (ECHCG) by preemergent application on the same day as planting the crop was also determined with the results reported in the table below.

TABLE

CASOB, SEBEX and ECHCG Weed Control Efficacy 28 DAT

| Product Formulation | Rate g AI/ha | CASOB 28 DAT | SEBEX 28 DAT | ECHCG 28 DAT |
|---|---|---|---|---|
| 410P9M | 840 | 8.8 | 8.8 | 87.5 |
| 410P9M | 1260 | 23.8 | 18.8 | 100.0 |
| COBRA | 175 | 12.5 | 10.0 | 75.0 |
| COBRA | 262 | 26.3 | 23.8 | 68.8 |
| SPARTAN 4L | 233 | 25.0 | 3.8 | 80.0 |
| SPARTAN 4L | 350 | 15.0 | 23.8 | 100.0 |
| PROWL | 1120 | 21.3 | 7.5 | 100.0 |
| PROWL | 1680 | 22.5 | 16.3 | 100.0 |

| Product Formulation | Rate g AI/ha | CASOB 28 DAT | SEBEX 28 DAT | ECHCG 28 DAT |
|---|---|---|---|---|
| 410P9M COBRA | 840 175 | 20.0 | 50.0 | 100.0 |
| 410P9M COBRA | 1260 175 | 32.0 | 55.0 | 100.0 |
| 410P9M COBRA | 840 262 | 32.5 | 57.5 | 95.0 |
| 410P9M COBRA | 1260 262 | 31.3 | 67.5 | 100.0 |
| 410P9M SPARTAN 4L | 840 233 | 18.8 | 30.0 | 100.0 |
| 410P9M SPARTAN 4L | 1260 233 | 26.3 | 42.5 | 100.0 |
| 410P9M SPARTAN 4L | 840 350 | 33.8 | 50.0 | 100.0 |
| 410P9M SPARTAN 4L | 1260 350 | 28.8 | 56.3 | 91.3 |
| 410P9M PROWL | 840 1120 | 23.8 | 12.5 | 100.0 |
| 410P9M PROWL | 1260 1120 | 28.8 | 26.3 | 100.0 |
| 410P9M PROWL | 840 1680 | 28.8 | 28.8 | 100.0 |
| 410P9M PROWL | 1260 1680 | 38.8 | 37.5 | 100.0 |

The encapsulated acetochlor formulation 410P9M in combination with COBRA, SPARTAN 4L or PROWL provide 91.3% or greater control of ECHCG. No herbicide alone or in combination provided greater than 38.8% control of CASOB or greater than 67.5% control of SEBEX.

The efficacy of the same formulations on crowfootgrass (DTTAE), signalgrass (BRAPP) and goosegrass (ELEIN) by preemergent application on the same day as planting the crop was also determined with the results reported in the table below.

TABLE

DTTAE, BRAPP and ELEIN Weed Control Efficacy 28 DAT

| Product Formulation | Rate g AI/ha | DTTAE 28 DAT | BRAPP 28 DAT | ELEIN 28 DAT |
|---|---|---|---|---|
| 410P9M | 840 | 100.0 | 82.5 | 100.0 |
| 410P9M | 1260 | 92.5 | 88.8 | 100.0 |
| COBRA | 175 | 57.5 | 0.0 | 100.0 |
| COBRA | 262 | 45.0 | 0.0 | 100.0 |
| SPARTAN 4L | 233 | 92.5 | 22.5 | 95.0 |
| SPARTAN 4L | 350 | 98.8 | 100.0 | 100.0 |
| PROWL | 1120 | 100.0 | 72.5 | 100.0 |
| PROWL | 1680 | 100.0 | 62.5 | 100.0 |
| 410P9M COBRA | 840 175 | 100.0 | 70.0 | 100.0 |
| 410P9M COBRA | 1260 175 | 100.0 | 87.5 | 100.0 |
| 410P9M COBRA | 840 262 | 90.0 | 81.3 | 92.5 |
| 410P9M COBRA | 1260 262 | 87.5 | 93.8 | 100.0 |
| 410P9M SPARTAN 4L | 840 233 | 100.0 | 97.5 | 100.0 |
| 410P9M SPARTAN 4L | 1260 233 | 92.5 | 100.0 | 92.5 |
| 410P9M SPARTAN 4L | 840 350 | 96.3 | 100.0 | 100.0 |
| 410P9M SPARTAN 4L | 1260 350 | 100.0 | 100.0 | 100.0 |
| 410P9M PROWL | 840 1120 | 92.5 | 96.3 | 100.0 |
| 410P9M PROWL | 1260 1120 | 100.0 | 85.0 | 100.0 |
| 410P9M PROWL | 840 1680 | 100.0 | 93.8 | 100.0 |
| 410P9M PROWL | 1260 1680 | 93.8 | 92.5 | 100.0 |

The encapsulated acetochlor formulation 410P9M both alone and in combination with COBRA, SPARTAN 4L or PROWL provided at least 92.5% control of ELEIN.

The encapsulated acetochlor formulation 410P9M in combination with SPARTAN 4L provided at least 97.5% control of BRAPP.

The efficacy of the same formulations on amaranth (AMARE), velvetleaf (ABUTH) and crabgrass (DIGSA) by preemergent application on the same day as planting the crop was also determined with the results reported in the table below.

TABLE

AMARE, ABUTH and DIGSA Weed Control Efficacy at 28 DAT

| Product Formulation | Rate g AI/ha | AMARE 28 DAT | ABUTH 28 DAT | DIGSA 28 DAT |
|---|---|---|---|---|
| 410P9M | 840 | 70.0 | 7.5 | 100.0 |
| 410P9M | 1260 | 92.5 | 3.8 | 100.0 |
| COBRA | 175 | 35.0 | 38.8 | 71.3 |
| COBRA | 262 | 55.0 | 63.8 | 62.5 |
| SPARTAN 4L | 233 | 100.0 | 44.5 | 77.5 |
| SPARTAN 4L | 350 | 100.0 | 70.0 | 75.0 |
| PROWL | 1120 | 32.5 | 63.8 | 90.0 |
| PROWL | 1680 | 33.8 | 80.0 | 88.8 |
| 410P9M COBRA | 840 175 | 75.0 | 50.0 | 91.3 |
| 410P9M COBRA | 1260 175 | 81.3 | 51.3 | 90.0 |
| 410P9M COBRA | 840 262 | 90.0 | 58.3 | 91.3 |
| 410P9M COBRA | 1260 262 | 69.5 | 60.0 | 100.0 |
| 410P9M SPARTAN 4L | 840 233 | 100.0 | 47.5 | 100.0 |
| 410P9M SPARTAN 4L | 1260 233 | 100.0 | 70.0 | 100.0 |
| 410P9M SPARTAN 4L | 840 350 | 100.0 | 58.8 | 91.3 |
| 410P9M SPARTAN 4L | 1260 350 | 100.0 | 100.0 | 100.0 |
| 410P9M PROWL | 840 1120 | 63.8 | 72.5 | 100.0 |
| 410P9M PROWL | 1260 1120 | 91.3 | 72.5 | 100.0 |
| 410P9M PROWL | 840 1680 | 82.5 | 75.0 | 100.0 |
| 410P9M PROWL | 1260 1680 | 100.0 | 85.0 | 100.0 |

DIGSA was controlled at least 90% at all rates of tank mixtures of the encapsulated acetochlor formulation 410P9M and COBRA, SPARTAN 4L, or PROWL. AMARE was controlled most effectively with SPARTAN alone and in tank mixtures with the encapsulated acetochlor formulation 410P9M and with PROWL in tank mixtures at the highest rate tested.

The efficacy of the same formulations on prickly *sida* (SIDSP), hemp sesbania (SEBEX) and sicklepod (CASOB) by preemergent application on the same day as planting the crop was also determined with the results reported in the table below.

TABLE

SIDSP, SEBEX and CASOB Weed Control Efficacy 28 DAT

| Product Formulation | Rate g AI/ha | SIDSP 28 DAT | SEBEX 28 DAT | CASOB 28 DAT |
|---|---|---|---|---|
| 410P9M | 840 | 15.0 | 0.0 | 12.5 |
| 410P9M | 1260 | 25.0 | 18.8 | 15.0 |
| COBRA | 175 | 17.5 | 27.5 | 21.3 |
| COBRA | 262 | 31.3 | 36.3 | 33.8 |
| SPARTAN 4L | 233 | 65.0 | 25.0 | 16.3 |
| SPARTAN 4L | 350 | 80.0 | 36.3 | 17.5 |
| PROWL | 1120 | 62.5 | 12.5 | 23.8 |
| PROWL | 1680 | 70.0 | 23.8 | 31.3 |
| 410P9M<br>COBRA | 840<br>175 | 47.5 | 43.8 | 32.5 |
| 410P9M<br>COBRA | 1260<br>175 | 56.3 | 52.8 | 45.0 |
| 410P9M<br>COBRA | 840<br>262 | 63.8 | 45.0 | 38.3 |
| 410P9M<br>COBRA | 1260<br>262 | 63.8 | 50.8 | 38.8 |
| 410P9M<br>SPARTAN 4L | 840<br>233 | 92.5 | 35.0 | 15.0 |
| 410P9M<br>SPARTAN 4L | 1260<br>233 | 95.0 | 52.0 | 18.8 |
| 410P9M<br>SPARTAN 4L | 840<br>350 | 93.8 | 50.0 | 21.3 |
| 410P9M<br>SPARTAN 4L | 1260<br>350 | 97.5 | 67.5 | 23.8 |
| 410P9M<br>PROWL | 840<br>1120 | 63.3 | 27.5 | 23.8 |
| 410P9M<br>PROWL | 1260<br>1120 | 83.8 | 43.8 | 26.3 |
| 410P9M<br>PROWL | 840<br>1680 | 88.8 | 26.3 | 27.5 |
| 410P9M<br>PROWL | 1260<br>1680 | 90.0 | 41.3 | 34.5 |

Tank mixtures of the encapsulated acetochlor formulation 410P9M and SPARTAN 4L showed commercially acceptable levels of weed control in SIDSP. Neither SEBEX nor CASOB were effectively controlled in this trial with a single herbicide treatment or with a mixture of two herbicides.

The efficacy of the same formulations on barnyardgrass (ECHCG) by preemergent application on the same day as planting the crop was also determined with the results reported in the table below.

TABLE

ECHCG Weed Control Efficacy 28 DAT

| Product Formulation | Rate g AI/ha | ECHCG 28 DAT |
|---|---|---|
| 410P9M | 840 | 97.5 |
| 410P9M | 1260 | 100.0 |
| COBRA | 175 | 62.5 |
| COBRA | 262 | 82.5 |
| SPARTAN 4L | 233 | 100.0 |
| SPARTAN 4L | 350 | 100.0 |
| PROWL | 1120 | 100.0 |
| PROWL | 1680 | 100.0 |
| 410P9M<br>COBRA | 840<br>175 | 100.0 |
| 410P9M<br>COBRA | 1260<br>175 | 100.0 |
| 410P9M<br>COBRA | 840<br>262 | 97.5 |
| 410P9M<br>COBRA | 1260<br>262 | 95.0 |
| 410P9M<br>SPARTAN 4L | 840<br>233 | 100.0 |
| 410P9M<br>SPARTAN 4L | 1260<br>233 | 100.0 |
| 410P9M<br>SPARTAN 4L | 840<br>350 | 100.0 |
| 410P9M<br>SPARTAN 4L | 1260<br>350 | 100.0 |
| 410P9M<br>PROWL | 840<br>1120 | 100.0 |
| 410P9M<br>PROWL | 1260<br>1120 | 100.0 |
| 410P9M<br>PROWL | 840<br>1680 | 100.0 |
| 410P9M<br>PROWL | 1260<br>1680 | 100.0 |

All tank mixtures of the encapsulated acetochlor formulation 410P9M showed commercially acceptable levels of weed control of ECHCG.

Example 7

Field Trial Study of Weed Control Efficacy and Soybean and Cotton Safety in Preemergent Crop Application of Microencapsulated Acetochlor Formulations and Tank Mixtures with Other Herbicides

Aqueous dispersions of microencapsulated acetochlor formulation 410P9M prepared in Example 2, alone and in tank mix combination with GOAL 2XL (oxyfluorfen), REFLEX (fomesafen), or SHARPEN (saflufenacil) were tested on glyphosate-tolerant ROUNDUP READY Flex Cotton or ROUNDUP READY Soy and various weeds. All treatments were applied to soil seeded with ROUNDUP READY soybeans or ROUNDUP READY Flex Cotton on the same day as planting and the associated crop injury was evaluated. The results from three field trials are reported in the tables below.

TABLE

RR Flex Cotton % Crop Injury 14 DAT in Three Field Trials

| Product Formulation | Rate g AI/ha | Trial 2010530043 % GR | Trial 2010530043 % SR | Trial 2010530044 % GR | Trial 2010530044 % SR | Trial 2010530045 % GR | Trial 2010530045 % SR |
|---|---|---|---|---|---|---|---|
| 410P9M | 840 | 1.3 | 0.0 | 6.8 | 0.0 | 12.5 | 6.3 |
| 410P9M | 1260 | 2.5 | 1.3 | 18.8 | 0.0 | 16.3 | 12.5 |
| GOAL 2XL | 188 | 0.0 | 0.0 | 41.3 | 2.5 | 25.0 | 16.3 |
| GOAL 2XL | 280 | 0.0 | 0.0 | 47.5 | 6.3 | 35.0 | 17.5 |
| REFLEX | 280 | 0.0 | 1.3 | 0.0 | 0.0 | 7.5 | 1.3 |
| REFLEX | 420 | 7.5 | 5.0 | 3.8 | 1.3 | 12.5 | 7.5 |
| SHARPEN | 16.8 | 0.0 | 0.0 | 0.0 | 0.0 | 6.3 | 5.0 |
| SHARPEN | 24.7 | 0.0 | 0.0 | 1.3 | 0.0 | 11.3 | 7.5 |
| 410P9M<br>GOAL 2XL | 840<br>188 | 0.0 | 2.0 | 47.5 | 5.0 | 28.8 | 15.0 |
| 410P9M<br>GOAL 2XL | 1260<br>188 | 0.0 | 1.3 | 46.3 | 6.3 | 28.8 | 16.3 |
| 410P9M<br>GOAL 2XL | 840<br>280 | 2.5 | 1.3 | 55.0 | 8.8 | 42.5 | 18.8 |
| 410P9M<br>GOAL 2XL | 1260<br>280 | 0.0 | 0.0 | 53.8 | 13.8 | 45.0 | 15.0 |
| 410P9M<br>REFLEX | 840<br>280 | 1.3 | 2.5 | 10.8 | 1.3 | 15.3 | 8.8 |
| 410P9M<br>REFLEX | 1260<br>280 | 0.0 | 3.8 | 27.5 | 7.5 | 22.5 | 13.8 |
| 410P9M<br>REFLEX | 840<br>420 | 2.5 | 1.3 | 31.3 | 10.0 | 23.3 | 15.0 |

TABLE-continued

RR Flex Cotton % Crop Injury 14 DAT in Three Field Trials

| Product Formulation | Rate g AI/ha | Trial 2010530043 % GR | Trial 2010530043 % SR | Trial 2010530044 % GR | Trial 2010530044 % SR | Trial 2010530045 % GR | Trial 2010530045 % SR |
|---|---|---|---|---|---|---|---|
| 410P9M REFLEX | 1260 420 | 1.3 | 2.5 | 40.0 | 11.3 | 26.3 | 13.8 |
| 410P9M SHARPEN | 840 16.8 | 0.0 | 0.0 | 10.3 | 5.0 | 17.5 | 13.8 |
| 410P9M SHARPEN | 1260 16.8 | 0.0 | 0.0 | 16.3 | 5.0 | 18.8 | 13.8 |
| 410P9M SHARPEN | 840 24.7 | 0.0 | 0.0 | 18.8 | 10.0 | 11.3 | 11.3 |
| 410P9M SHARPEN | 1260 24.7 | 1.3 | 2.5 | 20.8 | 8.8 | 27.5 | 15.0 |

TABLE

RR Soybean % Crop Injury 14 DAT in Three Field Trials

| Product Formulation | Rate g AI/ha | Trial 2010530043 % GR | Trial 2010530043 % LF Crinkle | Trial 2010530044 % GR | Trial 2010530044 % LF Crinkle | Trial 2010530045 % GR | Trial 2010530045 % LF Crinkle |
|---|---|---|---|---|---|---|---|
| 410P9M | 840 | 0.0 | 0.8 | 1.3 | 5.3 | 13.8 | 8.8 |
| 410P9M | 1260 | 0.0 | 2.3 | 8.8 | 9.3 | 15.0 | 13.8 |
| GOAL 2XL | 188 | 0.0 | 0.8 | 30.0 | 7.5 | 27.5 | 4.5 |
| GOAL 2XL | 280 | 0.0 | 0.8 | 45.0 | 11.3 | 41.3 | 8.3 |
| REFLEX | 280 | 0.0 | 0.0 | 1.3 | 0.0 | 2.5 | 0.0 |
| REFLEX | 420 | 0.0 | 0.0 | 3.8 | 0.0 | 7.5 | 0.0 |
| SHARPEN | 16.8 | 0.0 | 0.0 | 1.3 | 0.0 | 17.5 | 0.0 |
| SHARPEN | 24.7 | 0.0 | 0.0 | 1.3 | 0.0 | 28.8 | 0.0 |
| 410P9M GOAL 2XL | 840 188 | 0.0 | 7.8 | 45.0 | 16.3 | 35.0 | 13.8 |
| 410P9M GOAL 2XL | 1260 188 | 0.0 | 6.0 | 41.3 | 22.5 | 45.0 | 18.8 |
| 410P9M GOAL 2XL | 840 280 | 0.0 | 7.0 | 57.5 | 22.5 | 51.3 | 17.5 |
| 410P9M GOAL 2XL | 1260 280 | 0.0 | 9.8 | 58.8 | 28.8 | 48.8 | 15.8 |
| 410P9M REFLEX | 840 280 | 0.0 | 2.8 | 3.8 | 6.3 | 21.3 | 14.5 |
| 410P9M REFLEX | 1260 280 | 0.0 | 5.3 | 6.3 | 8.8 | 20.0 | 17.5 |
| 410P9M REFLEX | 840 420 | 0.0 | 2.5 | 5.0 | 8.3 | 16.3 | 13.8 |
| 410P9M REFLEX | 1260 420 | 0.0 | 3.5 | 3.8 | 11.3 | 20.0 | 15.0 |
| 410P9M SHARPEN | 840 16.8 | 0.0 | 2.0 | 10.0 | 6.3 | 25.0 | 12.5 |
| 410P9M SHARPEN | 1260 16.8 | 0.0 | 2.3 | 7.5 | 9.5 | 33.3 | 15.0 |
| 410P9M SHARPEN | 840 24.7 | 0.0 | 0.8 | 7.5 | 7.5 | 35.0 | 10.8 |
| 410P9M SHARPEN | 1260 24.7 | 0.0 | 2.3 | 21.3 | 8.8 | 37.5 | 18.8 |

In Field Trial 2010530043, RR Flex Cotton growth exhibited a slight reduction in growth (7.5%) with preemergent applications of REFLEX (fomesafen) at 420 g ai/ha. All other treatments with formulations of the encapsulated acetochlor formulation 410P9M, GOAL 2XL (oxyfluorfen), low rate of REFLEX (fomesafen), or SHARPEN (saflufenacil) at the rates evaluated in this trial had less than 2.5% growth reduction. No significant differences in cotton stand reduction were observed in this trial.

RR Soybeans had no growth reduction from the individual treatments or tank mix combinations. The combination of the encapsulated acetochlor formulation 410P9M and GOAL 2XL had the greatest % Leaf crinkle in this trial between 6.0 and 9.8%, which was significantly greater than the individual products.

In Field Trial 2010530044, RR Flex Cotton growth was impacted the least by low rate application of formulations of the encapsulated acetochlor formulation 410P9M (840 g ai/ha) and both rates of REFLEX (fomesafen) and SHARPEN (saflufenacil). GOAL 2XL (oxyfluorfen) and tank mixes of the encapsulated acetochlor formulation 410P9M with GOAL 2XL had growth reduction between 41.3-55.0%. Stand reduction was lowest for formulations of encapsulated acetochlor formulation 410P9M, REFLEX and SHARPEN, while the tank mix combinations of the encapsulated acetochlor formulation 410P9M with REFLEX or SHARPEN tended to have the greatest stand reductions.

RR Soybeans had slight growth reduction from applications of encapsulated acetochlor formulation 410P9M, REFLEX, SHARPEN and the tank mix combinations of composition 410P9M with REFLEX or SHARPEN. GOAL 2XL and tank mix combinations of the encapsulated acetochlor formulation 410P9M with GOAL 2XL had growth reduction between 30-58.8% in this trial. Leaf crinkle was greatest for tank mix combinations of composition 410P9M with GOAL 2XL and least for composition 410P9M tank mixed with REFLEX or SHARPEN.

In Field Trial 2010530045, RR Flex Cotton growth reduction ranged from 6.3% to 45.0% for all treatments. Tank mixes of the encapsulated acetochlor formulation 410P9M in combination with GOAL 2XL had the highest % growth reduction in this trial. A similar trend was identified in % stand reduction with REFLEX and SHARPEN having the least and GOAL 2XL having the greatest impact on RR Flex Cotton.

For RR Soybeans, REFLEX<the encapsulated acetochlor formulation 410P9M<SHARPEN<GOAL 2XL with respect to growth reduction as individual products. The tank mix combination of composition 410P9M with GOAL 2XL had the greatest % growth reduction, while composition 410P9M tank mixed with REFLEX had the least. No leaf crinkle was observed with either REFLEX or SHARPEN and a slight amount was detected with GOAL 2XL. The tank mix combinations of the encapsulated acetochlor formulation 410P9M with GOAL 2XL or REFLEX or SHARPEN had less than 18.8% leaf crinkle in this trial.

This trial was initiated when temperatures and humidity are much higher than typically found during cotton or soybean planting time. These conditions can promote rapid crop growth and uptake of herbicides thus causing elevated amounts of crop injury not typically observed.

The efficacy of the same formulations on morningglory (IPOHE), amaranthus (AMASS) and sicklepod (CASOB) by preemergent application on the same day as planting the crop was also determined with the results reported in the table below.

TABLE

IPOHE, AMASS and CASOB Weed Control Efficacy 28 and 56 DAT

| Product Formulation | Rate g AI/ha | IPOHE 28 DAT | IPOHE 56 DAT | AMASS 28 DAT | AMASS 56 DAT | CASOB 28 DAT | CASOB 56 DAT |
|---|---|---|---|---|---|---|---|
| 410P9M | 840 | 0.0 | 0.0 | 100.0 | 85.0 | 38.8 | 17.5 |
| 410P9M | 1260 | 3.8 | 0.0 | 87.5 | 75.0 | 27.5 | 5.0 |
| GOAL 2XL | 188 | 5.0 | 0.0 | 100.0 | 25.0 | 42.5 | 17.5 |
| GOAL 2XL | 280 | 3.8 | 0.0 | 100.0 | 17.5 | 20.0 | 0.0 |
| REFLEX | 280 | 17.5 | 17.5 | 100.0 | 96.3 | 30.0 | 6.3 |
| REFLEX | 420 | 17.5 | 0.0 | 100.0 | 75.0 | 20.0 | 0.0 |
| SHARPEN | 16.8 | 17.5 | 0.0 | 25.0 | 0.0 | 0.0 | 0.0 |
| SHARPEN | 24.7 | 12.5 | 12.5 | 36.3 | 0.0 | 13.8 | 0.0 |
| 410P9M GOAL 2XL | 840 188 | 0.0 | 0.0 | 100.0 | 100.0 | 10.0 | 0.0 |
| 410P9M GOAL 2XL | 1260 188 | 7.5 | 0.0 | 100.0 | 100.0 | 31.3 | 5.0 |
| 410P9M GOAL 2XL | 840 280 | 3.8 | 5.0 | 100.0 | 100.0 | 23.8 | 25.0 |
| 410P9M GOAL 2XL | 1260 280 | 7.5 | 0.0 | 100.0 | 100.0 | 20.0 | 0.0 |
| 410P9M REFLEX | 840 280 | 32.5 | 17.5 | 100.0 | 100.0 | 38.8 | 17.5 |
| 410P9M REFLEX | 1260 280 | 13.8 | 10.0 | 100.0 | 100.0 | 41.3 | 12.5 |
| 410P9M REFLEX | 840 420 | 38.8 | 43.8 | 100.0 | 100.0 | 22.5 | 0.0 |
| 410P9M REFLEX | 1260 420 | 41.3 | 25.0 | 100.0 | 100.0 | 26.3 | 6.3 |
| 410P9M SHARPEN | 840 16.8 | 16.3 | 17.5 | 100.0 | 92.5 | 22.5 | 5.0 |
| 410P9M SHARPEN | 1260 16.8 | 43.8 | 20.0 | 100.0 | 100.0 | 20.0 | 0.0 |
| 410P9M SHARPEN | 840 24.7 | 55.0 | 37.5 | 100.0 | 100.0 | 32.5 | 6.3 |
| 410P9M SHARPEN | 1260 24.7 | 20.0 | 10.0 | 100.0 | 100.0 | 46.3 | 25.0 |

The encapsulated acetochlor formulation 410P9M provided commercially acceptable levels of weed control for AMASS with GOAL 2XL, REFLEX, and SHARPEN as tank mix partners. IPOHE and CASOB were not effectively controlled by any herbicide treatment in this trial.

The efficacy of the same formulations on velvetleaf (ABUTH), barnyardgrass (ECHCG) and signalgrass (BRAPP) by preemergent application on the same day as planting the crop was also determined with the results reported in the table below.

TABLE

ABUTH, ECHCG and BRAPP Weed Control Efficacy 28 and 56 DAT

| Product Formulation | Rate g AI/ha | ABUTH 28 DAT | ABUTH 56 DAT | ECHCG 28 DAT | ECHCG 56 DAT | BRAPP 28 DAT | BRAPP 56 DAT |
|---|---|---|---|---|---|---|---|
| 410P9M | 840 | 7.5 | 0.0 | 82.5 | 50.0 | 18.8 | 5.0 |
| 410P9M | 1260 | 0.0 | 0.0 | 100.0 | 100.0 | 35.0 | 0.0 |
| GOAL 2XL | 188 | 11.3 | 0.0 | 72.5 | 25.0 | 36.3 | 0.0 |
| GOAL 2XL | 280 | 10.0 | 0.0 | 61.3 | 17.5 | 22.5 | 0.0 |
| REFLEX | 280 | 21.3 | 5.0 | 50.0 | 35.0 | 0.0 | 0.0 |
| REFLEX | 420 | 20.0 | 0.0 | 53.8 | 10.0 | 5.0 | 0.0 |
| SHARPEN | 16.8 | 8.8 | 0.0 | 0.0 | 0.0 | 0.0 | 0.0 |
| SHARPEN | 24.7 | 11.3 | 0.0 | 0.0 | 0.0 | 0.0 | 0.0 |
| 410P9M GOAL 2XL | 840 188 | 16.3 | 0.0 | 97.5 | 80.0 | 60.0 | 30.0 |
| 410P9M GOAL 2XL | 1260 188 | 17.5 | 0.0 | 97.5 | 75.0 | 72.5 | 25.0 |
| 410P9M GOAL 2XL | 840 280 | 21.3 | 10.0 | 100.0 | 100.0 | 37.5 | 5.0 |
| 410P9M GOAL 2XL | 1260 280 | 25.0 | 5.0 | 97.5 | 100.0 | 57.5 | 0.0 |
| 410P9M REFLEX | 840 280 | 26.3 | 10.0 | 97.5 | 87.5 | 35.0 | 5.0 |
| 410P9M REFLEX | 1260 280 | 20.0 | 7.5 | 100.0 | 100.0 | 40.0 | 0.0 |
| 410P9M REFLEX | 840 420 | 47.5 | 47.5 | 100.0 | 92.5 | 26.3 | 0.0 |
| 410P9M REFLEX | 1260 420 | 27.5 | 5.0 | 100.0 | 92.5 | 76.3 | 30.0 |

TABLE-continued

ABUTH, ECHCG and BRAPP Weed Control Efficacy 28 and 56 DAT

| Product Formulation | Rate g AI/ha | ABUTH 28 DAT | ABUTH 56 DAT | ECHCG 28 DAT | ECHCG 56 DAT | BRAPP 28 DAT | BRAPP 56 DAT |
|---|---|---|---|---|---|---|---|
| 410P9M SHARPEN | 840 16.8 | 21.3 | 0.0 | 65.0 | 17.5 | 12.5 | 5.0 |
| 410P9M SHARPEN | 1260 16.8 | 21.3 | 12.5 | 95.0 | 100.0 | 55.0 | 10.0 |
| 410P9M SHARPEN | 840 24.7 | 38.8 | 17.5 | 90.0 | 85.0 | 30.0 | 5.0 |
| 410P9M SHARPEN | 1260 24.7 | 25.0 | 5.0 | 92.5 | 75.0 | 38.8 | 5.0 |

Tank mix combinations of the encapsulated acetochlor formulation 410P9M and REFLEX provided the best control of ECHCG. Some tank mix combinations of composition 410P9M and SHARPEN and GOAL 2XL also provided acceptable levels of weed control.

The efficacy of the same formulations on *amaranthus* (AMARE), prickly *sida* (SIDSP) and velvetleaf (ABUTH) by preemergent application on the same day as planting the crop was also determined with the results reported in the table below.

TABLE

AMARE, SIDSP and ABUTH Weed Control Efficacy 28 DAT

| Product Formulation | Rate g AI/ha | AMARE 28 DAT | SIDSP 28 DAT | ABUTH 28 DAT |
|---|---|---|---|---|
| 410P9M | 840 | 100.0 | 25.0 | 12.5 |
| 410P9M | 1260 | 100.0 | 56.0 | 7.5 |
| GOAL 2XL | 188 | 93.8 | 88.8 | 95.0 |
| GOAL 2XL | 280 | 92.5 | 95.0 | 95.0 |
| REFLEX | 280 | 100.0 | 21.3 | 15.0 |
| REFLEX | 420 | 100.0 | 70.0 | 23.8 |
| SHARPEN | 16.8 | 35.0 | 17.5 | 3.8 |
| SHARPEN | 24.7 | 76.3 | 35.0 | 11.3 |
| 410P9M GOAL 2XL | 840 188 | 96.3 | 92.5 | 96.3 |
| 410P9M GOAL 2XL | 1260 188 | 100.0 | 95.0 | 92.5 |
| 410P9M GOAL 2XL | 840 280 | 92.5 | 95.0 | 98.8 |
| 410P9M GOAL 2XL | 1260 280 | 98.8 | 98.8 | 97.5 |
| 410P9M REFLEX | 840 280 | 100.0 | 87.0 | 33.8 |
| 410P9M REFLEX | 1260 280 | 100.0 | 95.8 | 36.3 |
| 410P9M REFLEX | 840 420 | 100.0 | 97.5 | 36.3 |
| 410P9M REFLEX | 1260 420 | 100.0 | 94.5 | 46.3 |
| 410P9M SHARPEN | 840 16.8 | 100.0 | 83.8 | 25.8 |
| 410P9M SHARPEN | 1260 16.8 | 100.0 | 97.5 | 28.8 |
| 410P9M SHARPEN | 840 24.7 | 100.0 | 87.5 | 32.5 |
| 410P9M SHARPEN | 1260 24.7 | 100.0 | 98.8 | 62.5 |

Tank mixtures of the encapsulated acetochlor formulation 410P9M with GOAL 2XL provided commercially acceptable levels of weed control for all weeds tested in this trial (AMARE, SIDSP and ABUTH). REFLEX and SHARPEN also provided effective weed control for AMARE and SIDSP.

The efficacy of the same formulations on barnyardgrass (ECHCG), morningglory (IPOHE) and crabgrass (DIGSA) by preemergent application on the same day as planting the crop was also determined with the results reported in the table below.

TABLE

ECHCG, IPOHE and DIGSA Weed Control Efficacy 28 DAT

| Product Formulation | Rate g AI/ha | ECHCG 28 DAT | IPOHE 28 DAT | DIGSA 28 DAT |
|---|---|---|---|---|
| 410P9M | 840 | 100.0 | 0.0 | 100.0 |
| 410P9M | 1260 | 100.0 | 7.5 | 100.0 |
| GOAL 2XL | 188 | 100.0 | 17.5 | 100.0 |
| GOAL 2XL | 280 | 100.0 | 36.3 | 100.0 |
| REFLEX | 280 | 100.0 | 17.5 | 97.5 |
| REFLEX | 420 | 97.5 | 11.3 | 100.0 |
| SHARPEN | 16.8 | 77.5 | 12.5 | 62.5 |
| SHARPEN | 24.7 | 91.3 | 17.5 | 72.5 |
| 410P9M GOAL 2XL | 840 + 188 | 100.0 | 20.0 | 100.0 |
| 410P9M GOAL 2XL | 1260 + 188 | 100.0 | 21.3 | 100.0 |
| 410P9M GOAL 2XL | 840 280 | 100.0 | 53.8 | 100.0 |
| 410P9M GOAL 2XL | 1260 280 | 100.0 | 51.3 | 100.0 |
| 410P9M REFLEX | 840 280 | 100.0 | 46.3 | 100.0 |
| 410P9M REFLEX | 1260 280 | 100.0 | 43.8 | 100.0 |
| 410P9M REFLEX | 840 420 | 100.0 | 46.3 | 100.0 |
| 410P9M REFLEX | 1260 420 | 100.0 | 49.5 | 100.0 |
| 410P9M SHARPEN | 840 16.8 | 100.0 | 38.8 | 100.0 |
| 410P9M SHARPEN | 1260 16.8 | 100.0 | 36.3 | 100.0 |
| 410P9M SHARPEN | 840 24.7 | 100.0 | 61.3 | 100.0 |
| 410P9M SHARPEN | 1260 24.7 | 100.0 | 50.0 | 100.0 |

ECHCG and DIGSA were effectively controlled with all tank mixtures tested in this trial. IPOHE was not effectively controlled with any herbicide alone or in combination.

The efficacy of the same formulations on hemp sesbania (SEBEX) and crowfootgrass (DTTAE) by preemergent application on the same day as planting the crop was also determined with the results reported in the table below.

TABLE

SEBEX and DTTAE Weed Control Efficacy 28 DAT

| Product Formulation | Rate g AI/ha | SEBEX 28 DAT | DTTAE 28 DAT |
|---|---|---|---|
| 410P9M | 840 | 18.8 | 100.0 |
| 410P9M | 1260 | 35.0 | 100.0 |
| GOAL 2XL | 188 | 51.3 | 100.0 |
| GOAL 2XL | 280 | 62.5 | 100.0 |
| REFLEX | 280 | 10.0 | 92.5 |
| REFLEX | 420 | 16.3 | 100.0 |
| SHARPEN | 16.8 | 3.8 | 82.5 |
| SHARPEN | 24.7 | 0.0 | 90.0 |
| 410P9M GOAL 2XL | 840 188 | 63.8 | 100.0 |
| 410P9M GOAL 2XL | 1260 188 | 74.8 | 100.0 |
| 410P9M GOAL 2XL | 840 280 | 68.3 | 100.0 |
| 410P9M GOAL 2XL | 1260 280 | 67.0 | 100.0 |
| 410P9M REFLEX | 840 280 | 59.0 | 100.0 |
| 410P9M REFLEX | 1260 280 | 65.8 | 100.0 |
| 410P9M REFLEX | 840 420 | 71.3 | 100.0 |
| 410P9M REFLEX | 1260 420 | 73.8 | 100.0 |
| 410P9M SHARPEN | 840 16.8 | 40.0 | 100.0 |
| 410P9M SHARPEN | 1260 16.8 | 50.3 | 100.0 |
| 410P9M SHARPEN | 840 24.7 | 50.0 | 100.0 |
| 410P9M SHARPEN | 1260 24.7 | 57.0 | 100.0 |

In this trial, all mixtures tested with 410P9M provided complete control of DTTAE.

The efficacy of the same formulations on *amaranthus* (AMARE), velvetleaf (ABUTH) and crabgrass (DIGSA) by preemergent application on the same day as planting the crop was also determined with the results reported in the table below.

TABLE

AMARE, ABUTH and DIGSA Weed Control Efficacy 28 DAT

| Product Formulation | Rate g AI/ha | AMARE 28 DAT | ABUTH 28 DAT | DIGSA 28 DAT |
|---|---|---|---|---|
| 410P9M | 840 | 92.5 | 10.0 | 100.0 |
| 410P9M | 1260 | 91.3 | 0.0 | 100.0 |
| GOAL 2XL | 188 | 40.0 | 46.3 | 61.3 |
| GOAL 2XL | 280 | 20.0 | 61.3 | 75.0 |
| REFLEX | 280 | 100.0 | 7.5 | 100.0 |
| REFLEX | 420 | 100.0 | 15.0 | 100.0 |
| SHARPEN | 16.8 | 72.5 | 18.8 | 8.8 |
| SHARPEN | 24.7 | 75.0 | 27.5 | 10.0 |
| 410P9M GOAL 2XL | 840 188 | 72.5 | 55.0 | 100.0 |
| 410P9M GOAL 2XL | 1260 188 | 90.0 | 60.0 | 100.0 |
| 410P9M GOAL 2XL | 840 280 | 67.5 | 62.5 | 87.5 |
| 410P9M GOAL 2XL | 1260 280 | 82.5 | 70.8 | 100.0 |
| 410P9M REFLEX | 840 280 | 100.0 | 12.5 | 100.0 |
| 410P9M REFLEX | 1260 280 | 95.0 | 11.3 | 100.0 |
| 410P9M REFLEX | 840 420 | 100.0 | 28.8 | 100.0 |
| 410P9M REFLEX | 1260 420 | 100.0 | 17.5 | 100.0 |
| 410P9M SHARPEN | 840 16.8 | 90.0 | 47.0 | 90.0 |
| 410P9M SHARPEN | 1260 16.8 | 100.0 | 40.0 | 100.0 |
| 410P9M SHARPEN | 840 24.7 | 92.5 | 45.0 | 77.5 |
| 410P9M SHARPEN | 1260 24.7 | 100.0 | 38.8 | 95.0 |

DIGSA was controlled between 77.5 to 100% for all tank mixtures tested. The encapsulated acetochlor formulation 410P9M in combination with REFLEX showed the greatest control of AMARE and DIGSA. ABUTH was not effectively controlled with any herbicide in this trial.

The efficacy of the same formulations on prickly *sida* (SIDSP), hemp sesbania (SEBEX) and sicklepod (CASOB) by preemergent application on the same day as planting the crop was also determined with the results reported in the table below.

TABLE

SIDSP, SEBEX and CASOB Weed Control Efficacy 28 DAT

| Product Formulation | Rate g AI/ha | SIDSP 28 DAT | SEBEX 28 DAT | CASOB 28 DAT |
|---|---|---|---|---|
| 410P9M | 840 | 21.3 | 12.5 | 21.3 |
| 410P9M | 1260 | 20.0 | 22.5 | 12.5 |
| GOAL 2XL | 188 | 52.5 | 27.5 | 22.5 |
| GOAL 2XL | 280 | 62.5 | 33.8 | 20.0 |
| REFLEX | 280 | 37.5 | 17.5 | 7.5 |
| REFLEX | 420 | 58.8 | 31.3 | 22.5 |
| SHARPEN | 16.8 | 46.3 | 3.8 | 3.8 |
| SHARPEN | 24.7 | 43.8 | 11.3 | 16.3 |
| 410P9M GOAL 2XL | 840 188 | 63.8 | 38.3 | 18.8 |
| 410P9M GOAL 2XL | 1260 188 | 65.0 | 41.3 | 27.5 |
| 410P9M GOAL 2XL | 840 280 | 66.3 | 43.8 | 27.5 |
| 410P9M GOAL 2XL | 1260 280 | 73.8 | 51.3 | 30.0 |
| 410P9M REFLEX | 840 280 | 80.0 | 41.3 | 21.3 |
| 410P9M REFLEX | 1260 280 | 65.0 | 37.5 | 20.0 |
| 410P9M REFLEX | 840 420 | 75.0 | 36.3 | 26.3 |
| 410P9M REFLEX | 1260 420 | 73.8 | 51.5 | 26.3 |
| 410P9M SHARPEN | 840 16.8 | 69.5 | 27.5 | 20.0 |
| 410P9M SHARPEN | 1260 16.8 | 75.0 | 31.3 | 12.5 |
| 410P9M SHARPEN | 840 + 24.7 | 57.5 | 21.3 | 18.8 |
| 410P9M SHARPEN | 1260 + 24.7 | 78.8 | 33.8 | 12.5 |

SIDSP, SEBEX and CASOB were not effectively controlled by any treatment in this trial.

The efficacy of the same formulations on barnyardgrass (ECHCG) by preemergent application on the same day as planting the crop was also determined with the results reported in the table below.

TABLE

ECHCG Weed Control Efficacy 28 DAT

| Product Formulation | Rate g AI/ha | ECHCG 28 DAT |
|---|---|---|
| 410P9M | 840 | 100.0 |
| 410P9M | 1260 | 100.0 |
| GOAL 2XL | 188 | 93.8 |
| GOAL 2XL | 280 | 82.5 |
| REFLEX | 280 | 92.5 |
| REFLEX | 420 | 100.0 |
| SHARPEN | 16.8 | 67.5 |
| SHARPEN | 24.7 | 95.0 |
| 410P9M + GOAL 2XL | 840 + 188 | 100.0 |
| 410P9M + GOAL 2XL | 1260 + 188 | 97.5 |
| 410P9M + GOAL 2XL | 840 + 280 | 97.5 |
| 410P9M + GOAL 2XL | 1260 + 280 | 100.0 |
| 410P9M + REFLEX | 840 + 280 | 100.0 |
| 410P9M + REFLEX | 1260 + 280 | 97.5 |
| 410P9M + REFLEX | 840 + 420 | 100.0 |
| 410P9M + REFLEX | 1260 + 420 | 100.0 |
| 410P9M + SHARPEN | 840 + 16.8 | 96.3 |
| 410P9M + SHARPEN | 1260 + 16.8 | 100.0 |
| 410P9M + SHARPEN | 840 + 24.7 | 87.5 |
| 410P9M + SHARPEN | 1260 + 24.7 | 96.3 |

In this trial, commercially acceptable levels of weed control were observed with all except one rate of the tank mixtures with the encapsulated acetochlor formulation 410P9M.

Example 8

Field Trial Study of Weed Control Efficacy and Soybean and Cotton Safety in Preemergent Crop Application of Microencapsulated Acetochlor Formulations and Blends Aqueous dispersions of microencapsulated acetochlor formulations 410P9M and 403U7N prepared in Example 2, alone and in blended combinations were tested on glyphosate-tolerant ROUNDUP READY Flex Cotton or ROUNDUP READY Soy and various weeds. The commercial formulation DUAL MAGNUM, available from Syngenta and comprising s-metalochlor as the active ingredient and proprietary ingredients was also tested. All treatments were applied to soil seeded with ROUNDUP READY Flex Cotton or ROUNDUP READY soybeans on the same day as planting and the associated crop injury was evaluated at 14-16 DAT. The results from three field trials are reported in the tables below.

TABLE

RR Flex Cotton % Crop Injury 14-16 DAT in Three Field Trials

| Product Formulation | Ratio | Rate g AI/ha | Trial 201053034 % GR | % SR | Trial 2010530035 % GR | % SR | Trial 201053036 % GR | % SR |
|---|---|---|---|---|---|---|---|---|
| 410P9M | NA | 1260 | 0.0 | 0.0 | 10.0 | 7.5 | 16.3 | 0.0 |
| 410P9M | NA | 1480 | 5.0 | 2.5 | 15.3 | 7.5 | 32.5 | 5.0 |
| 410P9M | NA | 1820 | 0.0 | 0.0 | 16.3 | 6.3 | 35.0 | 5.0 |
| 403U7N | NA | 1260 | 0.0 | 0.0 | 10.0 | 2.5 | 15.0 | 3.8 |
| 403U7N | NA | 1480 | 2.5 | 0.0 | 17.0 | 7.5 | 16.3 | 2.5 |
| 403U7N | NA | 1820 | 3.8 | 0.0 | 13.0 | 3.8 | 22.5 | 3.8 |
| 403U7N + 410P9M | 25 / 75 | 1260 | 0.0 | 1.3 | 13.3 | 7.5 | 20.0 | 6.3 |
| 403U7N + 410P9M | 25 / 75 | 1480 | 5.0 | 1.3 | 17.5 | 6.3 | 25.0 | 3.8 |
| 403U7N + 410P9M | 25 / 75 | 1820 | 2.5 | 1.3 | 20.0 | 5.0 | 32.5 | 0.0 |
| 403U7N + 410P9M | 50 / 50 | 1260 | 0.0 | 1.3 | 6.3 | 1.3 | 18.3 | 3.8 |
| 403U7N + 410P9M | 50 / 50 | 1480 | 3.8 | 2.5 | 10.8 | 0.0 | 25.0 | 5.0 |
| 403U7N + 410P9M | 50 / 50 | 1820 | 1.3 | 1.3 | 17.0 | 2.5 | 31.3 | 5.0 |
| 403U7N + 410P9M | 75 / 25 | 1260 | 2.5 | 2.5 | 12.5 | 3.8 | 12.5 | 1.3 |
| 403U7N + 410P9M | 75 / 25 | 1480 | 3.8 | 2.5 | 10.0 | 5.0 | 25.0 | 5.0 |
| 403U7N + 410P9M | 75 / 25 | 1820 | 3.8 | 1.3 | 17.0 | 3.8 | 31.3 | 5.0 |
| DUAL MAGNUM | NA | 1400 | 4.5 | 0.0 | 2.5 | 0.0 | 18.8 | 3.8 |
| DUAL MAGNUM | NA | 1680 | 13.8 | 3.8 | 2.5 | 1.3 | 32.5 | 6.3 |
| DUAL MAGNUM | NA | 1960 | 18.3 | 5.0 | 1.3 | 1.3 | 33.8 | 3.8 |

TABLE

RR Soybean % Crop Injury 14-16 DAT in Three Field Trials

| Product Formulation | Ratio | Rate g AI/ha | Trial 2010530034 % GR | Trial 2010530034 % LF Cupp | Trial 2010530035 % GR | Trial 2010530035 % LF Crink | Trial 2010530036 % GR | Trial 2010530036 % LF Crink |
|---|---|---|---|---|---|---|---|---|
| 410P9M | NA | 1260 | 0.0 | 0.0 | 7.5 | 16.3 | 15.0 | 13.8 |
| 410P9M | NA | 1480 | 0.0 | 5.8 | 11.5 | 19.5 | 15.0 | 15.0 |
| 410P9M | NA | 1820 | 0.0 | 5.3 | 10.8 | 21.3 | 17.5 | 15.0 |
| 403U7N | NA | 1260 | 0.0 | 0.0 | 6.3 | 16.8 | 15.0 | 13.8 |
| 403U7N | NA | 1480 | 0.0 | 4.5 | 12.8 | 22.5 | 11.3 | 12.0 |
| 403U7N | NA | 1820 | 0.0 | 4.5 | 9.5 | 23.8 | 15.0 | 13.8 |
| 403U7N / 410P9M | 25 / 75 | 1260 | 0.0 | 1.5 | 10.8 | 20.8 | 11.3 | 13.8 |
| 403U7N / 410P9M | 25 / 75 | 1480 | 0.0 | 4.5 | 20.8 | 23.3 | 18.8 | 13.8 |
| 403U7N / 410P9M | 25 / 75 | 1820 | 0.0 | 4.0 | 15.0 | 27.5 | 17.5 | 13.8 |
| 403U7N / 410P9M | 50 / 50 | 1260 | 0.0 | 2.3 | 8.8 | 18.8 | 10.0 | 11.3 |
| 403U7N / 410P9M | 50 / 50 | 1480 | 1.3 | 9.0 | 9.8 | 20.8 | 12.5 | 10.0 |
| 403U7N / 410P9M | 50 / 50 | 1820 | 0.0 | 5.8 | 15.0 | 22.5 | 15.0 | 13.8 |
| 403U7N / 410P9M | 75 / 25 | 1260 | 0.1 | 1.3 | 9.3 | 18.3 | 8.8 | 8.8 |
| 403U7N / 410P9M | 75 / 25 | 1480 | 0.0 | 3.3 | 11.3 | 21.3 | 16.3 | 13.8 |
| 403U7N / 410P9M | 75 / 25 | 1820 | 0.0 | 8.0 | 13.8 | 22.5 | 17.5 | 15.0 |
| DUAL MAGNUM | NA | 1400 | 0.0 | 0.0 | 3.3 | 6.3 | 13.8 | 10.8 |
| DUAL MAGNUM | NA | 1680 | 0.0 | 4.8 | 2.5 | 6.8 | 13.8 | 15.0 |
| DUAL MAGNUM | NA | 1960 | 0.0 | 4.5 | 3.8 | 5.8 | 15.0 | 12.5 |

The efficacy of the same encapsulated acetochlor formulations and blends on various weed species by preemergent application on the same day as planting the crop was also determined. The associated weed control was evaluated and the results are reported in the tables below.

TABLE

IPOHE and AMASS Weed Control Efficacy

| Product Formulation | Ratio | Rate g AI/ha | IPOHE 23 DAT | IPOHE 41 DAT | IPOHE 57 DAT | AMASS 23 DAT | AMASS 41 DAT | AMASS 57 DAT |
|---|---|---|---|---|---|---|---|---|
| 410P9M | NA | 1260 | 17.5 | 10.0 | 12.5 | 77.5 | 55.0 | 45.0 |
| 410P9M | NA | 1480 | 13.8 | 0.0 | 12.5 | 100.0 | 100.0 | 90.0 |
| 410P9M | NA | 1820 | 26.3 | 0.0 | 0.0 | 97.5 | 100.0 | 96.3 |
| 403U7N | NA | 1260 | 0.0 | 0.0 | 0.0 | 91.3 | 67.5 | 75.0 |
| 403U7N | NA | 1480 | 15.0 | 5.0 | 0.0 | 100.0 | 65.0 | 77.5 |
| 403U7N | NA | 1820 | 16.3 | 7.5 | 0.0 | 100.0 | 100.0 | 100.0 |
| 403U7N / 410P9M | 25 / 75 | 1260 | 13.8 | 5.0 | 0.0 | 100.0 | 100.0 | 92.5 |
| 403U7N / 410P9M | 25 / 75 | 1480 | 0.0 | 0.0 | 0.0 | 100.0 | 100.0 | 100.0 |
| 403U7N / 410P9M | 25 / 75 | 1820 | 10.0 | 0.0 | 0.0 | 100.0 | 100.0 | 97.5 |
| 403U7N / 410P9M | 50 / 50 | 1260 | 6.3 | 0.0 | 0.0 | 96.3 | 87.5 | 80.0 |
| 403U7N / 410P9M | 50 / 50 | 1480 | 0.0 | 0.0 | 0.0 | 92.5 | 75.0 | 75.0 |
| 403U7N / 410P9M | 50 / 50 | 1820 | 7.5 | 0.0 | 0.0 | 100.0 | 100.0 | 95.0 |
| 403U7N / 410P9M | 75 / 25 | 1260 | 12.5 | 10.0 | 12.5 | 95.0 | 80.0 | 50.0 |
| 403U7N / 410P9M | 75 / 25 | 1480 | 7.5 | 0.0 | 0.0 | 100.0 | 100.0 | 82.5 |
| 403U7N / 410P9M | 75 / 25 | 1820 | 5.0 | 0.0 | 0.0 | 100.0 | 100.0 | 100.0 |
| DUAL MAGNUM | NA | 1400 | 22.5 | 15.0 | 0.0 | 100.0 | 87.5 | 82.5 |
| DUAL MAGNUM | NA | 1680 | 15.0 | 0.0 | 0.0 | 100.0 | 87.5 | 77.5 |
| DUAL MAGNUM | NA | 1960 | 45.0 | 12.5 | 0.0 | 100.0 | 100.0 | 100.0 |

TABLE

CASOB and ABUTH Weed Control Efficacy

| Product Formulation | Ratio | Rate g AI/ha | CASOB 23 DAT | CASOB 41 DAT | CASOB 57 DAT | ABUTH 23 DAT | ABUTH 41 DAT | ABUTH 57 DAT |
|---|---|---|---|---|---|---|---|---|
| 410P9M | NA | 1260 | 32.5 | 5.0 | 10.0 | 3.8 | 0.0 | 0.0 |
| 410P9M | NA | 1480 | 22.5 | 0.0 | 10.0 | 16.3 | 11.3 | 5.0 |
| 410P9M | NA | 1820 | 33.8 | 5.0 | 0.0 | 0.0 | 0.0 | 0.0 |
| 403U7N | NA | 1260 | 30.0 | 10.0 | 0.0 | 10.0 | 0.0 | 0.0 |

TABLE-continued

CASOB and ABUTH Weed Control Efficacy

| Product Formulation | Ratio | Rate g AI/ha | CASOB 23 DAT | CASOB 41 DAT | CASOB 57 DAT | ABUTH 23 DAT | ABUTH 41 DAT | ABUTH 57 DAT |
|---|---|---|---|---|---|---|---|---|
| 403U7N | NA | 1480 | 27.5 | 12.5 | 5.0 | 11.3 | 5.0 | 0.0 |
| 403U7N | NA | 1820 | 26.3 | 6.3 | 0.0 | 5.0 | 6.3 | 0.0 |
| 403U7N 410P9M | 25 75 | 1260 | 46.3 | 15.0 | 0.0 | 2.5 | 5.0 | 0.0 |
| 403U7N 410P9M | 25 75 | 1480 | 28.8 | 5.0 | 5.0 | 7.5 | 5.0 | 5.0 |
| 403U7N 410P9M | 25 75 | 1820 | 37.5 | 15.0 | 10.0 | 2.5 | 0.0 | 0.0 |
| 403U7N 410P9M | 50 50 | 1260 | 18.8 | 5.0 | 0.0 | 5.0 | 3.8 | 0.0 |
| 403U7N 410P9M | 50 50 | 1480 | 55.0 | 35.0 | 18.8 | 6.3 | 5.0 | 0.0 |
| 403U7N 410P9M | 50 50 | 1820 | 56.3 | 32.5 | 20.0 | 12.5 | 0.0 | 0.0 |
| 403U7N 410P9M | 75 25 | 1260 | 23.8 | 0.0 | 0.0 | 2.5 | 0.0 | 0.0 |
| 403U7N 410P9M | 75 25 | 1480 | 22.5 | 7.5 | 20.0 | 0.0 | 0.0 | 0.0 |
| 403U7N 410P9M | 75 25 | 1820 | 21.3 | 6.3 | 5.0 | 2.5 | 6.3 | 5.0 |
| DUAL MAGNUM | NA | 1400 | 35.0 | 17.5 | 7.5 | 55.0 | 22.5 | 10.0 |
| DUAL MAGNUM | NA | 1680 | 51.3 | 22.5 | 20.0 | 66.3 | 40.0 | 25.0 |
| DUAL MAGNUM | NA | 1960 | 47.5 | 20.0 | 0.0 | 67.5 | 52.5 | 42.5 |

TABLE

ESHCG and BRAPP Weed Control Efficacy

| Product Formulation | Ratio | Rate g AI/ha | ECHCG 23 DAT | ECHCG 41 DAT | ECHCG 57 DAT | BRAPP 23 DAT | BRAPP 41 DAT | BRAPP 57 DAT |
|---|---|---|---|---|---|---|---|---|
| 410P9M | NA | 1260 | 91.3 | 80.0 | 92.5 | 71.3 | 27.5 | 0.0 |
| 410P9M | NA | 1480 | 97.5 | 100.0 | 100.0 | 72.5 | 36.3 | 0.0 |
| 410P9M | NA | 1820 | 96.3 | 100.0 | 100.0 | 95.0 | 57.5 | 0.0 |
| 403U7N | NA | 1260 | 96.3 | 100.0 | 100.0 | 87.5 | 32.5 | 0.0 |
| 403U7N | NA | 1480 | 100.0 | 85.0 | 72.5 | 86.3 | 32.5 | 10.0 |
| 403U7N | NA | 1820 | 100.0 | 100.0 | 100.0 | 80.0 | 20.0 | 0.0 |
| 403U7N 410P9M | 25 75 | 1260 | 100.0 | 97.5 | 88.8 | 80.0 | 27.5 | 12.5 |
| 403U7N 410P9M | 25 75 | 1480 | 100.0 | 99.5 | 100.0 | 71.3 | 23.8 | 0.0 |
| 403U7N 410P9M | 25 75 | 1820 | 100.0 | 100.0 | 96.3 | 88.3 | 20.0 | 0.0 |
| 403U7N 410P9M | 50 50 | 1260 | 88.8 | 97.5 | 100.0 | 85.0 | 16.3 | 0.0 |
| 403U7N 410P9M | 50 50 | 1480 | 100.0 | 97.5 | 100.0 | 87.0 | 27.5 | 22.5 |
| 403U7N 410P9M | 50 50 | 1820 | 100.0 | 100.0 | 96.3 | 87.0 | 20.0 | 12.5 |
| 403U7N 410P9M | 75 25 | 1260 | 92.5 | 100.0 | 75.0 | 91.3 | 13.8 | 0.0 |
| 403U7N 410P9M | 75 25 | 1480 | 100.0 | 100.0 | 100.0 | 81.3 | 15.0 | 10.0 |
| 403U7N 410P9M | 75 25 | 1820 | 100.0 | 100.0 | 100.0 | 88.8 | 22.5 | 0.0 |
| DUAL MAGNUM | NA | 1400 | 100.0 | 100.0 | 95.0 | 98.8 | 77.5 | 25.0 |
| DUAL MAGNUM | NA | 1680 | 100.0 | 100.0 | 100.0 | 100.0 | 50.0 | 17.5 |
| DUAL MAGNUM | NA | 1960 | 100.0 | 100.0 | 98.8 | 98.8 | 85.0 | 47.5 |

TABLE

AMARE and SIDSP Weed Control Efficacy

| Product Formulation | Ratio | Rate g AI/ha | AMARE 21 DAT | AMARE 42 DAT | SIDSP 21 DAT | SIDSP 42 DAT |
|---|---|---|---|---|---|---|
| 410P9M | NA | 1260 | 100.0 | 100.0 | 78.3 | 45.0 |
| 410P9M | NA | 1480 | 100.0 | 100.0 | 96.3 | 73.8 |
| 410P9M | NA | 1820 | 100.0 | 100.0 | 93.8 | 62.5 |
| 403U7N | NA | 1260 | 100.0 | 100.0 | 76.3 | 50.0 |
| 403U7N | NA | 1480 | 100.0 | 100.0 | 78.8 | 52.5 |
| 403U7N | NA | 1820 | 100.0 | 100.0 | 91.3 | 81.3 |
| 403U7N | 25 | | | | | |
| 410P9M | 75 | 1260 | 100.0 | 100.0 | 62.5 | 43.8 |
| 403U7N | 25 | | | | | |
| 410P9M | 75 | 1480 | 100.0 | 100.0 | 88.8 | 61.3 |
| 403U7N | 25 | | | | | |
| 410P9M | 75 | 1820 | 100.0 | 100.0 | 92.3 | 65.0 |
| 403U7N | 50 | | | | | |
| 410P9M | 50 | 1260 | 100.0 | 100.0 | 66.3 | 28.8 |
| 403U7N | 50 | | | | | |
| 410P9M | 50 | 1480 | 100.0 | 100.0 | 73.3 | 37.5 |
| 403U7N | 50 | | | | | |
| 410P9M | 50 | 1820 | 100.0 | 100.0 | 90.0 | 66.3 |
| 403U7N | 75 | | | | | |
| 410P9M | 25 | 1260 | 100.0 | 100.0 | 66.3 | 33.8 |
| 403U7N | 75 | | | | | |
| 410P9M | 25 | 1480 | 100.0 | 100.0 | 80.0 | 61.3 |
| 403U7N | 75 | | | | | |
| 410P9M | 25 | 1820 | 100.0 | 100.0 | 93.8 | 70.0 |
| DUAL MAGNUM | NA | 1400 | 100.0 | 100.0 | 40.0 | 18.8 |
| DUAL MAGNUM | NA | 1680 | 100.0 | 100.0 | 57.5 | 17.5 |
| DUAL MAGNUM | NA | 1960 | 100.0 | 100.0 | 50.0 | 12.5 |

TABLE

SEBEX and DTTAE Weed Control Efficacy

| Product Formulation | Ratio | Rate g AI/ha | SEBEX 21 DAT | SEBEX 42 DAT | DTTAE 21 DAT | DTTAE 42 DAT |
|---|---|---|---|---|---|---|
| 410P9M | NA | 1260 | 65.8 | 27.5 | 78.8 | 50.0 |
| 410P9M | NA | 1480 | 72.0 | 55.0 | 88.8 | 87.5 |
| 410P9M | NA | 1820 | 80.0 | 60.0 | 100.0 | 100.0 |
| 403U7N | NA | 1260 | 63.3 | 30.0 | 95.0 | 91.3 |
| 403U7N | NA | 1480 | 65.0 | 31.3 | 82.5 | 67.5 |
| 403U7N | NA | 1820 | 78.3 | 65.8 | 100.0 | 95.0 |
| 403U7N | 25 | | | | | |
| 410P9M | 75 | 1260 | 52.5 | 17.5 | 93.8 | 82.5 |
| 403U7N | 25 | | | | | |
| 410P9M | 75 | 1480 | 70.8 | 47.5 | 91.3 | 85.0 |
| 403U7N | 25 | | | | | |
| 410P9M | 75 | 1820 | 73.8 | 51.3 | 93.8 | 90.0 |
| 403U7N | 50 | 1260 | 50.0 | 28.8 | 100.0 | 100.0 |
| 410P9M | 50 | | | | | |
| 403U7N | 50 | | | | | |
| 410P9M | 50 | 1480 | 55.0 | 22.5 | 100.0 | 97.5 |
| 403U7N | 50 | | | | | |
| 410P9M | 50 | 1820 | 71.3 | 56.3 | 100.0 | 100.0 |
| 403U7N | 75 | | | | | |
| 410P9M | 25 | 1260 | 38.8 | 17.5 | 95.0 | 92.5 |
| 403U7N | 75 | | | | | |
| 410P9M | 25 | 1480 | 71.3 | 42.5 | 100.0 | 97.5 |
| 403U7N | 75 | | | | | |
| 410P9M | 25 | 1820 | 65.0 | 49.5 | 100.0 | 97.5 |
| DUAL MAGNUM | NA | 1400 | 26.3 | 6.3 | 100.0 | 100.0 |
| DUAL MAGNUM | NA | 1680 | 28.8 | 6.3 | 100.0 | 100.0 |
| DUAL MAGNUM | NA | 1960 | 38.8 | 12.5 | 100.0 | 100.0 |

TABLE

ABUTH and IPOHE Weed Control Efficacy

| Product Formulation | Ratio | Rate g AI/ha | ABUTH 21 DAT | ABUTH 42 DAT | IPOHE 21 DAT | IPOHE 42 DAT |
|---|---|---|---|---|---|---|
| 410P9M | NA | 1260 | 8.8 | 7.5 | 18.8 | 7.5 |
| 410P9M | NA | 1480 | 20.0 | 7.5 | 17.5 | 3.8 |
| 410P9M | NA | 1820 | 21.3 | 8.8 | 25.0 | 7.5 |
| 403U7N | NA | 1260 | 18.8 | 7.5 | 21.3 | 7.5 |
| 403U7N | NA | 1480 | 22.5 | 3.8 | 20.0 | 3.8 |
| 403U7N | NA | 1820 | 16.3 | 10.0 | 23.8 | 3.8 |
| 403U7N | 25 | | | | | |
| 410P9M | 75 | 1260 | 20.0 | 3.8 | 15.0 | 7.5 |
| 403U7N | 25 | | | | | |
| 410P9M | 75 | 1480 | 22.5 | 3.8 | 17.5 | 10.0 |
| 403U7N | 25 | | | | | |
| 410P9M | 75 | 1820 | 21.3 | 12.5 | 18.8 | 7.5 |
| 403U7N | 50 | | | | | |
| 410P9M | 50 | 1260 | 11.3 | 13.8 | 7.5 | 7.5 |
| 403U7N | 50 | | | | | |
| 410P9M | 50 | 1480 | 22.5 | 12.5 | 18.8 | 6.3 |
| 403U7N | 50 | | | | | |
| 410P9M | 50 | 1820 | 22.5 | 7.5 | 18.8 | 3.8 |
| 410P9M | 25 | 1260 | 20.0 | 3.8 | 21.3 | 10.0 |
| 75403U7N | 75 | | | | | |
| 410P9M | 25 | 1480 | 26.3 | 7.5 | 18.8 | 0.0 |
| 403U7N | 75 | | | | | |
| 410P9M | 25 | 1820 | 12.5 | 5.0 | 17.5 | 3.8 |
| DUAL MAGNUM | NA | 1400 | 16.3 | 5.0 | 11.3 | 8.8 |
| DUAL MAGNUM | NA | 1680 | 20.0 | 7.5 | 10.0 | 5.0 |
| DUAL MAGNUM | NA | 1960 | 18.8 | 6.3 | 33.8 | 3.8 |

TABLE

ELEIN and ECHCG Weed Control Efficacy

| Product Formulation | Ratio | Rate g AI/ha | ELEIN 21 DAT | ELEIN 42 DAT | ECHCG 21 DAT | ECHCG 42 DAT |
|---|---|---|---|---|---|---|
| 410P9M | NA | 1260 | 100.0 | 100.0 | 72.5 | 32.5 |
| 410P9M | NA | 1480 | 100.0 | 100.0 | 81.3 | 82.5 |
| 410P9M | NA | 1820 | 100.0 | 100.0 | 61.3 | 53.8 |
| 403U7N | NA | 1260 | 95.0 | 87.5 | 60.0 | 61.3 |
| 403U7N | NA | 1480 | 100.0 | 100.0 | 88.8 | 85.0 |
| 403U7N | NA | 1820 | 100.0 | 100.0 | 81.3 | 75.0 |
| 403U7N | 25 | | | | | |
| 410P9M | 75 | 1260 | 100.0 | 100.0 | 77.5 | 75.0 |
| 403U7N | 25 | | | | | |
| 410P9M | 75 | 1480 | 95.0 | 90.0 | 71.3 | 60.0 |
| 403U7N | 25 | | | | | |
| 410P9M | 75 | 1820 | 100.0 | 100.0 | 83.8 | 77.5 |
| 403U7N | 50 | | | | | |
| 410P9M | 50 | 1260 | 100.0 | 100.0 | 66.3 | 47.5 |
| 403U7N | 50 | | | | | |
| 410P9M | 50 | 1480 | 95.0 | 100.0 | 68.8 | 56.3 |
| 403U7N | 50 | | | | | |
| 410P9M | 50 | 1820 | 100.0 | 100.0 | 71.3 | 60.0 |
| 403U7N | 75 | | | | | |
| 410P9M | 25 | 1260 | 100.0 | 100.0 | 85.0 | 72.5 |
| 403U7N | 75 | | | | | |
| 410P9M | 25 | 1480 | 100.0 | 100.0 | 78.8 | 75.0 |
| 403U7N | 75 | | | | | |
| 410P9M | 25 | 1820 | 100.0 | 100.0 | 78.8 | 71.3 |
| DUAL MAGNUM | NA | 1400 | 100.0 | 100.0 | 83.8 | 82.5 |
| DUAL MAGNUM | NA | 1680 | 100.0 | 100.0 | 73.8 | 46.3 |
| DUAL MAGNUM | NA | 1960 | 100.0 | 100.0 | 75.0 | 73.8 |

TABLE

CASOB and SEBEX Weed Control Efficacy

| Product Formulation | Ratio | Rate g AI/ha | CASOB 21 DAT | SEBEX 21 DAT |
|---|---|---|---|---|
| 410P9M | NA | 1260 | 18.8 | 40.8 |
| 410P9M | NA | 1480 | 22.5 | 48.8 |
| 410P9M | NA | 1820 | 26.3 | 52.0 |
| 403U7N | NA | 1260 | 20.0 | 31.3 |
| 403U7N | NA | 1480 | 28.8 | 30.8 |
| 403U7N | NA | 1820 | 27.5 | 44.5 |
| 403U7N | 25 | | | |
| 410P9M | 75 | 1260 | 22.5 | 36.3 |
| 403U7N | 25 | | | |
| 410P9M | 75 | 1480 | 26.3 | 46.3 |
| 403U7N | 25 | | | |
| 410P9M | 75 | 1820 | 26.3 | 49.5 |
| 403U7N | 50 | | | |
| 410P9M | 50 | 1260 | 16.3 | 31.3 |
| 403U7N | 50 | | | |
| 410P9M | 50 | 1480 | 26.3 | 33.8 |
| 403U7N | 50 | | | |
| 410P9M | 50 | 1820 | 27.5 | 41.3 |
| 403U7N | 75 | | | |
| 410P9M | 25 | 1260 | 17.5 | 26.3 |
| 403U7N | 75 | | | |
| 410P9M | 25 | 1480 | 18.8 | 33.8 |
| 403U7N | 75 | | | |
| 410P9M | 25 | 1820 | 28.8 | 33.8 |
| DUAL MAGNUM | NA | 1400 | 15.0 | 26.3 |
| DUAL MAGNUM | NA | 1680 | 30.0 | 38.8 |
| DUAL MAGNUM | NA | 1960 | 23.8 | 46.3 |

TABLE

SIDSP and DIGSA Weed Control Efficacy

| Product Formulation | Ratio | Rate g AI/ha | SIDSP 21 DAT | DIGSA 21 DAT |
|---|---|---|---|---|
| 410P9M | NA | 1260 | 67.3 | 100.0 |
| 410P9M | NA | 1480 | 67.0 | 100.0 |
| 410P9M | NA | 1820 | 77.0 | 100.0 |
| 403U7N | NA | 1260 | 58.8 | 100.0 |
| 403U7N | NA | 1480 | 55.0 | 100.0 |
| 403U7N | NA | 1820 | 70.0 | 100.0 |
| 403U7N | 25 | | | |
| 410P9M | 75 | 1260 | 61.3 | 100.0 |
| 403U7N | 25 | 1480 | 67.5 | 100.0 |
| 410P9M | 75 | | | |
| 403U7N | 25 | | | |
| 410P9M | 75 | 1820 | 71.3 | 100.0 |
| 403U7N | 50 | | | |
| 410P9M | 50 | 1260 | 52.0 | 100.0 |
| 403U7N | 50 | | | |
| 410P9M | 50 | 1480 | 61.3 | 100.0 |
| 403U7N | 50 | | | |
| 410P9M | 50 | 1820 | 71.3 | 100.0 |
| 403U7N | 75 | | | |
| 410P9M | 25 | 1260 | 56.5 | 95.0 |
| 403U7N | 75 | | | |
| 410P9M | 25 | 1480 | 55.0 | 97.5 |
| 403U7N | 75 | | | |
| 410P9M | 25 | 1820 | 66.3 | 99.8 |
| DUAL MAGNUM | NA | 1400 | 47.5 | 100.0 |
| DUAL MAGNUM | NA | 1680 | 61.3 | 100.0 |
| DUAL MAGNUM | NA | 1960 | 67.5 | 100.0 |

TABLE

ABUTH and AMARE Weed Control Efficacy

| Product Formulation | Ratio | Rate g AI/ha | ABUTH 21 DAT | AMARE 21 DAT |
|---|---|---|---|---|
| 410P9M | NA | 1260 | 30.0 | 100.0 |
| 410P9M | NA | 1480 | 35.0 | 100.0 |
| 410P9M | NA | 1820 | 25.0 | 100.0 |
| 403U7N | NA | 1260 | 23.8 | 100.0 |
| 403U7N | NA | 1480 | 28.8 | 100.0 |
| 403U7N | NA | 1820 | 27.5 | 100.0 |
| 403U7N | 25 | | | |
| 410P9M | 75 | 1260 | 38.8 | 100.0 |
| 403U7N | 25 | | | |
| 410P9M | 75 | 1480 | 24.5 | 100.0 |
| 403U7N | 25 | | | |
| 410P9M | 75 | 1820 | 31.3 | 100.0 |
| 403U7N | 50 | | | |
| 410P9M | 50 | 1260 | 17.5 | 100.0 |
| 403U7N | 50 | | | |
| 410P9M | 50 | 1480 | 23.8 | 100.0 |
| 403U7N | 50 | | | |
| 410P9M | 50 | 1820 | 26.3 | 100.0 |
| 403U7N | 75 | 1260 | 25.0 | 97.5 |
| 410P9M | 25 | | | |
| 403U7N | 75 | | | |
| 410P9M | 25 | 1480 | 23.8 | 100.0 |
| 403U7N | 75 | | | |
| 410P9M | 25 | 1820 | 26.3 | 100.0 |
| DUAL MAGNUM | NA | 1400 | 27.5 | 97.5 |
| DUAL MAGNUM | NA | 1680 | 30.0 | 100.0 |
| DUAL MAGNUM | NA | 1960 | 26.3 | 100.0 |

TABLE

ECHCG Weed Control Efficacy

| Product Formulation | Ratio | Rate g AI/ha | ECHCG 21 DAT |
|---|---|---|---|
| 410P9M | NA | 1260 | 100.0 |
| 410P9M | NA | 1480 | 100.0 |
| 410P9M | NA | 1820 | 100.0 |
| 403U7N | NA | 1260 | 100.0 |
| 403U7N | NA | 1480 | 100.0 |
| 403U7N | NA | 1820 | 100.0 |
| 403U7N | 25 | | |
| 410P9M | 75 | 1260 | 100.0 |
| 403U7N | 25 | | |
| 410P9M | 75 | 1480 | 100.0 |
| 403U7N | 25 | | |
| 410P9M | 75 | 1820 | 100.0 |
| 403U7N | 50 | | |
| 410P9M | 50 | 1260 | 100.0 |
| 403U7N | 50 | | |
| 410P9M | 50 | 1480 | 100.0 |
| 403U7N | 50 | | |
| 410P9M | 50 | 1820 | 100.0 |
| 403U7N | 75 | | |
| 410P9M | 25 | 1260 | 99.8 |
| 403U7N | 75 | | |
| 410P9M | 25 | 1480 | 100.0 |
| 403U7N | 75 | | |
| 410P9M | 25 | 1820 | 100.0 |
| DUAL MAGNUM | NA | 1400 | 100.0 |
| DUAL MAGNUM | NA | 1680 | 100.0 |
| DUAL MAGNUM | NA | 1960 | 100.0 |

In the above tables that show the results from Field Trial 2010530034, control of *amaranthus* (AMASS) was greater as application rate increased with each formulation evaluated. At the earliest sampling date (23 DAT), the 403U7N:410P9M encapsulated acetochlor formulation blends provided better control than formulations of composition 410P9M alone at the field application rate of 1260 g ai/ha (1.125 lb ai/A). At the second sampling date (41 DAT), both the 25:75 and 50:50 blends of 403U7N:410P9M provided 87.5% or better control of AMASS compared to only 55% control with composition 410P9M alone. Only the 25:75 blend of 403U7N:410P9M provided greater than 90% AMASS control at 57 DAT at field application rates.

Barnyardgrass (ECHCG) efficacy was similar among the various encapsulated acetochlor formulations evaluated at all three sampling dates with 90% or greater control for 410P9M, 403U7N alone and the 50:50 blend of 403U7N:410P9M nearly 2 months after application (57 DAT) at field use rates. Signalgrass (BRAPP) efficacy was only commercially acceptable (>85%) for the encapsulated acetochlor formulations 403U7N alone and the 50:50 and 75:25 blends of 403U7N:410P9M at the first evaluation date (23 DAT).

Large seeded dicots, such as morningglory (IPOHE), sicklepod (CASOB) and velvetleaf (ABUTH), were not controlled in this trial with the encapsulated acetochlor formulations. This is not unexpected as previous greenhouse trials have demonstrated limited impact on these species.

In the above tables that show the results from Field Trial 2010530035, all encapsulated acetochlor formulations provided 100% control of common *amaranthus* (AMARE) at both 21 and 42 DAT. At field use rates, no formulation provided acceptable prickly *sida* (SIDSP) control. At both the 1480 and 1820 g ai/ha application rates, encapsulated acetochlor formulation 410P9M provided greater than 93.6% control of SIDSP for 21 DAT. Only the highest application rate of 1820 g ai/ha provided 90% or greater control of SIDSP for the various 403U7N:410P9M formulation blends at 21 DAT. No application rate or formulation provided acceptable SIDSP control at 42 DAT.

Goosegrass (ELEIN) efficacy was 100% at both 21 and 42 DAT for all encapsulated acetochlor formulations except 403U7N, which had 95 and 87.5% efficacy at 21 and 42 DAT, respectively. Field use rates of all encapsulated acetochlor formulations provided 93.8% or better efficacy for Crowfootgrass (DTTAE) except for composition 410P9M, which required application rates of 1480 g ai/ha (1.325 lb ai/A) to provide similar control 21 DAT. At 42 DAT, 403U7N alone and the 50:50 and the 75:25 403U7N:410P9M blends provided 91.3% or greater DTTAE efficacy. Barnyardgrass (ECHCG) efficacy was below commercially accepted levels at field use rates for all encapsulated acetochlor formulations except the 75:25 403U7N:410P9M blend at 21 DAT.

Large seeded dicots, such as morningglory (IPOHE), hemp sesbania (SEBEX) and velvetleaf (ABUTH), were not controlled in this trial with the encapsulated acetochlor formulations. This is not unexpected as previous greenhouse trials have demonstrated limited impact on these species.

In the above tables that shows results from Field Trial 2010530036, all encapsulated acetochlor formulations provided 97.5% or greater control of common *amaranthus* (AMARE) at 21 DAT. In this trial, prickly *sida* (SIDSP) had less than acceptable control (67.3% or less) for all encapsulated acetochlor formulations at field use application rate of 1260 g ai/ha. Both crabgrass (DIGSA) and barnyardgrass (ECHCG) had 95% or better control at 21 DAT with all rates and formulations evaluated in this trial.

Large seeded dicots, such as hemp sesbania (SEBEX), sicklepod (CASOB) and velvetleaf (ABUTH), were not controlled in this trial with the encapsulated acetochlor formulations. This is not unexpected as previous greenhouse trials have demonstrated limited impact on these species.

Overall, weed control efficacy is equal to or better with the 403U7N:410P9M encapsulated acetochlor blended formulations as compared to composition 410P9M alone and may provide slightly longer control with some weed species.

Example 9

Field Trial Study of Weed Control Efficacy and Soybean Safety in Pre-Plant, At Planting, At Cracking and Early Post Emergence Applications of Microencapsulated Acetochlor Tank Mixtures Tank mixtures containing aqueous dispersions of microencapsulated acetochlor formulation 410P9M prepared in Example 2 were evaluated in pre-plant (EPP), at planting (AP), at cracking (ACR) and early post emergence (EPOE) applications for crop safety in soybeans and weed control efficacy.

ROUNDUP READY Soybeans were planted in four row plots with a spray area of 2.08 m×6 m. The center two rows were utilized for crop safety evaluations. Rows 1 and 4 were sprayed with buffer. The whole plot was used for weed control evaluation. Unsprayed buffer between the plots of two rows provided a running check for weed control evaluation. Each treatment was run in four replicates.

The early pre-plant application (EPP) was made 14 days prior to planting the crop. The at cracking (ACR) application was made 5 days after planting. The early post-emergence application (EPOE) was made at the V1 or V2 growth stage.

The crop injury ratings were taken at 21 and 42 days after treatment and were based on the European Weed Research Scale (EWRS) as follows:
EWRS 1: injury of 0% (100% normal plants);
EWRS 2: injury of 0-2% (plants normally in a 98-100%);
EWRS 3: injury of 2-5% (plants normally in a 95-98%);
EWRS 4: injury of 5-10% (plants normally in a 90-95%);
EWRS 5: injury of 10-20%;
EWRS 6: injury of 20-40%;
EWRS 7: injury of 40-70%; and
EWRS 8: injury of 70-99%.

Weed control efficacy was evaluated at 21 and 42 days after treatment.

ROUNDUP READY soybeans were planted as described above. Tank mixtures containing encapsulated acetochlor formulation 410P9M with ROUNDUP (Rup) were compared to DUAL MAGNUM tank mixed with ROUNDUP and ROUNDUP alone. ROUNDUP in tank mixture and alone was applied at a rate of 840 g/ha.

RR Soybean crop injury at early (21 DAT) and late (42 DAT) evaluations from the combined data from 7 field trials is shown in the table below. Mean separation is within individual application and rating timings.

TABLE

| Rating Timing | Application Timing | Product Formulation/Rate (g/ha) | Injury (LS Mean) | SE | Mean Separation |
|---|---|---|---|---|---|
| Early | At Plant | Rup + 410P9M 1960 | 2.3 | 0.2 | A |
| Early | At Plant | Rup + 410P9M 1680 | 2.2 | 0.2 | A |
| Early | At Plant | Rup + 410P9M 1260 | 2.1 | 0.2 | A |
| Early | At Plant | Rup + DUAL MAGNUM 1960 | 2.0 | 0.2 | A |
| Early | At Plant | Rup + 410P9M 1120 | 2.0 | 0.2 | A |
| Early | At Plant | Rup + DUAL MAGNUM 1680 | 1.6 | 0.2 | B |
| Early | At Plant | Rup + DUAL MAGNUM 1400 | 1.5 | 0.2 | BC |
| Early | At Plant | Rup + DUAL MAGNUM 1120 | 1.3 | 0.2 | BC |

TABLE-continued

| Rating Timing | Application Timing | Product Formulation/Rate (g/ha) | Injury (LS Mean) | SE | Mean Separation |
|---|---|---|---|---|---|
| Early | At Plant | Rup 840 | 1.1 | 0.2 | C |
| Early | Cracking | Rup + 410P9M 1960 | 3.5 | 0.2 | A |
| Early | Cracking | Rup + 410P9M 1680 | 3.3 | 0.2 | AB |
| Early | Cracking | Rup + 410P9M 1260 | 3.1 | 0.2 | B |
| Early | Cracking | Rup + 410P9M 1120 | 2.7 | 0.2 | C |
| Early | Cracking | Rup + DUAL MAGNUM 1960 | 2.4 | 0.2 | CD |
| Early | Cracking | Rup + DUAL MAGNUM 1680 | 2.2 | 0.2 | DE |
| Early | Cracking | Rup + DUAL MAGNUM 1400 | 2.0 | 0.2 | EF |
| Early | Cracking | Rup + DUAL MAGNUM 1120 | 1.7 | 0.2 | F |
| Early | Cracking | Rup 840 | 1.2 | 0.2 | G |
| Early | Pre-Plant | Rup + 410P9M 1960 | 2.0 | 0.2 | A |
| Early | Pre-Plant | Rup + 410P9M 1260 | 1.8 | 0.2 | AB |
| Early | Pre-Plant | Rup + 410P9M 1680 | 1.8 | 0.2 | AB |
| Early | Pre-Plant | Rup + DUAL MAGNUM 1960 | 1.6 | 0.2 | ABC |
| Early | Pre-Plant | Rup + DUAL MAGNUM 1680 | 1.5 | 0.2 | BCD |
| Early | Pre-Plant | Rup + 410P9M 1120 | 1.5 | 0.2 | BCD |
| Early | Pre-Plant | Rup + DUAL MAGNUM 1400 | 1.3 | 0.2 | CDE |
| Early | Pre-Plant | Rup + DUAL MAGNUM 1120 | 1.2 | 0.2 | DE |
| Early | Pre-Plant | Rup 840 | 1.0 | 0.2 | E |
| Early | V2 | Rup + 410P9M 1960 | 3.7 | 0.2 | A |
| Early | V2 | Rup + DUAL MAGNUM 1960 | 3.4 | 0.2 | AB |
| Early | V2 | Rup + 410P9M_1680 | 3.3 | 0.2 | BC |
| Early | V2 | Rup + DUAL MAGNUM 1680 | 3.2 | 0.2 | BC |
| Early | V2 | Rup + 410P9M 1260 | 3.1 | 0.2 | BC |
| Early | V2 | Rup + DUAL MAGNUM 1400 | 3.0 | 0.2 | CD |
| Early | V2 | Rup + 410P9M 1120 | 2.7 | 0.2 | DE |
| Early | V2 | Rup + DUAL MAGNUM 1120 | 2.4 | 0.2 | E |
| Early | V2 | Rup 840 | 1.2 | 0.2 | F |
| Late | At Plant | Rup + 410P9M 1960 | 1.6 | 0.1 | A |
| Late | At Plant | Rup + 410P9M 1680 | 1.5 | 0.1 | A |
| Late | At Plant | Rup + DUAL MAGNUM 1960 | 1.4 | 0.1 | AB |
| Late | At Plant | Rup + 410P9M 1120 | 1.3 | 0.1 | ABC |
| Late | At Plant | Rup + 410P9M 1260 | 1.3 | 0.1 | ABC |
| Late | At Plant | Rup + DUAL MAGNUM 1120 | 1.2 | 0.1 | BC |
| Late | At Plant | Rup + DUAL MAGNUM 1680 | 1.2 | 0.1 | BC |
| Late | At Plant | Rup + DUAL MAGNUM 1400 | 1.1 | 0.1 | BC |
| Late | At Plant | Rup 840 | 1.0 | 0.1 | C |
| Late | Cracking | Rup + 410P9M 1960 | 1.9 | 0.1 | A |
| Late | Cracking | Rup + 410P9M 1260 | 1.7 | 0.1 | A |
| Late | Cracking | Rup + 410P9M 1680 | 1.6 | 0.1 | AB |
| Late | Cracking | Rup + DUAL MAGNUM 1960 | 1.6 | 0.1 | ABC |
| Late | Cracking | Rup + DUAL MAGNUM 1680 | 1.4 | 0.1 | BCD |
| Late | Cracking | Rup + 410P9M 1120 | 1.4 | 0.1 | BCD |
| Late | Cracking | Rup + DUAL MAGNUM 1400 | 1.3 | 0.1 | CD |
| Late | Cracking | Rup + DUAL MAGNUM 1120 | 1.1 | 0.1 | DE |
| Late | Cracking | Rup 840 | 1.0 | 0.1 | E |
| Late | Pre-Plant | Rup + 410P9M 1260 | 1.2 | 0.1 | A |
| Late | Pre-Plant | Rup + 410P9M 1960 | 1.1 | 0.1 | A |
| Late | Pre-Plant | Rup + DUAL MAGNUM 1960 | 1.1 | 0.1 | A |
| Late | Pre-Plant | Rup + 410P9M 1680 | 1.1 | 0.1 | A |
| Late | Pre-Plant | Rup + DUAL MAGNUM 1400 | 1.0 | 0.1 | A |
| Late | Pre-Plant | Rup + DUAL MAGNUM 1680 | 1.0 | 0.1 | A |
| Late | Pre-Plant | Rup + 410P9M 1120 | 1.0 | 0.1 | A |
| Late | Pre-Plant | Rup 840 | 1.0 | 0.1 | A |
| Late | Pre-Plant | Rup + DUAL MAGNUM 1120 | 1.0 | 0.1 | A |
| Late | V2 | Rup + 410P9M 1960 | 2.7 | 0.1 | A |
| Late | V2 | Rup + DUAL MAGNUM 1960 | 2.5 | 0.1 | AB |
| Late | V2 | Rup + 410P9M 1680 | 2.3 | 0.1 | BC |
| Late | V2 | Rup + DUAL MAGNUM 1680 | 2.2 | 0.1 | CD |
| Late | V2 | Rup + 410P9M 1120 | 2.1 | 0.1 | CDE |
| Late | V2 | Rup + 410P9M 1260 | 2.1 | 0.1 | CDE |
| Late | V2 | Rup + DUAL MAGNUM 1400 | 2.0 | 0.1 | DE |
| Late | V2 | Rup + DUAL MAGNUM 1120 | 1.8 | 0.1 | E |
| Late | V2 | Rup 840 | 1.1 | 0.1 | F |

Crop injury at 21 DAT with early pre-plant application ranged from 1.0 (no injury) for ROUNDUP alone up to 2.0 (0-2% injury) for ROUNDUP tank mixed with the encapsulated acetochlor formulation 410P9M at 1960 g ai/ha. Comparing the current field application rates of 410P9M (1260 g ai/ha) to DUAL MAGNUM (1400 g ai/ha), the encapsulated acetochlor formulation 410P9M had significantly greater injury level than DUAL MAGNUM (1.8 (0-2% injury) versus 1.3 (0-1% injury)). However, this is not a level of injury that would be noticeable in the field without untreated controls present. By the late evaluation date (42 DAT), there was no significant difference in crop injury with any of the treatments.

Crop injury at 21 DAT with at planting application ranged from 1.1 (no injury) for ROUNDUP alone to 2.3 (2% injury) for ROUNDUP tank mixed with the encapsulated acetochlor formulation 410P9M at 1960 g ai/ha. The level of injury with composition 410P9M at 1260 g ai/ha was significantly greater than found on plants treated with DUAL MAGNUM at 1400 g ai/ha, 2.1 (2% injury) compared to 1.5 (1% injury). While these differences are statistically different they would not be noticeable under field conditions without untreated controls present. By the late evaluation (42 DAT), foliar injury levels were 1.6 or less (<2% injury) for all treatments with field use rates of the encapsulated acetochlor formulation 410P9M and DUAL MAGNUM having similar levels of injury.

For the at cracking application timing, the injury level for the encapsulated acetochlor formulation 410P9M was greater than DUAL MAGNUM at all application rates. Crop injury at 21 DAT with at cracking application ranged from 1.2 (no injury) for ROUNDUP alone to 3.5 (2-5% injury) for ROUNDUP tank mixed with composition 410P9M at 1960 g ai/ha. The level of injury with composition 410P9M at 1260 g ai/ha was significantly greater than found on plants treated with DUAL MAGNUM at 1400 g ai/ha, 3.1 (2-5% injury) compared to 2.0 (0-2% injury). These differences between treatments may be noticeable, but would still be considered minor and not a threat to crop yield. At 42 DAT, all injury ratings were 1.9 or less (0-2% injury) for all treatments. Field use rates of the encapsulated acetochlor formulation 410P9M (1260 g ai/ha) were significantly greater than that of DUAL MAGNUM (1400 g ai/ha), 1.7 (0-2% injury) versus 0.3 (0-1% injury).

For the early post application timing, the injury level of the encapsulated acetochlor formulation 410P9M was similar to DUAL MAGNUM within each application rate. Crop injury at 21 DAT with an early post application ranged from 1.2 (no injury) for ROUNDUP alone to 3.7 (5% injury) for ROUNDUP tank mixed with the encapsulated acetochlor formulation 410P9M at 1960 g ai/ha. The level of injury with composition 410P9M at 1260 g ai/ha was similar to that found on plants treated with DUAL MAGNUM at 1400 g ai/ha, 3.1 versus 3.0 (2-5% injury). At the 42 DAT evaluation, both the encapsulated acetochlor formulation 410P9M and DUAL MAGNUM at field use rates had similar levels of crop injury of 2.0-2.1 (0-2% injury).

No crop injury was observed for the early pre-plant or at planting application of the herbicides at the six trial locations. For the at cracking applications, injury was observed at one trial location at 21 DAT. No significant differences in crop injury were observed with this application timing based on treatment or rate. Injury was minor with 5% or less reported at this trial location. No injury was reported at 42 DAT.

Three trial locations reported injury with the early post application timing at 21 DAT. At two locations, DUAL MAGNUM applications caused significantly greater injury than formulations of composition 410P9M at field use rates. DUAL MAGNUM (1400 g ai/ha) caused between 8.1-12.5% injury, while the encapsulated acetochlor formulation 410P9M (1260 g ai/ha) had no injury observed. In the third trial, composition 410P9M (1260 g ai/ha) had 6.0% injury, while no injury was noted with DUAL MAGNUM (1400 g ai/ha). These levels of injury are not considered high enough to cause reductions in crop yield with RR Soybeans.

Weed efficacy on crabgrass (DIGSA), purslane (POROL), and *quitensis amaranthus* (AMAQU) at early (21 DAT) and late (42 DAT) evaluations from the combined data from 7 field trials is shown in the table below. Mean separation is within individual application and rating timings.

TABLE

| Weed Species | DAT | Application Timing | Product Formulation/ Rate (g/ha) | Weed Control (LS Mean) | SE | Mean Separation |
|---|---|---|---|---|---|---|
| DIGSA | 21 | At Plant | Rup + DUAL MAGNUM 1680 | 92 | 3.9 | A |
| DIGSA | 21 | At Plant | Rup + 410P9M 1960 | 90 | 3.9 | AB |
| DIGSA | 21 | At Plant | Rup + DUAL MAGNUM 1960 | 90 | 3.9 | AB |
| DIGSA | 21 | At Plant | Rup + DUAL MAGNUM 1400 | 89 | 3.9 | AB |
| DIGSA | 21 | At Plant | Rup + DUAL MAGNUM 1120 | 89 | 3.9 | ABC |
| DIGSA | 21 | At Plant | Rup + 410P9M 1680 | 87 | 3.9 | BC |
| DIGSA | 21 | At Plant | Rup + 410P9M 1260 | 86 | 3.9 | C |
| DIGSA | 21 | At Plant | Rup + 410P9M 1120 | 85 | 3.9 | CD |
| DIGSA | 21 | At Plant | Rup 840 | 82 | 3.9 | D |
| DIGSA | 21 | Cracking | Rup + DUAL MAGNUM 1960 | 97 | 3.0 | A |
| DIGSA | 21 | Cracking | Rup + 410P9M 1680 | 97 | 3.0 | A |
| DIGSA | 21 | Cracking | Rup + 410P9M 1960 | 96 | 3.0 | A |
| DIGSA | 21 | Cracking | Rup + 410P9M 1120 | 96 | 3.0 | A |
| DIGSA | 21 | Cracking | Rup + 410P9M 1260 | 95 | 3.0 | AB |
| DIGSA | 21 | Cracking | Rup + DUAL MAGNUM 1680 | 94 | 3.0 | ABC |
| DIGSA | 21 | Cracking | Rup + DUAL MAGNUM 1400 | 91 | 3.0 | BCD |
| DIGSA | 21 | Cracking | Rup 840 | 90 | 3.0 | CD |
| DIGSA | 21 | Cracking | Rup + DUAL MAGNUM 1120 | 89 | 3.0 | D |
| DIGSA | 21 | Pre-Plant | Rup + 410P9M 1960 | 82 | 8.4 | A |
| DIGSA | 21 | Pre-Plant | Rup + DUAL MAGNUM 1960 | 78 | 8.4 | AB |
| DIGSA | 21 | Pre-Plant | Rup + 410P9M 1680 | 73 | 8.4 | ABC |
| DIGSA | 21 | Pre-Plant | Rup + DUAL MAGNUM 1680 | 72 | 8.4 | BC |
| DIGSA | 21 | Pre-Plant | Rup + 410P9M 1260 | 70 | 8.4 | BC |

TABLE-continued

| Weed Species | DAT | Application Timing | Product Formulation/ Rate (g/ha) | Weed Control (LS Mean) | SE | Mean Separation |
|---|---|---|---|---|---|---|
| DIGSA | 21 | Pre-Plant | Rup + DUAL MAGNUM 1400 | 70 | 8.4 | BC |
| DIGSA | 21 | Pre-Plant | Rup + 410P9M 1120 | 67 | 8.4 | C |
| DIGSA | 21 | Pre-Plant | Rup + DUAL MAGNUM 1120 | 66 | 8.4 | C |
| DIGSA | 21 | Pre-Plant | Rup 840 | 43 | 8.4 | D |
| DIGSA | 21 | V2 | Rup + DUAL MAGNUM 1960 | 99 | 1.1 | A |
| DIGSA | 21 | V2 | Rup + DUAL MAGNUM 1400 | 98 | 1.1 | AB |
| DIGSA | 21 | V2 | Rup + DUAL MAGNUM 1680 | 98 | 1.1 | AB |
| DIGSA | 21 | V2 | Rup + 410P9M 1680 | 98 | 1.1 | AB |
| DIGSA | 21 | V2 | Rup + 410P9M 1260 | 97 | 1.1 | AB |
| DIGSA | 21 | V2 | Rup + 410P9M 1960 | 97 | 1.1 | AB |
| DIGSA | 21 | V2 | Rup + DUAL MAGNUM 1120 | 97 | 1.1 | B |
| DIGSA | 21 | V2 | Rup + 410P9M 1120 | 97 | 1.1 | B |
| DIGSA | 21 | V2 | Rup 840 | 95 | 1.1 | C |
| DIGSA | 42 | At Plant | Rup + DUAL MAGNUM 1680 | 76 | 7.7 | A |
| DIGSA | 42 | At Plant | Rup + 410P9M 1960 | 74 | 7.7 | AB |
| DIGSA | 42 | At Plant | Rup + DUAL MAGNUM 1960 | 74 | 7.7 | AB |
| DIGSA | 42 | At Plant | Rup + 410P9M 1680 | 69 | 7.7 | ABC |
| DIGSA | 42 | At Plant | Rup + 410P9M 1260 | 68 | 7.7 | BC |
| DIGSA | 42 | At Plant | Rup + 410P9M 1120 | 66 | 7.7 | C |
| DIGSA | 42 | At Plant | Rup + DUAL MAGNUM 1400 | 66 | 7.7 | C |
| DIGSA | 42 | At Plant | Rup + DUAL MAGNUM 1120 | 64 | 7.7 | C |
| DIGSA | 42 | At Plant | Rup 840 | 49 | 7.7 | D |
| DIGSA | 42 | Cracking | Rup + 410P9M 1680 | 92 | 5.6 | A |
| DIGSA | 42 | Cracking | Rup + 410P9M 1960 | 89 | 5.6 | AB |
| DIGSA | 42 | Cracking | Rup + DUAL MAGNUM1960 | 89 | 5.6 | AB |
| DIGSA | 42 | Cracking | Rup + DUAL MAGNUM 1400 | 85 | 5.6 | AB |
| DIGSA | 42 | Cracking | Rup + 410P9M 1260 | 85 | 5.6 | AB |
| DIGSA | 42 | Cracking | Rup + DUAL MAGNUM 1680 | 83 | 5.6 | B |
| DIGSA | 42 | Cracking | Rup + 410P9M 1120 | 82 | 5.6 | B |
| DIGSA | 42 | Cracking | Rup + DUAL MAGNUM 1120 | 72 | 5.6 | C |
| DIGSA | 42 | Cracking | Rup 840 | 68 | 5.6 | C |
| DIGSA | 42 | Pre-Plant | Rup + 410P9M 1680 | 62 | 8.5 | A |
| DIGSA | 42 | Pre-Plant | Rup + DUAL MAGNUM 1960 | 59 | 8.5 | AB |

TABLE-continued

| Weed Species | DAT | Application Timing | Product Formulation/ Rate (g/ha) | Weed Control (LS Mean) | SE | Mean Separation |
|---|---|---|---|---|---|---|
| DIGSA | 42 | Pre-Plant | Rup + 410P9M 1960 | 58 | 8.5 | AB |
| DIGSA | 42 | Pre-Plant | Rup + 410P9M 1260 | 55 | 8.5 | BC |
| DIGSA | 42 | Pre-Plant | Rup + DUAL MAGNUM 1680 | 54 | 8.5 | BC |
| DIGSA | 42 | Pre-Plant | Rup + DUAL MAGNUM 1400 | 54 | 8.5 | BC |
| DIGSA | 42 | Pre-Plant | Rup + 410P9M 1120 | 50 | 8.5 | C |
| DIGSA | 42 | Pre-Plant | Rup + DUAL MAGNUM 1120 | 48 | 8.5 | C |
| DIGSA | 42 | Pre-Plant | Rup 840 | 25 | 8.5 | D |
| DIGSA | 42 | V2 | Rup + DUAL MAGNUM 1400 | 96 | 2.6 | A |
| DIGSA | 42 | V2 | Rup + DUAL MAGNUM 1960 | 95 | 2.6 | AB |
| DIGSA | 42 | V2 | Rup + DUAL MAGNUM 1680 | 94 | 2.6 | ABC |
| DIGSA | 42 | V2 | Rup + DUAL MAGNUM 1120 | 92 | 2.6 | ABCD |
| DIGSA | 42 | V2 | Rup + 410P9M 1960 | 92 | 2.6 | ABCD |
| DIGSA | 42 | V2 | Rup + 410P9M 1680 | 90 | 2.6 | BCD |
| DIGSA | 42 | V2 | Rup + 410P9M 1120 | 89 | 2.6 | CD |
| DIGSA | 42 | V2 | Rup + 410P9M 1260 | 88 | 2.6 | D |
| DIGSA | 42 | V2 | Rup 840 | 83 | 2.6 | E |
| POROL | 21 | At Plant | Rup + 410P9M 1960 | 84 | 8.8 | A |
| POROL | 21 | At Plant | Rup + 410P9M 1680 | 82 | 8.8 | A |
| POROL | 21 | At Plant | Rup + 410P9M 1120 | 79 | 8.8 | A |
| POROL | 21 | At Plant | Rup + 410P9M 1260 | 79 | 8.8 | A |
| POROL | 21 | At Plant | Rup + DUAL MAGNUM 1960 | 78 | 8.8 | A |
| POROL | 21 | At Plant | Rup + DUAL MAGNUM 1400 | 77 | 8.8 | A |
| POROL | 21 | At Plant | Rup + DUAL MAGNUM 1120 | 75 | 8.8 | A |
| POROL | 21 | At Plant | Rup840 | 75 | 8.8 | A |
| POROL | 21 | At Plant | Rup + DUAL MAGNUM 1680 | 74 | 8.8 | A |
| POROL | 21 | Cracking | Rup + 410P9M 1680 | 92 | 6.7 | A |
| POROL | 21 | Cracking | Rup + DUAL MAGNUM 1960 | 91 | 6.7 | A |
| POROL | 21 | Cracking | Rup + DUAL MAGNUM 1120 | 87 | 6.7 | A |
| POROL | 21 | Cracking | Rup + 410P9M 1260 | 87 | 6.7 | A |
| POROL | 21 | Cracking | Rup + 410P9M 1960 | 87 | 6.7 | A |
| POROL | 21 | Cracking | Rup + DUAL MAGNUM1400 | 86 | 6.7 | A |
| POROL | 21 | Cracking | Rup + DUAL MAGNUM 1680 | 85 | 6.7 | A |

TABLE-continued

| Weed Species | DAT | Application Timing | Product Formulation/ Rate (g/ha) | Weed Control (LS Mean) | SE | Mean Separation |
|---|---|---|---|---|---|---|
| POROL | 21 | Cracking | Rup + 410P9M 1120 | 83 | 6.7 | A |
| POROL | 21 | Cracking | Rup 840 | 81 | 6.7 | A |
| POROL | 21 | Pre-Plant | Rup + 410P9M 1960 | 74 | 13.5 | A |
| POROL | 21 | Pre-Plant | Rup + DUAL MAGNUM 1400 | 70 | 13.5 | AB |
| POROL | 21 | Pre-Plant | Rup + 410P9M 1680 | 67 | 13.5 | AB |
| POROL | 21 | Pre-Plant | Rup + 410P9M 1260 | 65 | 13.5 | AB |
| POROL | 21 | Pre-Plant | Rup + 410P9M 1120 | 65 | 13.5 | AB |
| POROL | 21 | Pre-Plant | Rup + DUAL MAGNUM 1960 | 64 | 13.5 | AB |
| POROL | 21 | Pre-Plant | Rup + DUAL MAGNUM 1680 | 58 | 13.5 | ABC |
| POROL | 21 | Pre-Plant | Rup + DUAL MAGNUM 1120 | 57 | 13.5 | BC |
| POROL | 21 | Pre-Plant | Rup 840 | 43 | 13.5 | C |
| POROL | 21 | V2 | Rup + DUAL MAGNUM 1960 | 92 | 6.4 | A |
| POROL | 21 | V2 | Rup + 410P9M 1960 | 91 | 6.4 | A |
| POROL | 21 | V2 | Rup + DUAL MAGNUM 1120 | 91 | 6.4 | A |
| POROL | 21 | V2 | Rup + DUAL MAGNUM 1680 | 90 | 6.4 | A |
| POROL | 21 | V2 | Rup 840 | 90 | 6.4 | A |
| POROL | 21 | V2 | Rup + 410P9M 1680 | 88 | 6.4 | A |
| POROL | 21 | V2 | Rup + 410P9M 1260 | 88 | 6.4 | A |
| POROL | 21 | V2 | Rup + DUAL MAGNUM 1400 | 88 | 6.4 | A |
| POROL | 21 | V2 | Rup + 410P9M 1120 | 86 | 6.4 | A |
| POROL | 42 | At Plant | Rup + 410P9M 1960 | 65 | 22.7 | A |
| POROL | 42 | At Plant | Rup + 410P9M 1680 | 60 | 22.7 | A |
| POROL | 42 | At Plant | Rup + DUAL MAGNUM 1680 | 57 | 22.7 | A |
| POROL | 42 | At Plant | Rup 840 | 56 | 22.7 | A |
| POROL | 42 | At Plant | Rup + DUAL MAGNUM 400 | 56 | 22.7 | A |
| POROL | 42 | At Plant | Rup + DUAL MAGNUM 960 | 56 | 22.7 | A |
| POROL | 42 | At Plant | Rup + 410P9M 1260 | 56 | 22.7 | A |
| POROL | 42 | At Plant | Rup + DUAL MAGNUM 1120 | 53 | 22.7 | A |
| POROL | 42 | At Plant | Rup + 410P9M 1120 | 52 | 22.7 | A |
| POROL | 42 | Cracking | Rup + 410P9M 1680 | 79 | 19.0 | A |
| POROL | 42 | Cracking | Rup + 410P9M 1260 | 70 | 19.0 | AB |
| POROL | 42 | Cracking | Rup + 410P9M 1960 | 69 | 19.0 | AB |
| POROL | 42 | Cracking | Rup + 410P9M 1120 | 66 | 19.0 | B |
| POROL | 42 | Cracking | Rup + DUAL MAGNUM 1680 | 61 | 19.0 | BC |

TABLE-continued

| Weed Species | DAT | Application Timing | Product Formulation/ Rate (g/ha) | Weed Control (LS Mean) | SE | Mean Separation |
|---|---|---|---|---|---|---|
| POROL | 42 | Cracking | Rup + DUAL MAGNUM 1400 | 61 | 19.0 | BC |
| POROL | 42 | Cracking | Rup + DUAL MAGNUM 1120 | 60 | 19.0 | BC |
| POROL | 42 | Cracking | Rup + DUAL MAGNUM 1960 | 58 | 19.0 | BC |
| POROL | 42 | Cracking | Rup 840 | 53 | 19.0 | C |
| POROL | 42 | Pre-Plant | Rup + 410P9M 1960 | 65 | 22.6 | A |
| POROL | 42 | Pre-Plant | Rup + 410P9M 1120 | 57 | 22.6 | AB |
| POROL | 42 | Pre-Plant | Rup + 410P9M 1260 | 54 | 22.6 | ABC |
| POROL | 42 | Pre-Plant | Rup + 410P9M 1680 | 47 | 22.6 | BC |
| POROL | 42 | Pre-Plant | Rup + DUAL MAGNUM 1400 | 43 | 22.6 | BCD |
| POROL | 42 | Pre-Plant | Rup + DUAL MAGNUM 1960 | 43 | 22.6 | BCD |
| POROL | 42 | Pre-Plant | Rup + DUAL MAGNUM 1120 | 40 | 22.6 | CD |
| POROL | 42 | Pre-Plant | Rup + DUAL MAGNUM 1680 | 39 | 22.6 | CD |
| POROL | 42 | Pre-Plant | Rup 840 | 28 | 22.6 | D |
| POROL | 42 | V2 | Rup + DUAL MAGNUM 1680 | 91 | 11.4 | A |
| POROL | 42 | V2 | Rup + DUAL MAGNUM 1960 | 90 | 11.4 | A |
| POROL | 42 | V2 | Rup + DUAL MAGNUM 1120 | 84 | 11.4 | AB |
| POROL | 42 | V2 | Rup + DUAL MAGNUM 1400 | 81 | 11.4 | ABC |
| POROL | 42 | V2 | Rup + 410P9M 1960 | 80 | 11.4 | ABC |
| POROL | 42 | V2 | Rup + 410P9M 1680 | 78 | 11.4 | BC |
| POROL | 42 | V2 | Rup 840 | 78 | 11.4 | BC |
| POROL | 42 | V2 | Rup + 410P9M 1260 | 73 | 11.4 | C |
| POROL | 42 | V2 | Rup + 410P9M 1120 | 73 | 11.4 | C |
| AMAQU | 21 | At Plant | Rup + DUAL MAGNUM 1680 | 100 | 0.2 | A |
| AMAQU | 21 | At Plant | Rup + 410P9M 1260 | 100 | 0.2 | A |
| AMAQU | 21 | At Plant | Rup + 410P9M 1680 | 100 | 0.2 | A |
| AMAQU | 21 | At Plant | Rup + 410P9M 1960 | 100 | 0.2 | A |
| AMAQU | 21 | At Plant | Rup + DUAL MAGNUM 1120 | 100 | 0.2 | A |
| AMAQU | 21 | At Plant | Rup + DUAL MAGNUM 1400 | 100 | 0.2 | A |
| AMAQU | 21 | At Plant | Rup + DUAL MAGNUM 1960 | 100 | 0.2 | A |
| AMAQU | 21 | At Plant | Rup + 410P9M 1120 | 100 | 0.2 | A |
| AMAQU | 21 | At Plant | Rup 840 | 98 | 0.2 | B |
| AMAQU | 21 | Cracking | Rup + DUAL MAGNUM 1400 | 100 | 1.1 | A |

TABLE-continued

| Weed Species | DAT | Application Timing | Product Formulation/ Rate (g/ha) | Weed Control (LS Mean) | SE | Mean Separation |
|---|---|---|---|---|---|---|
| AMAQU | 21 | Cracking | Rup + DUAL MAGNUM 1960 | 100 | 1.1 | A |
| AMAQU | 21 | Cracking | Rup + 410P9M 1680 | 100 | 1.1 | A |
| AMAQU | 21 | Cracking | Rup + 410P9M 1960 | 100 | 1.1 | A |
| AMAQU | 21 | Cracking | Rup + 410P9M 1120 | 99 | 1.1 | AB |
| AMAQU | 21 | Cracking | Rup + DUAL MAGNUM 1120 | 99 | 1.1 | AB |
| AMAQU | 21 | Cracking | Rup + DUAL MAGNUM 1680 | 99 | 1.1 | AB |
| AMAQU | 21 | Cracking | Rup + 410P9M 1260 | 99 | 1.1 | AB |
| AMAQU | 21 | Cracking | Rup 840 | 97 | 1.1 | B |
| AMAQU | 21 | Pre-Plant | Rup + 410P9M 1960 | 99 | 1.8 | A |
| AMAQU | 21 | Pre-Plant | Rup + 410P9M 1680 | 99 | 1.8 | AB |
| AMAQU | 21 | Pre-Plant | Rup + 410P9M 1260 | 98 | 1.8 | AB |
| AMAQU | 21 | Pre-Plant | Rup + DUAL MAGNUM 1680 | 98 | 1.8 | AB |
| AMAQU | 21 | Pre-Plant | Rup + DUAL MAGNUM 1960 | 98 | 1.8 | AB |
| AMAQU | 21 | Pre-Plant | Rup + 410P9M 1120 | 98 | 1.8 | AB |
| AMAQU | 21 | Pre-Plant | Rup + DUAL MAGNUM 1400 | 97 | 1.8 | AB |
| AMAQU | 21 | Pre-Plant | Rup + DUAL MAGNUM 1120 | 95 | 1.8 | B |
| AMAQU | 21 | Pre-Plant | Rup 840 | 88 | 1.8 | C |
| AMAQU | 42 | At Plant | Rup + 410P9M 1120 | 100 | 14.1 | A |
| AMAQU | 42 | At Plant | Rup + DUAL MAGNUM 1680 | 78 | 14.1 | AB |
| AMAQU | 42 | At Plant | Rup + 410P9M 1680 | 78 | 14.1 | AB |
| AMAQU | 42 | At Plant | Rup + DUAL MAGNUM 1120 | 70 | 14.1 | AB |
| AMAQU | 42 | At Plant | Rup 840 | 67 | 14.1 | AB |
| AMAQU | 42 | At Plant | Rup + 410P9M 1260 | 64 | 14.1 | B |
| AMAQU | 42 | At Plant | Rup + DUAL MAGNUM 1400 | 63 | 14.1 | B |
| AMAQU | 42 | At Plant | Rup + DUAL MAGNUM 1960 | 63 | 14.1 | B |
| AMAQU | 42 | At Plant | Rup + 410P9M 1960 | 58 | 14.1 | B |
| AMAQU | 42 | Cracking | Rup + DUAL MAGNUM 1120 | 89 | 16.8 | A |
| AMAQU | 42 | Cracking | Rup + DUAL MAGNUM 1400 | 81 | 16.8 | A |
| AMAQU | 42 | Cracking | Rup + 410P9M 1960 | 80 | 16.8 | A |
| AMAQU | 42 | Cracking | Rup + 410P9M 1260 | 79 | 16.8 | A |
| AMAQU | 42 | Cracking | Rup + 410P9M 1680 | 79 | 16.8 | A |
| AMAQU | 42 | Cracking | Rup + 410P9M 1120 | 74 | 16.8 | A |

TABLE-continued

| Weed Species | DAT | Application Timing | Product Formulation/ Rate (g/ha) | Weed Control (LS Mean) | SE | Mean Separation |
|---|---|---|---|---|---|---|
| AMAQU | 42 | Cracking | Rup + DUAL MAGNUM 1960 | 71 | 16.8 | A |
| AMAQU | 42 | Cracking | Rup + DUAL MAGNUM 1680 | 66 | 16.8 | A |
| AMAQU | 42 | Cracking | Rup 840 | 59 | 16.8 | A |
| AMAQU | 42 | Pre-Plant | Rup + DUAL MAGNUM 1680 | 98 | 14.0 | A |
| AMAQU | 42 | Pre-Plant | Rup + 410P9M 1260 | 98 | 14.0 | A |
| AMAQU | 42 | Pre-Plant | Rup + DUAL MAGNUM1400 | 80 | 14.0 | A |
| AMAQU | 42 | Pre-Plant | Rup + 410P9M 1120 | 78 | 14.0 | A |
| AMAQU | 42 | Pre-Plant | Rup + DUAL MAGNUM 1120 | 70 | 14.0 | A |
| AMAQU | 42 | Pre-Plant | Rup + 410P9M 1960 | 68 | 14.0 | A |
| AMAQU | 42 | Pre-Plant | Rup + DUAL MAGNUM 960 | 65 | 14.0 | A |
| AMAQU | 42 | Pre-Plant | Rup 840 | 65 | 14.0 | A |
| AMAQU | 42 | Pre-Plant | Rup + 410P9M 1680 | 60 | 14.0 | A |
| AMAQU | 42 | V2 | Rup + 410P9M 1680 | 100 | 9.7 | A |
| AMAQU | 42 | V2 | Rup + 410P9M 1960 | 100 | 9.7 | A |
| AMAQU | 42 | V2 | Rup + DUAL MAGNUM 1120 | 93 | 9.7 | A |
| AMAQU | 42 | V2 | Rup + DUAL MAGNUM 1960 | 89 | 9.7 | A |
| AMAQU | 42 | V2 | Rup + 410P9M 1260 | 89 | 9.7 | A |
| AMAQU | 42 | V2 | Rup + DUAL MAGNUM 1400 | 83 | 9.7 | A |
| AMAQU | 42 | V2 | Rup 840 | 79 | 9.7 | A |
| AMAQU | 42 | V2 | Rup + DUAL MAGNUM 1680 | 71 | 9.7 | A |
| AMAQU | 42 | V2 | Rup + 410P9M 1120 | 71 | 9.7 | A |

In this study, Crabgrass (DIGSA) efficacy was similar for field use rates of the encapsulated acetochlor formulation 410P9M (1260 g ai/ha) and DUAL MAGNUM (1400 g ai/ha) for the early pre-plant, at cracking and early post applications. With the at planting application, DUAL MAGNUM was more efficacious than the encapsulated acetochlor formulation 410P9M (89% versus 86%) at 21 DAT. Both the at cracking and early post applications provided greater than 90% DIGSA efficacy 21 DAT.

At the second sampling date, 42 DAT, DIGSA efficacy was similar for field use rates of the encapsulated acetochlor formulation 410P9M and DUAL MAGNUM for the early pre-plant, at planting and at cracking application. With the early post application, DUAL MAGNUM provided significantly greater DIGSA control than the encapsulated acetochlor formulation 410P9M (96% versus 88%).

Common purslane (POROL) efficacy was similar for both formulations of the encapsulated acetochlor formulation 410P9M and DUAL MAGNUM at all application timings with field application rates at 21 DAT. At-cracking applications provided 87% control and early post application provided 88% control of POROL. At 42 DAT, no application timing provided commercially acceptable POROL control with field use rates of these herbicides.

*Quitensis amaranthus* (AMAQU) efficacy was similar for field use rates of the encapsulated acetochlor formulation 410P9M and DUAL MAGNUM for the early pre-plant, at planting and at cracking applications with greater than 97% control at 21 DAT. No data was taken for the 21 DAT rating for the early post applications. At 42 DAT, efficacy was statistically the same for field use rates of the encapsulated acetochlor formulation 410P9M and DUAL MAGNUM, but only composition 410P9M provided acceptable AMAQU control with the early pre-plant and early post applications.

Weed efficacy on smooth pigweed (AMACH), lambsquarters (CHEAL), *datura* (DATFE), and wild marigold (TAGMI) at early (21 DAT) and late (42 DAT) evaluations from the combined data from 6 field trials is shown in the table below. Mean separation is within individual application and rating timings.

TABLE

| Weed Species | DAT | Application Timing | Product Formulation/ Rate (g/ha) | % Efficacy (LS Mean) | SE | Mean Separation |
|---|---|---|---|---|---|---|
| AMACH | 21 | At Plant | Rup + DUAL MAGNUM 1400 | 100.0 | 3.74 | A |
| AMACH | 21 | At Plant | Rup + DUAL MAGNUM 1680 | 100.0 | 3.74 | A |
| AMACH | 21 | At Plant | Rup + DUAL MAGNUM 1960 | 100.0 | 3.74 | A |
| AMACH | 21 | At Plant | Rup + 410P9M 1680 | 99.5 | 3.74 | A |
| AMACH | 21 | At Plant | Rup + 410P9M 1960 | 98.8 | 3.74 | A |
| AMACH | 21 | At Plant | Rup + 410P9M 1260 | 98.3 | 4.32 | A |
| AMACH | 21 | At Plant | Rup + DUAL MAGNUM 1120 | 96.3 | 3.74 | A |
| AMACH | 21 | At Plant | Rup + 410P9M 1120 | 77.5 | 3.74 | B |
| AMACH | 21 | At Plant | Rup 840 | 62.5 | 3.74 | C |
| AMACH | 21 | Cracking | Rup + 410P9M 1260 | 99.0 | 4.82 | A |
| AMACH | 21 | Cracking | Rup + 410P9M 1120 | 98.8 | 4.75 | A |
| AMACH | 21 | Cracking | Rup + 410P9M 1960 | 98.8 | 4.75 | A |
| AMACH | 21 | Cracking | Rup + 410P9M 1680 | 97.3 | 4.75 | A |
| AMACH | 21 | Cracking | Rup + DUAL MAGNUM 1960 | 96.8 | 4.82 | A |
| AMACH | 21 | Cracking | Rup + DUAL MAGNUM 1680 | 95.3 | 5.23 | A |
| AMACH | 21 | Cracking | Rup + DUAL MAGNUM 1400 | 91.6 | 4.75 | A |
| AMACH | 21 | Cracking | Rup + DUAL MAGNUM 1120 | 87.0 | 4.82 | A |
| AMACH | 21 | Cracking | Rup 840 | 85.6 | 4.82 | A |
| AMACH | 21 | Pre-Plant | Rup + DUAL MAGNUM 1680 | 100.0 | 1.50 | A |
| AMACH | 21 | Pre-Plant | Rup + DUAL MAGNUM 1960 | 100.0 | 1.50 | A |
| AMACH | 21 | Pre-Plant | Rup + 410P9M 1120 | 100.0 | 1.50 | A |
| AMACH | 21 | Pre-Plant | Rup 840 | 100.0 | 1.50 | A |
| AMACH | 21 | Pre-Plant | Rup + DUAL MAGNUM 1400 | 99.4 | 1.50 | A |
| AMACH | 21 | Pre-Plant | Rup + 410P9M 1680 | 99.4 | 1.50 | A |
| AMACH | 21 | Pre-Plant | Rup + 410P9M 1960 | 99.4 | 1.50 | A |
| AMACH | 21 | Pre-Plant | Rup + 410P9M 1260 | 97.5 | 1.50 | A |
| AMACH | 21 | Pre-Plant | Rup + DUAL MAGNUM 1120 | 96.6 | 1.50 | A |
| AMACH | 21 | V2 | Rup + DUAL MAGNUM 1400 | 100.0 | 2.55 | A |
| AMACH | 21 | V2 | Rup + 410P9M 1960 | 99.9 | 2.61 | A |
| AMACH | 21 | V2 | Rup + 410P9M 1120 | 98.8 | 2.57 | A |
| AMACH | 21 | V2 | Rup + DUAL MAGNUM 1680 | 98.7 | 2.55 | A |
| AMACH | 21 | V2 | Rup + DUAL MAGNUM 1120 | 98.6 | 2.57 | A |
| AMACH | 21 | V2 | Rup + DUAL MAGNUM 1960 | 97.9 | 2.57 | A |
| AMACH | 21 | V2 | Rup + 410P9M 1680 | 97.5 | 2.57 | A |
| AMACH | 21 | V2 | Rup + 410P9M 1260 | 97.2 | 2.55 | A |
| AMACH | 21 | V2 | Rup 840 | 93.4 | 2.55 | A |
| AMACH | 42 | At Plant | Rup + DUAL MAGNUM 1960 | 99.4 | 10.56 | A |
| AMACH | 42 | At Plant | Rup + 410P9M 1680 | 96.2 | 10.56 | A |
| AMACH | 42 | At Plant | Rup + DUAL MAGNUM 1680 | 95.0 | 10.56 | A |
| AMACH | 42 | At Plant | Rup + DUAL MAGNUM 1400 | 94.4 | 10.56 | A |

TABLE-continued

| Weed Species | DAT | Application Timing | Product Formulation/ Rate (g/ha) | % Efficacy (LS Mean) | SE | Mean Separation |
|---|---|---|---|---|---|---|
| AMACH | 42 | At Plant | Rup + 410P9M 1960 | 89.6 | 10.66 | A |
| AMACH | 42 | At Plant | Rup + DUAL MAGNUM 1120 | 89.4 | 10.56 | A |
| AMACH | 42 | At Plant | Rup + 410P9M 1260 | 88.7 | 10.56 | A |
| AMACH | 42 | At Plant | Rup + 410P9M 1120 | 71.9 | 10.56 | A |
| AMACH | 42 | At Plant | Rup 840 | 59.7 | 10.66 | A |
| AMACH | 42 | Cracking | Rup + DUAL MAGNUM 1680 | 95.7 | 8.28 | A |
| AMACH | 42 | Cracking | Rup + DUAL MAGNUM 1960 | 93.8 | 8.11 | A |
| AMACH | 42 | Cracking | Rup + 410P9M 1680 | 91.3 | 8.11 | AB |
| AMACH | 42 | Cracking | Rup + 410P9M 1960 | 91.0 | 8.11 | AB |
| AMACH | 42 | Cracking | Rup + 410P9M 1260 | 90.6 | 8.11 | AB |
| AMACH | 42 | Cracking | Rup + 410P9M 1120 | 89.2 | 8.28 | AB |
| AMACH | 42 | Cracking | Rup + DUAL MAGNUM 1400 | 81.3 | 8.11 | B |
| AMACH | 42 | Cracking | Rup 840 | 66.2 | 8.28 | C |
| AMACH | 42 | Cracking | Rup + DUAL MAGNUM 1120 | 63.9 | 8.51 | C |
| AMACH | 42 | Pre-Plant | Rup + 410P9M 1960 | 91.2 | 12.86 | A |
| AMACH | 42 | Pre-Plant | Rup + DUAL MAGNUM 1960 | 91.2 | 12.86 | A |
| AMACH | 42 | Pre-Plant | Rup + 410P9M 1680 | 88.1 | 12.86 | A |
| AMACH | 42 | Pre-Plant | Rup + 410P9M 1120 | 87.2 | 12.86 | A |
| AMACH | 42 | Pre-Plant | Rup + DUAL MAGNUM 1400 | 85.0 | 12.86 | A |
| AMACH | 42 | Pre-Plant | Rup + DUAL MAGNUM 1680 | 84.4 | 12.86 | A |
| AMACH | 42 | Pre-Plant | Rup + 410P9M 1260 | 82.2 | 12.86 | A |
| AMACH | 42 | Pre-Plant | Rup + DUAL MAGNUM 1120 | 81.6 | 12.86 | A |
| AMACH | 42 | Pre-Plant | Rup 840 | 77.2 | 12.86 | A |
| AMACH | 42 | V2 | Rup + 410P9M 1960 | 100.0 | 2.35 | A |
| AMACH | 42 | V2 | Rup + DUAL MAGNUM 1400 | 100.0 | 2.20 | A |
| AMACH | 42 | V2 | Rup + 410P9M 1260 | 98.8 | 2.20 | AB |
| AMACH | 42 | V2 | Rup + DUAL MAGNUM 1680 | 98.8 | 2.20 | AB |
| AMACH | 42 | V2 | Rup + 410P9M 1120 | 97.9 | 2.35 | AB |
| AMACH | 42 | V2 | Rup + DUAL MAGNUM 960 | 97.4 | 2.35 | AB |
| AMACH | 42 | V2 | Rup + DUAL MAGNUM 1120 | 96.6 | 2.35 | AB |
| AMACH | 42 | V2 | Rup + 410P9M 1680 | 93.3 | 2.35 | BC |
| AMACH | 42 | V2 | Rup 840 | 87.5 | 2.20 | C |
| CHEAL | 21 | At Plant | Rup + DUAL MAGNUM 960 | 81.6 | 16.62 | A |
| CHEAL | 21 | At Plant | Rup + DUAL MAGNUM 1680 | 80.2 | 16.78 | A |
| CHEAL | 21 | At Plant | Rup + DUAL MAGNUM 1400 | 75.7 | 16.53 | A |
| CHEAL | 21 | At Plant | Rup + 410P9M 1960 | 75.0 | 16.53 | A |
| CHEAL | 21 | At Plant | Rup + 410P9M 1260 | 74.9 | 16.62 | A |
| CHEAL | 21 | At Plant | Rup + DUAL MAGNUM 1120 | 73.5 | 16.53 | A |
| CHEAL | 21 | At Plant | Rup + 410P9M 1680 | 73.4 | 16.62 | A |
| CHEAL | 21 | At Plant | Rup + 410P9M 1120 | 72.5 | 16.62 | A |

TABLE-continued

| Weed Species | DAT | Application Timing | Product Formulation/ Rate (g/ha) | % Efficacy (LS Mean) | SE | Mean Separation |
|---|---|---|---|---|---|---|
| CHEAL | 21 | At Plant | Rup 840 | 41.6 | 16.62 | A |
| CHEAL | 21 | Cracking | Rup + DUAL MAGNUM 1680 | 98.8 | 3.63 | A |
| CHEAL | 21 | Cracking | Rup + 410P9M 1120 | 96.4 | 3.63 | A |
| CHEAL | 21 | Cracking | Rup + DUAL MAGNUM 1120 | 95.8 | 3.63 | A |
| CHEAL | 21 | Cracking | Rup + 410P9M 1260 | 95.5 | 3.63 | A |
| CHEAL | 21 | Cracking | Rup + 410P9M 1680 | 94.8 | 3.63 | A |
| CHEAL | 21 | Cracking | Rup + 410P9M 1960 | 93.9 | 3.63 | A |
| CHEAL | 21 | Cracking | Rup + DUAL MAGNUM 1400 | 93.6 | 3.63 | A |
| CHEAL | 21 | Cracking | Rup + DUAL MAGNUM 1960 | 93.1 | 3.63 | A |
| CHEAL | 21 | Cracking | Rup 840 | 90.9 | 3.63 | A |
| CHEAL | 42 | At Plant | Rup + DUAL MAGNUM 1960 | 76.7 | 14.78 | A |
| CHEAL | 42 | At Plant | Rup + DUAL MAGNUM 1680 | 56.9 | 14.78 | A |
| CHEAL | 42 | At Plant | Rup + DUAL MAGNUM 1400 | 56.3 | 14.78 | A |
| CHEAL | 42 | At Plant | Rup + DUAL MAGNUM 1120 | 48.1 | 14.78 | A |
| CHEAL | 42 | At Plant | Rup + 410P9M 1120 | 46.3 | 14.78 | A |
| CHEAL | 42 | At Plant | Rup + 410P9M 1960 | 35.6 | 14.78 | A |
| CHEAL | 42 | At Plant | Rup + 410P9M 1680 | 35.6 | 14.78 | A |
| CHEAL | 42 | At Plant | Rup + 410P9M 1260 | 26.9 | 14.78 | A |
| CHEAL | 42 | At Plant | Rup 840 | 17.5 | 14.78 | A |
| CHEAL | 42 | Cracking | Rup + DUAL MAGNUM 1680 | 91.3 | 10.75 | A |
| CHEAL | 42 | Cracking | Rup + DUAL MAGNUM 1120 | 86.3 | 10.75 | A |
| CHEAL | 42 | Cracking | Rup + 410P9M 1260 | 85.9 | 10.75 | A |
| CHEAL | 42 | Cracking | Rup + 410P9M 1680 | 85.6 | 10.75 | A |
| CHEAL | 42 | Cracking | Rup + DUAL MAGNUM 1400 | 85.4 | 10.75 | A |
| CHEAL | 42 | Cracking | Rup + DUAL MAGNUM 1960 | 79.6 | 10.75 | A |
| CHEAL | 42 | Cracking | Rup + 410P9M 1120 | 79.4 | 10.75 | A |
| CHEAL | 42 | Cracking | Rup + 410P9M 1960 | 76.9 | 10.75 | A |
| CHEAL | 42 | Cracking | Rup 840 | 62.5 | 10.75 | A |
| DATFE | 21 | At Plant | Rup + DUAL MAGNUM 1680 | 97.7 | 5.97 | A |
| DATFE | 21 | At Plant | Rup + DUAL MAGNUM 1960 | 97.2 | 5.97 | A |
| DATFE | 21 | At Plant | Rup + DUAL MAGNUM 1120 | 96.7 | 5.97 | A |
| DATFE | 21 | At Plant | Rup + DUAL MAGNUM 1400 | 95.1 | 5.97 | A |
| DATFE | 21 | At Plant | Rup + 410P9M 1960 | 95.0 | 5.97 | A |
| DATFE | 21 | At Plant | Rup + 410P9M 1680 | 94.2 | 5.97 | A |
| DATFE | 21 | At Plant | Rup + 410P9M 1120 | 92.5 | 5.97 | A |
| DATFE | 21 | At Plant | Rup + 410P9M 1260 | 90.2 | 5.97 | A |
| DATFE | 21 | At Plant | Rup 840 | 89.0 | 5.97 | A |
| DATFE | 21 | Cracking | Rup + DUAL MAGNUM 1680 | 97.9 | 1.86 | A |
| DATFE | 21 | Cracking | Rup + DUAL MAGNUM 1960 | 96.8 | 1.86 | A |
| DATFE | 21 | Cracking | Rup + 410P9M 1680 | 96.0 | 1.86 | A |

TABLE-continued

| Weed Species | DAT | Application Timing | Product Formulation/ Rate (g/ha) | % Efficacy (LS Mean) | SE | Mean Separation |
|---|---|---|---|---|---|---|
| DATFE | 21 | Cracking | Rup + DUAL MAGNUM 1120 | 95.9 | 1.86 | A |
| DATFE | 21 | Cracking | Rup + 410P9M 1120 | 95.3 | 1.86 | A |
| DATFE | 21 | Cracking | Rup + DUAL MAGNUM 1400 | 95.1 | 1.86 | A |
| DATFE | 21 | Cracking | Rup + 410P9M 1260 | 94.6 | 1.86 | A |
| DATFE | 21 | Cracking | Rup + 410P9M 1960 | 94.1 | 1.86 | A |
| DATFE | 21 | Cracking | Rup 840 | 87.6 | 1.86 | A |
| DATFE | 21 | Pre-Plant | Rup + 410P9M 1680 | 99.5 | 1.11 | A |
| DATFE | 21 | Pre-Plant | Rup + DUAL MAGNUM 1960 | 99.1 | 1.11 | A |
| DATFE | 21 | Pre-Plant | Rup + DUAL MAGNUM 1680 | 99.0 | 1.11 | A |
| DATFE | 21 | Pre-Plant | Rup + 410P9M 1960 | 99.0 | 1.11 | A |
| DATFE | 21 | Pre-Plant | Rup 840 | 98.9 | 1.11 | A |
| DATFE | 21 | Pre-Plant | Rup + 410P9M 1120 | 98.7 | 1.11 | A |
| DATFE | 21 | Pre-Plant | Rup + DUAL MAGNUM 1400 | 98.6 | 1.11 | A |
| DATFE | 21 | Pre-Plant | Rup + 410P9M 1260 | 98.4 | 1.11 | A |
| DATFE | 21 | Pre-Plant | Rup + DUAL MAGNUM 1120 | 97.6 | 1.11 | A |
| DATFE | 21 | V2 | Rup + DUAL MAGNUM 1400 | 98.8 | 2.33 | A |
| DATFE | 21 | V2 | Rup + DUAL MAGNUM 1960 | 98.8 | 2.33 | A |
| DATFE | 21 | V2 | Rup + 410P9M 1260 | 98.5 | 2.33 | A |
| DATFE | 21 | V2 | Rup + 410P9M 1680 | 98.5 | 2.33 | A |
| DATFE | 21 | V2 | Rup + DUAL MAGNUM 1120 | 98.1 | 2.38 | A |
| DATFE | 21 | V2 | Rup + 410P9M 1960 | 98.1 | 2.33 | A |
| DATFE | 21 | V2 | Rup + DUAL MAGNUM 1680 | 97.8 | 2.33 | A |
| DATFE | 21 | V2 | Rup + 410P9M 1120 | 97.5 | 2.33 | A |
| DATFE | 21 | V2 | Rup 840 | 95.4 | 2.33 | A |
| DATFE | 42 | Cracking | Rup + 410P9M 1680 | 95.6 | 8.05 | A |
| DATFE | 42 | Cracking | Rup + DUAL MAGNUM 1400 | 95.1 | 8.05 | A |
| DATFE | 42 | Cracking | Rup + DUAL MAGNUM 1960 | 95.0 | 8.05 | A |
| DATFE | 42 | Cracking | Rup + 410P9M 1960 | 94.4 | 8.05 | A |
| DATFE | 42 | Cracking | Rup + DUAL MAGNUM 1680 | 93.9 | 8.05 | A |
| DATFE | 42 | Cracking | Rup + DUAL MAGNUM 1120 | 92.7 | 8.05 | A |
| DATFE | 42 | Cracking | Rup + 410P9M 1260 | 91.9 | 8.05 | A |
| DATFE | 42 | Cracking | Rup + 410P9M 1120 | 91.2 | 8.05 | A |
| DATFE | 42 | Cracking | Rup 840 | 77.1 | 8.05 | A |
| DATFE | 42 | Pre-Plant | Rup + DUAL MAGNUM 1960 | 93.2 | 5.18 | A |
| DATFE | 42 | Pre-Plant | Rup + DUAL MAGNUM 1680 | 91.6 | 5.18 | A |
| DATFE | 42 | Pre-Plant | Rup + DUAL MAGNUM 1400 | 90.9 | 5.18 | A |
| DATFE | 42 | Pre-Plant | Rup + 410P9M 1120 | 89.2 | 5.18 | A |
| DATFE | 42 | Pre-Plant | Rup + 410P9M 1960 | 88.5 | 5.18 | A |
| DATFE | 42 | Pre-Plant | Rup + 410P9M 1260 | 87.4 | 5.18 | A |
| DATFE | 42 | Pre-Plant | Rup + 410P9M 1680 | 86.7 | 5.18 | A |

TABLE-continued

| Weed Species | DAT | Application Timing | Product Formulation/ Rate (g/ha) | % Efficacy (LS Mean) | SE | Mean Separation |
|---|---|---|---|---|---|---|
| DATFE | 42 | Pre-Plant | Rup 840 | 85.4 | 5.18 | A |
| DATFE | 42 | Pre-Plant | Rup + DUAL MAGNUM 1120 | 85.2 | 5.18 | A |
| DATFE | 42 | V2 | Rup + 410P9M 1960 | 97.9 | 1.46 | A |
| DATFE | 42 | V2 | Rup + DUAL MAGNUM 1960 | 97.2 | 1.46 | A |
| DATFE | 42 | V2 | Rup + 410P9M 1680 | 97.0 | 1.46 | A |
| DATFE | 42 | V2 | Rup + 410P9M 1260 | 96.7 | 1.46 | A |
| DATFE | 42 | V2 | Rup + 410P9M 1120 | 96.4 | 1.46 | A |
| DATFE | 42 | V2 | Rup + DUAL MAGNUM 1680 | 96.2 | 1.46 | A |
| DATFE | 42 | V2 | Rup + DUAL MAGNUM 1400 | 95.7 | 1.46 | A |
| DATFE | 42 | V2 | Rup 840 | 95.1 | 1.46 | A |
| DATFE | 42 | V2 | Rup + DUAL MAGNUM 1120 | 95.0 | 1.46 | A |
| TAGMI | 21 | At Plant | Rup + DUAL MAGNUM 1960 | 92.3 | 6.72 | A |
| TAGMI | 21 | At Plant | Rup + DUAL MAGNUM 1680 | 91.5 | 6.74 | A |
| TAGMI | 21 | At Plant | Rup + DUAL MAGNUM 1400 | 91.2 | 6.74 | A |
| TAGMI | 21 | At Plant | Rup + 410P9M 1960 | 90.4 | 6.69 | A |
| TAGMI | 21 | At Plant | Rup + DUAL MAGNUM 1120 | 89.9 | 6.67 | A |
| TAGMI | 21 | At Plant | Rup + 410P9M 1260 | 88.6 | 6.71 | A |
| TAGMI | 21 | At Plant | Rup + 410P9M 1120 | 88.4 | 6.67 | A |
| TAGMI | 21 | At Plant | Rup + 410P9M 1680 | 87.6 | 6.67 | A |
| TAGMI | 21 | At Plant | Rup 840 | 81.2 | 6.78 | A |
| TAGMI | 21 | Cracking | Rup + DUAL MAGNUM 1960 | 90.5 | 5.59 | A |
| TAGMI | 21 | Cracking | Rup + DUAL MAGNUM 1680 | 90.0 | 5.57 | A |
| TAGMI | 21 | Cracking | Rup + 410P9M 1960 | 89.8 | 5.55 | A |
| TAGMI | 21 | Cracking | Rup + 410P9M 1680 | 89.4 | 5.55 | A |
| TAGMI | 21 | Cracking | Rup + 410P9M 1120 | 88.5 | 5.59 | A |
| TAGMI | 21 | Cracking | Rup + DUAL MAGNUM 1400 | 85.7 | 5.55 | AB |
| TAGMI | 21 | Cracking | Rup + DUAL MAGNUM 1120 | 85.4 | 5.55 | AB |
| TAGMI | 21 | Cracking | Rup + 410P9M 1260 | 85.1 | 5.65 | AB |
| TAGMI | 21 | Cracking | Rup 840 | 80.2 | 5.55 | B |
| TAGMI | 21 | Pre-Plant | Rup + 410P9M 1260 | 99.6 | 0.91 | A |
| TAGMI | 21 | Pre-Plant | Rup + 410P9M 1960 | 99.6 | 0.91 | A |
| TAGMI | 21 | Pre-Plant | Rup + DUAL MAGNUM 1120 | 99.4 | 0.92 | A |
| TAGMI | 21 | Pre-Plant | Rup + DUAL MAGNUM 1400 | 99.3 | 0.91 | A |
| TAGMI | 21 | Pre-Plant | Rup + 410P9M 1680 | 99.3 | 0.91 | A |
| TAGMI | 21 | Pre-Plant | Rup + DUAL MAGNUM 1960 | 99.2 | 0.91 | A |
| TAGMI | 21 | Pre-Plant | Rup + DUAL MAGNUM 1680 | 99.1 | 0.91 | A |
| TAGMI | 21 | Pre-Plant | Rup + 410P9M 1120 | 99.0 | 0.91 | A |
| TAGMI | 21 | Pre-Plant | Rup 840 | 98.2 | 0.91 | A |
| TAGMI | 21 | V2 | Rup + DUAL MAGNUM 1960 | 98.4 | 2.43 | A |
| TAGMI | 21 | V2 | Rup + 410P9M 1960 | 98.1 | 2.61 | A |

TABLE-continued

| Weed Species | DAT | Application Timing | Product Formulation/ Rate (g/ha) | % Efficacy (LS Mean) | SE | Mean Separation |
|---|---|---|---|---|---|---|
| TAGMI | 21 | V2 | Rup + 410P9M 1260 | 98.0 | 2.45 | A |
| TAGMI | 21 | V2 | Rup + 410P9M 1120 | 96.5 | 2.40 | A |
| TAGMI | 21 | V2 | Rup + DUAL MAGNUM 1680 | 96.1 | 2.42 | A |
| TAGMI | 21 | V2 | Rup + 410P9M 1680 | 96.0 | 2.48 | A |
| TAGMI | 21 | V2 | Rup + DUAL MAGNUM1120 | 95.1 | 2.40 | A |
| TAGMI | 21 | V2 | Rup + DUAL MAGNUM 1400 | 93.5 | 2.54 | A |
| TAGMI | 21 | V2 | Rup 840 | 92.6 | 2.40 | A |
| TAGMI | 42 | At Plant | Rup + DUAL MAGNUM 1960 | 86.6 | 12.17 | A |
| TAGMI | 42 | At Plant | Rup + DUAL MAGNUM 1680 | 81.5 | 12.27 | A |
| TAGMI | 42 | At Plant | Rup + 410P9M 1120 | 79.3 | 12.17 | A |
| TAGMI | 42 | At Plant | Rup + DUAL MAGNUM 1400 | 79.1 | 12.27 | A |
| TAGMI | 42 | At Plant | Rup + DUAL MAGNUM 1120 | 77.2 | 12.20 | A |
| TAGMI | 42 | At Plant | Rup + 410P9M 1960 | 77.1 | 12.17 | A |
| TAGMI | 42 | At Plant | Rup + 410P9M 1680 | 75.8 | 12.20 | A |
| TAGMI | 42 | At Plant | Rup + 410P9M 1260 | 74.4 | 12.20 | A |
| TAGMI | 42 | At Plant | Rup 840 | 67.8 | 12.24 | A |
| TAGMI | 42 | Cracking | Rup + DUAL MAGNUM 1680 | 84.6 | 7.99 | A |
| TAGMI | 42 | Cracking | Rup + DUAL MAGNUM 1960 | 83.6 | 8.02 | A |
| TAGMI | 42 | Cracking | Rup + 410P9M 1680 | 81.4 | 7.96 | A |
| TAGMI | 42 | Cracking | Rup + DUAL MAGNUM 1400 | 79.9 | 8.02 | A |
| TAGMI | 42 | Cracking | Rup + 410P9M 1120 | 78.9 | 7.99 | A |
| TAGMI | 42 | Cracking | Rup + 410P9M 1260 | 78.5 | 8.02 | A |
| TAGMI | 42 | Cracking | Rup + 410P9M 1960 | 78.2 | 7.99 | A |
| TAGMI | 42 | Cracking | Rup + DUAL MAGNUM 1120 | 77.9 | 7.96 | A |
| TAGMI | 42 | Cracking | Rup 840 | 68.8 | 7.96 | B |
| TAGMI | 42 | Pre-Plant | Rup + 410P9M 1960 | 84.7 | 8.45 | A |
| TAGMI | 42 | Pre-Plant | Rup + DUAL MAGNUM 1680 | 80.9 | 8.45 | A |
| TAGMI | 42 | Pre-Plant | Rup + DUAL MAGNUM 1960 | 80.5 | 8.45 | A |
| TAGMI | 42 | Pre-Plant | Rup + 410P9M 1680 | 79.8 | 8.45 | A |
| TAGMI | 42 | Pre-Plant | Rup + 410P9M 1260 | 77.7 | 8.45 | A |
| TAGMI | 42 | Pre-Plant | Rup + DUAL MAGNUM 1120 | 76.1 | 8.45 | A |
| TAGMI | 42 | Pre-Plant | Rup + 410P9M 1120 | 74.0 | 8.45 | A |
| TAGMI | 42 | Pre-Plant | Rup + DUAL MAGNUM 1400 | 70.6 | 8.45 | A |
| TAGMI | 42 | Pre-Plant | Rup 840 | 70.3 | 8.45 | A |
| TAGMI | 42 | V2 | Rup + DUAL MAGNUM 1960 | 94.4 | 4.97 | A |
| TAGMI | 42 | V2 | Rup + DUAL MAGNUM 1680 | 93.9 | 4.92 | A |
| TAGMI | 42 | V2 | Rup + DUAL MAGNUM 1400 | 93.4 | 4.95 | A |
| TAGMI | 42 | V2 | Rup + 410P9M 1960 | 92.8 | 4.94 | A |
| TAGMI | 42 | V2 | Rup + 410P9M 1680 | 92.0 | 5.03 | A |
| TAGMI | 42 | V2 | Rup + 410P9M 1260 | 91.0 | 4.95 | A |

TABLE-continued

| Weed Species | DAT | Application Timing | Product Formulation/ Rate (g/ha) | % Efficacy (LS Mean) | SE | Mean Separation |
|---|---|---|---|---|---|---|
| TAGMI | 42 | V2 | Rup + 410P9M 1120 | 90.0 | 4.92 | A |
| TAGMI | 42 | V2 | Rup + DUAL MAGNUM 1120 | 86.5 | 4.94 | A |
| TAGMI | 42 | V2 | Rup 840 | 81.5 | 4.96 | A |

Smooth pigweed (AMACH) control was 97.2% or greater at 21 DAT for all four application timings in these trials with field use rates of both the encapsulated acetochlor formulation 410P9M (1260 g ai/ha) and DUAL MAGNUM (1400 g ai/ha). Pre-plant, at-planting, at-cracking and early post applications of DUAL MAGNUM and composition 410P9M were similar at 42 DAT with field use rates of each product. The early post application at field use rates provided 98.8% or better AMACH control at 42 DAT.

Lambsquarter (CHEAL) control was evaluated only with the at-planting and at-cracking applications. The at-planting application did not provide commercially acceptable levels of CHEAL control at 21 and 42 DAT. At-cracking applications of both DUAL MAGNUM and the encapsulated acetochlor formulation 410P9M provided 93.6% and 95.5% efficacy, respectively, at 21 DAT. At the later sampling date, 42 DAT, the at-cracking application provided 85.4-85.9% for CHEAL.

Datura (DATFE) efficacy was similar for the encapsulated acetochlor formulation 410P9M and DUAL MAGNUM at field application rates for all four application timings at 21 DAT. DATFE efficacy was 90.2% or greater with these application rates. At 42 DAT, DATFE efficacy was similar for both composition 410P9M and DUAL MAGNUM at field use rates with all four application timings and efficacy was 87.4% or greater.

Wild marigold (TAGMI) efficacy was similar for both DUAL MAGNUM and composition 410P9M at the early pre-plant application with 99.3-99.6% control at 21 DAT using field use rates of each product. At-planting applications of DUAL MAGNUM provided 91.2% control, which was similar to the control achieved with composition 410P9M with 88.6% TAGMI efficacy. Early post application of composition 410P9M at 1260 g ai/ha provided 98.0% efficacy, which was similar to the 93.5% control provided by DUAL MAGNUM at 1400 g ai/ha. The pre-planting, at-planting, and at-cracking application of composition 410P9M and DUAL MAGNUM provided less than 80.0% TAGMI efficacy at 42 DAT. The early post applications provided 91.0% efficacy for 410P9M and 93.4% for DUAL MAGNUM at 42 DAT.

Example 10

Preparation of Aqueous Dispersions of Microencapsulated Acetochlor

Various aqueous dispersions of microencapsulated acetochlor were prepared. The formulations were prepared using an amine component (TETA or a combination of TETA and XDA) and an isocyanate component (DES N3200 or MISTAFLEX, which is a blend of polyisocyanates comprising DES N3200 and DES W). Typically, the formulations contain an internal phase solvents such as NORPAR 15, ISOPAR V, ISOPAR L, EXXSOL D-130, or EXXSOL D-110, with the exception of formulations 2805A, 2805B, and 2805C. The formulations were prepared using an excess of amine equivalents. To prepare these formulations, batches of each of the internal phase, the external phase, the amine solution, and the stabilizer solution were prepared containing the components and amounts shown in the table below.

The aqueous dispersions of microcapsules were prepared substantially as described above in Example 1. The amine solutions were used to initiate polymerization. During emulsification, the mixer speed was varied by controlling the blender to achieve mean particle sizes as shown in the particle size table below. The particle size parameters were measured using a Beckman Coulter LS Particle Size Analyzer.

The acetochlor loading was varied among the formulations. For example, in formulations 609A, 609B, 609C, 660A, 660B, 660C, 664A, 664B, 664C, 668A, 668B, 668C, 672A, 672B, 672C, 680A, 680B, 680C, 684A, 684B, 684C, and 684D, the acetochlor loading was approximately 33% by weight, which is relatively lower than the acetochlor loading in DEGREE. In formulations 993A, 993B, and 993C, the acetochlor loading was approximately 38% by weight, which is relatively lower than the acetochlor loading in DEGREE. In formulations 997A, 997B, and 997C, the acetochlor loading was approximately 40% by weight, which is relatively lower than the acetochlor loading in DEGREE. In formulations 601A, 601B, and 601C, the acetochlor loading was approximately equal to DEGREE.

The proportion of shell wall components was varied among the formulations. For example, formulations 613A, 613B, and 613C were prepared using a higher proportion of shell wall components compared to commercially available DEGREE. The formulation for DEGREE employs about 8% by weight shell wall components compared to the acetochlor loading. By comparison, formulations 613A, 613B, and 613C were prepared with 16% by weight shell wall components compared to the acetochlor loading. Formulations 617A, 617B, and 617C were prepared using a similar relative proportion of shell wall components compared to DEGREE. Formulations 621A, 621B, 621C, and 621D were prepared using a higher proportion of shell wall components compared to DEGREE, but a lower proportion compared to formulations 613A, 613B, and 613C. Formulations 621A, 621B, 621C, and 621D were prepared with 12% by weight shell wall components compared to the acetochlor loading.

The weight ratio of acetochlor and internal phase solvent was also varied among the formulations. For example, the weight ratio of acetochlor to NORPAR 15 diluent was approximately 16:1 in formulations 684A, 684B, 684C, and 684D compared to about 19:1 in the formulations 680A, 680B, and 680C.

TABLE

| | | Formulation Components | | | | | | | | |
|---|---|---|---|---|---|---|---|---|---|---|
| | | Internal Phase | | | | Iso- | External Phase | | | |
| Form. | Molar Ratio Amine:Iso-cyanate | Acetochlor (g) | Solvent | Solvent mass (g) | Isocyanate | cyanate mass (g) | Glycerin (g) | Sokalan CP9 (g) | Ammonium Caseinate (g) | Acid (g) | Water (g) |
| 3993 | 1.29:1 | 175.0 | NORPAR 15 | 9.3 | DES N3200 | 13.01 | 32.5 | 9.45 | 0.19 | 0.72 | 115.0 |
| 3995 | 1.26:1 | 175.0 | NORPAR 15 | 9.3 | DES N3200 | 12.87 | 32.0 | 9.48 | 0.19 | 0.75 | 115.0 |
| 3997 | 1.25:1 | 175.0 | NORPAR 15 | 9.11 | DES N3200 | 12.79 | 32.0 | 9.41 | 0.19 | 0.72 | 115.0 |
| 2805A | 1.03:1-1.04 | 530.0 | — | — | DES N3200, DES W | 31.99, 5.65 | 104.0 | 30.6 | 0.60 | 2.22 | 373.0 |
| 2805B | 1.03:1-1.04 | 530.0 | — | — | DES N3200, DES W | 31.99, 5.65 | 104.0 | 30.6 | 0.60 | 2.22 | 373.0 |
| 2805C | 1.03:1-1.04 | 530.0 | — | — | DES N3200, DES W | 31.99, 5.65 | 104.0 | 30.6 | 0.60 | 2.22 | 373.0 |
| 831A | 1.04:1-1.05:1 | 504.01 | NORPAR 15 | 26.27 | MISTAFLEX H9915 | 36.60 | 103.05 | 30.38 | 0.61 | 2.35 | 372.01 |
| 831B | 1.04:1-1.05:1 | 504.01 | NORPAR 15 | 26.27 | MISTAFLEX H9915 | 36.60 | 103.05 | 30.38 | 0.61 | 2.35 | 372.01 |
| 831D | 1.04:1-1.05:1 | 504.01 | NORPAR 15 | 26.27 | MISTAFLEX H9915 | 36.60 | 103.05 | 30.38 | 0.61 | 2.35 | 372.01 |
| 838A | 1.04:1-1.05:1 | 669.0 | NORPAR 15 | 34.92 | MISTAFLEX H9915 | 49.10 | 137.0 | 40.45 | 0.81 | 3.10 | 494.00 |
| 838B | 1.04:1-1.05:1 | 669.0 | NORPAR 15 | 34.92 | MISTAFLEX H9915 | 49.10 | 137.0 | 40.45 | 0.81 | 3.10 | 494.00 |
| 838C | 1.04:1-1.05:1 | 669.0 | NORPAR 15 | 34.92 | MISTAFLEX H9915 | 49.10 | 137.0 | 40.45 | 0.81 | 3.10 | 494.00 |
| 838D | 1.04:1-1.05:1 | 669.0 | NORPAR 15 | 34.92 | MISTAFLEX H9915 | 49.10 | 137.0 | 40.45 | 0.81 | 3.10 | 494.00 |
| 843A | 1.04:1-1.05:1 | 669.0 | NORPAR 15 | 35.0 | MISTAFLEX H9915 | 49.58 | 137.10 | 40.4 | 0.81 | 3.0 | 494.02 |
| 843B | 1.04:1-1.05:1 | 669.0 | NORPAR 15 | 35.0 | MISTAFLEX H9915 | 49.58 | 137.10 | 40.40 | 0.81 | 3.0 | 494.02 |
| 843C | 1.04:1-1.05:1 | 669.0 | NORPAR 15 | 35.0 | MISTAFLEX H9915 | 49.58 | 137.10 | 40.40 | 0.81 | 3.0 | 494.02 |
| 843D | 1.04:1-1.05:1 | 669.0 | NORPAR 15 | 35.0 | MISTAFLEX H9915 | 49.58 | 137.10 | 40.40 | 0.81 | 3.0 | 494.02 |
| 874A | 1.2:1 | 352.70 | NORPAR 15 | 18.43 | MISTAFLEX H9916 | 25.73 | 64.60 | 19.06 | 0.38 | 1.39 | 232.80 |
| 874B | 1.2:1 | 352.70 | NORPAR 15 | 18.43 | MISTAFLEX H9917 | 25.73 | 64.60 | 19.06 | 0.38 | 1.39 | 232.80 |
| 877A | 1.1:1 | 353.0 | NORPAR 15 | 18.43 | MISTAFLEX H9915 | 26.30 | 64.69 | 19.1 | 0.38 | 1.40 | 233.08 |
| 877B | 1.1:1 | 353.0 | NORPAR 15 | 18.43 | MISTAFLEX H9915 | 26.30 | 64.69 | 19.1 | 0.38 | 1.40 | 233.08 |
| 880A | 1.3:1 | 353.0 | NORPAR 15 | 18.42 | MISTAFLEX H9915 | 25.33 | 64.50 | 19.05 | 0.37 | 1.40 | 232.5 |
| 880B | 1.3:1 | 353.0 | NORPAR 15 | 18.42 | MISTAFLEX H9915 | 25.33 | 64.50 | 19.05 | 0.37 | 1.40 | 232.5 |
| 883A | 1.15:1 | 352.75 | NORPAR 15 | 18.44 | MISTAFLEX H9915 | 25.97 | 64.65 | 19.07 | 0.38 | 1.37 | 232.92 |
| 885A | 1.25:1 | 174.18 | NORPAR 15 | 9.10 | MISTAFLEX H9915 | 12.65 | 32.0 | 9.4 | 0.19 | 0.70 | 115.0 |
| 911A | 1.2:1 | 352.7 | NORPAR 15 | 18.41 | DES N3200, DES W | 12.59, 12.59 | 64.50 | 19.0 | 0.4 | 1.39 | 232.3 |
| 911B | 1.2:1 | 352.7 | NORPAR 15 | 18.41 | DES N3200, DES W | 12.59, 12.59 | 64.50 | 19.0 | 0.4 | 1.39 | 232.3 |
| 914A | 1.2:1 | 352.70 | NORPAR 15 | 18.40 | DES N3200, DES W | 21.99, 4.0 | 64.60 | 19.1 | 0.4 | 1.38 | 232.77 |
| 914C | 1.2:1 | 352.70 | NORPAR 15 | 18.40 | DES N3200, DES W | 21.99, 4.0 | 64.60 | 19.1 | 0.4 | 1.38 | 232.77 |
| 917A | 1.2:1 | 352.65 | NORPAR 15 | 18.40 | DES N3200, DES W | 17.85, 7.66 | 64.57 | 19.01 | 0.38 | 1.41 | 232.60 |
| 917B | 1.2:1 | 352.65 | NORPAR 15 | 18.40 | DES N3200, DES W | 17.85, 7.66 | 64.57 | 19.01 | 0.38 | 1.41 | 232.60 |
| 934 | 1.05:1 | 175.50 | ISOPAR L | 9.10 | MISTAFLEX H9915 | 13.06 | 32.0 | 9.57 | 0.20 | 0.75 | 116.0 |
| 939 | 1.05:1 | 174.20 | ISOPAR L | 18.20 | MISTAFLEX H9915 | 13.70 | 30.00 | 8.90 | 0.18 | 0.75 | 108.0 |
| 936A | 1.05:1 | 352.70 | ISOPAR L | 18.40 | MISTAFLEX H9915 | 26.40 | 64.70 | 19.10 | 0.38 | 1.42 | 233.3 |
| 936B | 1.05:1 | 352.70 | ISOPAR L | 18.40 | MISTAFLEX H9915 | 26.40 | 64.70 | 19.10 | 0.38 | 1.42 | 233.3 |

TABLE-continued

Formulation Components

| | | | | | | | | | | | |
|---|---|---|---|---|---|---|---|---|---|---|---|
| 941A | 1.05:1 | 529.0 | ISOPAR V | 55.30 | MISTAFLEX H9915 | 41.60 | 90.90 | 26.80 | 0.54 | 2.09 | 327.60 |
| 941B | 1.05:1 | 529.0 | ISOPAR V | 55.30 | MISTAFLEX H9915 | 41.60 | 90.90 | 26.80 | 0.54 | 2.09 | 327.60 |
| 941C | 1.05:1 | 529.0 | ISOPAR V | 55.30 | MISTAFLEX H9915 | 41.60 | 90.90 | 26.80 | 0.54 | 2.09 | 327.60 |
| 945A | 1.05:1 | 529.0 | ISOPAR V | 27.65 | MISTAFLEX H9915 | 39.60 | 97.1 | 28.70 | 0.57 | 2.25 | 350.0 |
| 945B | 1.05:1 | 529.0 | ISOPAR V | 27.65 | MISTAFLEX H9915 | 39.60 | 97.1 | 28.70 | 0.57 | 2.25 | 350.0 |
| 945C | 1.05:1 | 529.0 | ISOPAR V | 27.65 | MISTAFLEX H9915 | 39.60 | 97.1 | 28.70 | 0.57 | 2.25 | 350.0 |
| 949 | 1.05:1 | 174.25 | Exxsol D-130 | 9.1 | MISTAFLEX H9915 | 13.1 | 32.0 | 9.5 | 0.2 | 0.75 | 115.3 |
| 951A | 1.05:1 | 352.70 | ISOPAR V | 18.42 | MISTAFLEX H9915 | 26.40 | 64.70 | 19.10 | 0.39 | 1.45 | 233.3 |
| 951B | 1.05:1 | 352.70 | ISOPAR V | 18.42 | MISTAFLEX H9915 | 26.40 | 64.70 | 19.10 | 0.39 | 1.45 | 233.3 |
| 954A | 1.05:1 | 352.7 | Exxsol D-130 | 36.85 | MISTAFLEX | 27.71 | 60.80 | 17.9 | 0.37 | 1.28 | 218.39 |
| 954B | 1.05:1 | 352.7 | Exxsol D-130 | 36.85 | MISTAFLEX | 27.71 | 60.80 | 17.9 | 0.37 | 1.28 | 218.39 |
| 957A | 1.05:1 | 353.0 | ISOPAR L | 36.90 | MISTAFLEX H9915 | 27.7 | 60.6 | 17.9 | 0.37 | 1.35 | 218.40 |
| 957B | 1.05:1 | 353.0 | ISOPAR L | 36.90 | MISTAFLEX H9915 | 27.7 | 60.6 | 17.9 | 0.37 | 1.35 | 218.40 |
| 960A | 1.05:1 | 352.70 | Exxsol D-130 | 36.83 | MISTAFLEX H9915 | 27.70 | 60.6 | 17.9 | 0.37 | 1.35 | 218.40 |
| 960B | 1.05:1 | 352.70 | Exxsol D-130 | 36.83 | MISTAFLEX H9915 | 27.70 | 60.6 | 17.9 | 0.37 | 1.35 | 218.40 |
| 993A | 1.2:1 | 483.0 | NORPAR 15 | 25.0 | MISTAFLEX H9915 | 35.20 | 108.0 | 31.82 | 0.64 | 2.40 | 389.0 |
| 993B | 1.2:1 | 483.0 | NORPAR 15 | 25.0 | MISTAFLEX H9915 | 35.20 | 108.0 | 31.82 | 0.64 | 2.40 | 389.0 |
| 993C | 1.2:1 | 483.0 | NORPAR 15 | 25.0 | MISTAFLEX H9915 | 35.20 | 108.0 | 31.82 | 0.64 | 2.40 | 389.0 |
| 997A | 1.2:1 | 508.40 | NORPAR 15 | 26.30 | MISTAFLEX H9915 | 37.10 | 101.90 | 30.05 | 0.61 | 2.25 | 367.0 |
| 997B | 1.2:1 | 508.40 | NORPAR 15 | 26.30 | MISTAFLEX H9915 | 37.10 | 101.90 | 30.05 | 0.61 | 2.25 | 367.0 |
| 997C | 1.2:1 | 508.40 | NORPAR 15 | 26.30 | MISTAFLEX H9915 | 37.10 | 101.90 | 30.05 | 0.61 | 2.25 | 367.0 |
| 601A | 1.2:1 | 534.60 | NORPAR 15 | 27.65 | MISTAFLEX H9915 | 39.0 | 95.66 | 28.22 | 0.58 | 2.25 | 345.0 |
| 601B | 1.2:1 | 534.60 | NORPAR 15 | 27.65 | MISTAFLEX H9915 | 39.0 | 95.66 | 28.22 | 0.58 | 2.25 | 345.0 |
| 601C | 1.2:1 | 534.60 | NORPAR 15 | 27.65 | MISTAFLEX H9915 | 39.0 | 95.66 | 28.22 | 0.58 | 2.25 | 345.0 |
| 609A | 1.2:1 | 418.10 | NORPAR 15 | 21.70 | MISTAFLEX H9915 | 30.56 | 123.10 | 36.32 | 0.74 | 2.84 | 443.6 |
| 609B | 1.2:1 | 418.10 | NORPAR 15 | 21.70 | MISTAFLEX H9915 | 30.56 | 123.10 | 36.32 | 0.74 | 2.84 | 443.6 |
| 609C | 1.2:1 | 418.10 | NORPAR 15 | 21.70 | MISTAFLEX H9915 | 30.56 | 123.10 | 36.32 | 0.74 | 2.84 | 443.6 |
| 613A | 1.2:1 | 507.0 | NORPAR 15 | 26.30 | MISTAFLEX H9915 | 81.01 | 88.81 | 26.2 | 0.52 | 1.96 | 320.0 |
| 613B | 1.2:1 | 507.0 | NORPAR 15 | 26.30 | MISTAFLEX H9915 | 81.01 | 88.81 | 26.2 | 0.52 | 1.96 | 320.0 |
| 613C | 1.2:1 | 507.0 | NORPAR 15 | 26.30 | MISTAFLEX H9915 | 81.01 | 88.81 | 26.2 | 0.52 | 1.96 | 320.0 |
| 617A | 1.25:1 | 506.78 | NORPAR 15 | 26.33 | MISTAFLEX H9915 | 35.48 | 102.2 | 31.1 | 0.62 | 2.85 | 368.3 |
| 617B | 1.25:1 | 506.78 | NORPAR 15 | 26.33 | MISTAFLEX H9915 | 35.48 | 102.2 | 31.1 | 0.62 | 2.85 | 368.3 |
| 617C | 1.25:1 | 506.78 | NORPAR 15 | 26.33 | MISTAFLEX H9915 | 35.48 | 102.2 | 31.1 | 0.62 | 2.85 | 368.3 |
| 621A | 1.2:1 | 675.72 | NORPAR 15 | 35.10 | MISTAFLEX H9915 | 77.3 | 127.6 | 37.90 | 0.25 | 3.0 | 461.0 |
| 621B | 1.2:1 | 675.72 | NORPAR 15 | 35.10 | MISTAFLEX H9915 | 77.3 | 127.6 | 37.90 | 0.25 | 3.0 | 461.0 |
| 621C | 1.2:1 | 675.72 | NORPAR 15 | 35.10 | MISTAFLEX H9915 | 77.3 | 127.6 | 37.90 | 0.25 | 3.0 | 461.0 |
| 621D | 1.2:1 | 675.72 | NORPAR 15 | 35.10 | MISTAFLEX H9915 | 77.3 | 127.6 | 37.90 | 0.25 | 3.0 | 461.0 |
| 660A | 1.2:1 | 524.1 | NORPAR 15 | 27.0 | MISTAFLEX H9915 | 38.32 | 146.40 | 43.22 | 0.88 | 3.15 | 527.40 |
| 660B | 1.2:1 | 524.1 | NORPAR 15 | 27.0 | MISTAFLEX H9915 | 38.32 | 146.40 | 43.22 | 0.88 | 3.15 | 527.40 |

| | | | | | Formulation Components | | | | | | |
|---|---|---|---|---|---|---|---|---|---|---|---|
| 660C | 1.2:1 | 524.1 | NORPAR 15 | 27.0 | MISTAFLEX H9915 | 38.32 | 146.40 | 43.22 | 0.88 | 3.15 | 527.40 |
| 664A | 1.2:1 | 524.10 | ISOPAR L | 54.10 | MISTAFLEX H9915 | 40.15 | 140.40 | 41.40 | — | 3.10 | 506.0 |
| 664B | 1.2:1 | 524.10 | ISOPAR L | 54.10 | MISTAFLEX H9915 | 40.15 | 140.40 | 41.40 | — | 3.10 | 506.0 |
| 664C | 1.2:1 | 524.10 | ISOPAR L | 54.10 | MISTAFLEX H9915 | 40.15 | 140.40 | 41.40 | — | 3.10 | 506.0 |
| 668A | 1.2:1 | 524.10 | Exxsol D-110 | 54.10 | MISTAFLEX H9915 | 40.15 | 140.30 | 41.40 | 0.85 | 3.05 | 506.0 |
| 668B | 1.2:1 | 524.10 | Exxsol D-110 | 54.10 | MISTAFLEX H9915 | 40.15 | 140.30 | 41.40 | 0.85 | 3.05 | 506.0 |
| 668C | 1.2:1 | 524.10 | Exxsol D-110 | 54.10 | MISTAFLEX H9915 | 40.15 | 140.30 | 41.40 | 0.85 | 3.05 | 506.0 |
| 672A | 1.2:1 | 524.1 | ISOPAR V | 27.1 | MISTAFLEX H9915 | 38.3 | 146.4 | 43.2 | 0.88 | 3.25 | 521.4 |
| 672B | 1.2:1 | 524.1 | ISOPAR V | 27.1 | MISTAFLEX H9915 | 38.3 | 146.4 | 43.2 | 0.88 | 3.25 | 521.4 |
| 672C | 1.2:1 | 524.1 | ISOPAR V | 27.1 | MISTAFLEX H9915 | 38.3 | 146.4 | 43.2 | 0.88 | 3.25 | 521.4 |
| 680A | 1.2:1 | 524.10 | NORPAR 15 | 27.10 | MISTAFLEX H9915 | 38.3 | 146.4 | 43.20 | 0.88 | 3.50 | 527.40 |
| 680B | 1.2:1 | 524.10 | NORPAR 15 | 27.10 | MISTAFLEX H9915 | 38.3 | 146.4 | 43.20 | 0.88 | 3.50 | 527.40 |
| 680C | 1.2:1 | 524.10 | NORPAR 15 | 27.10 | MISTAFLEX H9915 | 38.3 | 146.4 | 43.20 | 0.88 | 3.50 | 527.40 |
| 684A | 1.2:1 | 524.10 | NORPAR 15 | 32.50 | MISTAFLEX H9915 | 38.60 | 145.2 | 42.90 | 0.88 | 3.30 | 523.0 |
| 684B | 1.2:1 | 524.10 | NORPAR 15 | 32.50 | MISTAFLEX H9915 | 38.60 | 145.2 | 42.90 | 0.88 | 3.30 | 523.0 |
| 684C | 1.2:1 | 524.10 | NORPAR 15 | 32.50 | MISTAFLEX H9915 | 38.60 | 145.2 | 42.90 | 0.88 | 3.30 | 523.0 |

| | | External Phase | | | | | | | |
|---|---|---|---|---|---|---|---|---|---|
| Form. | Molar Ratio Amine:Isocyanate | TETA, 50% sol. (g) | Xylylene-diamine, 50% sol. (g) | Invalon (g) | Kelzan CC (g) | Anti-foam (g) | Glycerin (g) | Proxel GXL (g) | Caustic (g) | Buffer (g) |
| 3993 | 1.29:1 | 6.71 | — | 23.65 | 0.21 | 0.0 | 15.85 | 0.21 | 0.07 | 0.47 |
| 3995 | 1.26:1 | 6.5 | — | 23.65 | 0.21 | 0.0 | 15.85 | 0.21 | 0.07 | 0.47 |
| 3997 | 1.25:1 | 6.4 | — | 23.65 | 0.21 | 0.0 | 15.85 | 0.21 | 0.07 | 0.47 |
| 2805A | 1.03:1-1.04 | 5.48 | — | 71.83 | 0.64 | 0.01 | 48.15 | 0.64 | 0.22 | 1.43 |
| 2805B | 1.03:1-1.04 | 5.50 | — | 71.83 | 0.64 | 0.01 | 48.15 | 0.64 | 0.22 | 1.43 |
| 2805C | 1.03:1-1.04 | 5.39 | — | 71.83 | 0.64 | 0.01 | 48.15 | 0.64 | 0.22 | 1.43 |
| 831A | 1.04:1-1.05:1 | 4.35 | 1.90 | 71.83 | 0.01 | 0.22 | 0.64 | 48.15 | 0.64 | 1.43 |
| 831B | 1.04:1-1.05:1 | 4.38 | 1.91 | 71.83 | 0.01 | 0.22 | 0.64 | 48.15 | 0.64 | 1.43 |
| 831D | 1.04:1-1.05:1 | 4.37 | 1.87 | 71.83 | 0.01 | 0.22 | 0.64 | 48.15 | 0.64 | 1.43 |
| 838A | 1.04:1-1.05:1 | 4.80 | 1.2 | 95.48 | 0.02 | 0.29 | 0.86 | 64.0 | 0.86 | 1.91 |
| 838B | 1.04:1-1.05:1 | 4.79 | 1.21 | 95.48 | 0.02 | 0.29 | 0.86 | 64.0 | 0.86 | 1.91 |
| 838C | 1.04:1-1.05:1 | 4.78 | 1.22 | 95.48 | 0.02 | 0.29 | 0.86 | 64.0 | 0.86 | 1.91 |
| 838D | 1.04:1-1.05:1 | 4.80 | 1.21 | 95.48 | 0.02 | 0.29 | 0.86 | 64.0 | 0.86 | 1.91 |
| 843A | 1.04:1-1.05:1 | 5.17 | 0.59 | 95.48 | 0.02 | 0.29 | 0.86 | 64.0 | 0.86 | 1.91 |
| 843B | 1.04:1-1.05:1 | 5.18 | 0.6 | 95.48 | 0.02 | 0.29 | 0.86 | 64.0 | 0.86 | 1.91 |
| 843C | 1.04:1-1.05:1 | 5.16 | 0.58 | 95.48 | 0.02 | 0.29 | 0.86 | 64.0 | 0.86 | 1.91 |
| 843D | 1.04:1-1.05:1 | 5.17 | 0.59 | 95.48 | 0.02 | 0.29 | 0.86 | 64.0 | 0.86 | 1.91 |
| 874A | 1.2:1 | 6.46 | — | 47.89 | 0.01 | 0.15 | 0.43 | 32.10 | 0.43 | 0.96 |
| 874B | 1.2:1 | 6.45 | — | 47.89 | 0.01 | 0.15 | 0.43 | 32.10 | 0.43 | 0.96 |
| 877A | 1.1:1 | 6.02 | — | 47.89 | 0.01 | 0.15 | 0.43 | 32.10 | 0.43 | 0.96 |
| 877B | 1.1:1 | 6.02 | — | 47.89 | 0.01 | 0.15 | 0.43 | 32.10 | 0.43 | 0.96 |
| 880A | 1.3:1 | 6.88 | — | 47.89 | 0.01 | 0.15 | 0.43 | 32.10 | 0.43 | 0.96 |
| 880B | 1.3:1 | 6.87 | — | 47.89 | 0.01 | 0.15 | 0.43 | 32.10 | 0.43 | 0.96 |
| 883A | 1.15:1 | 12.63 | — | 47.89 | 0.43 | 0.01 | 32.10 | 0.43 | 0.15 | 0.96 |
| 885A | 1.25:1 | 6.67 | — | 23.65 | 0.21 | 0.0 | 15.85 | 0.21 | 0.07 | 0.47 |
| 911A | 1.2:1 | 7.1 | — | 47.89 | 0.43 | 0.01 | 32.10 | 0.43 | 0.15 | 0.96 |
| 911B | 1.2:1 | 7.1 | — | 47.89 | 0.43 | 0.01 | 32.10 | 0.43 | 0.15 | 0.96 |
| 914A | 1.2:1 | 6.46 | — | 47.89 | 0.43 | 0.01 | 32.10 | 0.43 | 0.15 | 0.96 |
| 914C | 1.2:1 | 6.46 | — | 47.89 | 0.43 | 0.01 | 32.10 | 0.43 | 0.15 | 0.96 |
| 917A | 1.2:1 | 6.74 | — | 47.89 | 0.43 | 0.01 | 32.10 | 0.43 | 0.15 | 0.96 |
| 917B | 1.2:1 | 6.74 | — | 47.89 | 0.43 | 0.01 | 32.10 | 0.43 | 0.15 | 0.96 |
| 934 | 1.05:1 | 5.79 | — | 23.65 | 0.21 | 0.0 | 15.85 | 0.21 | 0.07 | 0.47 |
| 939 | 1.05:1 | 6.08 | — | 23.65 | 0.21 | 0.0 | 15.85 | 0.21 | 0.07 | 0.47 |
| 936A | 1.05:1 | 5.79 | — | 47.89 | 0.43 | 0.01 | 32.10 | 0.43 | 0.15 | 0.96 |
| 936B | 1.05:1 | 5.79 | — | 47.89 | 0.43 | 0.01 | 32.10 | 0.43 | 0.15 | 0.96 |
| 941A | 1.05:1 | 6.09 | — | 71.83 | 0.64 | 0.01 | 48.15 | 0.64 | 0.22 | 1.43 |
| 941B | 1.05:1 | 6.10 | — | 71.83 | 0.64 | 0.01 | 48.15 | 0.64 | 0.22 | 1.43 |

TABLE-continued

Formulation Components

| | | | | | | | | | | |
|---|---|---|---|---|---|---|---|---|---|---|
| 941C | 1.05:1 | 6.10 | — | 71.83 | 0.64 | 0.01 | 48.15 | 0.64 | 0.22 | 1.43 |
| 945A | 1.05:1 | 17.6 | — | 71.83 | 0.64 | 0.01 | 48.15 | 0.64 | 0.22 | 1.43 |
| 945B | 1.05:1 | 17.6 | — | 71.83 | 0.64 | 0.01 | 48.15 | 0.64 | 0.22 | 1.43 |
| 945C | 1.05:1 | 17.6 | — | 71.83 | 0.64 | 0.01 | 48.15 | 0.64 | 0.22 | 1.43 |
| 949 | 1.05:1 | 5.8 | — | 23.65 | 0.21 | 0.0 | 15.85 | 0.21 | 0.07 | 0.47 |
| 951A | 1.05:1 | 11.73 | — | 47.89 | 0.43 | 0.01 | 32.10 | 0.43 | 0.15 | 0.96 |
| 951B | 1.05:1 | 11.73 | — | 47.89 | 0.43 | 0.01 | 32.10 | 0.43 | 0.15 | 0.96 |
| 954A | 1.05:1 | 12.31 | — | 47.89 | 0.43 | 0.01 | 32.10 | 0.43 | 0.15 | 0.96 |
| 954B | 1.05:1 | 12.31 | — | 47.89 | 0.43 | 0.01 | 32.10 | 0.43 | 0.15 | 0.96 |
| 957A | 1.05:1 | 12.31 | — | 47.89 | 0.43 | 0.01 | 32.10 | 0.43 | 0.15 | 0.96 |
| 957B | 1.05:1 | 12.31 | — | 47.89 | 0.43 | 0.01 | 32.10 | 0.43 | 0.15 | 0.96 |
| 960A | 1.05:1 | 6.10 | — | 47.89 | 0.43 | 0.01 | 32.10 | 0.43 | 0.15 | 0.96 |
| 960B | 1.05:1 | 6.09 | — | 47.89 | 0.43 | 0.01 | 32.10 | 0.43 | 0.15 | 0.96 |
| 993A | 1.2:1 | 5.90 | — | 71.83 | 0.64 | 0.01 | 48.15 | 0.64 | 0.22 | 1.43 |
| 993B | 1.2:1 | 5.87 | — | 71.83 | 0.64 | 0.01 | 48.15 | 0.64 | 0.22 | 1.43 |
| 993C | 1.2:1 | 5.86 | — | 71.83 | 0.64 | 0.01 | 48.15 | 0.64 | 0.22 | 1.43 |
| 997A | 1.2:1 | 6.21 | — | 71.83 | 0.64 | 0.01 | 48.15 | 0.64 | 0.22 | 1.43 |
| 997B | 1.2:1 | 6.23 | — | 71.83 | 0.64 | 0.01 | 48.15 | 0.64 | 0.22 | 1.43 |
| 997C | 1.2:1 | 6.22 | — | 71.83 | 0.64 | 0.01 | 48.15 | 0.64 | 0.22 | 1.43 |
| 601A | 1.2:1 | 6.54 | — | 71.83 | 0.64 | 0.01 | 48.15 | 0.64 | 0.22 | 1.43 |
| 601B | 1.2:1 | 6.53 | — | 71.83 | 0.64 | 0.01 | 48.15 | 0.64 | 0.22 | 1.43 |
| 601C | 1.2:1 | 6.54 | — | 71.83 | 0.64 | 0.01 | 48.15 | 0.64 | 0.22 | 1.43 |
| 609A | 1.2:1 | 5.12 | — | 71.83 | 0.64 | 0.01 | 48.15 | 0.64 | 0.22 | 1.43 |
| 609B | 1.2:1 | 5.11 | — | 71.83 | 0.64 | 0.01 | 48.15 | 0.64 | 0.22 | 1.43 |
| 609C | 1.2:1 | 5.13 | — | 71.83 | 0.64 | 0.01 | 48.15 | 0.64 | 0.22 | 1.43 |
| 613A | 1.2:1 | 13.56 | — | 71.83 | 0.64 | 0.01 | 48.15 | 0.64 | 0.22 | 1.43 |
| 613B | 1.2:1 | 13.56 | — | 71.83 | 0.64 | 0.01 | 48.15 | 0.64 | 0.22 | 1.43 |
| 613C | 1.2:1 | 13.57 | — | 71.83 | 0.64 | 0.01 | 48.15 | 0.64 | 0.22 | 1.43 |
| 617A | 1.25:1 | 6.20 | — | 71.83 | 0.64 | 0.01 | 48.15 | 0.64 | 0.22 | 1.43 |
| 617B | 1.25:1 | 6.20 | — | 71.83 | 0.64 | 0.01 | 48.15 | 0.64 | 0.22 | 1.43 |
| 617C | 1.25:1 | 6.21 | — | 71.83 | 0.64 | 0.01 | 48.15 | 0.64 | 0.22 | 1.43 |
| 621A | 1.2:1 | 9.72 | — | 95.77 | 0.86 | 0.02 | 64.20 | 0.86 | 0.29 | 1.91 |
| 621B | 1.2:1 | 9.72 | — | 95.77 | 0.86 | 0.02 | 64.20 | 0.86 | 0.29 | 1.91 |
| 621C | 1.2:1 | 9.72 | — | 95.77 | 0.86 | 0.02 | 64.20 | 0.86 | 0.29 | 1.91 |
| 621D | 1.2:1 | 9.73 | — | 95.77 | 0.86 | 0.02 | 64.20 | 0.86 | 0.29 | 1.91 |
| 660A | 1.2:1 | 6.43 | — | 108.38 | 0.97 | 0.02 | 72.65 | 0.97 | 0.33 | 2.16 |
| 660B | 1.2:1 | 6.42 | — | 108.38 | 0.97 | 0.02 | 72.65 | 0.97 | 0.33 | 2.16 |
| 660C | 1.2:1 | 6.45 | — | 108.38 | 0.97 | 0.02 | 72.65 | 0.97 | 0.33 | 2.16 |
| 664A | 1.2:1 | 6.75 | — | 108.38 | 0.97 | 0.02 | 72.65 | 0.97 | 0.33 | 2.16 |
| 664B | 1.2:1 | 6.75 | — | 108.38 | 0.97 | 0.02 | 72.65 | 0.97 | 0.33 | 2.16 |
| 664C | 1.2:1 | 6.74 | — | 108.38 | 0.97 | 0.02 | 72.65 | 0.97 | 0.33 | 2.16 |
| 668A | 1.2:1 | 20.36 | — | 108.38 | 0.97 | 0.02 | 72.65 | 0.97 | 0.33 | 2.16 |
| 668B | 1.2:1 | 20.36 | — | 108.38 | 0.97 | 0.02 | 72.65 | 0.97 | 0.33 | 2.16 |
| 668C | 1.2:1 | 20.36 | — | 108.38 | 0.97 | 0.02 | 72.65 | 0.97 | 0.33 | 2.16 |
| 672A | 1.2:1 | 6.40 | — | 108.38 | 0.97 | 0.02 | 72.65 | 0.97 | 0.33 | 2.16 |
| 672B | 1.2:1 | 6.42 | — | 108.38 | 0.97 | 0.02 | 72.65 | 0.97 | 0.33 | 2.16 |
| 672C | 1.2:1 | 6.43 | — | 108.38 | 0.97 | 0.02 | 72.65 | 0.97 | 0.33 | 2.16 |
| 680A | 1.2:1 | 6.42 | — | 108.38 | 0.97 | 0.02 | 72.65 | 0.97 | 0.33 | 2.16 |
| 680B | 1.2:1 | 6.43 | — | 108.38 | 0.97 | 0.02 | 72.65 | 0.97 | 0.33 | 2.16 |
| 680C | 1.2:1 | 6.42 | — | 108.38 | 0.97 | 0.02 | 72.65 | 0.97 | 0.33 | 2.16 |
| 684A | 1.2:1 | 6.49 | — | 108.38 | 0.97 | 0.02 | 72.65 | 0.97 | 0.33 | 2.16 |
| 684B | 1.2:1 | 6.48 | — | 108.38 | 0.97 | 0.02 | 72.65 | 0.97 | 0.33 | 2.16 |
| 684C | 1.2:1 | 6.49 | — | 108.38 | 0.97 | 0.02 | 72.65 | 0.97 | 0.33 | 2.16 |

TABLE

Particle Size Parameters

| Formulation | Mean Particle size (μm) | Standard Deviation (μm) |
|---|---|---|
| 3993 | 2.01 | 1.14 |
| 3995 | 9.49 | 6.31 |
| 3997 | 10.8 | 7.9 |
| 2805A | 2.26 | 1.27 |
| 2805B | 9.73 | 6.33 |
| 2805C | 15.89 | 12.51 |
| 831A | 2.11 | 1.22 |
| 831B | 8.48 | 5.82 |
| 831D | 11.7 | — |
| 838A | 2.06 | 1.12 |
| 838B | 6.74 | 4.44 |
| 838C | 12.84 | 8.16 |
| 838D | 8.35 | 5.49 |
| 843A | 2.18 | 1.16 |
| 843B | 7.62 | 5.05 |
| 843C | 11.68 | 7.92 |
| 843D | 5.58 | 3.74 |
| 874A | 2.02 | 1.06 |
| 874B | 7.33 | 7.93 |
| 877A | 2.08 | 1.13 |
| 877B | 7.68 | 5.14 |
| 880A | 2.17 | 1.15 |
| 880B | 8.21 | 5.20 |
| 883A | 2.27 | 2.28 |

TABLE-continued

Particle Size Parameters

| Formulation | Mean Particle size (μm) | Standard Deviation (μm) |
|---|---|---|
| 885A | 1.94 | 1.06 |
| 911A | 7.73 | 5.64 |
| 911B | 2.62 | 2.94 |
| 914A | 2.21 | 1.25 |
| 914C | 7.43 | 5.05 |
| 917A | 1.99 | 1.1 |
| 917B | 7.55 | 5.01 |
| 934 | 10.69 | 8.33 |
| 939 | 9.75 | 5.96 |
| 936A | 10.16 | 6.34 |
| 936B | 8.36 | 5.46 |
| 941A | 8.90 | 5.56 |
| 941B | 11.67 | 6.76 |
| 941C | 10.98 | 6.52 |
| 945A | 9.72 | 6.02 |
| 945B | 13.22 | 8.23 |
| 945C | 12.48 | 7.84 |
| 949 | 10.59 | 6.45 |
| 951A | 11.28 | 7.53 |
| 951B | 8.30 | 5.48 |
| 954A | 9.83 | 6.04 |
| 954B | 7.7 | — |
| 957A | 10.46 | 6.38 |
| 957B | 8.01 | 5.13 |
| 960A | 10.60 | 6.51 |
| 960B | 6.65 | 4.55 |
| 993A | 7.86 | 5.36 |
| 993B | 10.95 | 6.64 |
| 993C | 13.9 | 10.4 |
| 997A | 7.73 | 5.17 |
| 997B | 10.56 | 6.66 |
| 997C | 13.38 | 9.21 |
| 601A | 8.13 | 5.23 |
| 601B | 11.08 | 7.44 |
| 601C | 14.64 | 10.46 |
| 609A | 3.28 | 2.63 |
| 609B | 11.61 | 7.22 |
| 609C | 12.65 | 7.66 |
| 613A | 3.24 | 3.37 |
| 613B | 7.73 | 5.18 |
| 613C | 10.90 | 7.88 |
| 617A | 7.10 | 4.67 |
| 617B | 8.93 | 5.75 |
| 617C | 11.23 | 6.86 |
| 621A | 6.70 | 4.42 |
| 621B | 8.88 | 5.89 |
| 621C | 2.48 | 2.43 |
| 621D | 11.53 | 7.02 |
| 660A | 12.50 | 8.59 |
| 660B | 10.13 | 7.69 |
| 660C | 6.83 | 4.77 |
| 664A | 6.84 | 5.24 |
| 664B | 8.27 | 5.47 |
| 664C | 9.35 | 5.95 |
| 668A | 6.75 | 4.55 |
| 668B | 7.02 | 4.75 |
| 668C | 9.75 | 6.16 |
| 672A | 8.13 | 5.35 |
| 672B | 8.82 | 5.71 |
| 672C | 10.82 | 7.59 |
| 680A | 9.29 | 6.08 |
| 680B | 7.60 | 5.04 |
| 680C | 6.70 | 4.51 |
| 684A | 8.36 | 5.59 |
| 684B | 7.04 | 4.78 |
| 684C | 6.33 | 4.35 |
| 684D | 10.3 | — |

Example 11

Release Rates of Microencapsulated Acetochlor Formulations

The release rates for some of the formulations prepared above in Example 10 were measured according to the above described protocol wherein a dispersion of 1% by weight of the encapsulated acetochlor in deionized water was agitated at 150 RPM and 25° C. in a SOTAX AT-7 agitated dissolution test apparatus and sampled at 6 hours and 24 hours. The release rates of the tested formulations are reported in the following table. For comparison, the release rates from DEGREE formulations were also measured and reported.

TABLE

Release Rates

| Formulation | Release at 6 hours (ppm) | Release at 24 hours (ppm) |
|---|---|---|
| 3993 | 211 | 280 |
| 3995 | 80 | 104 |
| 3997 | 96 | 128 |
| 2805A | 179 | 312 |
| 2805B | 91 | 152 |
| 2805C | 88 | 140 |
| DEGREE | 129 | 200 |
| DEGREE | 123 | 200 |
| 831A | 245 | 305 |
| 831B | 168 | 191 |
| 831D | 156 | 182 |
| 838A | 186 | 275 |
| 838D | 170 | 214 |
| 838C | 73 | 90 |
| 843A | 188 | 286 |
| 843B | 94 | 123 |
| 843C | 96 | 134 |
| DEGREE | 131 | 202 |
| DEGREE | 136 | 200 |
| 911A | 137 | 146 |
| 911B | 307 | 320 |
| 914A | 221 | 321 |
| 914C | 96 | 136 |
| 917A | 278 | 329 |
| 917B | 93 | 125 |
| DEGREE | 130 | 202 |
| 934 | 58 | 73 |
| 936B | 70 | 90 |
| 941C | 52 | 63 |
| 951B | 78 | 95 |
| 954B | 54 | 63 |
| DEGREE | 129 | 179 |
| 960A | 52 | 64 |
| DEGREE | 129 | 179 |
| 941A | 56 | 64 |
| 954A | 53 | 64 |
| 957B | 68 | 87 |
| 960B | 70 | 86 |
| DEGREE | 129 | 179 |
| 936B | 70 | 90 |
| 951B | 78 | 95 |
| 960A | 52 | 64 |
| 960B | 70 | 86 |
| DEGREE | 129 | 179 |
| 957B | 68 | 87 |
| 960B | 70 | 86 |
| 951B | 78 | 95 |
| 936B | 70 | 90 |
| DEGREE | 129 | 179 |
| 993A | 81 | 108 |
| 993B | 64 | 86 |
| 993C | 50 | 69 |
| 997A | 79 | 106 |

| Formulation | Release at 6 hours (ppm) | Release at 24 hours (ppm) |
|---|---|---|
| 997C | 53 | 73 |
| 601C | 74 | 94 |
| DEGREE | 134 | 217 |
| 613B | 52 | 65 |
| 613C | 45 | 55 |
| 617A | 77 | 97 |
| 617B | 79 | 95 |
| 621A | 100 | 123 |
| 621B | 65 | 82 |
| DEGREE | 127 | 182 |
| DEGREE | 118 | 174 |
| 664A | 98 | 118 |
| 664B | 75 | 89 |
| 664C | 68 | 83 |
| 668B | 81 | 94 |
| 668C | 59 | 69 |
| 660C | 118 | 144 |
| 680A | 67 | 79 |
| 680B | 82 | 106 |
| 680C | 78 | 103 |
| 684A | 69 | 92 |
| 684C | 62 | 78 |
| 684D | 80 | 104 |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description shall be interpreted as illustrative and not in a limiting sense.

What is claimed is:

1. A method for controlling weeds in a field of crop plants selected from the group consisting of soybeans, cotton, peanuts, rice, wheat, canola, alfalfa, sugarcane, sorghum and sunflowers, the method comprising applying an application mixture to the field in an herbicidally effective amount, wherein the application mixture comprises at least one particulate microencapsulated acetamide herbicide and the application mixture is applied to the field (i) prior to planting the crop plant or (ii) preemergence to the crop plant,
wherein the acetamide herbicide comprises acetochlor, and
wherein the microencapsulated acetamide herbicide comprises a water-immiscible core material comprising the acetamide herbicide and a microcapsule having a polyurea shell wall containing the core material, and wherein the shell wall is formed in a polymerization medium by a polymerization reaction between a polyisocyanate component comprising a polyisocyanate or mixture of polyisocyanates and a polyamine component comprising a polyamine or mixture of polyamines to form the polyurea and the ratio of amine molar equivalents contained in the polyamine component to isocyanate molar equivalents contained in the polyisocyanate component is from 1.15:1 to about 1.7:1.

2. The method of claim 1 wherein the crop plant is selected from the group consisting of soybeans, cotton and peanuts.

3. The method of claim 1 wherein the application mixture is applied to the field prior to planting the crop plant.

4. The method of claim 3 wherein the application mixture is applied to the field at any time during an interval from about 20 days prior to planting of the crop plant to immediately prior to planting the crop plant.

5. The method of claim 1 wherein the application mixture is applied to the field preemergence to the crop plant.

6. The method of claim 5 wherein the application mixture is applied to the field at any time during an interval from about 1 day after planting of the crop plant up to, but not including, emergence of the crop plant.

7. The method of claim 1 wherein the ratio of amine molar equivalents contained in the polyamine component to isocyanate molar equivalents contained in the polyisocyanate component is from 1.15:1 to about 1.4:1.

8. The method of claim 7 wherein the particulate microencapsulated acetamide herbicide has a mean particle size of from about 7 µm to about 15 µm.

9. The method of claim 8 wherein the particulate microencapsulated acetamide herbicide has a mean particle size of from about 8 µm to about 12 µm.

10. The method of claim 1 wherein the polyisocyanate component comprises an aliphatic polyisocyanate.

11. The method of claim 1 wherein the application mixture does not comprise a safener.

12. The method of claim 1 wherein the weeds comprise one or more glyphosate-resistant species, 2,4-D-resistant species, dicamba-resistant species and/or ALS inhibitor herbicide-resistant species.

13. The method of claim 1 wherein the weeds comprise one or more glyphosate-resistant species.

14. The method of claim 13 where the glyphosate-resistant weed species is selected from the group consisting of *Amaranthus palmeri, Amaranthus rudis, Ambrosia artemisiifolia, Ambrosia trifida, Conyza bonariensis, Conyza canadensis, Digitaria insularis, Echinochloa colona, Eleusine indica, Euphorbia heterophylla, Lolium multiflorum, Lolium rigidum, Plantago lancelata, Sorghum halepense, Plantago lancelata*, and *Urochloa panicoides*.

15. The method of claim 1 wherein the application mixture further comprises one or more co-herbicides.

16. The method of claim 15 wherein the co-herbicide is selected from acetyl CoA carboxylase inhibitors, enolpyruvyl shikimate-3-phosphate synthase inhibitors, glutamine synthetase inhibitors, synthetic auxins, photosystem II inhibitors, acetolactate synthase or acetohydroxy acid synthase inhibitors, photosystem I inhibitors, mitosis inhibitors, protoporphyrinogen oxidase inhibitors, cellulose inhibitors, oxidative phosphorylation uncouplers, dihydropteroate synthase inhibitors, fatty acid and lipid biosynthesis inhibitors, auxin transport inhibitors and carotenoid biosynthesis inhibitors, salts and esters thereof, racemic mixtures and resolved isomers thereof, and mixtures thereof.

17. The method of claim 15 wherein the co-herbicide is a photosystem II inhibitor selected from the group consisting of ametryn, amicarbazone, atrazine, bentazon, bromacil, bromoxynil, chlorotoluron, cyanazine, desmedipham, desmetryn, dimefuron, diuron, fluometuron, hexazinone, ioxynil, isoproturon, linuron, metamitron, methibenzuron, metoxuron, metribuzin, monolinuron, phenmedipham, prometon, prometryn, propanil, pyrazon, pyridate, siduron, simazine, simetryn, tebuthiuron, terbacil, terbumeton, terbuthylazine and trietazine, salts and esters thereof, and mixtures thereof.

18. The method of claim 15 wherein the co-herbicide is a protoporphyrinogen oxidase inhibitor selected from the group consisting of acifluorfen, azafenidin, bifenox, butafenacil, carfentrazone-ethyl, flufenpyr-ethyl, flumiclorac, flumiclorac-pentyl, flumioxazin, fluoroglycofen, fluthiacet-methyl, fomesafen, lactofen, oxadiargyl, oxadiazon, oxyfluorfen, pyraflufen-ethyl, saflufenacil and sulfentrazone, salts and esters thereof, and mixtures thereof.

19. The method of claim 15 wherein the co-herbicide is selected from the group consisting of glyphosate, glufosinate, flumioxazin, fomesafen, lactofen, sulfentrazone, oxyfluorfen, saflufenacil, metribuzin and fluometuron, salts and esters thereof, racemic mixtures and resolved isomers thereof, and mixtures thereof.

20. The method of claim 15 wherein the application mixture comprises a first co-herbicide and a second co-herbicide, wherein the first co-herbicide is a non-encapsulated protoporphyrinogen oxidase inhibitor and the second co-herbicide is a non-encapsulated photosystem II inhibitor.

21. The method of claim 1 wherein the application mixture further comprises flumioxazin co-herbicide and the crop plant is cotton or soybeans.

22. The method of claim 1 wherein the application mixture further comprises fomesafen co-herbicide and the crop plant is cotton or soybeans.

23. The method of claim 1 wherein the application mixture further comprises saflufenacil co-herbicide and the crop plant is cotton or soybeans.

24. The method of claim 1 wherein the application mixture further comprises mesotrione co-herbicide and the crop plant is cotton or soybeans.

25. The method of claim 1 wherein the application mixture further comprises isoxaflutole co-herbicide and the crop plant is cotton or soybeans.

26. The method of claim 15 wherein the co-herbicide is not encapsulated.

27. The method of claim 1 wherein the crop plants have one or more herbicide tolerant traits.

28. The method of claim 27 wherein the application mixture further comprises glyphosate co-herbicide and the crop plants are transgenic glyphosate-tolerant crop plants.

29. The method of claim 27 wherein the application mixture further comprises dicamba co-herbicide and the crop plants are transgenic dicamba-tolerant crop plants.

30. The method of claim 27 wherein the application mixture further comprises glufosinate co-herbicide and the crop plants are transgenic glufosinate-tolerant crop plants.

31. The method of claim 28 wherein the crop plants comprise transgenic glyphosate-tolerant cotton plants having increased glyphosate tolerance in vegetative and reproductive tissues such that application of a herbicidal glyphosate formulation to said crop and weeds in said field when at least five leaf nodes are present on a cotton plant of said crop does not incur significant glyphosate-mediated reproductive injury to said plant of said crop.

32. The method of claim 31 wherein the genome of the transgenic glyphosate-tolerant cotton plants comprises one or more DNA molecules selected from the group consisting of SEQ ID NO:1, SEQ ID NO:2, SEQ ID NO:3, and SEQ ID NO:4; or
the genome of the transgenic glyphosate-tolerant cotton plants in a DNA amplification method produces an amplicon comprising SEQ ID NO:1 or SEQ ID NO:2; or the transgenic glyphosate-tolerant cotton plants comprise a glyphosate tolerant trait that is genetically linked to a complement of a marker polynucleic acid, and the marker polynucleic acid molecule is homologous or complementary to a DNA molecule selected from the group consisting of SEQ ID NO:1 and SEQ ID NO:2.

33. The method of claim 31 wherein the crop of transgenic glyphosate-tolerant cotton plants comprises cotton plants grown from seed of cotton event designated MON 88913 and having representative seed deposited with American Type Culture Collection (ATCC) with Accession No. PTA-4854 or glyphosate-tolerant progeny thereof.

34. The method of claim 1 wherein the application mixture acetochlor loading is from about 0.1% to about 5% by weight on an active ingredient basis.

35. The method of claim 1 wherein a commercially acceptable rate of crop injury of not more than 10% is maintained for the time period of from 1 day to 28 days after the crop plants reach the six-leaf growth stage; and
a commercially acceptable rate of weed control of at least 80% is achieved for the time period of from application of the application mixture to 12 weeks after application of the application mixture.

36. The method of claim 1 wherein the application mixture further comprises fluometuron co-herbicide and the crop plant is cotton.

37. The method of claim 1 wherein the application mixture further comprises diuron co-herbicide and the crop plant is cotton.

38. The method of claim 1 wherein the application mixture further comprises sulfentrazone co-herbicide and the crop plant is soybeans.

39. The method of claim 1 wherein the application mixture further comprises metribuzin co-herbicide and the crop plant is soybeans.

40. The method of claim 1 wherein the acetochlor is applied to the field at an application rate of from 0.5 to 10 kilograms per hectare.

41. The method of claim 1 wherein the acetochlor is applied to the field at an application rate of from 1 to 10 kilograms per hectare.

42. The method of claim 1 wherein the acetochlor is applied to the field at an application rate of from 1 to 5 kilograms per hectare.

43. The method of claim 1 wherein the acetochlor is applied to the field at an application rate of from about 0.85 to about 1 kilograms per hectare.

44. The method of claim 1 wherein the acetochlor is applied to the field at an application rate of about 1.1 to about 1.4 kilograms per hectare.

* * * * *